United States Patent
Venkateshappa et al.

(10) Patent No.: US 11,629,135 B2
(45) Date of Patent: Apr. 18, 2023

(54) PYRIMIDINE DERIVATIVES AS INHIBITORS OF PD1/PD-L1 ACTIVATION

(71) Applicant: JUBILANT PRODEL LLC, Yardley, PA (US)

(72) Inventors: Chandregowda Venkateshappa, Bangalore (IN); Athisayamani Jeyaraj Duraiswamy, Bangalore (IN); Rama Kishore V P Putta, Bangalore (IN); Sridharan Rajagopal, Bangalore (IN)

(73) Assignee: JUBILANT PRODELL LLC, Yardley, PA (US)

( * ) Notice: Subject to any disclaimer, the term of this patent is extended or adjusted under 35 U.S.C. 154(b) by 0 days.

(21) Appl. No.: 16/761,792

(22) PCT Filed: Nov. 6, 2018

(86) PCT No.: PCT/IN2018/050716
§ 371 (c)(1),
(2) Date: May 5, 2020

(87) PCT Pub. No.: WO2019/087214
PCT Pub. Date: May 9, 2019

(65) Prior Publication Data
US 2021/0179580 A1    Jun. 17, 2021

(30) Foreign Application Priority Data

Nov. 6, 2017    (IN) .............................. 201741039535

(51) Int. Cl.
| | |
|---|---|
| *C07D 401/06* | (2006.01) |
| *A61P 35/04* | (2006.01) |
| *A61K 45/06* | (2006.01) |
| *C07D 239/52* | (2006.01) |
| *C07D 401/14* | (2006.01) |
| *C07D 405/14* | (2006.01) |

(52) U.S. Cl.
CPC ............ *C07D 401/06* (2013.01); *A61K 45/06* (2013.01); *A61P 35/04* (2018.01); *C07D 239/52* (2013.01); *C07D 401/14* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 3,565,896 A | 2/1971 | Ghielmetti et al. | |
| 3,970,753 A | 7/1976 | Durant | |
| 3,985,881 A | 10/1976 | Mehrhof et al. | |
| 4,246,274 A | 1/1981 | Regel et al. | |
| 4,315,855 A | 2/1982 | Schefczik | |

(Continued)

FOREIGN PATENT DOCUMENTS

| | | |
|---|---|---|
| CN | 101838264 | 9/2010 |
| CN | 105461693 A | 4/2016 |

(Continued)

OTHER PUBLICATIONS

Chemical Abstracts, STN Registry Database, Record for RN 1648388-87-7, Entered into STN Feb. 16, 2015.
Cromwell, et al., "Amino ketones. III. B-Tetrahydroisoquinolino ketones and derivatives. Reaction with Grignard reagents," Journal of the American Chemical Society (1944), 66, 872-3.

(Continued)

*Primary Examiner* — Brian J Davis
(74) *Attorney, Agent, or Firm* — Knobbe, Martens, Olson & Bear LLP

(57) ABSTRACT

The compounds of Formula Ib, Formula Ia, and Formula I are described herein along with their polymorphs, stereoisomers, tautomers, prodrugs, solvates, and pharmaceutically acceptable salts thereof. The process of preparation of the compounds of Formula Ib, Formula Ia, and Formula I is also described. The compounds described herein, their polymorphs, stereoisomers, tautomers, prodrugs, solvates, and pharmaceutically acceptable salts thereof are 2-(benzyloxy) pyrimidine derivatives that are inhibitors of PD-1/PD-L1 activation.

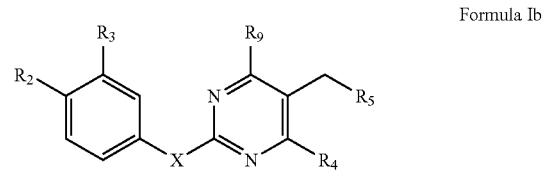

Formula Ib

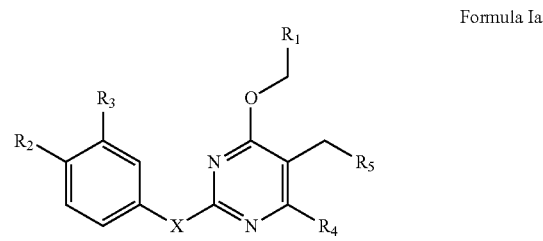

Formula Ia

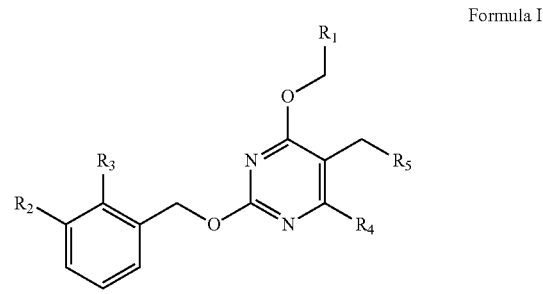

Formula I

16 Claims, 1 Drawing Sheet

(56) References Cited

U.S. PATENT DOCUMENTS

| | | |
|---|---|---|
| 4,495,191 A | 1/1985 | Ehrhardt et al. |
| 4,703,056 A | 10/1987 | Hideg et al. |
| 4,757,081 A | 7/1988 | Yonekura et al. |
| 4,871,735 A | 10/1989 | Heider et al. |
| 4,871,751 A | 10/1989 | Yonekura et al. |
| 4,962,113 A | 10/1990 | Tsushima et al. |
| 5,001,132 A | 3/1991 | Manoury et al. |
| 5,010,094 A | 4/1991 | Schade et al. |
| 5,047,411 A | 9/1991 | Takasugi et al. |
| 5,100,890 A | 3/1992 | Siegal et al. |
| 5,179,125 A | 1/1993 | Mimura et al. |
| 5,210,266 A | 5/1993 | Mimura et al. |
| 5,229,516 A | 7/1993 | Messer et al. |
| 5,244,908 A | 9/1993 | Takatani et al. |
| 5,273,980 A | 12/1993 | Frenette et al. |
| 5,330,989 A | 7/1994 | Soll et al. |
| 5,420,289 A | 5/1995 | Musser et al. |
| 5,541,033 A | 7/1996 | Blakeney et al. |
| 5,547,814 A | 8/1996 | Blakeney et al. |
| 5,550,162 A | 8/1996 | Frost et al. |
| 5,554,621 A | 9/1996 | Poindexter et al. |
| 5,663,183 A | 9/1997 | Frost et al. |
| 6,844,445 B2 | 1/2005 | Wierzbicki et al. |
| 6,887,868 B2 | 5/2005 | Fu |
| 8,148,408 B2 | 4/2012 | Bunnelle et al. |
| 8,642,660 B2 | 2/2014 | Goldfarb |
| 9,067,898 B1 | 6/2015 | Illig |
| 9,732,066 B2 | 8/2017 | Otsu |
| 2002/0094989 A1 | 7/2002 | Hale et al. |
| 2002/0173531 A1 | 11/2002 | Wierzbicki et al. |
| 2003/0018025 A1 | 1/2003 | Thurkauf et al. |
| 2004/0229160 A1 | 11/2004 | Naiini et al. |
| 2005/0159334 A1 | 7/2005 | Gluck et al. |
| 2005/0228014 A1 | 10/2005 | Marquess et al. |
| 2006/0270686 A1 | 11/2006 | Kelly et al. |
| 2007/0191371 A1 | 8/2007 | Bennett et al. |
| 2007/0219218 A1 | 9/2007 | Yu et al. |
| 2008/0280891 A1 | 11/2008 | Kelly et al. |
| 2009/0069373 A1 | 3/2009 | Wrobel et al. |
| 2009/0264433 A1 | 10/2009 | Russell et al. |
| 2010/0249127 A1 | 9/2010 | Namdev et al. |
| 2017/0105971 A1 | 4/2017 | Catrina et al. |
| 2017/0174672 A1 | 6/2017 | Amberg et al. |
| 2021/0015810 A1 | 1/2021 | Venkateshappa et al. |
| 2021/0371431 A1 | 12/2021 | Vadivelu et al. |

FOREIGN PATENT DOCUMENTS

| | | |
|---|---|---|
| CN | 107056630 A | 8/2017 |
| CN | 107163044 A | 9/2017 |
| CN | 108358917 A | 8/2018 |
| CN | 110105299 A | 8/2019 |
| CN | 110963997 A | 9/2019 |
| CN | 107056630 B | 1/2020 |
| CN | 111606904 A | 9/2020 |
| DE | 1961595 A | 6/1970 |
| DE | 2832677 A1 | 2/1980 |
| DE | 3210570 A1 | 10/1983 |
| DE | 3628545 A1 | 4/1987 |
| DE | 3901723 A1 | 7/1990 |
| DE | 4227522 A1 | 2/1994 |
| DE | 19717371 A1 | 10/1998 |
| DE | 19834751 | 2/2000 |
| EP | 0090269 A1 | 10/1983 |
| EP | 0218118 A1 | 4/1987 |
| EP | 0239391 A2 | 9/1987 |
| EP | 0259793 A1 | 3/1988 |
| EP | 0301751 A1 | 2/1989 |
| EP | 0370852 A1 | 5/1990 |
| EP | 0218118 B1 | 9/1991 |
| EP | 0471236 A1 | 2/1992 |
| EP | 0259793 B1 | 7/1992 |
| EP | 0301751 B1 | 3/1993 |
| EP | 0533056 A2 | 3/1993 |
| EP | 0535924 A1 | 4/1993 |
| EP | 0533056 A3 | 6/1993 |
| EP | 0666250 A1 | 8/1995 |
| EP | 0747378 A1 | 12/1996 |
| EP | 0764640 A1 | 3/1997 |
| EP | 0819977 A1 | 1/1998 |
| EP | 0666250 B1 | 2/1998 |
| EP | 1245565 A1 | 10/2002 |
| EP | 1245565 B1 | 9/2003 |
| EP | 1388342 A1 | 2/2004 |
| EP | 2194035 A2 | 6/2010 |
| EP | 2194035 A3 | 6/2010 |
| EP | 2194035 B1 | 11/2011 |
| EP | 3 112 362 A1 | 1/2017 |
| FR | 2102082 A2 | 4/1972 |
| FR | 2102082 B2 | 10/1974 |
| FR | 2706895 A1 | 12/1994 |
| FR | 2706895 B1 | 8/1995 |
| GB | 1230663 A | 5/1971 |
| GB | 1356789 A | 6/1974 |
| JP | 62187452 A | 8/1987 |
| JP | H 02215809 A | 8/1990 |
| JP | 06184076 | 12/1992 |
| JP | 07304770 | 5/1994 |
| JP | 11119379 A1 | 4/1999 |
| JP | 2001233712 A | 8/2001 |
| JP | 2005060247 A | 3/2005 |
| JP | 2008280344 A | 11/2008 |
| JP | 2009209090 A | 9/2009 |
| JP | 2009274984 | 11/2009 |
| JP | 2011063589 A | 3/2011 |
| JP | 2011207765 | 10/2011 |
| JP | 2019156770 A | 9/2019 |
| JP | 2021054909 | 4/2021 |
| RU | 2371444 C1 | 10/2009 |
| RU | 2632908 C2 | 10/2017 |
| WO | WO 86/05519 | 9/1986 |
| WO | WO 9106537 A2 | 5/1991 |
| WO | WO 9106537 A3 | 10/1991 |
| WO | WO 9301157 A1 | 1/1993 |
| WO | WO 9312094 A1 | 6/1993 |
| WO | WO 9320099 A2 | 10/1993 |
| WO | WO 9320099 A3 | 11/1993 |
| WO | WO 9401407 A2 | 1/1994 |
| WO | WO 9401407 A3 | 3/1994 |
| WO | WO 9422829 A2 | 10/1994 |
| WO | WO 9422834 A1 | 10/1994 |
| WO | WO 9427971 A1 | 12/1994 |
| WO | WO 9422829 A3 | 1/1995 |
| WO | WO 9509843 A1 | 4/1995 |
| WO | WO 9511226 A1 | 4/1995 |
| WO | WO 9521164 A1 | 8/1995 |
| WO | WO 9521832 A1 | 8/1995 |
| WO | WO 9610012 A1 | 4/1996 |
| WO | WO 9616040 A1 | 5/1996 |
| WO | WO 9709066 A1 | 3/1997 |
| WO | WO 9724119 A1 | 7/1997 |
| WO | WO 9740051 A1 | 10/1997 |
| WO | WO 9817648 A1 | 4/1998 |
| WO | WO 9824766 A1 | 6/1998 |
| WO | WO 9834609 A1 | 8/1998 |
| WO | WO 9836749 A1 | 8/1998 |
| WO | WO 9838156 A1 | 9/1998 |
| WO | WO 9906387 A2 | 2/1999 |
| WO | WO 9906387 A3 | 4/1999 |
| WO | WO 9932447 A2 | 7/1999 |
| WO | WO 9932447 A3 | 10/1999 |
| WO | WO 2000007978 A1 | 2/2000 |
| WO | WO 2000023420 A1 | 4/2000 |
| WO | WO 2000026203 A1 | 5/2000 |
| WO | WO 2001070731 A1 | 9/2001 |
| WO | WO 2001077075 A2 | 10/2001 |
| WO | WO 2001087293 A1 | 11/2001 |
| WO | WO 2002002518 A2 | 1/2002 |
| WO | WO 2002002520 A2 | 1/2002 |
| WO | WO 2002083673 A1 | 1/2002 |
| WO | WO 2001077075 A3 | 3/2002 |
| WO | WO 2002002518 A3 | 8/2002 |
| WO | WO 2002002520 A3 | 8/2002 |
| WO | WO 2002066478 A1 | 8/2002 |

(56) References Cited

FOREIGN PATENT DOCUMENTS

| | | |
|---|---|---|
| WO | WO 2002070510 A2 | 9/2002 |
| WO | WO 2002076964 A1 | 10/2002 |
| WO | WO 2002076979 A1 | 10/2002 |
| WO | WO 2002088089 A1 | 11/2002 |
| WO | WO 2002098869 A2 | 12/2002 |
| WO | WO 2002100813 A2 | 12/2002 |
| WO | WO 2002070510 A3 | 1/2003 |
| WO | WO 2008000408 A1 | 1/2003 |
| WO | WO 2003035076 A1 | 5/2003 |
| WO | WO 2003037887 A1 | 5/2003 |
| WO | WO 2003044016 A1 | 5/2003 |
| WO | WO 2003044017 A1 | 5/2003 |
| WO | WO 2003066613 A1 | 8/2003 |
| WO | WO 2003084916 A2 | 10/2003 |
| WO | WO 2002100813 A3 | 11/2003 |
| WO | WO 2003084916 A3 | 12/2003 |
| WO | WO 2002098869 A3 | 2/2004 |
| WO | WO 2004011430 A1 | 2/2004 |
| WO | WO 2004014372 A1 | 2/2004 |
| WO | WO 2004022558 A2 | 3/2004 |
| WO | WO 2004035579 A1 | 4/2004 |
| WO | WO 2004022558 A3 | 5/2004 |
| WO | WO 2004/052846 A1 | 6/2004 |
| WO | WO 2004048363 A1 | 6/2004 |
| WO | WO 2004058679 A2 | 7/2004 |
| WO | WO 2004058679 A3 | 8/2004 |
| WO | WO 2004078731 A1 | 9/2004 |
| WO | WO 2004109400 A2 | 12/2004 |
| WO | WO 2002034716 A2 | 5/2005 |
| WO | WO 2005058823 A1 | 6/2005 |
| WO | WO 2005092899 A1 | 10/2005 |
| WO | WO 2005100350 A1 | 10/2005 |
| WO | WO 2005105805 A1 | 11/2005 |
| WO | WO 2005105805 A9 | 1/2006 |
| WO | WO 2006048330 A1 | 5/2006 |
| WO | WO 2006062224 A1 | 6/2006 |
| WO | WO 2006069125 A1 | 6/2006 |
| WO | WO 2006102588 A1 | 9/2006 |
| WO | WO 2006105971 A1 | 10/2006 |
| WO | WO 2004109400 A3 | 11/2006 |
| WO | WO 2006125119 A1 | 11/2006 |
| WO | WO 2006130707 A2 | 12/2006 |
| WO | WO 2006133104 A2 | 12/2006 |
| WO | WO 2006130707 A3 | 1/2007 |
| WO | WO 2006133104 A3 | 4/2007 |
| WO | WO 2007073503 A2 | 6/2007 |
| WO | WO 2007087548 A2 | 8/2007 |
| WO | WO 2007105989 A2 | 9/2007 |
| WO | WO 2007106469 A2 | 9/2007 |
| WO | WO 2007073503 A3 | 11/2007 |
| WO | WO 2007105989 A3 | 11/2007 |
| WO | WO 2007133108 A1 | 11/2007 |
| WO | WO 2007106469 A3 | 12/2007 |
| WO | WO 2008008059 A1 | 1/2008 |
| WO | WO 2008022945 A1 | 2/2008 |
| WO | WO 2008051757 A1 | 5/2008 |
| WO | WO 2008064320 A2 | 5/2008 |
| WO | WO 2008065500 A2 | 6/2008 |
| WO | WO 2008065500 A3 | 6/2008 |
| WO | WO 2008066789 A2 | 6/2008 |
| WO | WO 2008079988 A2 | 7/2008 |
| WO | WO 2008104077 A1 | 9/2008 |
| WO | WO 2008112715 A2 | 9/2008 |
| WO | WO 2008064320 A3 | 10/2008 |
| WO | WO 2008121687 A2 | 10/2008 |
| WO | WO 2008123582 A1 | 10/2008 |
| WO | WO 2008112715 A3 | 11/2008 |
| WO | WO 2008135526 A1 | 11/2008 |
| WO | WO 2008156142 A1 | 12/2008 |
| WO | WO 2009010925 A2 | 1/2009 |
| WO | WO 2009023179 A2 | 2/2009 |
| WO | WO 2009038842 A2 | 3/2009 |
| WO | WO 2009048152 A2 | 4/2009 |
| WO | WO 2009054914 A1 | 4/2009 |
| WO | WO 2009010925 A3 | 7/2009 |
| WO | WO 2009080351 A1 | 7/2009 |
| WO | WO 2009104819 A1 | 8/2009 |
| WO | WO 2009048152 A3 | 9/2009 |
| WO | WO 2009112651 A1 | 9/2009 |
| WO | WO 2009137309 A2 | 11/2009 |
| WO | WO 2009140101 A2 | 11/2009 |
| WO | WO 2005123703 A2 | 12/2009 |
| WO | WO 2009038842 A3 | 12/2009 |
| WO | WO 2009153313 A1 | 12/2009 |
| WO | WO 2010048207 A2 | 4/2010 |
| WO | WO 2010075973 A1 | 7/2010 |
| WO | WO 2010077680 A2 | 7/2010 |
| WO | WO 2010091409 A1 | 8/2010 |
| WO | WO 2010098495 A1 | 9/2010 |
| WO | WO 2010151799 A2 | 12/2010 |
| WO | WO 2011023989 A1 | 3/2011 |
| WO | WO 2011086178 A1 | 7/2011 |
| WO | WO 2011100380 A1 | 8/2011 |
| WO | WO 2011123751 A2 | 10/2011 |
| WO | WO 2012006202 A1 | 1/2012 |
| WO | WO 2012006203 A1 | 1/2012 |
| WO | WO 2012022265 A1 | 2/2012 |
| WO | WO 2021028810 A1 | 2/2012 |
| WO | WO 20122022045 A1 | 2/2012 |
| WO | WO 2012058133 A1 | 5/2012 |
| WO | WO 2012087833 A1 | 6/2012 |
| WO | WO 2013000994 A1 | 1/2013 |
| WO | WO 2013002879 A1 | 1/2013 |
| WO | WO 2013002880 A1 | 1/2013 |
| WO | WO 2013018371 A1 | 2/2013 |
| WO | WO 2013025733 A1 | 2/2013 |
| WO | WO 2013068470 A1 | 5/2013 |
| WO | WO 2013096049 A1 | 6/2013 |
| WO | WO 2013096055 A1 | 6/2013 |
| WO | WO 2013096059 A1 | 6/2013 |
| WO | WO 2013096060 A1 | 6/2013 |
| WO | WO 2013096681 A1 | 6/2013 |
| WO | WO 2013120464 A1 | 8/2013 |
| WO | WO 2013127729 A1 | 9/2013 |
| WO | WO 2010077680 A3 | 10/2013 |
| WO | WO 2013174895 A1 | 11/2013 |
| WO | WO 2013178810 A1 | 12/2013 |
| WO | WO 2013192430 A2 | 12/2013 |
| WO | WO 2014013182 A1 | 1/2014 |
| WO | WO 2014015905 A1 | 1/2014 |
| WO | WO 2014031872 A2 | 2/2014 |
| WO | WO 2014031986 A1 | 2/2014 |
| WO | WO 2014031872 A3 | 4/2014 |
| WO | WO 2014077321 A1 | 5/2014 |
| WO | WO 2014/100719 A2 | 6/2014 |
| WO | WO 2014100764 A2 | 6/2014 |
| WO | WO 2014100764 A3 | 9/2014 |
| WO | WO 2014152018 A1 | 9/2014 |
| WO | WO 2015011397 A1 | 1/2015 |
| WO | WO 2015/034820 A1 * 3/2015 ........... C07D 211/60 |
| WO | WO 2015031295 A1 | 3/2015 |
| WO | WO 2015086512 A1 | 6/2015 |
| WO | WO 2015086527 A1 | 6/2015 |
| WO | WO 2015108038 A1 | 7/2015 |
| WO | WO 2015140051 A1 | 9/2015 |
| WO | WO 2015197028 A1 | 12/2015 |
| WO | WO 2016008433 A1 | 1/2016 |
| WO | WO 2016031815 A1 | 3/2016 |
| WO | WO 2016034675 A1 | 3/2016 |
| WO | WO 2016036636 A1 | 3/2016 |
| WO | WO 2016051306 A2 | 4/2016 |
| WO | WO 2016102727 A1 | 6/2016 |
| WO | WO 2006126939 A1 | 11/2016 |
| WO | WO 2016185279 A1 | 11/2016 |
| WO | WO 2017024180 A1 | 2/2017 |
| WO | WO 2017025510 A1 | 2/2017 |
| WO | WO 2017/042182 | 3/2017 |
| WO | WO 2017068412 A1 | 4/2017 |
| WO | WO 2017106634 A1 | 6/2017 |
| WO | WO 2017109095 A1 | 6/2017 |
| WO | WO 2017/118762 | 7/2017 |
| WO | WO 2017/147102 | 8/2017 |
| WO | WO 2017216281 A1 | 12/2017 |
| WO | WO 2018002848 A1 | 1/2018 |

(56) References Cited

FOREIGN PATENT DOCUMENTS

| | | |
|---|---|---|
| WO | WO 2018019204 A1 | 2/2018 |
| WO | WO 2018026971 A1 | 2/2018 |
| WO | WO 2018112843 A1 | 6/2018 |
| WO | WO 2018119036 A1 | 6/2018 |
| WO | WO 2018121610 A1 | 7/2018 |
| WO | WO 2018183411 A1 | 10/2018 |
| WO | WO 2018208985 A2 | 11/2018 |
| WO | WO 2018234342 A1 | 12/2018 |
| WO | WO 2019007696 A1 | 1/2019 |
| WO | WO 2019/058393 A1 | 3/2019 |
| WO | WO 2019/077631 A1 | 4/2019 |
| WO | WO 2019079783 A1 | 4/2019 |
| WO | WO 2019/102494 A1 | 5/2019 |
| WO | WO 2019126081 A1 | 6/2019 |
| WO | WO 2019154047 A1 | 8/2019 |
| WO | WO 2019160014 A1 | 8/2019 |
| WO | WO 2019175897 A1 | 9/2019 |
| WO | WO 2019205147 A1 | 10/2019 |
| WO | WO 2019213234 A1 | 11/2019 |
| WO | WO 2020028723 A1 | 2/2020 |
| WO | WO 2020029980 A1 | 2/2020 |
| WO | WO 2020045216 A1 | 3/2020 |
| WO | WO 2020083971 A2 | 4/2020 |
| WO | WO 2020092394 A1 | 5/2020 |
| WO | WO 2020201773 A1 | 10/2020 |
| WO | WO 2020246910 A1 | 12/2020 |
| WO | WO 2021014949 A1 | 1/2021 |
| WO | WO 2021018858 A1 | 2/2021 |
| WO | WO 2021060432 A1 | 4/2021 |
| WO | WO 2021096238 A1 | 5/2021 |
| WO | WO 2021096241 A1 | 5/2021 |

OTHER PUBLICATIONS

Evans, et al. "Phenoxyacetic acids as PPAR☐ partial agonists: Synthesis, optimization, and in vivo efficacy," Bioorganic & Medicinal Chemistry Letters (2011), 21(8), 2345-2350.

Fukagawa, Tomokichi, "The biuret reaction. VII. Primary-quaternary bases which give the biuret reaction," Z. physiol. Chem. (1931), 201, 40-6.

Goi, et al., "Synthesis and pharmacological properties of pyridinecarbonyl derivatives of 7-substituted theophyllines," Chimica Therapeutica (1973), 8(6), 634-7.

Hwang, et al., "Synthesis and evaluation of methylsulfonylnitrobenzamides (MSNBAs) as inhibitors of the thyroid hormone receptor-coactivator interaction," Bioorganic & Medicinal Chemistry Letters (2013), 23(6), 1891-1895.

Ivaschenko, et al., "Synthesis, biological evaluation and in silico modeling of novel integrase strand transfer inhibitors (INSTIs)," European Journal of Medicinal Chemistry (2020), 189, 112064.

Nicolaou, et al., "Synthesis of imides, N-acyl vinylogous carbamates and ureas, and nitriles by oxidation of amides and amines with Dess-Martin periodinane," Angewandte Chemie, International Edition (2005), 44(37), 5992-5997.

Piper, et al., "Synthesis of potential inhibitors of hypoxanthine-guanine phosphoribosyltransferase for testing as antiprotozoal agents. 1. 7-Substituted 6-oxopurines," Journal of Medicinal Chemistry (1980), 23(4), 357-64.

Spassova, et al., "Synthesis of N-(3-azido-2 hydroxypropyl), N-(3-phthalimido-2-hydroxypropyl) and N-(3-amino-2 hydroxypropyl) derivatives of heterocyclic bases," Collection of Czechoslovak Chemical Communications (1994), 59(5), 1153-74.

Uenishi, et al, "Structural effects of diazonaphthoquinone-photoactivecompound backbone on resist lithographic properties," Proceedings of SPIE—The International Society for Optical Engineering (1991), 1466(Adv. Resist Technol. Process. 8), 102-16.

Vooturi, et al., "Solution-phase parallel synthesis of novel membrane-targeted antibiotics," Journal of Combinatorial Chemistry (2010), 12(1), 151-160.

Zajdel, et al, "Solid-phase synthesis of aryl-alkylamine derivatives using protected aminoalcohol building blocks on SynPhase lanterns," QSAR & Combinatorial Science (2007), 26(2), 215-219.

Acharya et al., "Neuronal PAD4 expression and protein citrullination: Possible role in production of autoantibodies associated with neurodegenerative disease", J. Autoimmun., vol. 38, pp. 369-380, 2012.

Arisan, et al., "Putative Roles for Peptidylarginine Deiminases in COVID-19", International Journal of Molecular Sciences, vol. 21, No. 13, in 29 pages, 2020.

Barber, et al., "Restoring function in exhausted CD8 T cells during chronic viral infection", Nature, vol. 439, No. 7077, pp. 682-687, 2005.

Bardhan, et al., "The PD1:PD-L1/2 Pathway from Discovery to Clinical Implementation", Frontiers in Immunology, vol. 7, No. 550, pp. 1-17, 2016.

Barnes, et al., "Targeting potential drivers of COVID-19: Neutrophil extracellular traps", Journal of Experimental Medicine, vol. 217, No. 6, in 7 pages, 2020.

Bertini, et al., "Carbazole-containing arylcarboxamides as BACE1 inhibitors," Bioorganic & Medicinal Chemistry Letters (2011), 21 (22), 6657-6661.

Borregaard, "Neutrophils, from Marrow to Microbes", Immunity, vol. 33, No. 5, pp. 657-670, 2010.

Brinkmann, et al., "Neutrophil Extracellular Traps Kill Bacteria", Science, vol. 303, No. 5663, pp. 1532-1535, 2004.

Candi et al., "The Cornified Envelope: A Model of Cell Death in the Skin", Nat. Rev. Mol. Cell Biol., vol. 6, pp. 328-340, 2005.

Cedervall et al., NETosis in Cancer, Oncoscience, vol. 2, No. 11, pp. 900-901, 2015.

Chen, et al., "Anti-PD-1/PD-L1 therapy of human cancer: past, present, and future", Journal of Clinical Investigation, vol. 125, No. 9, pp. 3384-3391, 2015.

Chang et al., "Increased PADI4 expression in blood and tissues of patients with malignant tumors", BMC Cancer, vol. 9, pp. 40, 2009.

Chiummiento, et a;., "New indolic non-peptidic HIV protease inhibitors from (S)-glycidol: synthesis and preliminary biological activity," Tetrahedron (2009), 65(31), 5984-5989.

Christophorou et al., Citrullination regulated pluripotency and histone H1 binding to chromatin, Nature, vol. 507, pp. 104-108, 2014.

Chumanevich et al., "Suppression of colitis in mice by C1-amidine: a novel peptidylarginine deiminase inhibitor", Am. J. Physiol. Gastrointest. Liver Physiol., vol. 300, No. 6, pp. G929-G938, 2011.

Curiel, et al., "Blockade of B7-H1 improves myeloid dendritic cell-mediated antitumor or immunity", Nature Medicine, vol. 9, No. 5, pp. 562-567, 2003.

Dimauro et al., Discovery of Aminoquinazolines as Potent, Orally Bioavailable Inhibitor of Lck: Synthesis, SAR, and in Vivo Anti-inflammatory Activity, Journal of Medical Chemistry, vol. 49, No. 19, pp. 5671-5686, 2006.

Dong, et al., "Tumor-associated B7-H1 promotes T-cell apoptosis: A potential mechanism of immune evasion", Nature Medicine, vol. 8, No. 8, pp. 793-800, 2002.

Dong, et al., "PD-1 and its ligands are important immune checkpoints in cancer", Oncotarget, vol. 8, No. 2, pp. 2171-2186, 2017.

First Examination Report dated Sep. 8, 2021 received in Indian Patent Application No. 201741033768.

Flies, et al., "The New B7S: Playing a Pivotal Rose in Tumor Immunity", Immunotherapy, vol. 30, No. 3, pp. 251-260, 2007.

Flies, et al., "Blockade of the B7-H1/PD-1 Pathway for Cancer Immunotherapy", Yale J. Biology Medicine, vol. 84, No. 4, pp. 409-421, 2011.

Fuhrmann, Jakob, et al., "Chemical Biology of Protein Arginine Modifications in Epigenetic Regulation," Chemical Reviews, 2015, 115, 5413-5461.

Francisco, et al., "PD-L1 regulates the development, maintenance, and function of induced regulatory T cells", Journal of Experimental Medicine, vol. 206, No. 13, pp. 3015-3029, 2009.

Guo, et al., "Development of Benzophenone-Alkyne Bifunctional Sigma Receptor Ligands," ChemBioChem (2012), 13(15), 2277-2289.

Gyorgy et al., "Citrullination: A posttranslational modification in health and disease", Int. J. Biochem. Cell Biol., vol. 38, pp. 1662-1677, 2006.

(56) References Cited

OTHER PUBLICATIONS

Hamanishi, et al., "PD-1/PD-L1 blockade in cancer treatment: perspectives and issues", Int. J. Clin. Oncol., vol. 21, pp. 462-473, 2016.
Hankovsky, et al., "New antiarrhythmic agents. 2,2,5,5-Tetramethyl-3-pyrroline-3-carboxamides and 2,2,5,5 tetramethylpyrrolidine-3-carboxamides," Journal of Medicinal Chemistry (1986), 29(7), 1138-52.
He, et al., "Development of PD-1/PD-L1 Pathway in Tumor Immune Microenvironment and Treatment for Non-Small Cell Lung Cancer", Scientific Reports, vol. 5, pp. 1-9, 2015.
International Search Report and WritTen Opinion dated Nov. 12, 2018 for PCT/IN2018/050614.
International Search Report & written opinion, dated Feb. 14, 2019, in International Application No. PCT/IN2018/050671.
International Search Report & Written Opinion, dated Feb. 20, 2019, in International Application No. PCT/IN2018/050671.
International Search Report & Written Opinion, dated May 20, 2019 in International Application No. PCT/IN2019/050203.
Ireland et al., "Autophagy in antigen-presenting cells results in presentation of citrullinated peptides to CD4 T cells", J. Exp. Med., vol. 208, pp. 2625-2632, 2011.
Jones et al., "Protein arginine deiminase 4 (PAD4): current understanding and future therapeutic potential", Curr. Opin. Drug Discov. Devel., vol. 12, pp. 616-627, 2009.
Knight et al., "Peptidylarginine Deiminase Inhibition Reduces Vascular Damage and Modulates Innate Immune Responses in Murine Models of Atherosclerosis", Circ. Res., vol. 114, No. 6, pp. 947-956, 2014.
Kochi et al., "PADI4 polymorphism predisposes male smokers to rheumatoid arthritis", Ann. Rheum. Dis., vol. 70, pp. 512-515, 2011.
Labrie, et al., "In vitro activity of novel dual action MDR anthranilamide modulators with inhibitory activity at CYP450," Bioorganic & Medicinal Chemistry (2006), 14(23), 7972-7987.
Lai, et al., "A Novel PD-L1-targeting Antagonistic DNA Aptamer With Antitumor Effects", Mol. Therapy—Nucl. Acids, vol. 5, pp. e397, 2016.
Lakshmann, et al., "Synthesis and evaluation of novel N-substituted-6 methoxynaphthalene-2-carboxamides as potential chemosensitizing agents for cancer," Chemical & Pharmaceutical Bulletin (2008), 56(7), 894-896.
Lange et al., "Protein deiminases: New players in the developmentally regulated loss of neural regenerative ability", Dev. Biol., vol. 355, No. 2, pp. 205-214, 2011.
Lee, et al., Interferon regulatory factor-1 is prerequisite to the constitutive expression and IFN-γ-induced upregulation of B7-H1 (CD274), FEBS Letters, vol. 580, pp. 755-762, 2006.
"Letter to the Editors-in-Chief", Thrombosis Research 191, pp. 26-27, 2020.
Leung, et al., "The CD28-B7 Family in Anti-Tumor Immunity: Emerging Concepts in Cancer Immunotherapy", Immune Network, vol. 14, No. 6, pp. 265-276, 2014.
Lewis et al, "Inhibition of PAD4 activity is sufficient to disrupt mouse and human NET formation", Nature Chemical Biology 11(3), 189-191. 10.1038/nchembio.1735, 2015.
Li et al., "Regulation of p53 Target Gene Expression by Peptidylarginine Deiminase 4", Mol. Cell Biol., vol. 28, pp. 4745-4758, 2008.
Liu, G.-Y, et al., "Overexpression of peptidylarginine deiminase IV features in apoptosis of haematopoietic cells", Apoptosis, vol. 11, pp. 183-196, 2006.
Loos et al., "Citrullination of CXCL10 and CXCL11 by peptidylarginine deiminase: a naturally occurring posttranslational modification of chemokines and new dimension of immunoregulation", Blood, vol. 112, pp. 2648-2656, 2008.
Makrygiannakis et al., "Citrullination is an inflammation-dependent process", Ann. Rheum. Dis., vol. 65, pp. 1219-1222, 2006.
Mastronardi et al., "Increased Citrullination of Histone H3 in Multiple Sclerosis Brain and Animal Models of Demyelination: A Role for Tumor Necrosis Factor-Induced Peptidylarginine Deiminase 4 Translocation", The Journal of Neurosciences, vol. 26, pp. 11387-11396, 2006.
Mohanan, Sunish, et al., "Potential Role of Peptidylarginine Deiminase Enzymes and Protein Citrullination in Cancer Pathogenesis," Biochemistry Research International, vol. 2012, article ID 895343.
Muenst, et al., "Expression of programmed death ligand 1 (PD-L1) is associated with poor prognosis in human breast cancer", Breast Cancer Res. Treat., vol. 146, No. 1, pp. 15-24, 2014.
Nakashima et al., "Molecular Characterization of Peptidylarginine Deiminase in HL-60 Cells Induced by Retinoic Acid and 1α,25-Dihydroxyvitamin D3", J. Biol. Chem., vol. 274, pp. 27786-27792, 1999.
Nathan, "Neutrophils and COVID-19: Nots, NETs, and knots", The Journal of Experimental Medicine, vol. 217, No. 9, in 3 pages, 2020.
Neeli et al., "Histone Deimination as a Response to Inflammatory Stimuli in Neutrophils", J. Immunol., vol. 180, pp. 1895-1902, 2008.
Omran, et al., "Synthesis and biological evaluation of new Donepezil-like Thiaindanones as AChE inhibitors," Journal of Enzyme Inhibition and Medicinal Chemistry (2008), 23(5), 696-703.
Patsoukis, et al., "PD-1 inhibits T cell proliferation by upregulating p27 and p15 and suppressing Cdc25A", Cell Cycle, vol. 11, No. 23, pp. 4305-4309, 2012.
Schönrich, et al., "Neutrophil Extracellular Traps Go Viral", Frontiers in Immunology, vol. 7, No. 366 in 7 pages, 2016.
Sheppard, et al., "PD-1 inhibits T-cell receptor induced phosphorylation of the ZAP70/CD3 signalosome and downstream signaling to PKCθ", FEBS Letters, vol. 574, pp. 37-41, 2004.
Slack et al., "Protein arginine deiminase 4: a target for an epigenetic cancer therapy", Cellular and Molecular Life Sciences, vol. 68, No. 4, pp. 709-720, 2011.
Smahel, Michal, "PD-1/PD-L1 Blockade Therapy for Tumors with Downregulated MHC Class I Expression", Int. J. Mol. Sci., vol. 18, No. 6, pp. 1331, 2017.
Topalian, et al., "Targeting the PD-1/B7-H1 (PD-L1) pathway to activate anti-tumor immunity", Curr. Opin. Immunol., vol. 24, No. 2, pp. 207-212, 2012.
Vinay, et al., "Immune evasion in cancer: Mechanistic basis and therapeutic strategies", Seminars in Cancer Biology, vol. 35, pp. S185-S198, 2015.
Wang et al., "Histone hypercitrullination mediates chromatin decondensation and neutrophil extracellular trap formation", J. Cell Biol., vol. 184, pp. 205-213, 2009.
Wang, Shu, et al., "Peptidylarginine deiminases in citrullination, gene regulation, health and pathogenesis," Biochim Biophys Acta, Oct. 2013; 1829 (10): 1126-1135.
Wang, et al., "Prognostic significance of PD-L1 in solid tumor", Medicine Baltimore, vol. 96, No. 18, pp. e6369, 2017.
Wang, et al., "PD-LI expression in human cancers and its association with clinical outcomes", Oncotargets and Therapy, vol. 9, pp. 5023-5039, 2016.
Wei, Lianhu, et al., "Novel Inhibitors of Protein Arginine Deiminase with Potential Activity in Multiple Sclerosis Animal Model," Journal of Medicinal Chemistry, 2013, 56, 1715-1722.
Willis et al., N-α-Benzoyl-N5-(2-Chloro-1-Iminoethyl)-1-Ornithine Amine, a Protein Arginine Deiminase Inhibitor, Reduces the Severity of Murine Collagen-Induced Arthritis, J. Immunol., vol. 186, No. 7, pp. 4396-4404, 2011.
Zamarron, et al., "Dual Roles of Immune Cells and Their Factors in Cancer Development and Progression", Intl. J. Biol. Sciences, vol. 7, No. 5, pp. 651-658, 2011.
Zawrotniak, et al., "Neutrophil extracellular traps (NETs)—formation and implications", ACTA Biochimica Polonica, vol. 60, No. 3, pp. 277-284, 2013.
Zhuravel, et al, "Solution-phase synthesis of a combinatorial library of 3-[4-(Coumarin-3-yl)-1,3-thiazol-2-ylcarbamoyl]propanoic acid amides," Molecules (2005), 10(2), 444-456.
Zou, et al., "Neutrophil extracellular traps in COVID-19", JCI Insight, vol. 5, No. 11, pp. 1-11, 2020.
Zou, et al., "PD-L1 (B7-H1) and PD-1 pathway blockade for cancer therapy: Mechanisms, response biomarkers, and combinations", Sci. Transl. Med., vol. 8, No. 328, pp. 328rv4, 2016.

(56) References Cited

OTHER PUBLICATIONS

Database, chemcats [Online] CAS Sep. 19, 2017, XP002788163, Retrieved from STN accession No. A655743/ON Database accession No. 0234972813.
Search Report dated Sep. 2, 2021 in Russian Application 2020132944.
Office Action dated Oct. 11, 2022 in JP Application No. 2020-544707.
Chemcats, Registry (STN) [online], entered STN Sep. 2016 (search date: Aug. 2, 2022), CAS Registry No. 1987343-81-6; 1498689-38-5, [cited in Office Action in JP Application No. 2020-544707].
Chemcats, Registry (STN) [online], entered STN Feb. 2014 (search date: Aug. 2, 2022), CAS Registry No. 1545778-28-6; 1550927-86-0; 1547350-21-9, [cited in Office Action in JP Application No. 2020-544707].

* cited by examiner

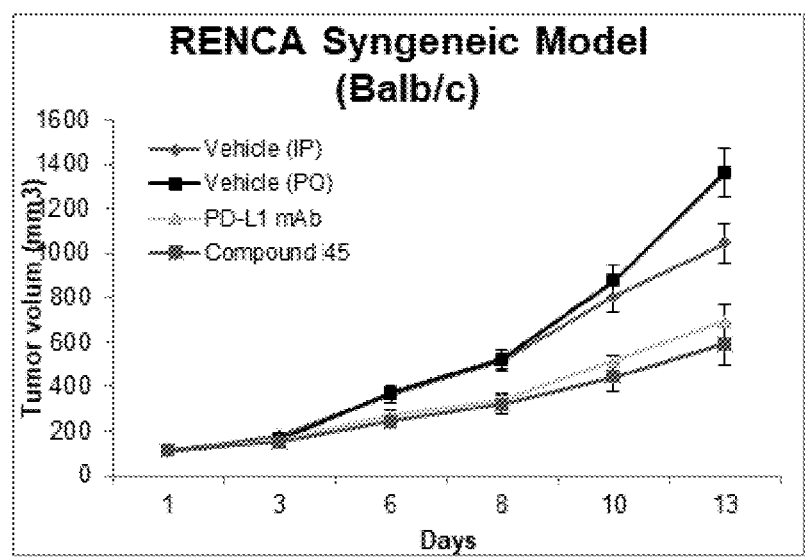

PYRIMIDINE DERIVATIVES AS INHIBITORS OF PD1/PD-L1 ACTIVATION

TECHNICAL FIELD OF THE INVENTION

The present invention relates to substituted 2-(benzyloxy) pyrimidine compounds of Formula Ib, Formula Ia, and Formula I along with their polymorphs, stereoisomers, tautomers, prodrugs, solvates, and pharmaceutically acceptable salts thereof which are inhibitors of PD1/PD-L1 activation. The present invention also relates to method of synthesizing the compounds of Formula Ib, Formula Ia, and Formula I.

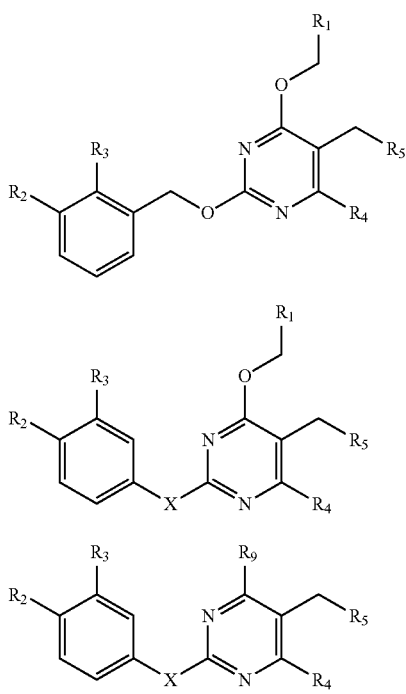

Formula I

Formula Ia

Formula Ib

The compounds described herein are inhibitors of PD1/PD-L1 activation and may be used in the treatment of cancer, and other diseases or conditions associated with activation of PD1/PD-L1.

BACKGROUND OF THE INVENTION

Tumor development and survival is a chaotically governed process involving the interplay between cancer cells, normal stromal cells and host defence mechanisms (Vinay D S et al., Seminars in Cancer Biology, 2015, 35: S185-S198). Generally, CD8+ cytotoxic T cells (CTLs) and CD4+ helper T (Th1) cells curb cancer development via mechanisms commonly involving the production of interferon (IFN)-γ and cytotoxins (Zamarron B F et al., Intl. J. Biol. Sciences, 2011, 7(5):651-658). Tumors have, however evolved a number of mechanisms to escape immune eradications. The PD-1/PD-L1 molecular pathway is one such primary mechanism of cancer immune evasion.

PD-1 is a type 1 trans-membrane protein encoded by the PDCD1 gene. It is a member of the extended CD28/CTLA-4 immunoglobulin family and one of the most important inhibitory co-receptors expressed by T cells (He J et al., Scientific Reports, 2015, 5:1-9). PD-1 is absent on resting T cells but is induced on activated T cells. It is also expressed on B cells, NK cells, dendritic cells (DCs) and macrophages. The programmed cell death protein (PD-1) down regulates the immune system and prevents it from killing cancerous cells present in the body. In cancer, high levels of PD-1 are detected in tumor infiltrating T cells and this expression has been associated with impaired CD8+ T cell function (Leung J et al., Immune Network, 2014, 14(6):265-276).

PD-1 has two ligands: PD-L1 (also named B7-H1; CD274) and PD-L2 (B7-DC; CD273), that are both co-inhibitory (Flies D B et al., Yale J. Biology Medicine, 2011, 84(4):409-421). PD-L1, expressed on almost all murine tumor cells, is the major ligand for PD-1 mediated immune suppression. It is constitutively expressed on APCs and can be broadly induced on cells in both lymphoid tissues and non-lymphoid peripheral tissues following cellular activation (Flies D B et al., Yale J. Biology Medicine, 2011, 84(4):409-421; Dong Y et al., Oncotarget, 2017, 8(2):2171-2186). The cytokine IFN-γ is particularly effective in up-regulating PD-L1 expression due to IFN-γ response elements in the PD-L1 promoter region (Lee S J et al., FEBS Letters, 2006, 580:755-762; Flies D B et al., Immunotherapy, 2007, 30(3):251-260). The expression of B7-DC/PD-L2 is largely restricted to myeloid dendritic cells (DCs) and macrophages in lymphoid compartments and is not broadly expressed in peripheral tissues (Flies D B et al., Yale J. Biology Medicine, 2011, 84(4):409-421). In cancer, PD-L1 is expressed on the surface of tumor cells in various solid malignancies such as squamous cell carcinoma of the head and neck, melanoma, carcinomas of the brain, thyroid, thymus, esophagus, lung, breast, gastrointestinal tract, colorectum, liver, pancreas, kidney etc. (Topalian S L et al., Curr. Opin. Immunol., 2012, 24(2):207-212; Wang X et al., Oncotargets and Therapy, 2016, 9:5023-5039). In hepatocellular carcinoma, melanoma and breast cancer, PD-L1 positivity was correlated with worse prognosis (Muenst S et al., Breast Cancer Res. Treat., 2014, 146(1):15-24; Leung J et al., Immune Network, 2014, 14(6):265-276; Wang Q et al., Medicine (Baltimore), 2017, 96(18): e6369). In contrast, normal human tissues seldom express PD-L1 protein on their cell surface, indicating that PD-L1 can be a selective target for anti-tumor therapy (Chen L et al., J Clin. Invest, 2015, 125(9):3384-3391).

Cancer microenvironment manipulates the PD-1/PD-L1 pathway; induction of PD-L1 expression is associated with inhibition of immune responses against cancer, thus permitting cancer progression and metastasis (He J et al., Scientific Reports, 2015, 5:1-9; Bardhan K et al., Frontiers in Immunology, 2016, 7(550):1-17). Activation of PD-1/PD-L1 pathway induces apoptosis of activated T cells (Dong H et al., Nature Medicine, 2002, 8(8):793-800; Curiel T J et al., Nature Medicine, 2003, 9(5):562-567), facilitates T cell anergy and exhaustion (Barber D L et al., Nature, 2005, 439(7077):682-687), enhances the function of regulatory T cells (Francisco L M et al., J. Exp. Med., 2009, 206(13): 3015-3029) and inhibits the proliferation of T cells (Sheppard K A et al., FEBS Letters, 2004, 574:37-41; Patsoukis N et al., Cell Cycle, 2012, 11(23):4305-4309). Therefore, blocking this pathway restores the proliferation and cytotoxicity of CTLs, inhibiting the function of regulatory T cells (Tregs), and results in decrease T cell apoptosis.

Blockade of the PD-1/PD-L1 pathway by therapeutic antibodies has been shown to prevent inhibitory signaling from cancer cells and enabling CTLs to elicit an immune response against the target/cancer cells (Zou W et al., Sci. Transl. Med., 2016, 8(328):328rv4; Smahel M, Int. J. Mol. Sci., 2017, 18(6):1331). A number of cancer immunotherapy agents targeting PD-1 have been developed till date and approved for a number of malignancies including Melanoma, Lung cancer, Kidney cancer, Hodgkin's lymphoma, Head and neck cancer and Urothelial cancer. The first therapeutic anti-PD-L1 antibody was approved by the FDA in May 2016, with a number of additional therapies in the pipeline (https://www.fda.gov/). Still, there are at least 500 clinical studies ongoing with PD-1/PD-L1 antibodies against 20 types of solid and hematological malignant tumors. However, there is still a need for potent and selective small molecule inhibitors of the PD-1/PD-L1 pathway.

Common drug-related adverse effects (AEs) of both anti-PD-1 and anti-PD-L1 antibodies include fatigue, rash, diarrhea, pruritus, decrease appetite, arthralgia and nausea. Immune-related AEs (irAEs) such as dermatitis, colitis, Hepatitis, vitiligo and thryoiditis have been reported and about 10% of patients develop grade 3 or 4 irAEs (Hamanishi J et al., Int. J. Clin. Oncol., 2016, 21:462-473). The long residence time of the monoclonal antibodies (mAbs) could contribute to these AEs, which may be partially circumvented using a small molecule inhibitor. In addition, studies using smaller cell penetrating Biologicals and DNA aptamers have shown to exert antibody-mimic functions and is advantageous over antibody for its chemically synthetic nature, low immunogenicity, and efficient tissue penetration (Lai W Y et al., Mol. Therapy—Nucl. Acids, 2016, 5: e397). Small molecule inhibitors, therefore, can provide increased oral bioavailability, increased bio-efficiency and shortened half-life activity for a more controllable treatment, particularly in the case of auto-immune or other adverse events.

As discussed, the PD-1/PD-L1 inhibitory compounds have vast utility in up-regulating the immune system for efficiently combating cancer. Therefore, the identification of a chemical moiety, especially small molecule inhibitors, that facilitates this inhibition is necessary. Therefore, the identification and development of new PD-1/PD-L1 inhibitor compounds treating cancer and other diseases or conditions associated with activation of PD-1/PD-L1 would open new opportunities in the realm of cancer treatment.

SUMMARY OF INVENTION

In an aspect of the present disclosure, there is provided a compound of Formula Ib

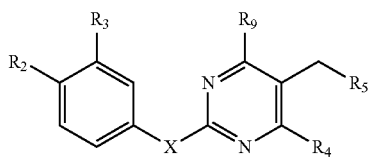

Formula Ib their polymorphs, stereoisomers, tautomers, prodrugs, solvates, and pharmaceutically acceptable salts thereof, wherein X is selected from —$CH_2O$—, —$OCH_2$—, —C(O)NH— or —NHC(O)—; $R_2$, $R_3$, $R_4$, and $R_9$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —$COOR_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, $C_{1-6}$ alkoxy, or $COOR_a$, wherein $C_{1-6}$ heterocyclyl is optionally substituted with one or more groups selected from hydroxy, halogen, or cyano; and $R_a$ is selected from hydrogen, halogen, cyano, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, or $C_{1-6}$ heteroarylalkyl; $R_5$ is —$NR_7R_8$, wherein $R_7$ and $R_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, $C(O)NH_2$, $C(O)CH_2CN$, $NHR_6$, COOH, $COOR_6$, $NHC(O)R_6$, $C_{1-6}$ alkyl, $C_{1-6}$ haloalkyl, $C_{3-10}$ cycloalkyl, $C_{5-6}$ aryl, $SR_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and $R_6$; or $R_7$ and $R_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of oxo, hydroxyl, halogen, $C_{1-6}$ alkyl, COOH, $COOR_6$, $R_6$, $NHR_6$, $C(O)NHR_6$, $C(O)NHSO_2R_6$, $C(O)(CH_2)_nNHC(O)CH_3$, and combinations thereof, wherein $C_{1-6}$ alkyl is further substituted with groups selected from hydroxyl, COOH, or $NHR_6$; n is 1-6; and $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In another aspect of the present disclosure there is provided a compound of Formula Ia

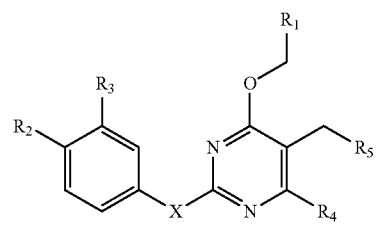

Formula Ia their polymorphs, stereoisomers, tautomers, prodrugs, solvates, and pharmaceutically acceptable salts thereof, wherein X is selected from —$CH_2O$, —$OCH_2$, C(O)NH or NHC(O); $R_1$, $R_2$, $R_3$, and $R_4$ are independently selected from hydrogen, cyano. $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{5-10}$ aryl, and 5-10 membered monocyclic or bicyclic heteroaryl, are optionally substituted with one or more of the groups selected from the group consisting of hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, —COOR$_a$, wherein $C_{1-6}$ alkyl, $C_{1-6}$ alkoxy, $C_{1-10}$ heterocyclyl are optionally substituted with one or more of the groups selected from $C_{1-6}$ alkyl, $C_{3-6}$ cycloalkyl, $C_{1-6}$ heterocyclyl, $C_{1-6}$ alkoxy, or COOR$_a$, wherein $C_{1-6}$ heterocyclyl is optionally substituted with one or more groups selected from hydroxy, halogen, or cyano, and $R_a$ is selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_5$ is —NR$_7$R$_8$, wherein R$_7$, and R$_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, $C(O)NH_2$, $C(O)CH_2CN$, NHR$_6$, COOH, COOR$_6$, NHC(O)R$_6$, $C_{1-6}$ alkyl, $C_{1-6}$ haloalkyl, $C_{3-10}$ cycloalkyl, $C_{5-6}$ aryl, SR$_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and R$_6$; or R$_7$ and R$_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic saturated or unsaturated heterocyclic ring is optionally substituted with substituents selected from the group consisting of oxo, hydroxyl, halogen, $C_{1-6}$ alkyl, COOH, COOR$_6$, R$_6$, NHR$_6$, C(O)NHR$_6$, C(O)NHSO$_2$R$_6$, $C(O)(CH_2)_n$NHC(O)CH$_3$, and combinations thereof, wherein $C_{1-6}$ alkyl is further substituted with groups selected from hydroxyl, COOH, or NHR$_6$; n is 1-6; and R$_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, NHR$_6$, NHC(O)NHR$_6$, and combinations thereof.

In another aspect of the present disclosure there is provided a compound of Formula I

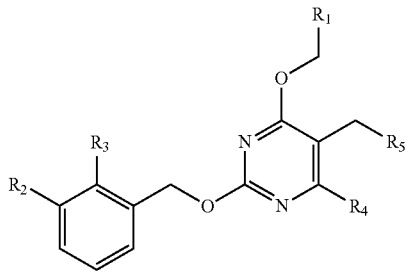

Formula I their polymorphs, stereoisomers, tautomers, prodrugs, solvates, and pharmaceutically acceptable salts thereof, wherein R$_1$, R$_2$, R$_3$, and R$_4$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, aminoC$_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, —COOR$_a$, wherein $C_{1-6}$ alkyl, $C_{1-6}$ alkoxy, and $C_{1-10}$ heterocyclyl are optionally substituted with one or more of the groups selected from $C_{1-6}$ alkyl, $C_{3-6}$ cycloalkyl, $C_{1-6}$ heterocyclyl, $C_{1-6}$ alkoxy, and COOR$_a$, wherein $C_{1-6}$ heterocyclyl is optionally substituted with one or more groups selected from hydroxy, halogen, or cyano, and $R_a$ is selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_5$ is —NR$_7$R$_8$, wherein R$_7$, and R$_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with the substituents selected from oxo, cyano, halogen, hydroxyl, morpholino, $C(O)NH_2$, $C(O)CH_2CN$, NHR$_6$, COOH, COOR$_6$, NHC(O)R$_6$, $C_{1-6}$ alkyl, $C_{1-6}$ haloalkyl, $C_{3-10}$ cycloalkyl, $C_{5-6}$ aryl, SR$_6$, 5-10 membered monocyclic or bicyclic saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and R$_6$; or R$_7$ and R$_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of oxo, hydroxyl, $C_{1-6}$ alkyl, COOH, COOR$_6$, R$_6$, NHR$_6$, C(O)NHR$_6$, C(O)NHSO$_2$R$_6$, $C(O)(CH_2)_n$NHC(O)CH$_3$, and combinations thereof, wherein $C_{1-6}$ alkyl is further substituted with groups selected from hydroxyl, COOH, or NHR$_6$; n is 1-6; and R$_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, NHR$_6$, NHC(O)NHR$_6$, and combinations thereof.

In an aspect of the present disclosure there is provided a process of preparation of compounds of Formula Ib, Formula Ia, and Formula I or their polymorphs, stereoisomers, tautomers, prodrugs, solvates, and pharmaceutically acceptable salts thereof.

In an aspect of the present disclosure there is provided a pharmaceutical composition comprising a compound of Formula Ib, Formula Ia, Formula I or a pharmaceutically acceptable salt thereof together with a pharmaceutically acceptable carrier, optionally in combination with one or more other pharmaceutical compositions.

In an aspect of the present disclosure there is provided a method for the treatment and/or prevention of various diseases, including cancer and infectious diseases, comprising administering to a subject suffering from the proliferative disorder or cancer a therapeutically effective amount of the compound of Formula Ib, Formula Ia, and Formula I or the pharmaceutical composition, with other clinically relevant cytotoxic agents or non-cytotoxic agents to a subject in need thereof.

In an aspect of the present disclosure there is provided a method of treatment and/or prevention of various diseases, including cancer and infectious diseases, comprising administering to a subject suffering from the viral infectious diseases such as HIV, Influenza, herpes virus, Hepatitis A, Hepatitis B, Hepatitis C, and Hepatitis D, a therapeutically effective amount of the compound of Formula Ib, Formula Ia, and Formula I or the pharmaceutical composition, with other clinically relevant anti-viral drugs to a subject in need thereof.

In an aspect of the present disclosure there is provided use of the compounds of Formula Ib, Formula Ia, and Formula I or the pharmaceutical composition for the treatment and/or prevention of various diseases including proliferative disorder or cancer; or treatment of cancer together with other clinically relevant cytotoxic agents or non-cytotoxic agents.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

BRIEF DESCRIPTION OF THE DRAWINGS

FIG. 1 illustrates the in vivo efficacy of compound-45 in RENCA renal model, in accordance with an implementation of the present disclosure.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.
Definitions For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

Furthermore, the compound of Formula Ib, Formula Ia, and Formula I can be their derivatives, analogs, stereoisomer's, diastereomers, geometrical isomers, polymorphs, solvates, co-crystals, intermediates, metabolites, prodrugs or pharmaceutically acceptable salts and pharmaceutical compositions.

The compounds of Formula Ib, Formula Ia, Formula I and their polymorphs, stereoisomers, prodrugs, solvates, co-crystals, intermediates, pharmaceutically acceptable salts, and metabolites thereof can also be referred as "compounds of the present disclosure".

The compounds according to Formula Ib, Formula Ia, and Formula I may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in Formula Ib, Formula Ia, and Formula I or in any chemical structure illustrated herein, is not specified, the structure is intended to encompass any stereoisomer and all mixtures thereof. Thus, compounds according to Formula Ib, Formula Ia, and Formula I containing one or more chiral centres may be used as racemic modifications including racemic mixtures and racemates, enantiomerically-enriched mixtures, or as enantiomerically-pure individual stereoisomers.

Individual stereoisomers of a compound according to Formula Ib, Formula Ia, and Formula I which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form.

Alternatively, specific stereoisomers may be synthesized by asymmetric synthesis using optically active reagents, substrates, catalysts or solvents, or by converting one enantiomer to the other by asymmetric transformation.

It is to be understood that the references herein to compounds of Formula Ib, Formula Ia, Formula I and salts thereof covers the compounds of Formula Ib. Formula Ia, and Formula I as free bases, or as salts thereof, for example as pharmaceutically acceptable salts thereof. Thus, in one embodiment, the invention is directed to compounds of Formula Ib, Formula Ia, and Formula I as the free base. In another embodiment, the invention is directed to compounds of Formula Ib. Formula Ia, Formula I, and salts thereof. In a further embodiment, the invention is directed to compounds of Formula Ib, Formula Ia, Formula I and pharmaceutically acceptable salts thereof.

It will be appreciated that pharmaceutically acceptable salts of the compounds according to Formula Ib, Formula Ia, and Formula I may be prepared. Indeed, in certain embodiments of the invention, pharmaceutically acceptable salts of the compounds according to Formula Ib, Formula Ia, and Formula I may be preferred over the respective free base because such salts impart greater stability or solubility to the molecule thereby facilitating formulation into a dosage form. Accordingly, the invention is further directed to compounds of Formula Ib, Formula Ia, Formula I, and pharmaceutically acceptable salts thereof.

Included within the scope of the "compounds of the invention" are all solvates (including hydrates), complexes, polymorphs, prodrugs, radiolabelled derivatives, and stereoisomers of the compounds of Formula Ib, Formula Ia, Formula I, and salts thereof.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, isopropyl alcohol, dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

The term "prodrugs" refers to the precursor of the compound of Formula Ib, Formula Ia, and Formula I which on administration undergoes chemical conversion by metabolic processes before becoming active pharmacological substances. In general, such prodrugs will be functional derivatives of a compound of the invention, which are readily convertible in vivo into a compound of the invention.

The term "effective amount" refers to an amount or concentration of the compound of Formula Ib, Formula Ia, and Formula I that produces a biological response either individually or when present in a pharmaceutical composition. The term effective amount or effective dose can be used interchangeably when measurements are taken either in vivo, or in vitro.

The term "alkyl" refers to a saturated hydrocarbon chain having the specified number of carbon atoms. For example, which are not limited, $C_{1-10}$ alkyl refers to an alkyl group having from 1-10 carbon atoms, 1-6 carbon atoms, or 1-4 carbon atoms. Alkyl groups may be straight or branched chained groups. Representative branched alkyl groups have one, two, or three branches. Preferred alkyl groups include, without limitation, methyl, ethyl, n-propyl, isopropyl, butyl, isobutyl, and t-butyl.

The term "alkoxy" refers to an alkyl group attached via an oxygen linkage to the rest of the molecule. For example, $C_{1-10}$ alkoxy refers to an alkyl group having from 1-10 carbon atoms, or 1-6 carbon atoms, or 1-4 carbon atoms, attached via an oxygen linkage to the rest of the molecule. Preferred alkoxy groups include, without limitation, —OCH$_3$ (methoxy), —OC$_2$H$_5$ (ethoxy) and the like.

The term "alkylamino" refers to an alkyl group as defined above attached via amino linkage to the rest of the molecule. For example, $C_{1-6}$ alkylamino refers to an alkyl group having from 1-6 carbon atoms, or 1-3 carbon atoms attached via amino linkage to the rest of the molecule. Preferred alkylamino groups include, without limitation, —NHCH$_3$, —N(CH$_3$)$_2$, and the like.

The term "acylamino" refers to an acyl group attached via amino linkage to the rest of the molecule. For example, $C_{1-6}$ acylamino refers to an acyl group having from 1-6 carbon atoms, or 1-3 carbon atoms attached via amino linkage to the rest of the molecule. Preferred acylamino groups include, without limitation, CH$_3$(CO)NH—, and the like.

The term "haloalkyl" refers to an alkyl group as defined above containing halogen and attached via alkyl linkage to the rest of the molecule. For example, $C_{1-6}$ haloalkyl refers to an alkyl group having from 1-6 carbon atoms, or 1-3 carbon atoms attached via halo linkage to the rest of the molecule. Preferred haloalkyl groups include, without limitation, —CH$_2$Cl, —CHCl$_2$, and the like.

The term "haloalkoxy" refers to an alkoxy group as defined above containing halogen and attached via oxygen atom of alkoxy linkage to the rest of the molecule. For example, $C_{1-6}$ haloalkoxy refers to an alkoxy group having from 1- 6 carbon atoms, or 1-3 carbon atoms attached via halo linkage to the rest of the molecule. Preferred haloalkoxy groups include, without limitation, —OCH$_2$Cl, —OCHCl$_2$, and the like.

The term "halogen" refers to a halogen radical, for example, fluoro, chloro, bromo, or iodo. "Haloalkyl" refers to an alkyl group, as herein before defined, in which at least one of the hydrogen atoms has been replaced with a halogen radical. "$C_{1-6}$ haloalkyl" refers to a $C_{1-6}$ alkyl group in which at least one of the hydrogen atoms has been replaced with a halogen radical. An example of 'haloalkyl' is trifluoromethyl or 2,2,2-trifluoroethyl.

The term "cycloalkyl" refers to a saturated hydrocarbon ring having a specified number of carbon atoms. For example, which are not limited, $C_{3-10}$ cycloalkyl refers to a cycloalkyl group having from 3 to 10 member atoms. Preferred cycloalkyl groups include, without limitation, cyclopropyl, cyclobutyl, cyclopentyl, cyclohexyl, Adamantane groups, and the like.

The term "aryl" refers to aromatic ring having a specified number of carbon atoms. For example, $C_{5-10}$ aryl refers to an aryl group having 5 to 10 member atoms. Preferred aryl groups include, without limitation, phenyl, benzyl, naphthyl, and the like.

The term "heteroaryl" refers to aromatic rings containing from 1 to 3 heteroatoms in the ring. "Heteroaryl" groups may be substituted with one or one or more substituents if so defined herein. The "$C_{1-6}$ heteroaryl" rings having 1 or 6 carbon as member atoms. The "heteroaryl" includes pyridinyl, tetrazolyl and pyrazolyl. "Heteroatom" refers to a nitrogen, sulfur, or oxygen atom, for example a nitrogen atom or an oxygen atom.

The term "heterocyclic" and "heterocyclyl" refer to saturated or unsaturated monocyclic aliphatic rings containing 5, 6, or 7 ring members including 1 or 2 heteroatoms or to saturated or unsaturated bicyclic aliphatic rings containing 5, 6 or 7 ring members including 1-5 heteroatoms. In certain embodiments, "heterocyclyl" groups are saturated. In other embodiments, "heterocyclyl" groups are unsaturated. "Heterocyclyl" groups containing more than one heteroatom may contain different heteroatoms. "Heterocyclyl" groups may be substituted with one or more substituents as defined herein. "Heterocyclyl" includes piperidinyl, tetrahydropyranyl, azepinyl, oxazepinyl, azabicyclo[3.1.0]hexanyl. In some embodiments, the heterocyclic ring is monocyclic or bicyclic or spiro cyclic ring which may be saturated or unsaturated. In some other embodiments, the monocyclic or bicyclic or spiro cyclic heterocyclic ring may contain one or more hetero atoms selected from N, S, or O.

The phrase "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free base form with a suitable acid.

Salts and solvates having non-pharmaceutically acceptable counter-ions or associated solvents are within the scope of the present invention, for example, for use as intermediates in the preparation of other compounds of Formula Ib, Formula Ia, Formula I, and their pharmaceutically acceptable salts. Thus, one embodiment of the invention embraces compounds of Formula Ib, Formula Ia, Formula I, and salts thereof. Compounds according to Formula Ib, Formula Ia, and Formula I contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methyl nitrate, sulfate, bisulfate, sulfamate, phosphate, acetate, hydroxyacetate, phenyl acetate, propionate, butyrate, iso-butyrate, valerate, maleate, hydroxymaleate, acrylate, fumarate, malate, tartrate, citrate, salicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), aminobenzenesulfonate, p-toluenesulfonate (tosylate), and naphthalene-2-sulfonate.

The term "PD-1/PD-L1 inhibitor or inhibitory compounds" or "inhibitors of PD-1/PD-L1 activation" is used to identify a compound, which is capable of blocking PD-1/PD-L1 pathway to prevent inhibitory signalling from cancer cells and enabling CTLs to elicit an immune response against the target/cancer cells and thus treat cancer and other diseases or conditions associated with activation of PD1/PD-L1.

A term once described, the same meaning applies for it, throughout the disclosure.

As discussed in the background section, the identification and development of new PD-1/PD-L1 inhibitor compounds for treating cancer and other diseases or conditions associated with activation of PD-1/PD-L1 would open new opportunities in the realm of cancer treatment.

The term "cytotoxic agents" or "inhibitors" is used to identify any agents or drugs which is capable of killing cells including cancer cells. These agents or inhibitors may stop cancer cells from growing and dividing and may cause tumors to shrink in size.

The term "non-cytotoxic agents" or "inhibitors" is used to identify any agents or inhibitors are which does not directly kill cells, but instead affects cellular transport and metabolic functions to ultimately produce cell death.

The term "immune checkpoint inhibitors agents" or "immune modulators agents" are used to identify any agents or inhibitors that blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. The immune checkpoint inhibitors include inhibitors against immune checkpoint molecules such as CD27, CD28, CD40, CD122, CD96, CD73, CD47, 0X40, GITR, CSF1R, JAK, PI3K delta, PI3K gamma, TAM, aiginase, CD137 (also known as 4-1BB), ICOS, A2AR, B7-H3, B7-H4, BTLA, CTLA-4, LAG3, TIM3, VISTA, PD-1, PD-L1 and PD-L2. The terms "immune modulators agents" and "immune checkpoint inhibitors" are used interchangeably throughout the present disclosure.

In an embodiment of the present disclosure, there is provided compounds of Formula Ib, their polymorphs, stereoisomers, tautomers, prodrugs, solvates, and pharmaceutically acceptable salts thereof, wherein Formula Ib

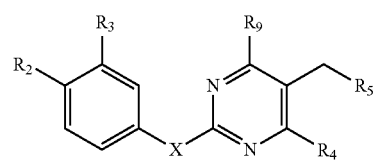

wherein X is selected from —$CH_2O$—, —$OCH_2$—, —C(O)NH— or —NHC(O)—; $R_2$, $R_3$, $R_4$, and $R_9$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —$COOR_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, $C_{1-6}$ alkoxy, or $COOR_a$, wherein $C_{1-6}$ heterocyclyl is optionally substituted with one or more groups selected from hydroxy, halogen, or cyano; and $R_a$ is selected from hydrogen, halogen, cyano, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, or $C_{1-6}$ heteroarylalkyl; $R_5$ is —$NR_7R_8$, wherein $R_7$ and $R_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, C(O)$NH_2$, C(O)$CH_2CN$, $NHR_6$, COOH, $COOR_6$, NHC(O)$R_6$, $C_{1-6}$ alkyl, $C_{1-6}$ haloalkyl, $C_{3-10}$ cycloalkyl, $C_{5-6}$ aryl, $SR_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and $R_6$; or $R_7$ and $R_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of oxo, hydroxyl, halogen, $C_{1-6}$ alkyl, COOH, $COOR_6$, $R_6$, $NHR_6$, C(O)$NHR_6$, C(O)$NHSO_2R_6$, C(O)$(CH_2)_n$NHC(O)$CH_3$, and combinations thereof, wherein $C_{1-6}$ alkyl is further substituted with groups selected from hydroxyl, COOH, or $NHR_6$; n is 1-6; and $R_6$ is selected from the group consisting of hydrogen, $C_{1-6}$ alkyl, C(O)$C_{1-6}$ alkyl, and combinations thereof, wherein $C_{1-6}$ alkyl, and C(O)$C_{1-6}$ alkyl are optionally substituted with substituents selected from the group consisting of hydroxyl, COOH, $NHR_6$, NHC(O)$NHR_6$, and combinations thereof.

In an embodiment of the present disclosure, there is provided a compound of Formula Ib their polymorphs, stereoisomers, tautomers, prodrugs, solvates, and pharmaceutically acceptable salts thereof, wherein X is —$CH_2O$—, wherein $CH_2$ of —$CH_2O$— is attached to the aryl ring and O— is attached to the heteroaryl ring; $R_2$, $R_3$, $R_4$, and $R_9$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —$COOR_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, $C_{1-6}$ alkoxy, or $COOR_a$, wherein $C_{1-6}$ heterocyclyl is optionally substituted with one or more groups selected from hydroxy, halogen, or cyano; and $R_a$ is selected from hydrogen, halogen, cyano, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, or $C_{1-6}$ heteroarylalkyl; $R_5$ is —$NR_7R_8$, wherein $R_7$ and $R_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, C(O)$NH_2$, C(O)$CH_2CN$, $NHR_6$, COOH, $COOR_6$, NHC(O)$R_6$, $C_{1-6}$ alkyl, $C_{1-6}$ haloalkyl, $C_{3-10}$ cycloalkyl, $C_{5-6}$ aryl, $SR_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and $R_6$; or $R_7$ and $R_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of oxo, hydroxyl, halogen, $C_{1-6}$ alkyl, COOH, $COOR_6$, $R_6$, $NHR_6$, C(O)$NHR_6$, C(O)$NHSO_2R_6$, C(O)$(CH_2)_n$NHC(O)$CH_3$, and combinations thereof, wherein $C_{1-6}$ alkyl is further substituted with groups selected from hydroxyl, COOH, or $NHR_6$; n is 1-6; and $R_6$ is selected from the group consisting of hydrogen, $C_{1-6}$ alkyl, C(O)$C_{1-6}$ alkyl, and combinations thereof, wherein $C_{1-6}$ alkyl, and C(O)$C_{1-6}$ alkyl are optionally substituted with substituents selected from the group consisting of hydroxyl, COOH, $NHR_6$, NHC(O)$NHR_6$, and combinations thereof.

In an embodiment of the present disclosure, there is provided a compound of Formula Ib their polymorphs, stereoisomers, tautomers, prodrugs, solvates, and pharmaceutically acceptable salts thereof, wherein X is —$CH_2O$—, wherein $CH_2$ of —$CH_2O$— is attached to the aryl ring and O— is attached to the heteroaryl ring; $R_2$, $R_3$, and $R_4$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —$COOR_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, $C_{1-6}$ alkoxy, or COOR$_a$, wherein $C_{1-6}$ heterocyclyl is optionally substituted with one or more groups selected from hydroxy, halogen, or cyano; and R$_a$ is selected from hydrogen, halogen, cyano, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, or $C_{1-6}$ heteroarylalkyl; R$_9$ is $C_{1-6}$ alkoxy, wherein $C_{1-6}$ alkoxy is optionally substituted with one or more groups selected from hydroxy, $C_{1-4}$ haloalkyl, $C_{5-6}$ aryl, or $C_{1-6}$ heteroaryl, wherein $C_{5-6}$ aryl, or $C_{1-6}$ heteroaryl are optionally substituted with one or more groups selected from halogen or cyano; R$_5$ is —NR$_7$R$_8$, wherein R$_7$ and R$_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, C(O)NH$_2$, C(O)CH$_2$CN, NHR$_6$, COOH, COOR$_6$, NHC(O)R$_6$, $C_{1-6}$ alkyl, $C_{1-6}$ haloalkyl, $C_{3-10}$ cycloalkyl, $C_{5-6}$ aryl, SR$_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and R$_6$; or R$_7$ and R$_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of oxo, hydroxyl, halogen, $C_{1-6}$ alkyl, COOH, COOR$_6$, R$_6$, NHR$_6$, C(O)NHR$_6$, C(O)NHSO$_2$R$_6$, C(O)(CH$_2$)$_n$NHC(O)CH$_3$, and combinations thereof, wherein $C_{1-6}$ alkyl is further substituted with groups selected from hydroxyl, COOH, or NHR$_6$; n is 1-6; and R$_6$ is selected from the group consisting of hydrogen, $C_{1-6}$ alkyl, C(O)C$_{1-6}$ alkyl, and combinations thereof, wherein $C_{1-6}$ alkyl, and C(O)C$_{1-6}$ alkyl are optionally substituted with substituents selected from the group consisting of hydroxyl, COOH, NHR$_6$, NHC(O)NHR$_6$, and combinations thereof.

In an embodiment of the present disclosure, there is provided a compound of Formula Ib their polymorphs, stereoisomers, tautomers, prodrugs, solvates, and pharmaceutically acceptable salts thereof, wherein X is —CH$_2$O—, wherein CH$_2$ of —CH$_2$O— is attached to the aryl ring and O— is attached to the heteroaryl ring; R$_2$, R$_3$, and R$_4$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, aminoC$_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —COOR$_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, $C_{1-6}$ alkoxy, or COOR$_a$, wherein $C_{1-6}$ heterocyclyl is optionally substituted with one or more groups selected from hydroxy, halogen, or cyano; and R$_a$ is selected from hydrogen, halogen, cyano, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, or $C_{1-6}$ heteroarylalkyl; R$_9$ is $C_{1-6}$ alkyl; R$_5$ is —NR$_7$R$_8$, wherein R$_7$ and R$_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, C(O)NH$_2$, C(O)CH$_2$CN, NHR$_6$, COOH, COOR$_6$, NHC(O)R$_6$, $C_{1-6}$ alkyl, $C_{1-6}$ haloalkyl, $C_{3-10}$ cycloalkyl, $C_{5-6}$ aryl, SR$_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and R$_6$; or R$_7$ and R$_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of oxo, hydroxyl, halogen, $C_{1-6}$ alkyl, COOH, COOR$_6$, R$_6$, NHR$_6$, C(O)NHR$_6$, C(O)NHSO$_2$R$_6$, C(O)(CH$_2$)$_n$NHC(O)CH$_3$, and combinations thereof, wherein $C_{1-6}$ alkyl is further substituted with groups selected from hydroxyl, COOH, or NHR$_6$; n is 1-6; and R$_6$ is selected from the group consisting of hydrogen, $C_{1-6}$ alkyl, C(O)C$_{1-6}$ alkyl, and combinations thereof, wherein $C_{1-6}$ alkyl, and C(O)C$_{1-6}$ alkyl are optionally substituted with substituents selected from the group consisting of hydroxyl, COOH, NHR$_6$, NHC(O)NHR$_6$, and combinations thereof.

In an embodiment of the present disclosure, there is provided a compound of Formula Ib their polymorphs, stereoisomers, tautomers, prodrugs, solvates, and pharmaceutically acceptable salts thereof, wherein X is —CH$_2$O—, wherein CH$_2$ of —CH$_2$O— is attached to the aryl ring and O— is attached to the heteroaryl ring; R$_2$ and R$_9$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, aminoC$_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —COOR$_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, $C_{1-6}$ alkoxy, or COOR$_a$, wherein $C_{1-6}$ heterocyclyl is optionally substituted with one or more groups selected from hydroxy, halogen, or cyano; and R$_a$ is selected from hydrogen, cyano, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, or $C_{1-6}$ heteroarylalkyl; R$_3$ and R$_4$ are independently selected from hydrogen, $C_{1-6}$ alkyl, and $C_{1-6}$ alkoxy; R$_5$ is —NR$_7$R$_8$, wherein R$_7$ and R$_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, $C(O)NH_2$, $C(O)CH_2CN$, $NHR_6$, COOH, $COOR_6$, $NHC(O)R_6$, $C_{1-6}$ alkyl, $C_{1-6}$ haloalkyl, $C_{3-10}$ cycloalkyl, $C_{5-6}$ aryl, $SR_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and $R_6$; or $R_7$ and $R_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of oxo, hydroxyl, halogen, $C_{1-6}$ alkyl, COOH, $COOR_6$, $R_6$, $NHR_6$, $C(O)NHR_6$, $C(O)NHSO_2R_6$, $C(O)(CH_2)_nNHC(O)CH_3$, and combinations thereof, wherein $C_{1-6}$ alkyl is further substituted with groups selected from hydroxyl, COOH, or $NHR_6$; n is 1-6; and $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided a compound of Formula Ib their polymorphs, stereoisomers, tautomers, prodrugs, solvates, and pharmaceutically acceptable salts thereof, wherein X is —$CH_2O$—, wherein $CH_2$ of —$CH_2O$— is attached to the aryl ring and O— is attached to the heteroaryl ring; $R_3$, $R_4$ and $R_9$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —$COOR_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, $C_{1-6}$ alkoxy, or $COOR_a$, wherein $C_{1-6}$ heterocyclyl is optionally substituted with one or more groups selected from hydroxy, halogen, or cyano; and $R_a$ is selected from hydrogen, halogen, cyano, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, or $C_{1-6}$ heteroarylalkyl; $R_2$ is selected from hydrogen, cyano, $C_{1-10}$ alkyl, $C_{1-10}$ alkoxy, $C_{5-10}$ aryl, and 5-10 membered monocyclic or bicyclic heteroaryl with 1-5 heteroatoms selected from N, S or O, wherein $C_{1-10}$ alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —$COOR_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, or $C_{1-6}$ alkoxy, wherein $C_{1-6}$ heterocyclyl is optionally substituted with one or more groups selected from hydroxy, halogen, or cyano; $R_5$ is —$NR_7R_8$, wherein $R_7$ and $R_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, $C(O)NH_2$, $C(O)CH_2CN$, $NHR_6$, COOH, $COOR_6$, $NHC(O)R_6$, $C_{1-6}$ alkyl, $C_{1-6}$ haloalkyl, $C_{3-10}$ cycloalkyl, $C_{5-6}$ aryl, $SR_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and $R_6$; or $R_7$ and $R_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of oxo, hydroxyl, halogen, $C_{1-6}$ alkyl, COOH, $COOR_6$, $R_6$, $NHR_6$, $C(O)NHR_6$, $C(O)NHSO_2R_6$, $C(O)(CH_2)_nNHC(O)CH_3$, and combinations thereof, wherein $C_{1-6}$ alkyl is further substituted with groups selected from hydroxyl, COOH, or $NHR_6$; n is 1-6; and $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided a compound of Formula Ib their polymorphs, stereoisomers, tautomers, prodrugs, solvates, and pharmaceutically acceptable salts thereof, wherein X is —$CH_2O$—, wherein $CH_2$ of —$CH_2O$— is attached to the aryl ring and O— is attached to the heteroaryl ring; $R_2$, $R_3$, $R_4$, and $R_9$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —$COOR_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, $C_{1-6}$ alkoxy, or $COOR_a$, wherein $C_{1-6}$ heterocyclyl is optionally substituted with one or more groups selected from hydroxy, halogen, or cyano; and $R_a$ is selected from hydrogen, halogen, cyano, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, or $C_{1-6}$ heteroarylalkyl; $R_5$ is selected from

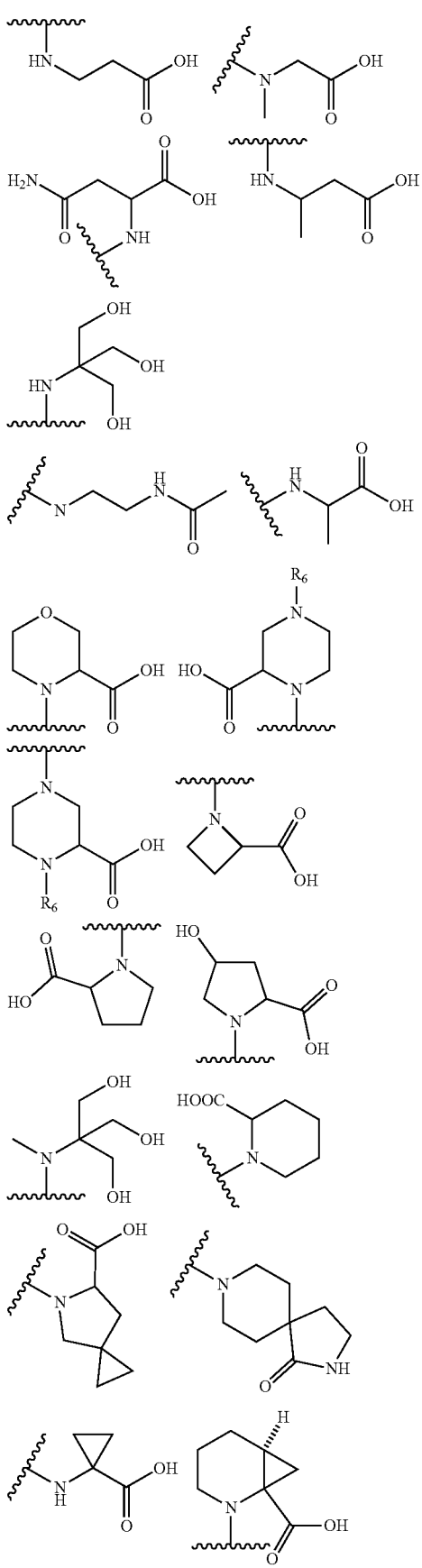
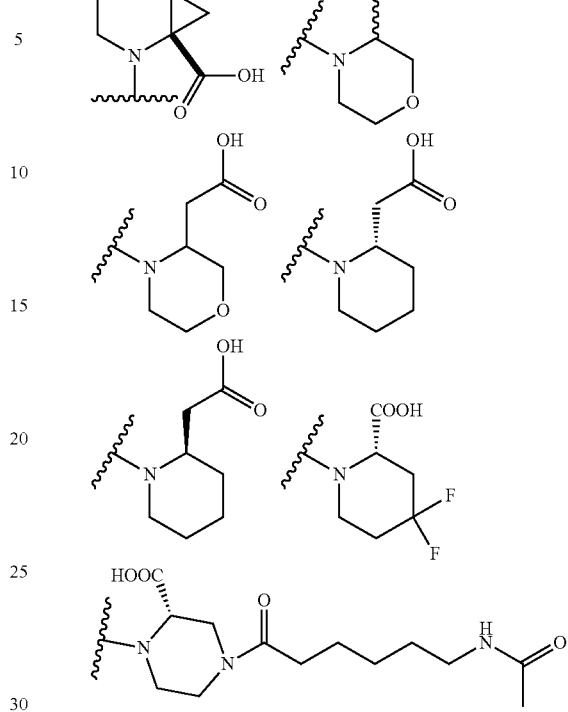
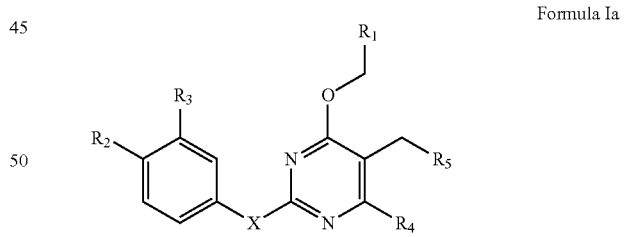

and $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided compounds of Formula Ia, their polymorphs, stereoisomers, tautomers, prodrugs, solvates, and pharmaceutically acceptable salts thereof, wherein Formula Ia wherein X is selected from —$CH_2O$—, —$OCH_2$—, —C(O)NH— or —NHC(O)—; $R_1$, $R_2$, $R_3$, and $R_4$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{5-10}$ aryl, and 5-10 membered monocyclic or bicyclic heteroaryl, are optionally substituted with one or more of the groups selected from the group consisting of hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, —COOR$_a$, wherein $C_{1-6}$ alkyl, $C_{1-6}$ alkoxy, $C_{1-10}$ heterocyclyl are optionally substituted with one or more of the groups selected from $C_{1-6}$ alkyl, $C_{3-6}$ cycloalkyl, $C_{1-6}$ heterocyclyl, $C_{1-6}$ alkoxy, or COOR$_a$, wherein $C_{1-6}$ heterocyclyl is optionally substituted with one or more groups selected from hydroxy, halogen, or cyano, and R$_a$ is selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; R$_5$ is —NR$_7$R$_8$, wherein R$_7$, and R$_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, C(O)NH$_2$, C(O)CH$_2$CN, NHR$_6$, COOH, COOR$_6$, NHC(O)R$_6$, $C_{1-6}$ alkyl, $C_{1-6}$ haloalkyl, $C_{3-10}$ cycloalkyl, $C_{5-6}$ aryl, SR$_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and R$_6$; or R$_7$ and R$_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic saturated or unsaturated heterocyclic ring is optionally substituted with substituents selected from the group consisting of oxo, hydroxyl, halogen, $C_{1-6}$ alkyl, COOH, COOR$_6$, R$_6$, NHR$_6$, C(O)NHR$_6$, C(O)NHSO$_2$R$_6$, C(O)(CH$_2$)$_n$NHC(O)CH$_3$, and combinations thereof, wherein $C_{1-6}$ alkyl is further substituted with groups selected from hydroxyl, COOH, or NHR$_6$; n is 1-6; and R$_6$ is selected from the group consisting of hydrogen, $C_{1-6}$ alkyl, C(O)$C_{1-6}$ alkyl, and combinations thereof, wherein $C_{1-6}$ alkyl, and C(O)$C_{1-6}$ alkyl are optionally substituted with substituents selected from the group consisting of hydroxyl, COOH, NHR$_6$, NHC(O)NHR$_6$, and combinations thereof.

In an embodiment of the present disclosure, there is provided a compound of Formula Ia their polymorphs, stereoisomers, tautomers, prodrugs, solvates, and pharmaceutically acceptable salts thereof, wherein X is —CH$_2$O—, wherein CH$_2$ of —CH$_2$O— is attached to the aryl ring and O— is attached to the heteroaryl ring; R$_1$, R$_2$, R$_3$, and R$_4$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{5-10}$ aryl, and 5-10 membered monocyclic or bicyclic heteroaryl, are optionally substituted with one or more of the groups selected from the group consisting of hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, —COOR$_a$, wherein $C_{1-6}$ alkyl, $C_{1-6}$ alkoxy, $C_{1-10}$ heterocyclyl are optionally substituted with one or more of the groups selected from $C_{1-6}$ alkyl, $C_{3-6}$ cycloalkyl, $C_{1-6}$ heterocyclyl, $C_{1-6}$ alkoxy, or COOR$_a$, wherein $C_{1-6}$ heterocyclyl is optionally substituted with one or more groups selected from hydroxy, halogen, or cyano, and R$_a$ is selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; R$_5$ is —NR$_7$R$_8$, wherein R$_7$, and R$_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring is optionally substituted with one or more substituents selected from oxo, cyano, halogen, hydroxyl, morpholino, C(O)NH$_2$, C(O)

CH$_2$CN, NHR$_6$, COOH, COOR$_6$, NHC(O)R$_6$, C$_{1-6}$ alkyl, C$_{1-6}$ haloalkyl, C$_{3-10}$ cycloalkyl, C$_{5-6}$ aryl, SR$_6$, or 5-10 membered monocyclic or bicyclic saturated or unsaturated heterocyclic ring with 1-3 heteroatoms selected from N, S or O, wherein C$_{1-6}$ alkyl, and the 5-10 membered monocyclic or bicyclic, saturated or unsaturated heterocyclic ring are independently substituted with one or more substituents selected from hydroxyl, and R$_6$; or R$_7$ and R$_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic saturated or unsaturated heterocyclic ring is optionally substituted with the substituents selected from the group consisting of oxo, hydroxyl, halogen, C$_{1-6}$ alkyl, COOH, COOR$_6$, R$_6$, NHR$_6$, C(O)NHR$_6$, C(O)NHSO$_2$R$_6$, C(O)(CH$_2$)$_n$NHC(O)CH$_3$, and combinations thereof, wherein C$_{1-6}$ alkyl is further substituted with groups selected from hydroxyl, COOH, or NHR$_6$; n is 1-6; and R$_6$ is selected from the group consisting of hydrogen, C$_{1-6}$ alkyl, C(O)C$_{1-6}$ alkyl, and combinations thereof, wherein C$_{1-6}$ alkyl, and C(O)C$_{1-6}$ alkyl are optionally substituted with substituents selected from the group consisting of hydroxyl, COOH, NHR$_6$, NHC(O)NHR$_6$, and combinations thereof.

In an embodiment of the present disclosure, there is provided a compound of Formula Ia their polymorphs, stereoisomers, tautomers, prodrugs, solvates, and pharmaceutically acceptable salts thereof, wherein X is —OCH$_2$—, wherein O of —OCH$_2$ is attached to the aryl ring and CH$_2$— is attached to the heteroaryl ring; R$_1$, R$_2$, R$_3$, and R$_4$ are independently selected from hydrogen, cyano, C$_{1-10}$ alkyl, C$_{1-10}$ alkoxy, C$_{1-6}$ haloalkyl, C$_{1-6}$ haloalkoxy, C$_{3-6}$ cycloalkyl, C$_{1-6}$ alkylamino, amino C$_{1-6}$ alkyl, C$_{1-6}$ alkoxyamino, C$_{1-6}$ acylamino, C$_{5-10}$ aryl, and 5-10 membered monocyclic or bicyclic heteroaryl with 1-5 heteroatoms selected from N, S or O, wherein C$_{1-10}$ alkyl, C$_{5-10}$ aryl, and 5-10 membered monocyclic or bicyclic heteroaryl, are optionally substituted with one or more of the groups selected from the group consisting of hydrogen, halogen, hydroxyl, cyano, C$_{1-6}$ alkyl, C$_{1-6}$ alkoxy, C$_{1-6}$ haloalkyl, C$_{1-6}$ haloalkoxy, C$_{3-6}$ cycloalkyl, C$_{1-6}$ alkylamino, C$_{1-6}$ alkoxyamino, C$_{1-6}$ acylamino, C$_{1-10}$ heterocyclyl, —COOR$_a$, wherein C$_{1-6}$ alkyl, C$_{1-6}$ alkoxy, C$_{1-10}$ heterocyclyl are optionally substituted with one or more of the groups selected from C$_{1-6}$ alkyl, C$_{3-6}$ cycloalkyl, C$_{1-6}$ heterocyclyl, C$_{1-6}$ alkoxy, or COOR$_a$, wherein C$_{1-6}$ heterocyclyl is optionally substituted with one or more groups selected from hydroxy, halogen, or cyano, and R$_a$ is selected from hydrogen, C$_{1-6}$ alkyl, C$_{3-8}$ cycloalkyl, C$_{5-6}$ aryl, C$_{5-6}$ arylalkyl, C$_{2-6}$ heterocyclyl, C$_{1-6}$ heteroaryl or C$_{1-6}$ heteroarylalkyl; R$_5$ is selected from

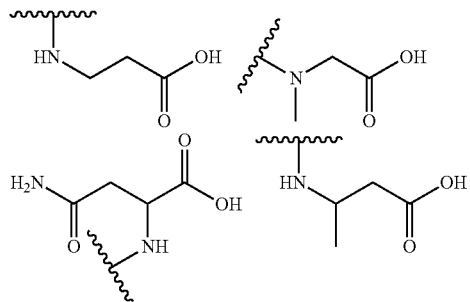

-continued

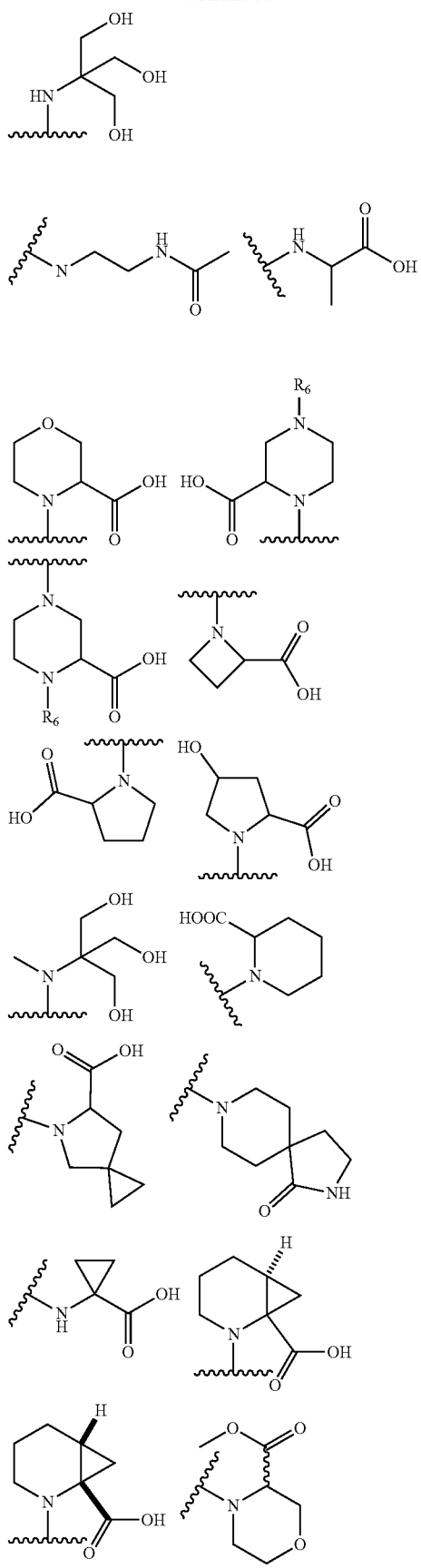

-continued

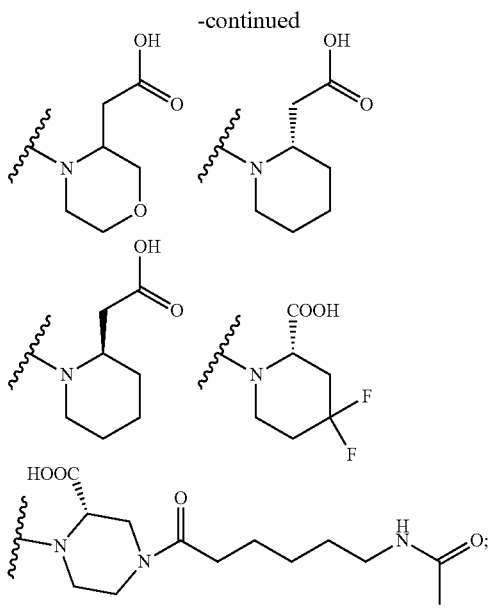

$R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided a compound of Formula Ia their polymorphs, stereoisomers, tautomers, prodrugs, solvates, and pharmaceutically acceptable salts thereof, wherein X is —C(O)NH—, wherein —C(O) of —C(O)NH is attached to the aryl ring and NH— is attached to the heteroaryl ring; $R_1$, $R_2$, $R_3$, and $R_4$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{5-10}$ aryl, and 5-10 membered monocyclic or bicyclic heteroaryl, are optionally substituted with one or more of the groups selected from the group consisting of hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, —$COOR_a$, wherein $C_{1-6}$ alkyl, $C_{1-6}$ alkoxy, $C_{1-10}$ heterocyclyl are optionally substituted with one or more of the groups selected from $C_{1-6}$ alkyl, $C_{3-6}$ cycloalkyl, $C_{1-6}$ heterocyclyl, $C_{1-6}$ alkoxy, or $COOR_a$, wherein $C_{1-6}$ heterocyclyl is optionally substituted with one or more groups selected from hydroxy, halogen, or cyano, and $R_a$ is selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_5$ is —$NR_7R_8$, wherein $R_7$, and $R_8$ are selected from the group consisting of hydrogen, $C_{3-10}$ cycloalkyl, $C_{1-6}$ alkyl, $C_{2-6}$ alkenyl, 5-10 membered monocyclic or bicyclic saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring is optionally substituted with one or more substituents selected from oxo, cyano, halogen, hydroxyl, morpholino, $C(O)NH_2$, $C(O)CH_2CN$, $NHR_6$, COOH, $COOR_6$, $NHC(O)R_6$, $C_{1-6}$ alkyl, $C_{1-6}$ haloalkyl, $C_{3-10}$ cycloalkyl, $C_{5-6}$ aryl, $SR_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and $R_6$; or $R_7$ and $R_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with the substituents selected from the group consisting of oxo, hydroxyl, halogen, $C_{1-6}$ alkyl, COOH, $COOR_6$, $R_6$, $NHR_6$, $C(O)NHR_6$, $C(O)NHSO_2R_6$, $C(O)(CH_2)_nNHC(O)CH_3$, and combinations thereof, wherein $C_{1-6}$ alkyl is further substituted with groups selected from hydroxyl, COOH, or $NHR_6$; n is 1-6; and $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided a compound of Formula Ia their polymorphs, stereoisomers, tautomers, prodrugs, solvates, and pharmaceutically acceptable salts thereof, wherein X is —NHC(O)—, wherein —NH of —NHC(O)— is attached to the aryl ring and C(O)— is attached to the heteroaryl ring; $R_1$, $R_2$, $R_3$, and $R_4$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{5-10}$ aryl, and 5-10 membered monocyclic or bicyclic heteroaryl, are optionally substituted with one or more of the groups selected from the group consisting of hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$cycloalkyl, $C_{1-6}$ alkylamino, $C_{1-6}$ alkoxyamino, $C_{1-6}$ acylamino, $C_{1-10}$ heterocyclyl, —$COOR_a$, wherein $C_{1-6}$ alkyl, $C_{1-6}$ alkoxy, $C_{1-10}$ heterocyclyl are optionally substituted with one or more of the groups selected from $C_{1-6}$ alkyl, $C_{3-6}$ cycloalkyl, $C_{1-6}$ heterocyclyl, $C_{1-6}$ alkoxy, or $COOR_a$, wherein $C_{1-6}$ heterocyclyl is optionally substituted with one or more groups selected from hydroxy, halogen, or cyano, and $R_a$ is selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_5$ is —$NR_7R_8$, wherein $R_7$, and $R_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring is optionally substituted with one or more substituents selected from oxo, cyano, halogen, hydroxyl, morpholino, $C(O)NH_2$, $C(O)CH_2CN$, $NHR_6$, COOH, $COOR_6$, $NHC(O)R_6$, $C_{1-6}$ alkyl, $C_{1-6}$ haloalkyl, $C_{3-10}$ cycloalkyl, $C_{5-6}$ aryl, $SR_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with the substituents selected from hydroxyl, and $R_6$; or $R_7$ and $R_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with the substituents selected from the group consisting of oxo, halogen, hydroxyl, $C_{1-6}$ alkyl, COOH, COOR$_6$, R$_6$, NHR$_6$, C(O)NHR$_6$, C(O)NHSO$_2$R$_6$, C(O)(CH$_2$)$_n$NHC(O)CH$_3$, and combinations thereof, wherein $C_{1-6}$ alkyl is further substituted with groups selected from hydroxyl, COOH, or NHR$_6$; n is 1-6; and R$_6$ is selected from the group consisting of hydrogen, $C_{1-6}$ alkyl, C(O)$C_{1-6}$ alkyl, and combinations thereof, wherein $C_{1-6}$ alkyl, and C(O)$C_{1-6}$ alkyl are optionally substituted with substituents selected from the group consisting of hydroxyl, COOH, NHR$_6$, NHC(O)NHR$_6$, and combinations thereof.

In an embodiment of the present disclosure, there is provided a compound of Formula I their polymorphs, stereoisomers, tautomers, prodrugs, solvates, and pharmaceutically acceptable salts thereof, wherein

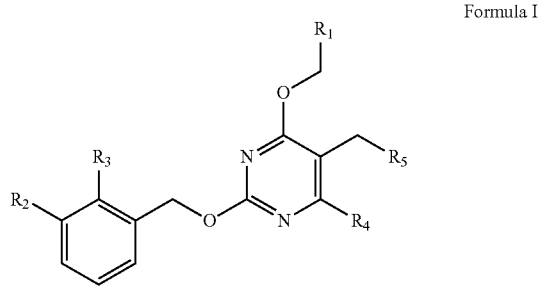

Formula I $R_1$, $R_2$, $R_3$, and $R_4$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{3-6}$ heterocyclyl, —COOR$_a$, wherein $C_{1-6}$ alkyl, $C_{1-6}$ alkoxy, and $C_{1-10}$ heterocyclyl are optionally substituted with one or more of the groups selected from $C_{1-6}$ alkyl, $C_{3-6}$ cycloalkyl, $C_{1-6}$ heterocyclyl, $C_{1-6}$ alkoxy, and COOR$_a$, wherein $C_{1-6}$ heterocyclyl is optionally substituted with one or more groups selected from hydroxy, halogen, or cyano, and R$_a$ is selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; R$_8$ is —NR$_7$R$_8$, wherein R$_7$, and R$_8$ are selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with the substituents selected from oxo, cyano, halogen, hydroxyl, morpholino, C(O)NH$_2$, C(O)CH$_2$CN, NHR$_6$, COOH, COOR$_6$, NHC(O)R$_6$, $C_{1-6}$ alkyl, $C_{1-6}$ haloalkyl, $C_{3-10}$ cycloalkyl, $C_{5-6}$ aryl, SR$_6$, 5-10 membered monocyclic or bicyclic saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and R$_6$; or R$_7$ and R$_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of oxo, hydroxyl, $C_{1-6}$ alkyl, COOH, COOR$_6$, R$_6$, NHR$_6$, C(O)NHR$_6$, C(O)NHSO$_2$R$_6$, C(O)(CH$_2$)$_n$NHC(O)CH$_3$, and combinations thereof, wherein $C_{1-6}$ alkyl is further substituted with groups selected from hydroxyl. COOH, or NHR$_6$; n is 1-6; and R$_6$ is selected from the group consisting of hydrogen, $C_{1-6}$ alkyl, C(O)$C_{1-6}$ alkyl, and combinations thereof, wherein $C_{1-6}$ alkyl, and C(O)$C_{1-6}$ alkyl are optionally substituted with substituents selected from the group consisting of hydroxyl, COOH, NHR$_6$, NHC(O)NHR$_6$, and combinations thereof.

In an embodiment of the present disclosure, there is provided a compound of Formula I their polymorphs, stereoisomers, tautomers, prodrugs, solvates, and pharmaceutically acceptable salts thereof, wherein $R_1$, $R_2$, $R_3$, and $R_4$ are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ alkyl, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-6}$ heterocyclyl, —COOR$_a$, wherein $C_{1-6}$ alkyl, $C_{1-6}$ alkoxy, and $C_{1-6}$ heterocyclyl are optionally substituted with one or more of the groups selected from $C_{1-6}$ alkyl, $C_{3-6}$ cycloalkyl, $C_{1-6}$ heterocyclyl, $C_{1-6}$ alkoxy, and COOR$_a$, wherein $C_{1-6}$ heterocyclyl is optionally substituted with one or more groups selected from hydroxy, halogen, or cyano, and R$_a$ is selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl, and R$_5$ is selected from

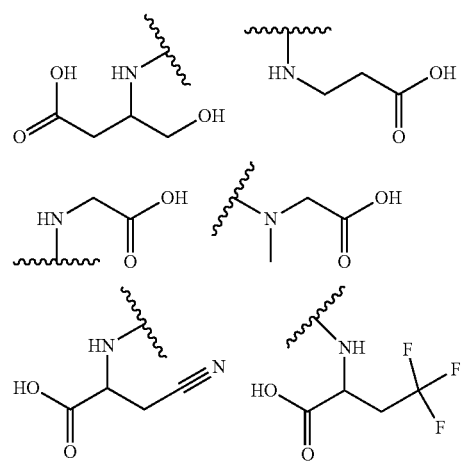

-continued
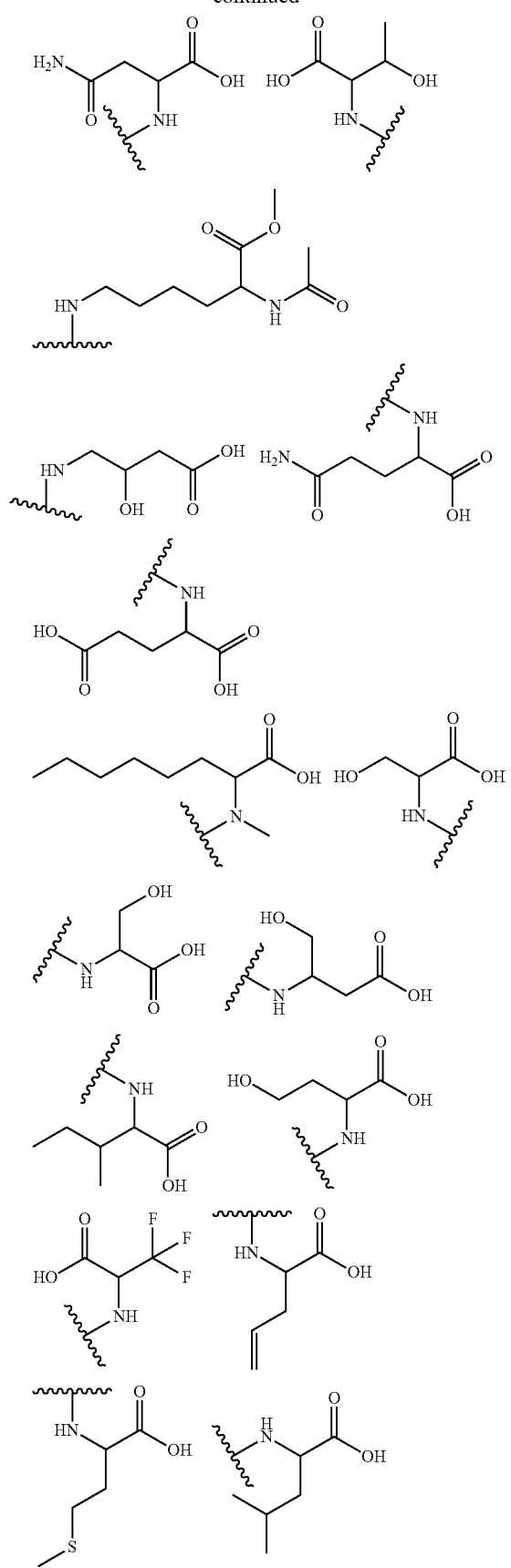
-continued
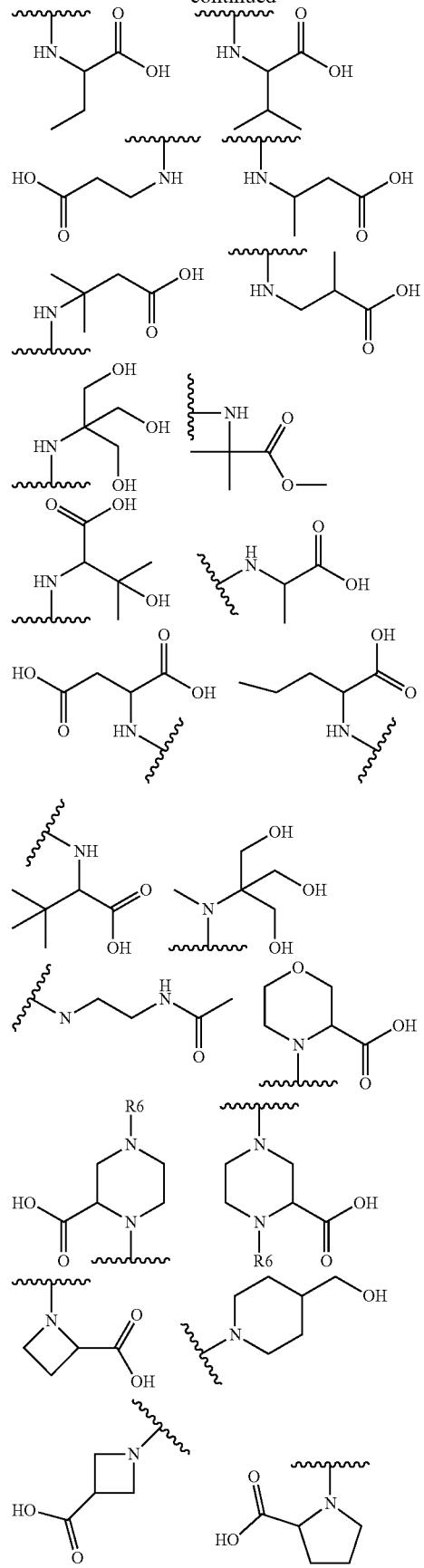

-continued
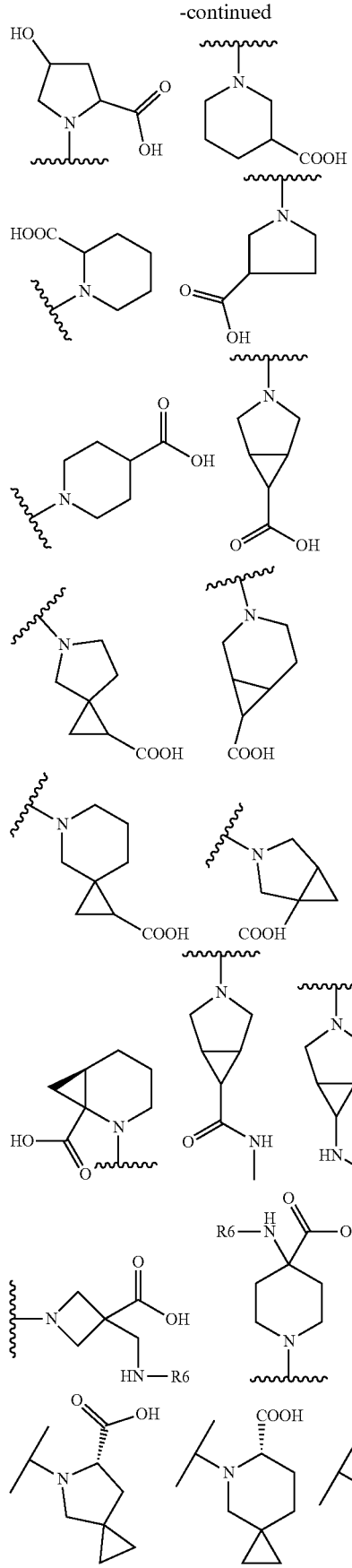
-continued
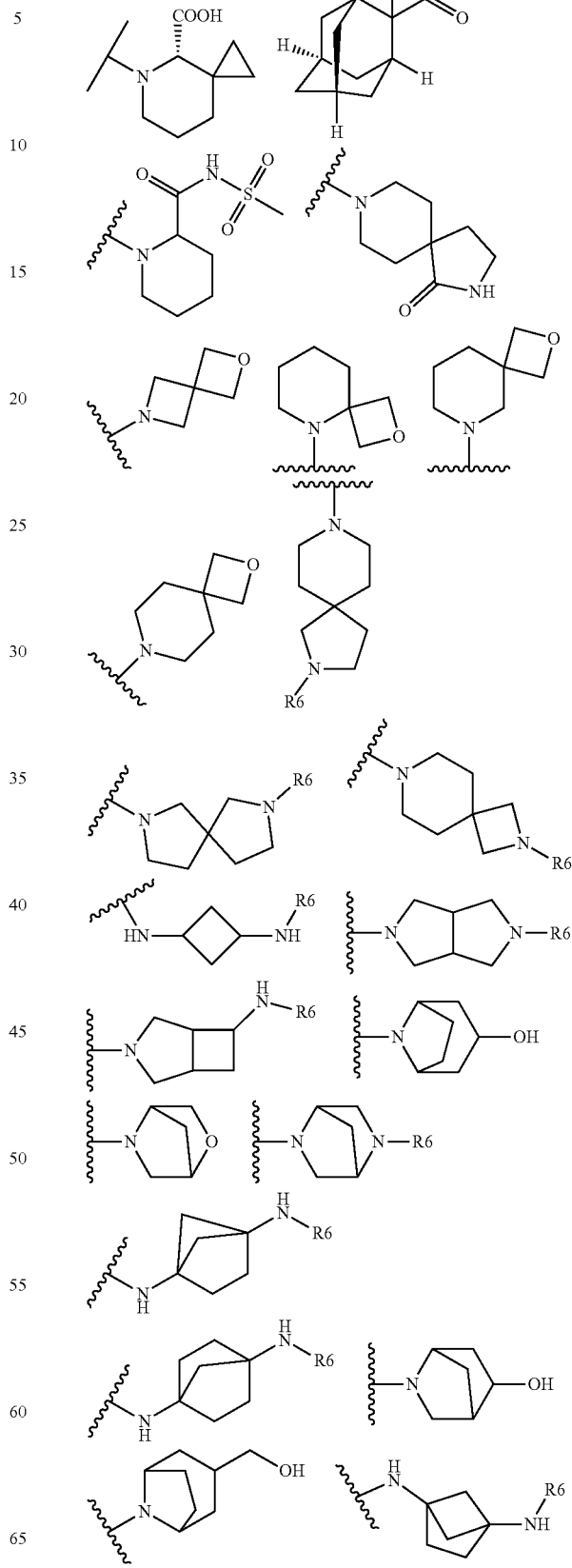

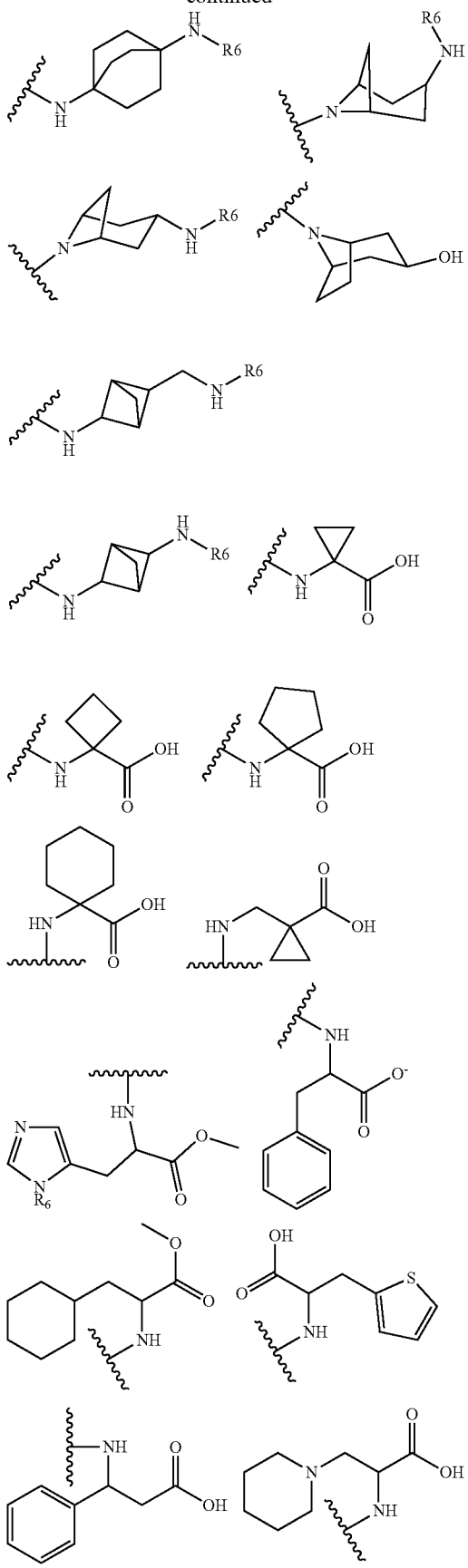
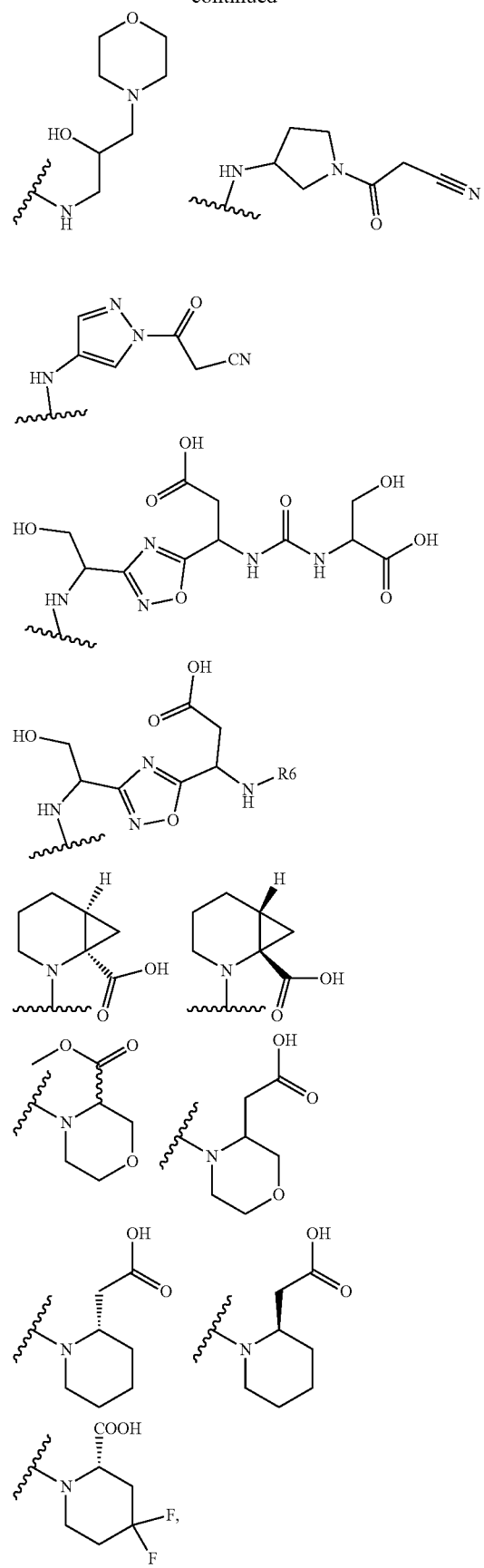

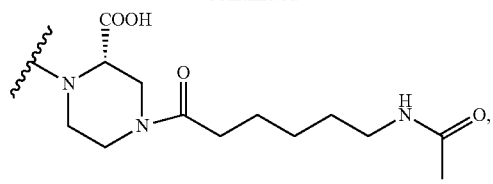

wherein R₆ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, NHR₆, NHC(O)NHR₆, and combinations thereof.

In an embodiment of the present disclosure, there is provided a compound of Formula I as described herein, wherein R₁, R₂, R₃, and R₄ are independently selected from hydrogen, cyano, $C_{1-6}$ alkyl, $C_{1-6}$ alkoxy, $C_{1-6}$ haloalkyl, $C_{1-4}$ haloalkoxy, $C_{3-6}$ cycloalkyl, $C_{1-4}$ alkylamino, amino$C_{1-4}$ alkyl, $C_{1-4}$ alkoxyamino, $C_{1-4}$ acylamino, $C_{5-6}$ aryl, and 5-10 membered monocyclic or bicyclic heteroaryl with 1-5 heteroatoms selected from N, S or O, wherein $C_{1-6}$ alkyl, $C_{5-6}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, CL-6 alkylamino, $C_{1-6}$ alkoxyamino, $C_{1-6}$ acylamino, $C_{1-10}$ heterocyclyl, —COOR$_a$, wherein $C_{1-6}$ alkyl, $C_{1-6}$ alkoxy, $C_{1-10}$ heterocyclyl are optionally substituted with one or more of the groups selected from $C_{1-6}$ alkyl, $C_{3-6}$ cycloalkyl, $C_{1-6}$ heterocyclyl, $C_{1-6}$ alkoxy, and COOR$_a$, wherein $C_{1-6}$ heterocyclyl is optionally substituted with one or more groups selected from hydroxy, halogen, or cyano, and R$_a$ is selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl $C_{1-6}$ heteroaryl or $C_{1-6}$ heteroarylalkyl and R₅ is selected from

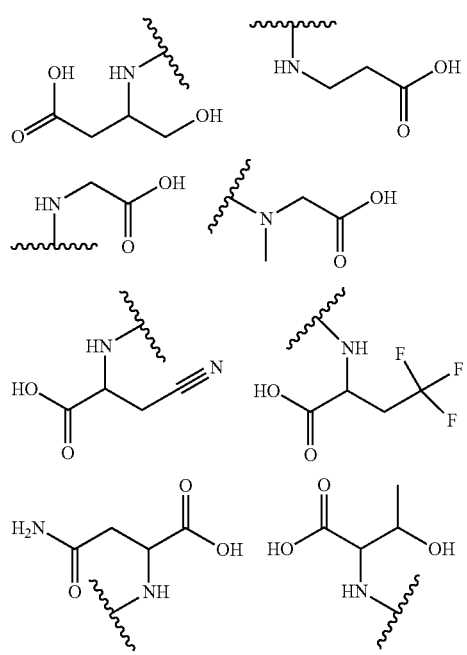

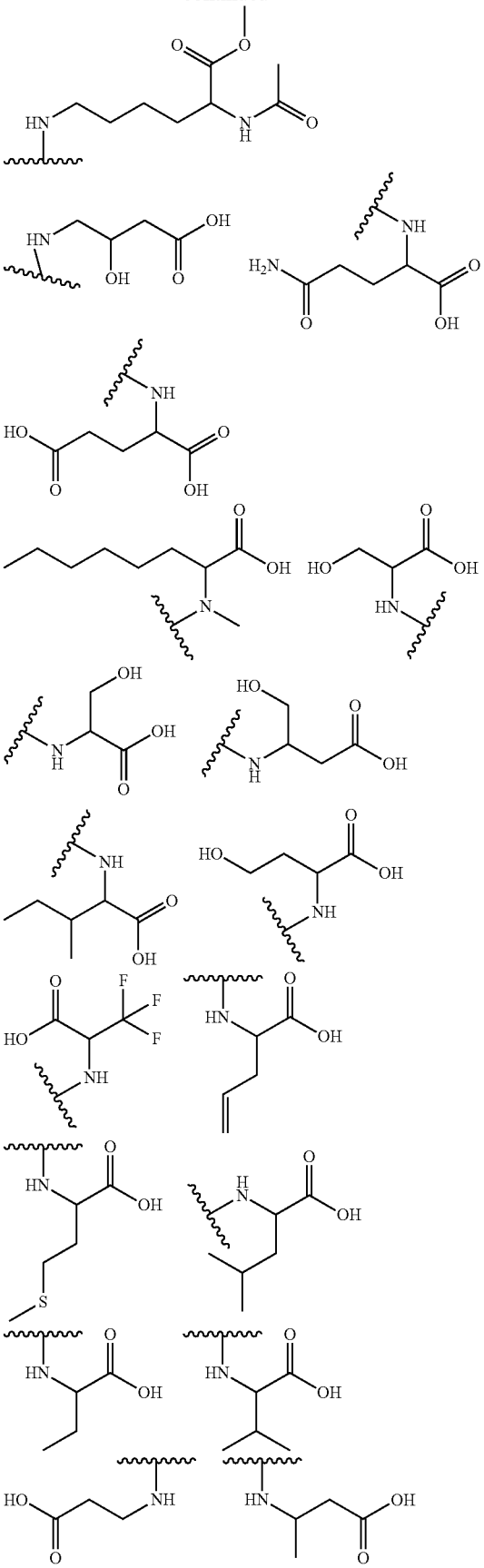

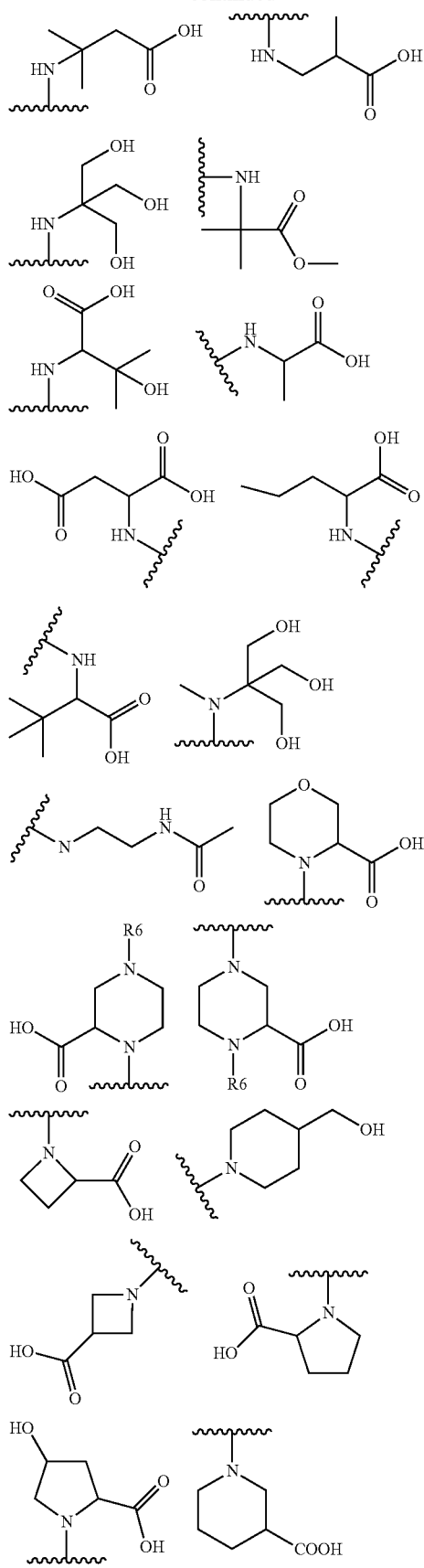
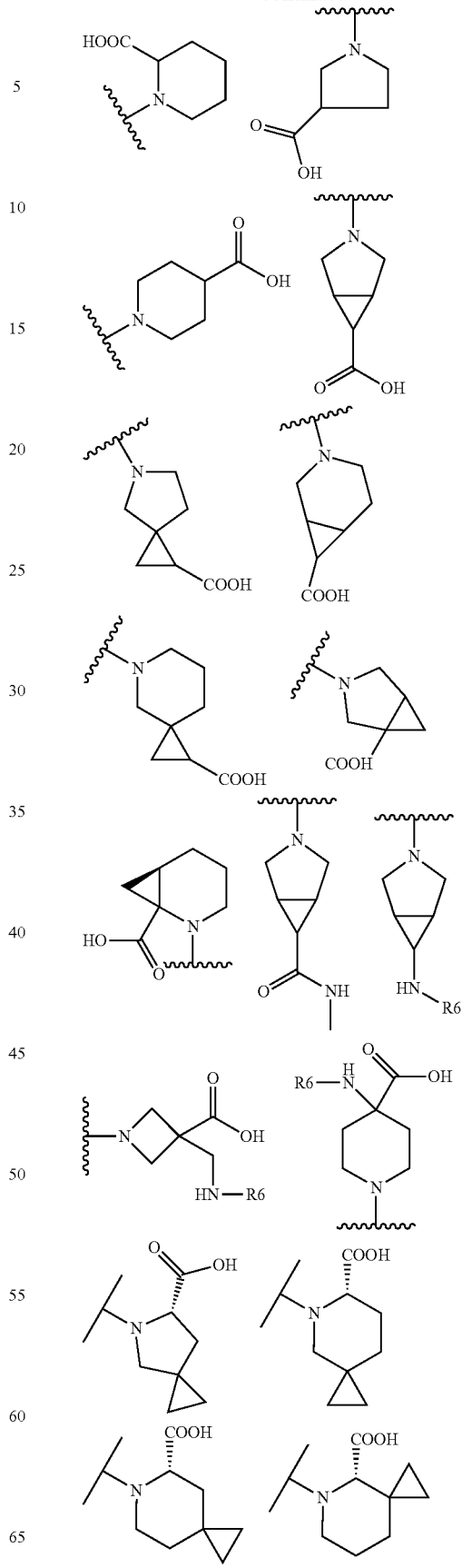

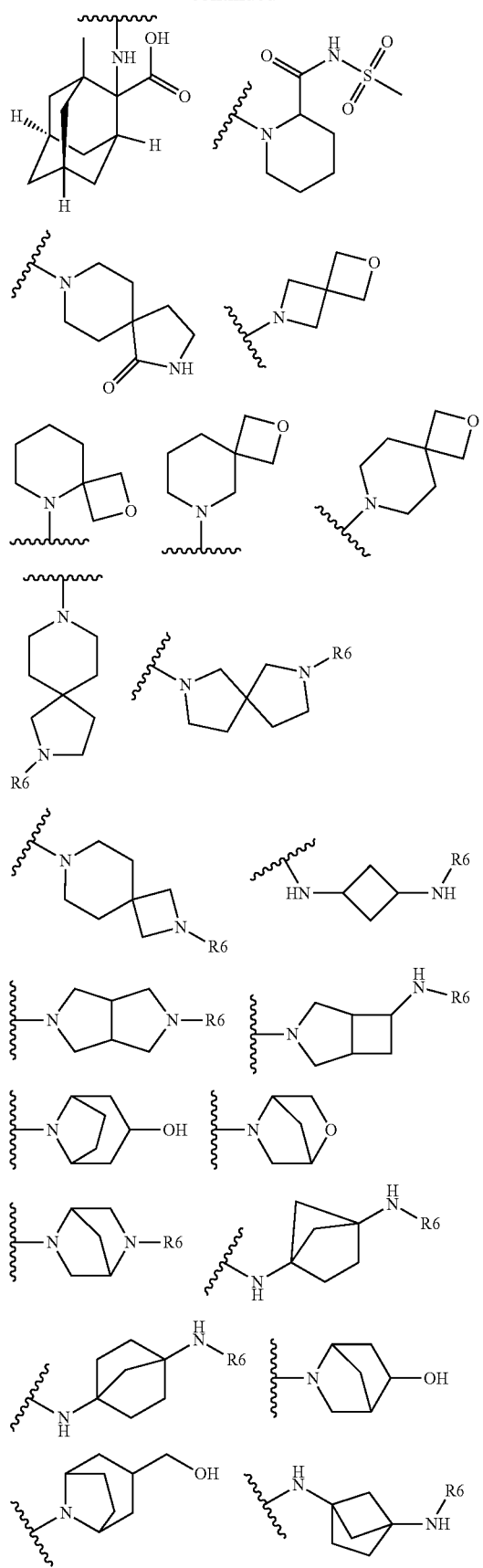
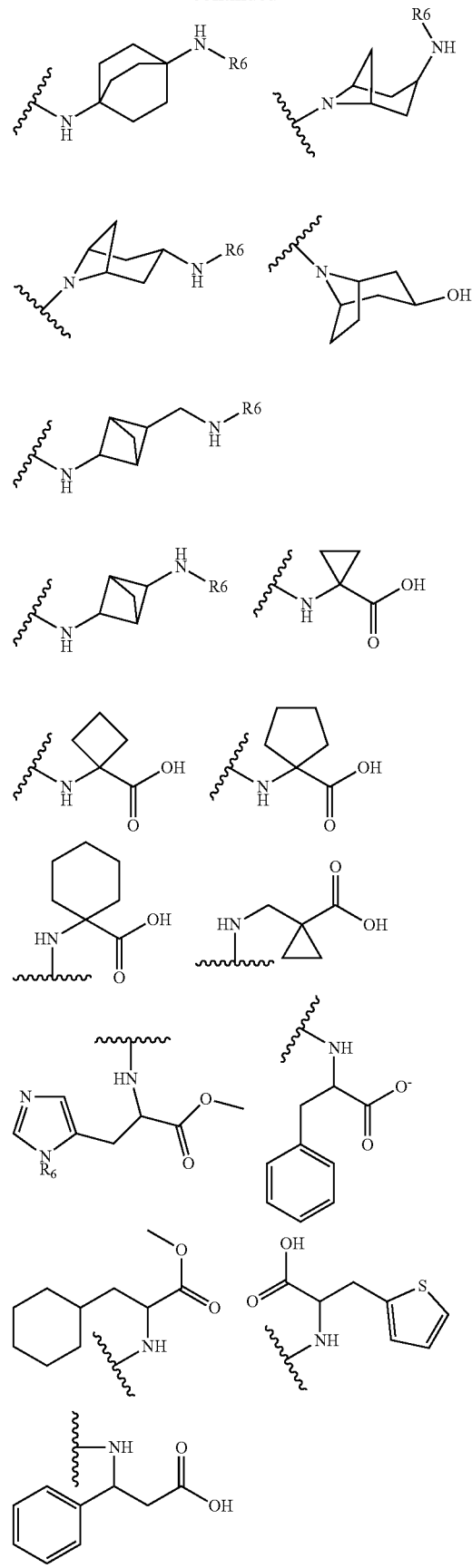

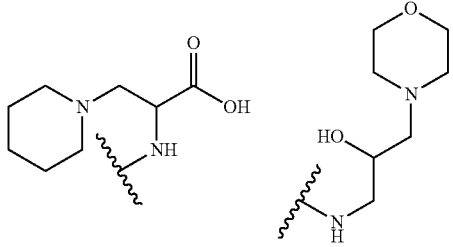
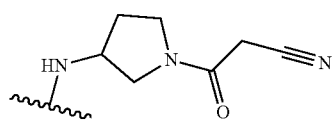
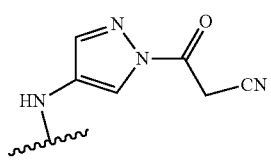
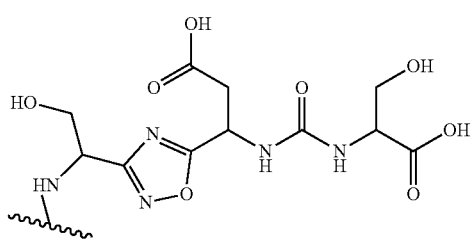
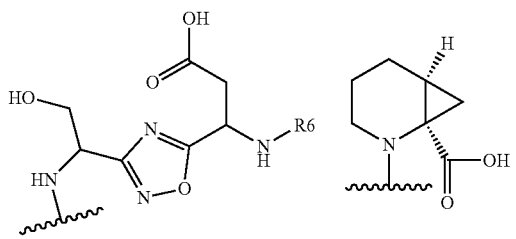
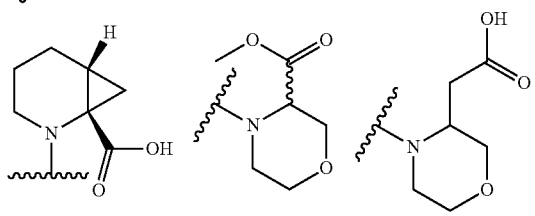
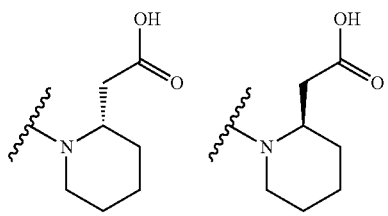
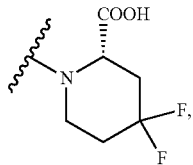

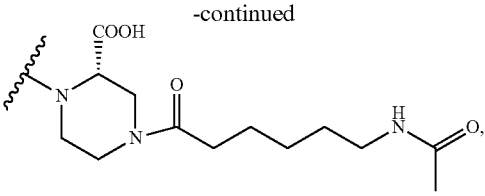

$R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided a compound of Formula I as described herein, wherein $R_1$ is selected from hydrogen, $C_{1-4}$ alkyl, $C_{3-6}$ cycloalkyl, $C_{5-6}$ aryl, and 5-9 membered monocyclic or bicyclic heteroaryl with 1-5 heteroatoms selected from N, S or O, wherein $C_{1-4}$ alkyl, $C_{5-6}$ aryl, and 5-9 membered monocyclic or bicyclic heteroaryl, is optionally substituted with one or more of the groups selected from hydrogen, halogen, hydroxyl, cyano, $C_{1-4}$ alkyl, $C_{1-4}$ alkoxy, $C_{1-4}$ haloalkyl, or $C_{1-4}$ haloalkoxy; $R_2$ is selected from hydrogen, $C_{5-6}$ aryl, and 5-10 membered monocyclic or bicyclic heteroaryl with 1-5 heteroatoms selected from N, S or O, wherein $C_{5-6}$ aryl, and 5-10 membered monocyclic or bicyclic heteroaryl, is optionally substituted with one or more of the groups selected from hydrogen, fluoro, chloro, bromo, iodo, hydroxyl, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, amino $C_{1-6}$ alkyl, $C_{1-4}$ alkoxyamino, $C_{1-4}$ acylamino, $C_{1-8}$ heterocyclyl, $COOR_a$, wherein $C_{1-4}$ alkyl, $C_{1-4}$ alkoxy, $C_{1-8}$ heterocyclyl is optionally substituted with one or more of the groups selected from $C_{1-4}$ alkyl, $C_{3-6}$ cycloalkyl, $C_{1-6}$ heterocyclyl, $C_{1-4}$ alkoxy, and $COOR_a$; wherein $C_{1-6}$ heterocyclyl is optionally substituted with one or more groups selected from hydroxy, halogen, or cyano, and $R_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_3$ and $R_4$ are independently selected from hydrogen, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, amino$C_{1-4}$ alkyl, $C_{1-4}$ alkoxyamino, $C_{1-4}$ acylamino, $C_{5-6}$ aryl, and 5-9 membered monocyclic or bicyclic heteroaryl with 1-5 heteroatoms selected from N, S or O, wherein $C_{5-6}$ aryl, and 5-9 membered monocyclic or bicyclic heteroaryl, is optionally substituted with one or more of the groups selected from hydrogen, halogen, hydroxyl, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, $C_{1-4}$ acylamino, or $C_{1-6}$ heterocyclyl; and $R_5$ is selected from

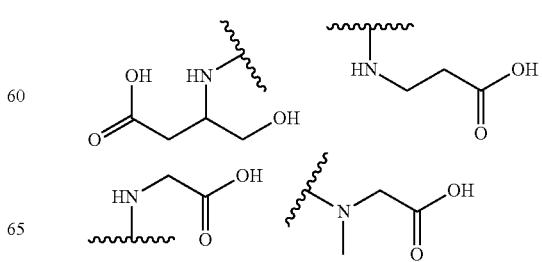

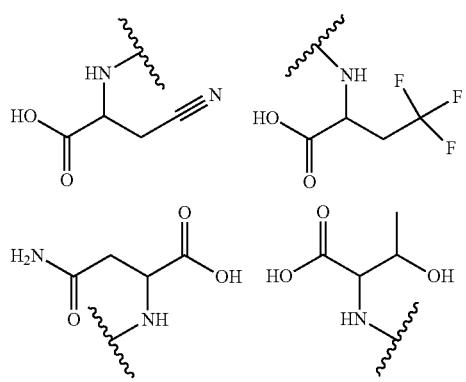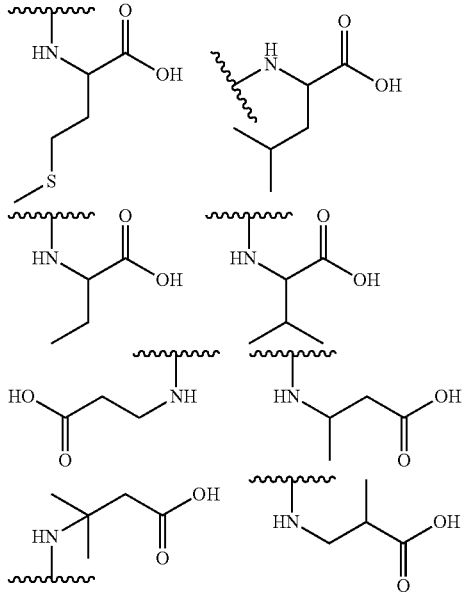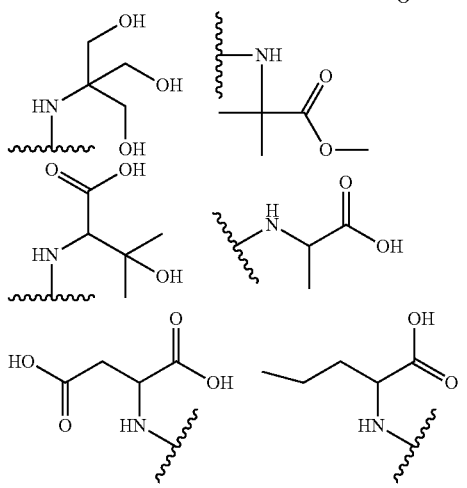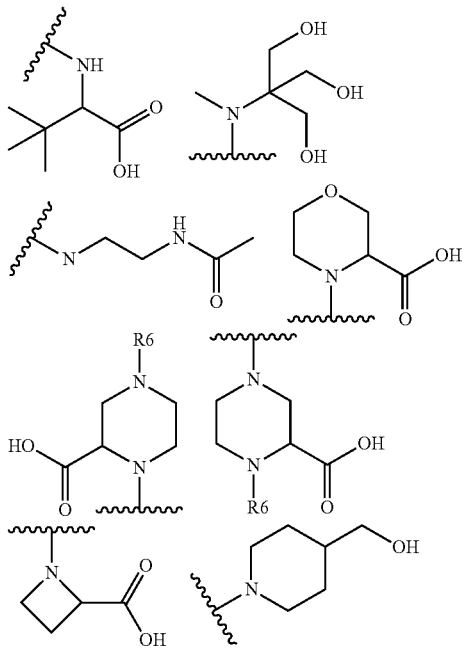

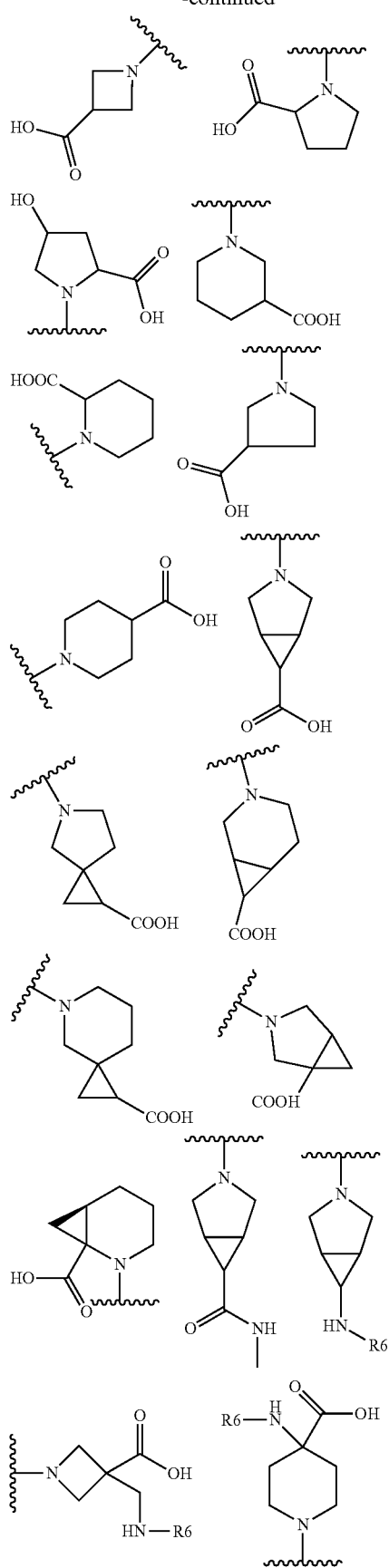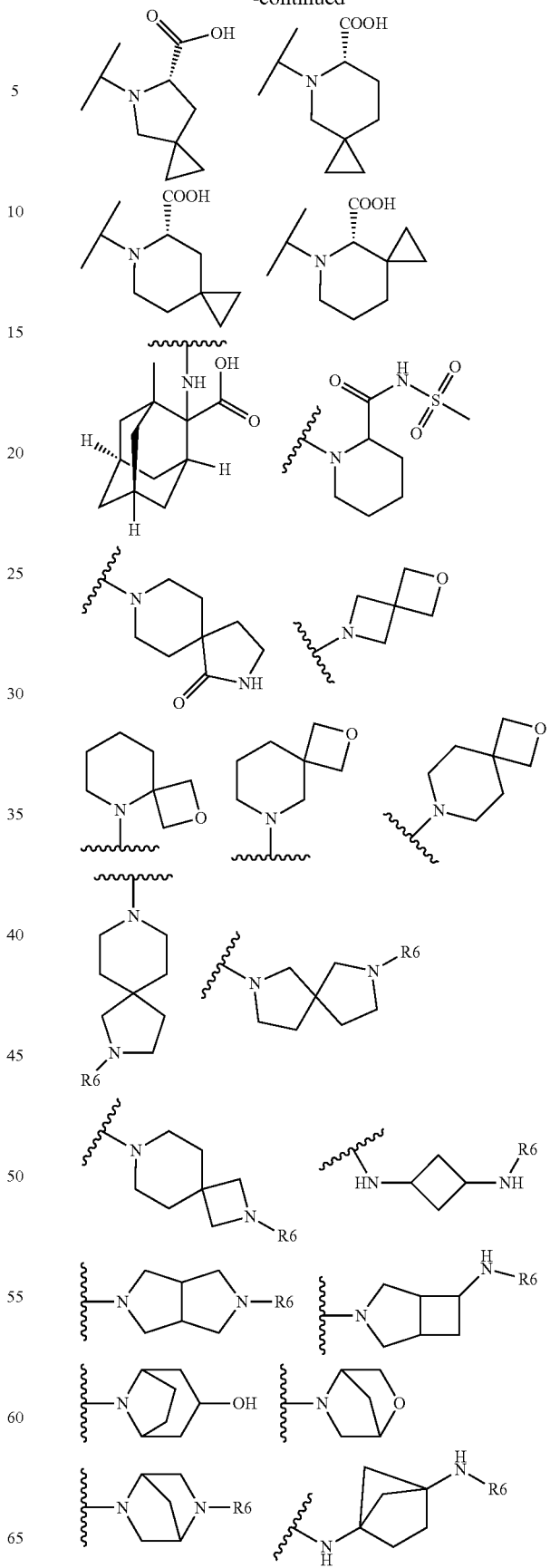

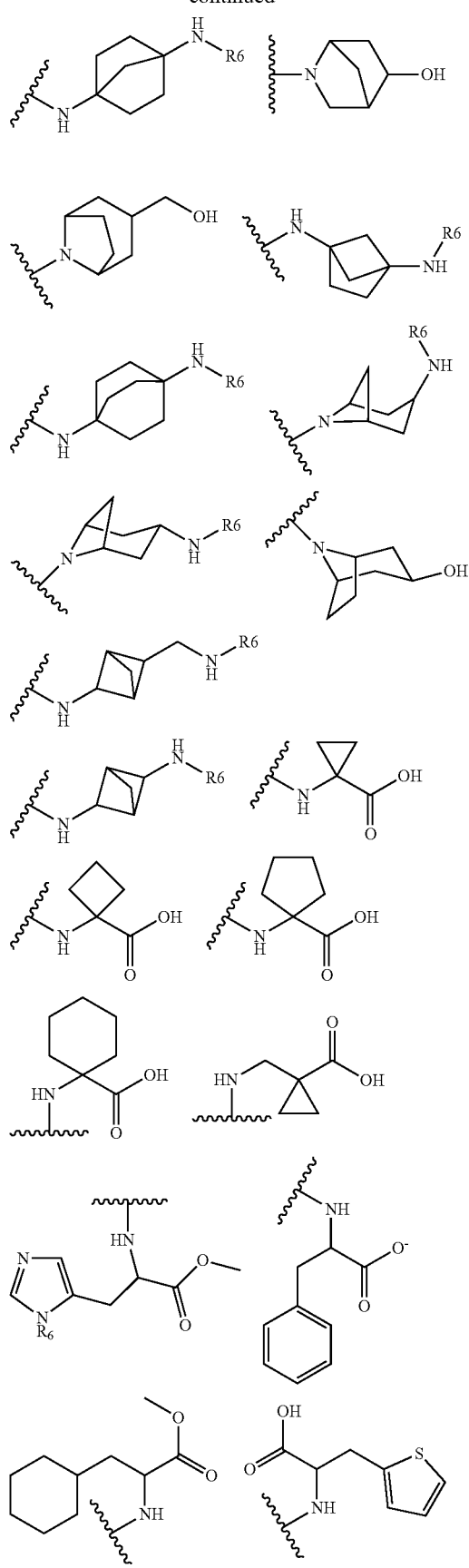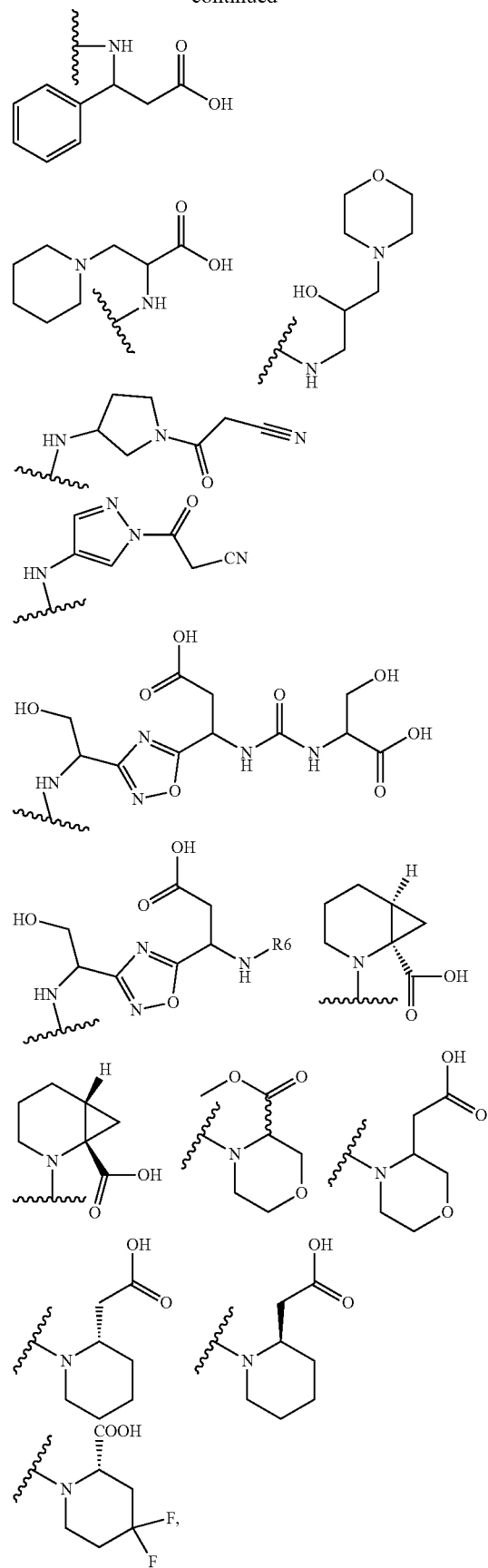

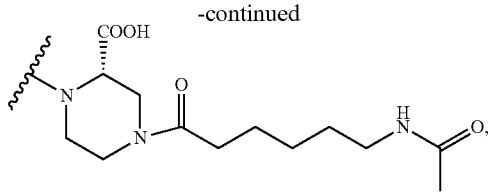

wherein $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided a compound of Formula I as described herein, wherein $R_1$, and $R_2$ are independently selected from hydrogen, $C_{1-6}$ alkyl, $C_{1-6}$ alkoxy, $C_{1-4}$ haloalkyl, $C_{1-4}$ haloalkoxy, $C_{3-6}$ cycloalkyl, $C_{1-4}$ alkylamino, amino$C_{1-4}$ alkyl, $C_{1-4}$ alkoxyamino, $C_{1-4}$ acylamino, $C_{5-6}$ aryl, and 5-10 membered monocyclic or bicyclic heteroaryl with 1-5 heteroatoms selected from N, S or O, wherein $C_{1-6}$ alkyl, $C_{5-6}$ aryl, and 5-10 membered monocyclic or bicyclic heteroaryl, are optionally substituted with one or more of the groups selected from hydrogen, halogen, hydroxyl, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, $C_{1-4}$ acylamino, $C_{1-6}$ heterocyclyl, $COOR_a$, wherein $C_{1-4}$ alkyl, $C_{1-4}$ alkoxy, and $C_{1-6}$ heterocyclyl are optionally substituted with one or more of the groups selected from $C_{1-4}$ alkyl, $C_{3-6}$ cycloalkyl, $C_{1-6}$ heterocyclyl, $C_{1-4}$ alkoxy, and $COOR_a$, wherein $C_{1-6}$ heterocyclyl is optionally substituted with one or more groups selected from hydroxy, halogen, or cyano, and $R_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_3$, and $R_4$ are independently selected from the group consisting of hydrogen, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, $C_{1-4}$ acylamino, and combinations thereof; and $R_5$ is selected from

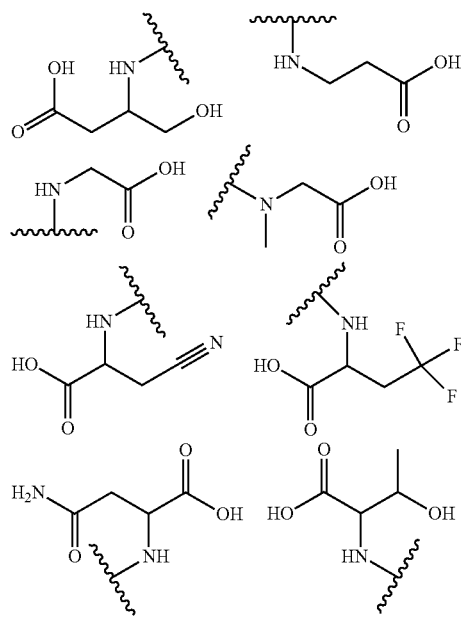

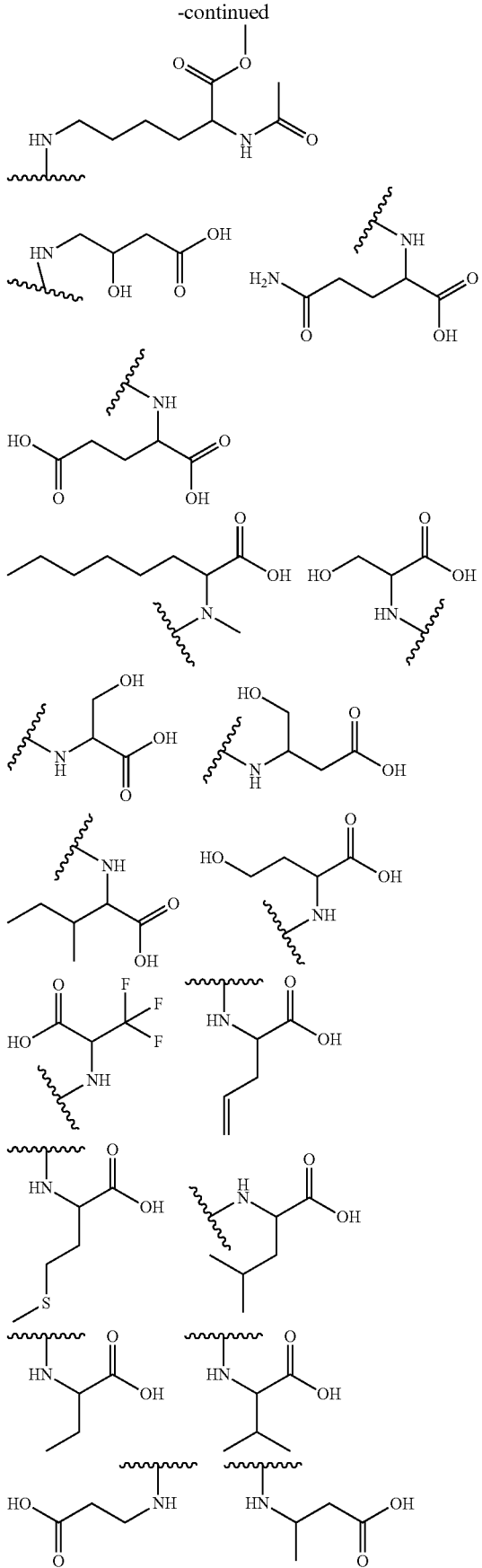

51
-continued
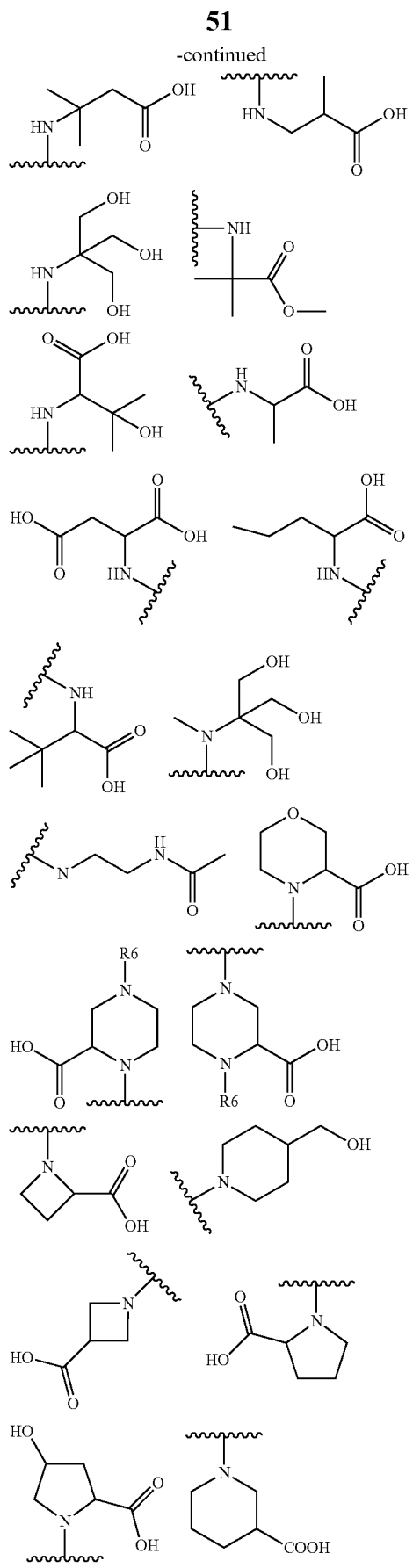
52
-continued
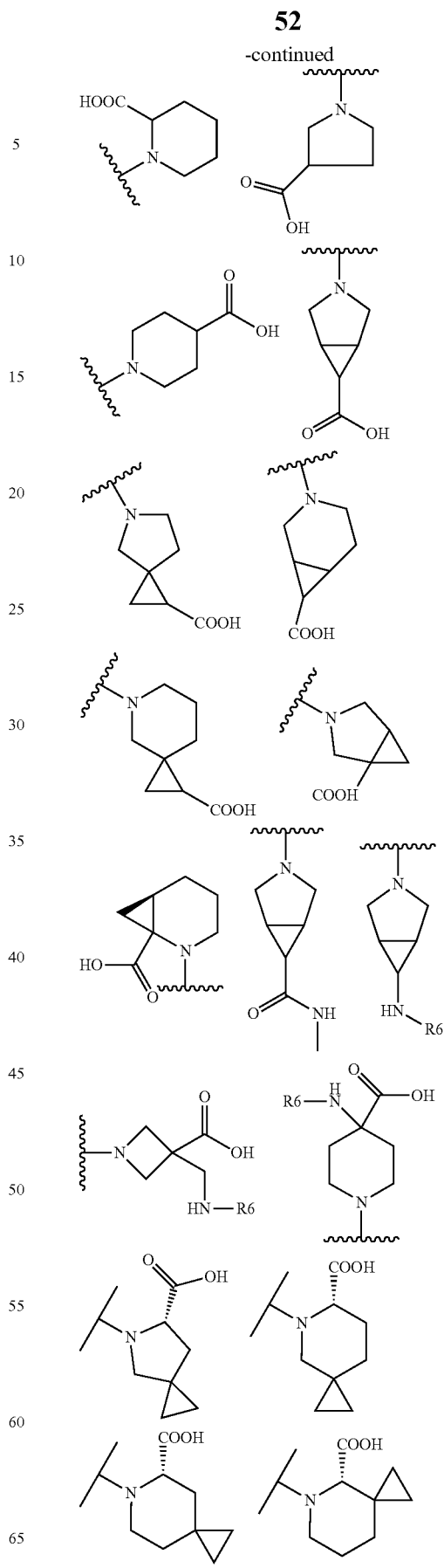

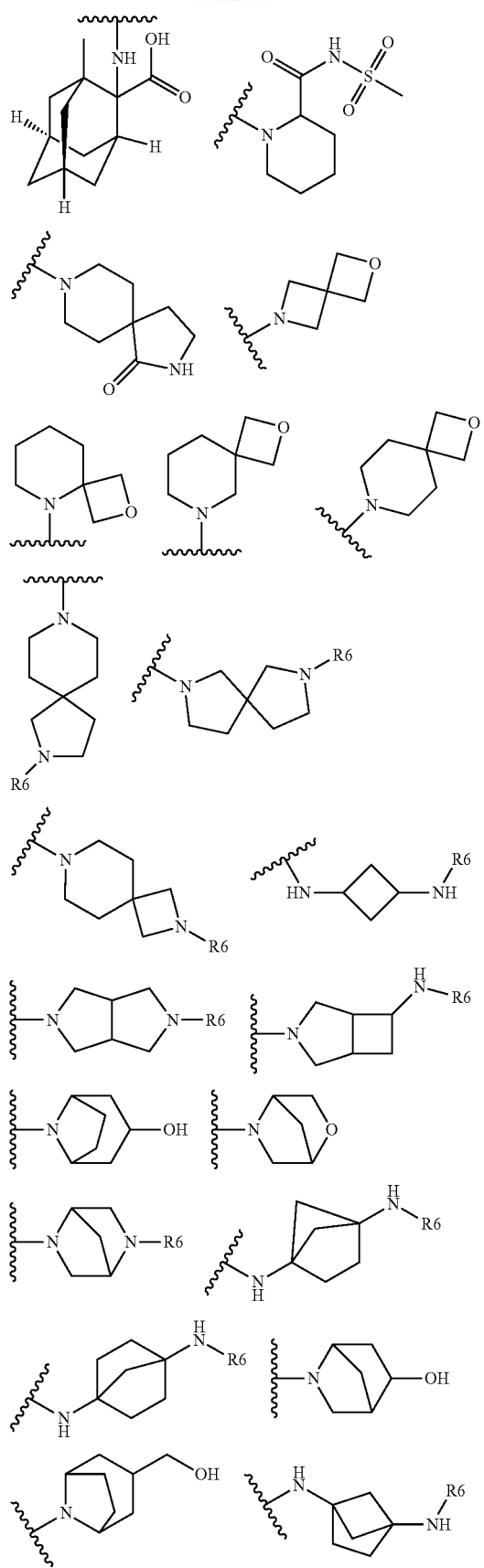
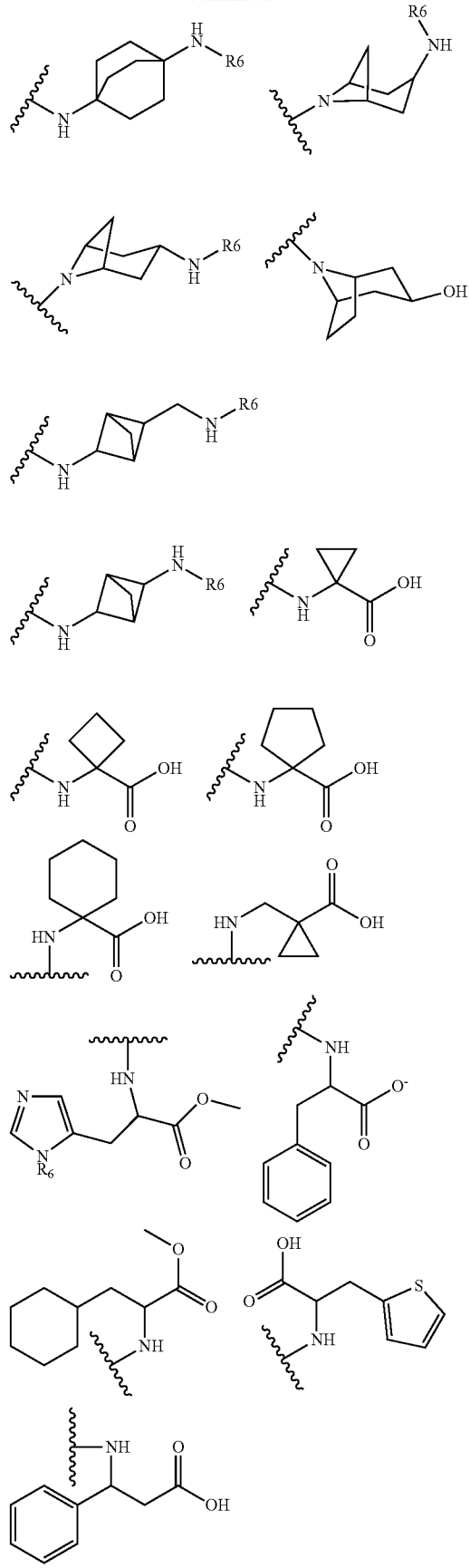

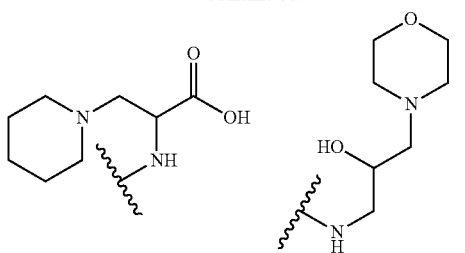
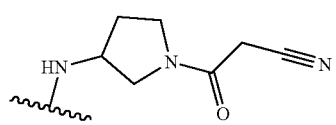
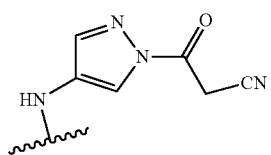
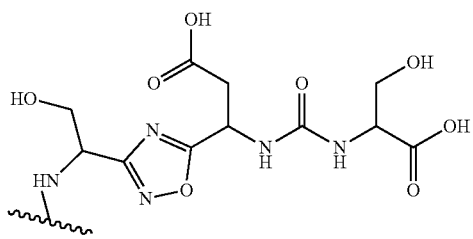
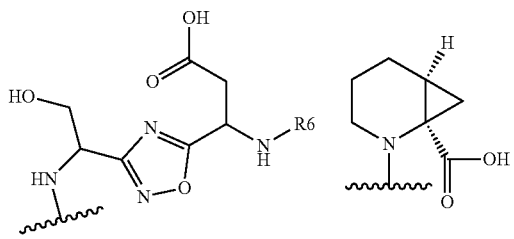
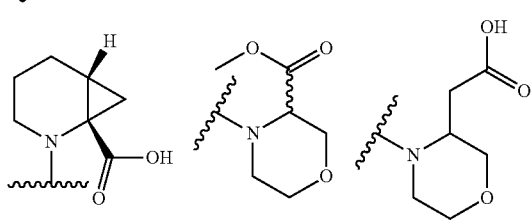
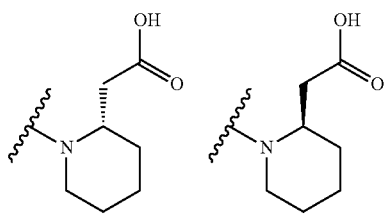
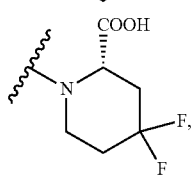

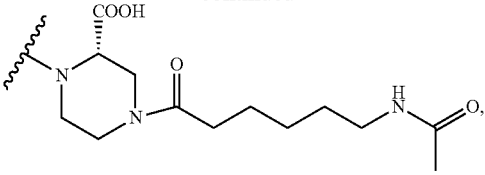

wherein $R_6$ is selected from hydrogen, $C_{1-6}$ alkyl, and $C(O)C_{1-6}$ alkyl.

In an embodiment of the present disclosure, there is provided a compound of Formula I as described herein, wherein $R_1$, $R_2$, $R_3$, and $R_4$ are independently selected from hydrogen, cyano, $C_{1-6}$ alkyl, $C_{1-6}$ alkoxy, $C_{1-4}$ haloalkyl, $C_{1-4}$ haloalkoxy, $C_{3-6}$ cycloalkyl, $C_{1-4}$ alkylamino, amino $C_{1-4}$ alkyl, $C_{1-4}$ alkoxyamino, $C_{1-4}$ acylamino, $C_{5-9}$ aryl, and 5-10 membered monocyclic or bicyclic heteroaryl with 1-5 heteroatoms selected from N, S or O, wherein $C_{1-6}$ alkyl, $C_{5-9}$ aryl, and 5-10 membered monocyclic or bicyclic heteroaryl, is optionally substituted with one or more of the groups selected from hydrogen, halogen, hydroxyl, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, $C_{1-4}$ acylamino, $C_{1-6}$ heterocyclyl, or —$COOR_a$, wherein $C_{1-4}$ alkyl, $C_{1-4}$ alkoxy, $C_{1-9}$ heterocyclyl are optionally substituted with one or more of the groups selected from $C_{1-4}$ alkyl, $C_{3-6}$ cycloalkyl, $C_{1-6}$ heterocyclyl, $C_{1-4}$ alkoxy, or $COOR_a$, wherein $C_{1-6}$ heterocyclyl is optionally substituted with one or more groups selected from hydroxy, halogen, or cyano; and $R_a$ is selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; and $R_5$ is selected from

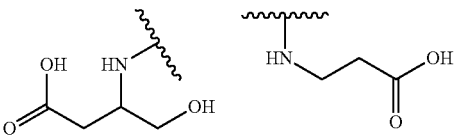
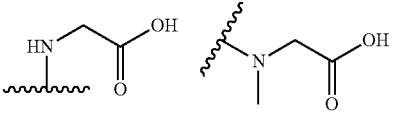
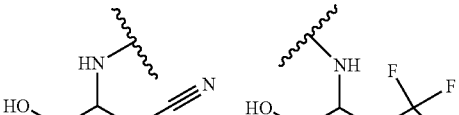
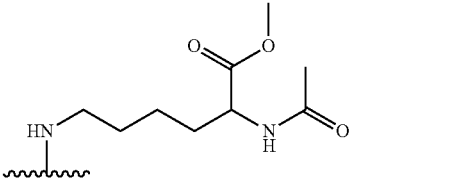

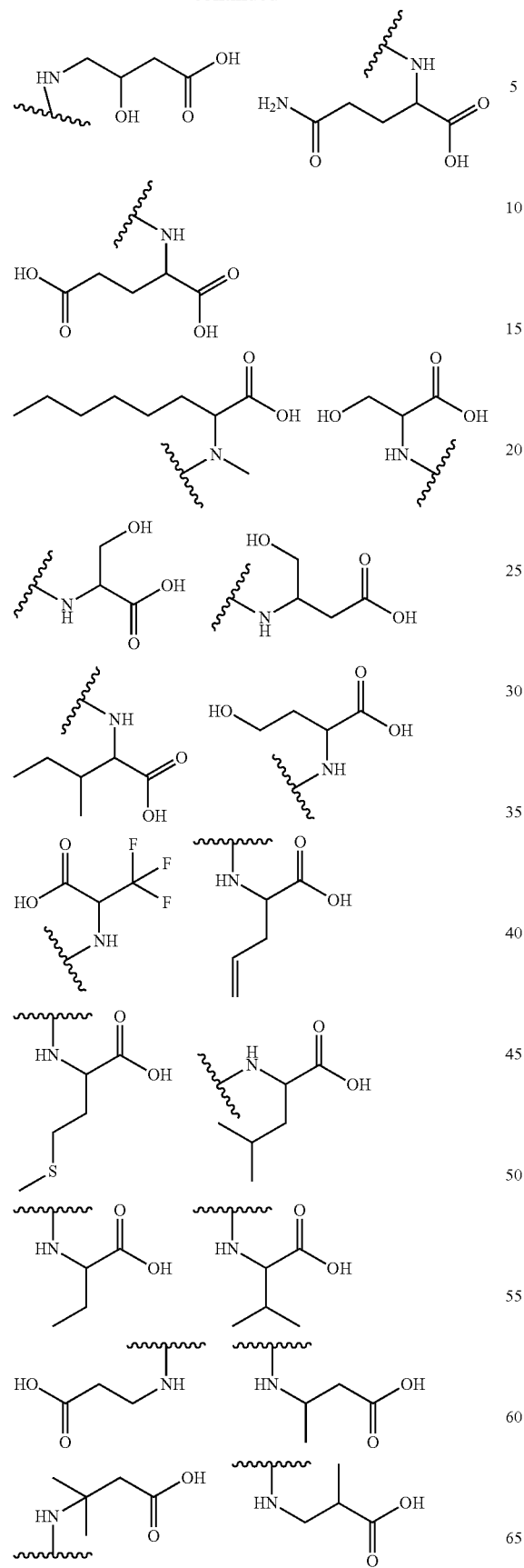
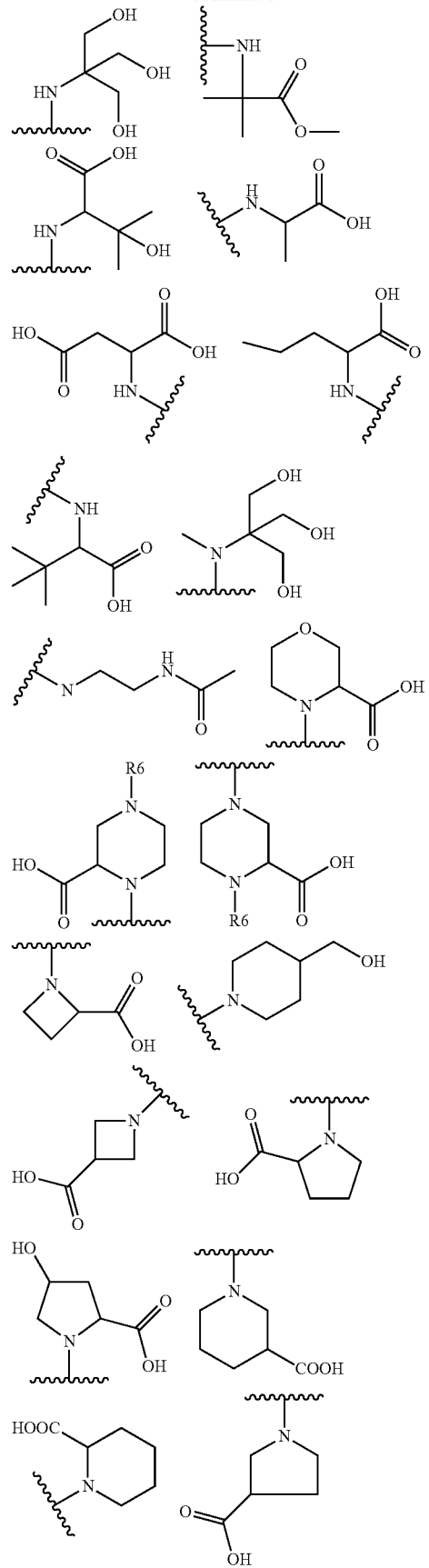

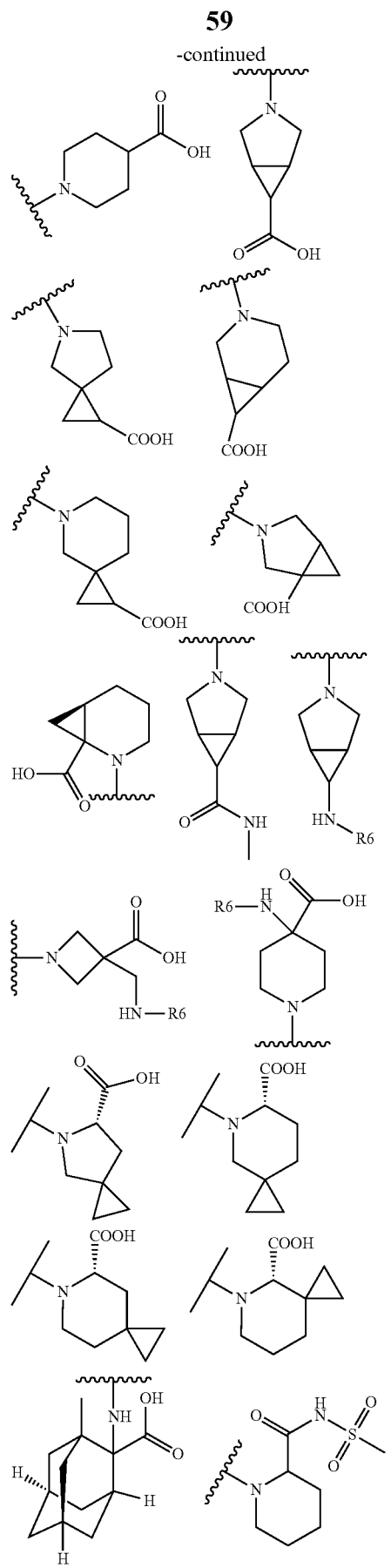
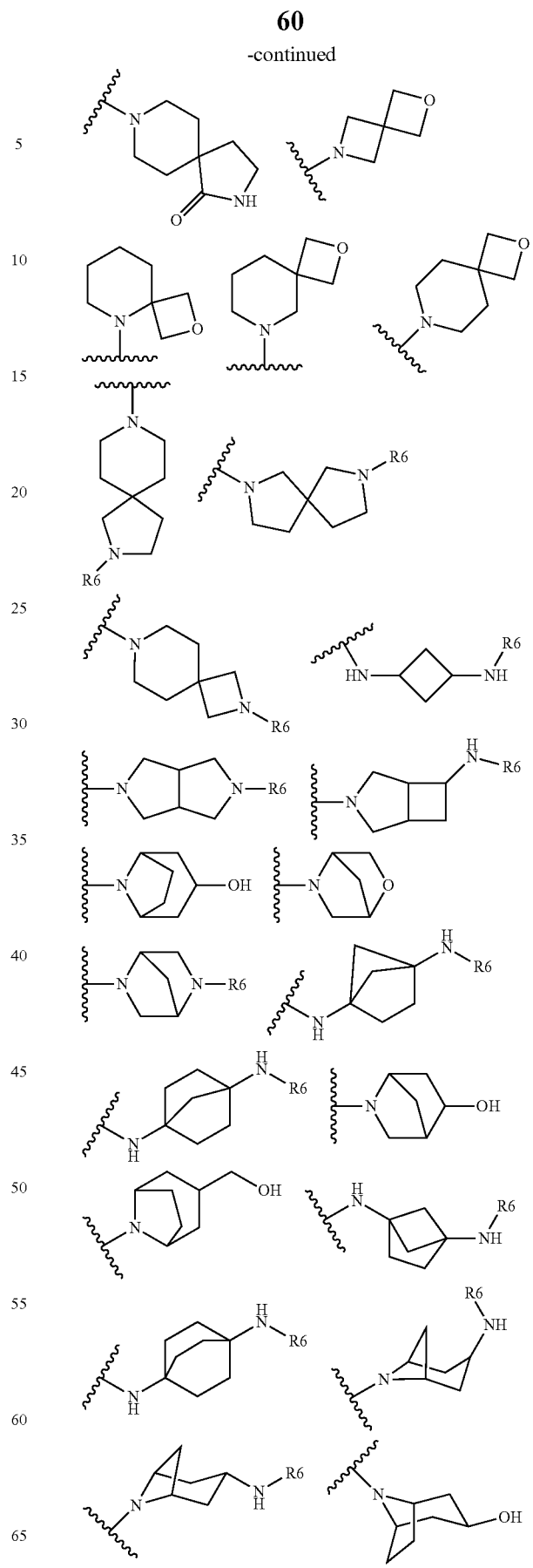

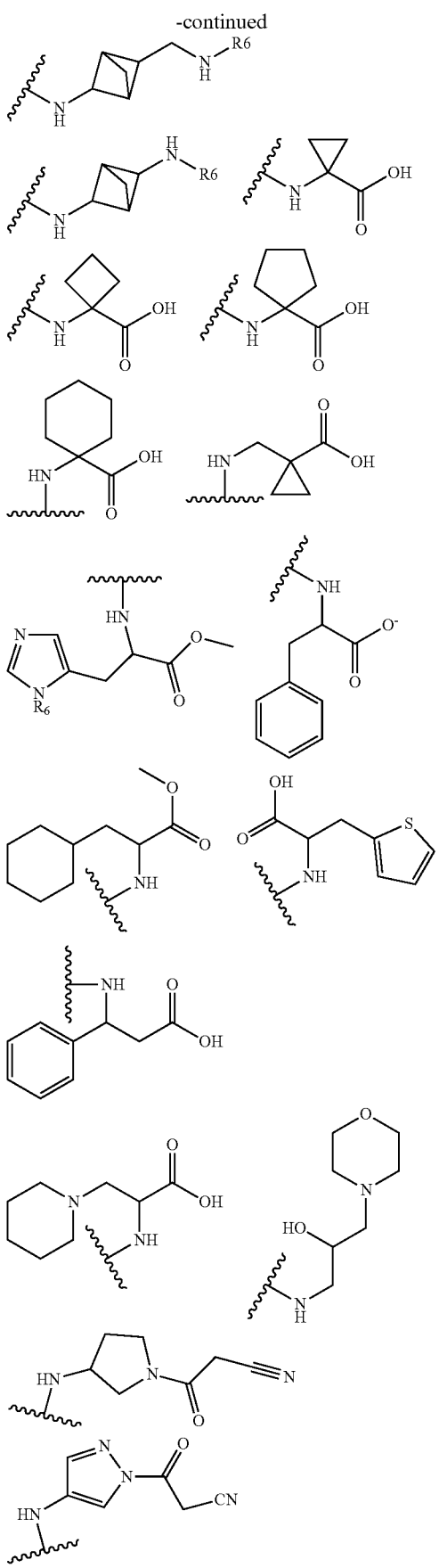
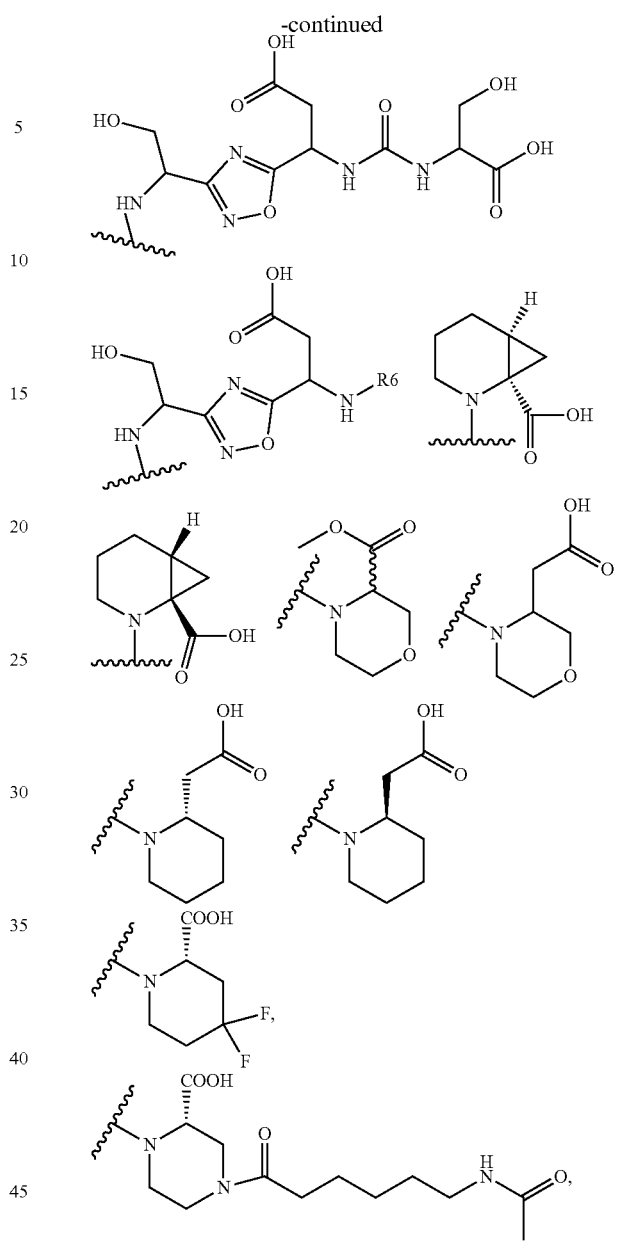

wherein $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided a compound of Formula I as described herein, wherein $R_1$ is selected from hydrogen, $C_{1-4}$ alkyl, $C_{3-6}$ cycloalkyl, $C_{5-6}$ aryl, and 5-10 membered monocyclic or bicyclic heteroaryl with 1-5 heteroatoms selected from N, S or O, wherein $C_{1-4}$ alkyl, $C_{5-6}$ aryl, and 5-10 membered monocyclic or bicyclic heteroaryl, are optionally substituted with one or more of the groups selected from hydrogen, halogen, hydroxyl, cyano, $C_{1-4}$ alkyl, $C_{1-4}$ alkoxy, $C_{1-4}$ haloalkyl, $C_{1-4}$ haloalkoxy, or $C_{1-6}$ heterocyclyl; $R_2$ is selected from hydrogen, $C_{5-6}$ aryl, and 5-10 membered monocyclic or bicyclic heteroaryl with 1-5 heteroatoms selected from N, S or O, wherein $C_{5-6}$ aryl, and 5-10 membered monocyclic or bicyclic heteroaryl, are optionally substituted with one or more of the groups selected from hydrogen, fluoro, chloro, bromo, iodo, hydroxyl, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, amino $C_{1-6}$ alkyl, $C_{1-4}$ alkoxyamino, $C_{1-4}$ acylamino, $C_{1-8}$ heterocyclyl, or $COOR_a$, wherein $C_{1-4}$ alkyl, $C_{1-4}$ alkoxy, and $C_{1-8}$ heterocyclyl are optionally substituted with one or more of the groups selected from $C_{1-4}$ alkyl, $C_{3-6}$ cycloalkyl, $C_{1-6}$ heterocyclyl, $C_{1-4}$ alkoxy, and $COOR_a$; wherein $C_{1-6}$ heterocyclyl is optionally substituted with one or more groups selected from hydroxy, halogen, or cyano; and $R_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_3$ and $R_4$ are independently selected from the group consisting of hydrogen, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, $C_{1-4}$ acylamino, and combinations thereof; and $R_5$ is selected from

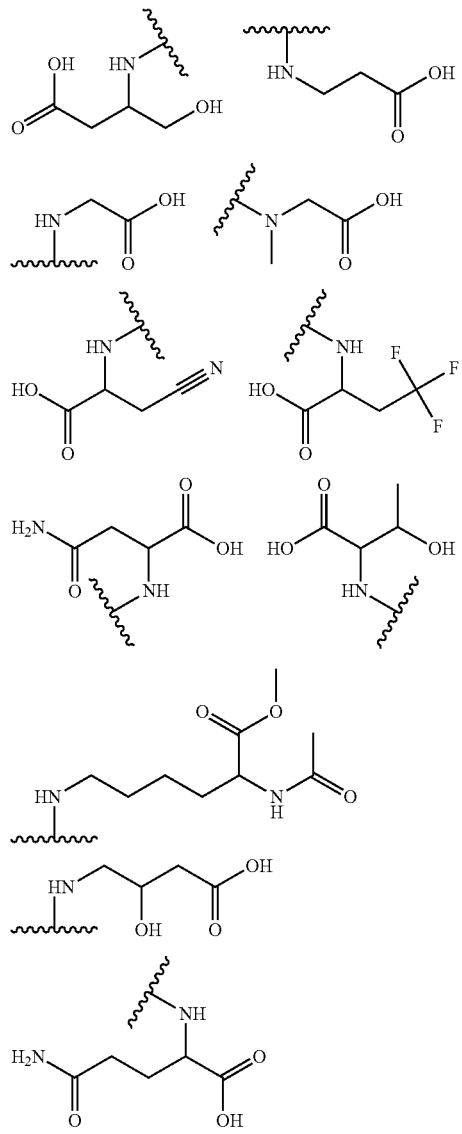

-continued

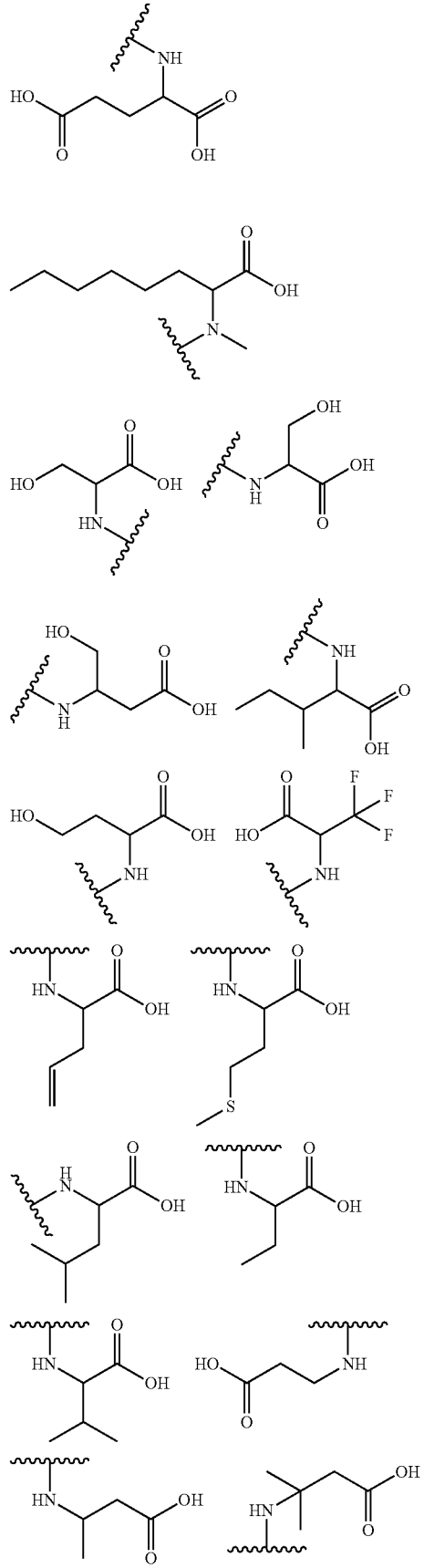

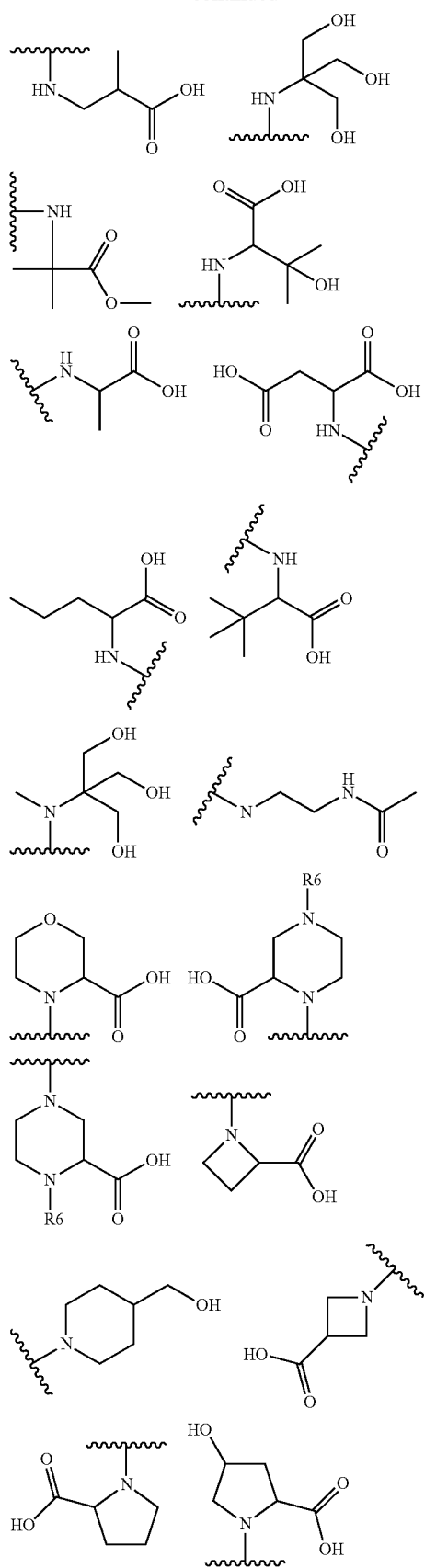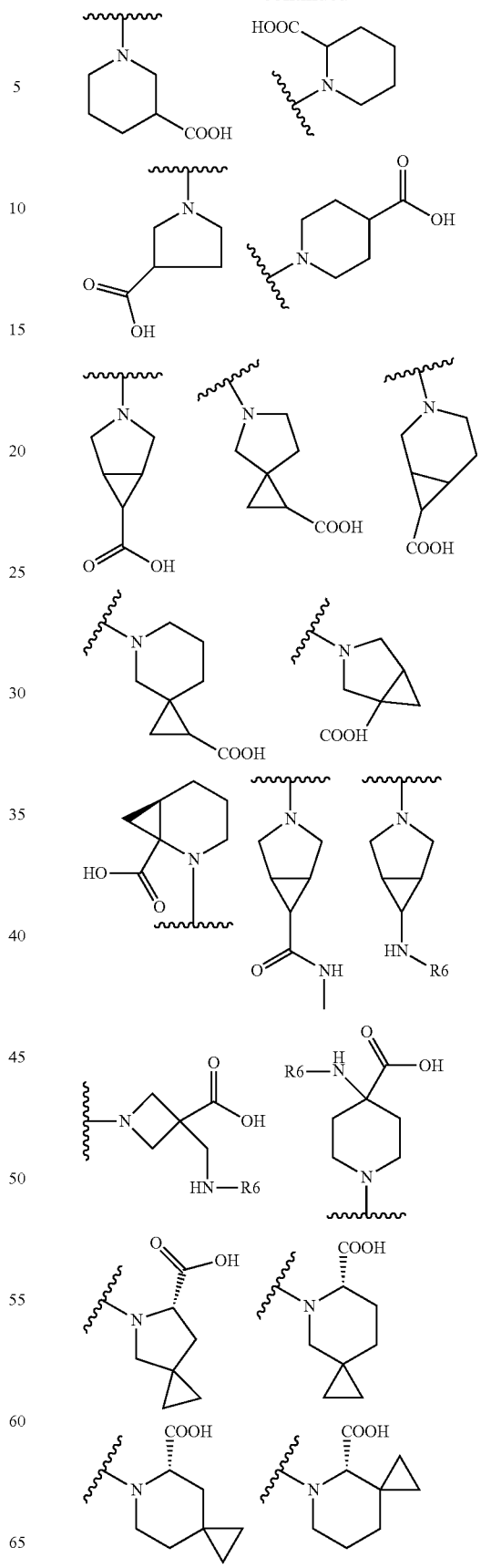

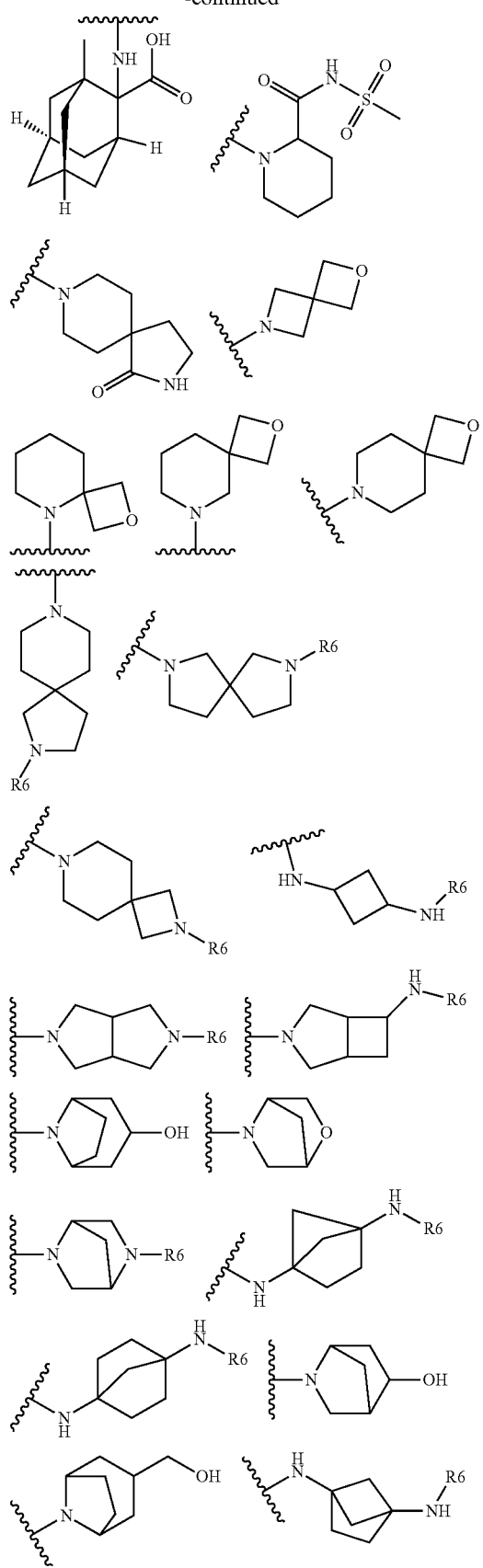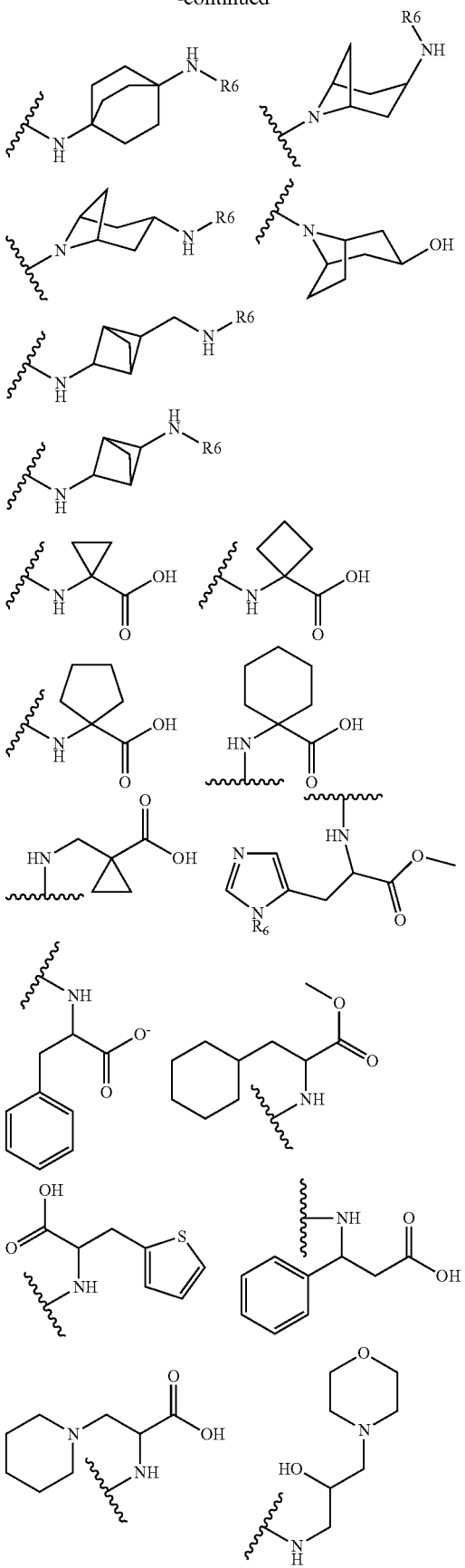

-continued

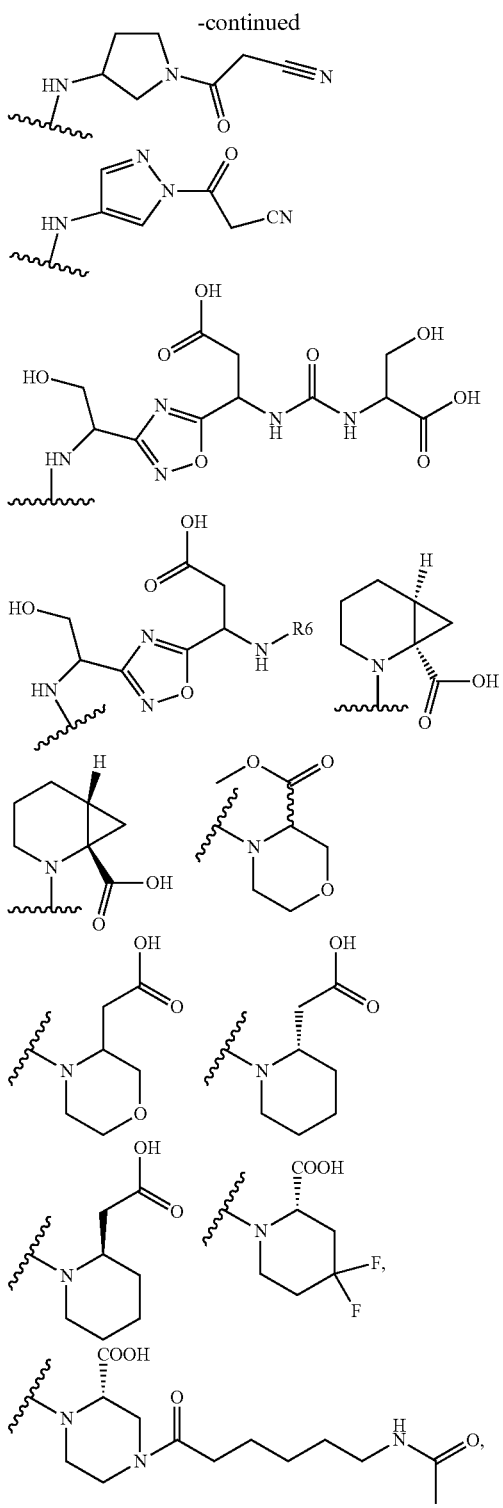

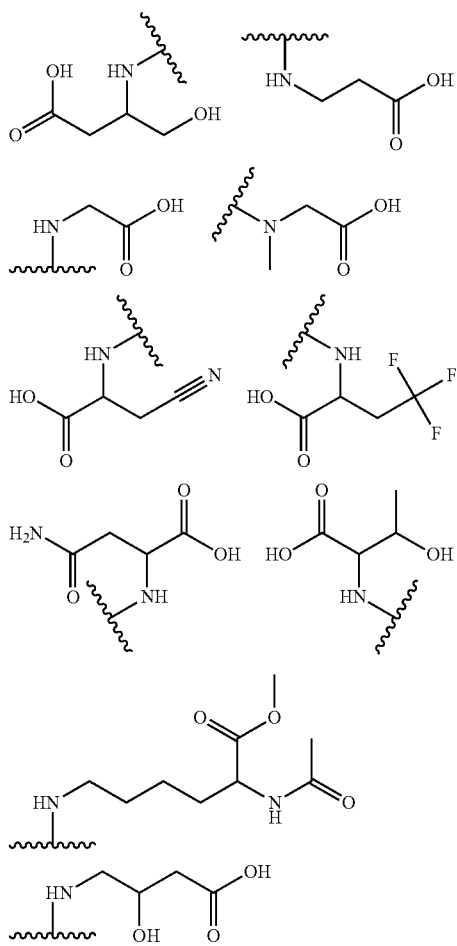

cycloalkyl, $C_{5-6}$ aryl, and 5-9 membered monocyclic or bicyclic heteroaryl with 1-5 heteroatoms selected from N, S or O, wherein $C_{1-4}$ alkyl, $C_{5-6}$ aryl, and 5-9 membered monocyclic or bicyclic heteroaryl, are optionally substituted with one or more groups selected from hydrogen, halogen, hydroxyl, cyano, $C_{1-4}$ alkyl, $C_{1-4}$ alkoxy, $C_{1-4}$ haloalkyl, $C_{1-4}$ haloalkoxy, $C_{1-6}$ heterocyclyl, or $COOR_a$, wherein $R_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_2$ is selected from hydrogen, $C_{5-6}$ aryl, and 5-10 membered monocyclic or bicyclic heteroaryl with 1-5 heteroatoms selected from N, S or O, wherein $C_{5-6}$ aryl, and 5-10 membered monocyclic or bicyclic heteroaryl, are optionally substituted with one or more groups selected from hydrogen, fluoro, chloro, bromo, iodo, hydroxyl, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, amino $C_{1-6}$ alkyl, $C_{1-4}$ alkoxyamino, $C_{1-4}$ acylamino, $C_{1-6}$ heterocyclyl, $COOR_a$, wherein $C_{1-4}$ alkyl, $C_{1-4}$ alkoxy, $C_{1-6}$ heterocyclyl are optionally substituted with one or more of the groups selected from $C_{1-4}$ alkyl, $C_{3-6}$ cycloalkyl, $C_{1-6}$ heterocyclyl, and $C_{1-4}$ alkoxy, wherein $C_{1-6}$ heterocyclyl is optionally substituted with one or more groups selected from hydroxy, halogen, or cyano; $R_3$ and $R_4$ are independently selected from hydrogen, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, or $C_{1-4}$ acylamino; and $R_5$ is selected from wherein $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, NH—C(O)NH—$R_6$, and combinations thereof.

In an embodiment of the present disclosure, there is provided a compound of Formula I as described herein, wherein $R_1$ is selected from hydrogen, $C_{1-4}$ alkyl, $C_{3-6}$ -continued
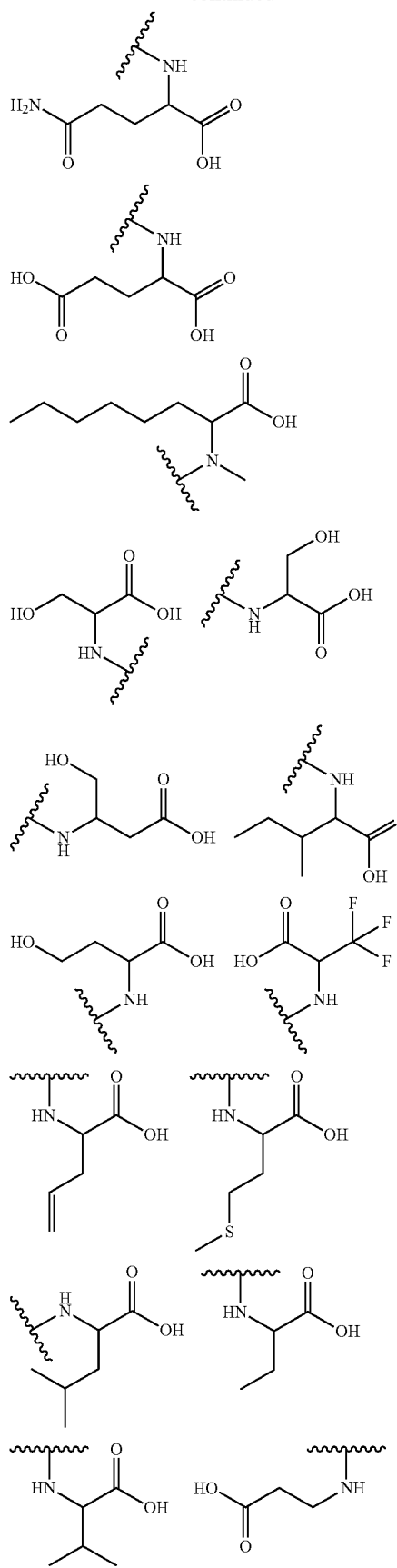
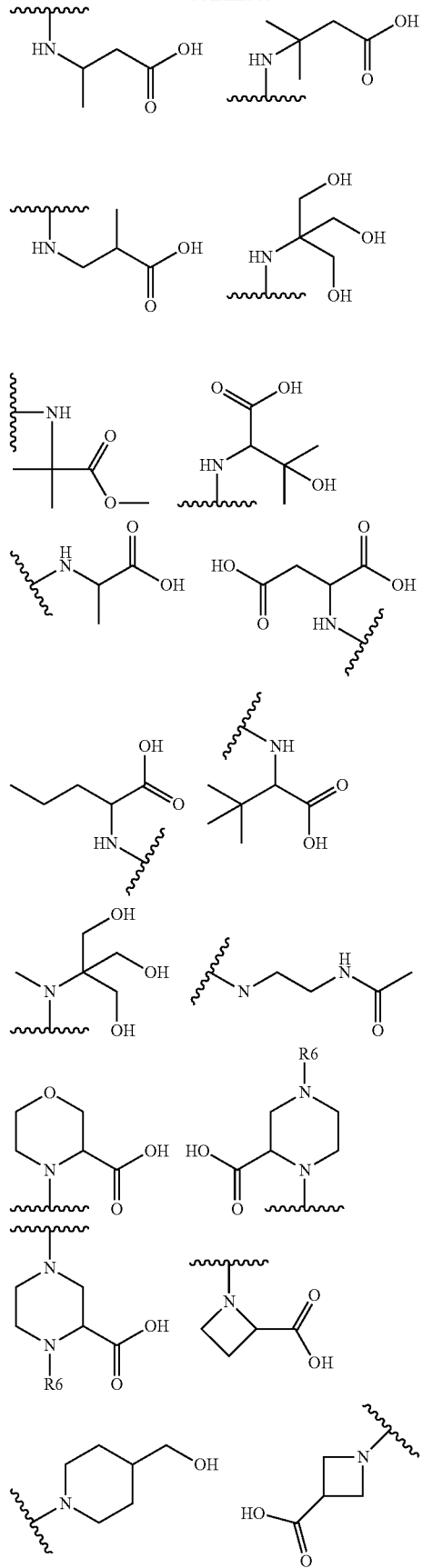

-continued
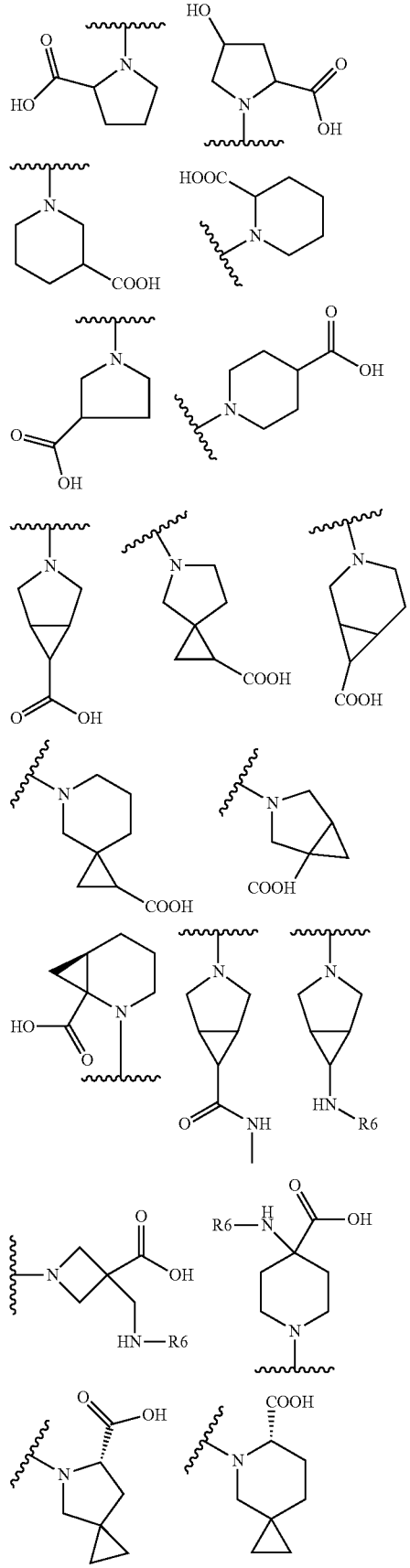
-continued
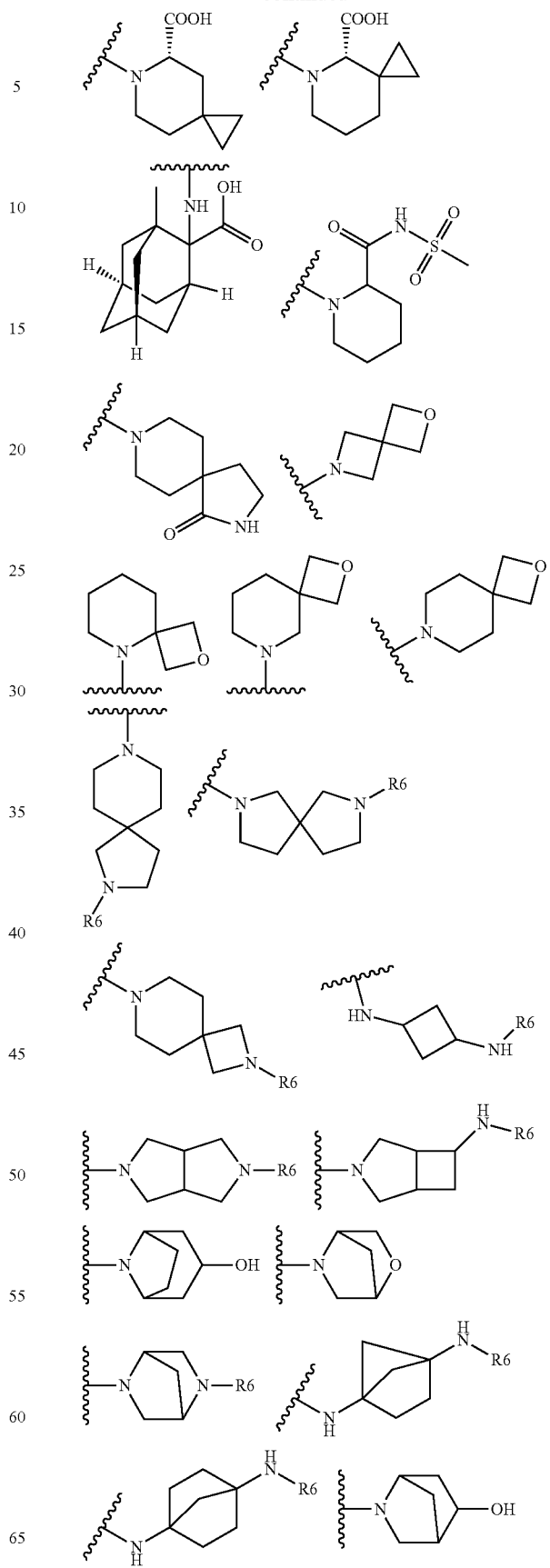

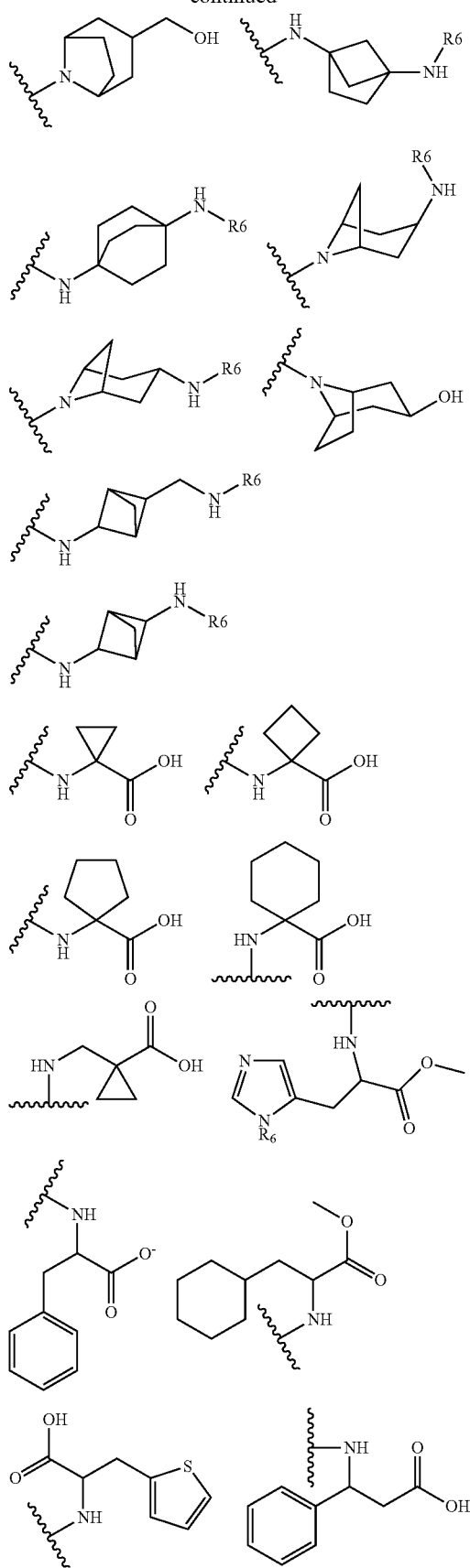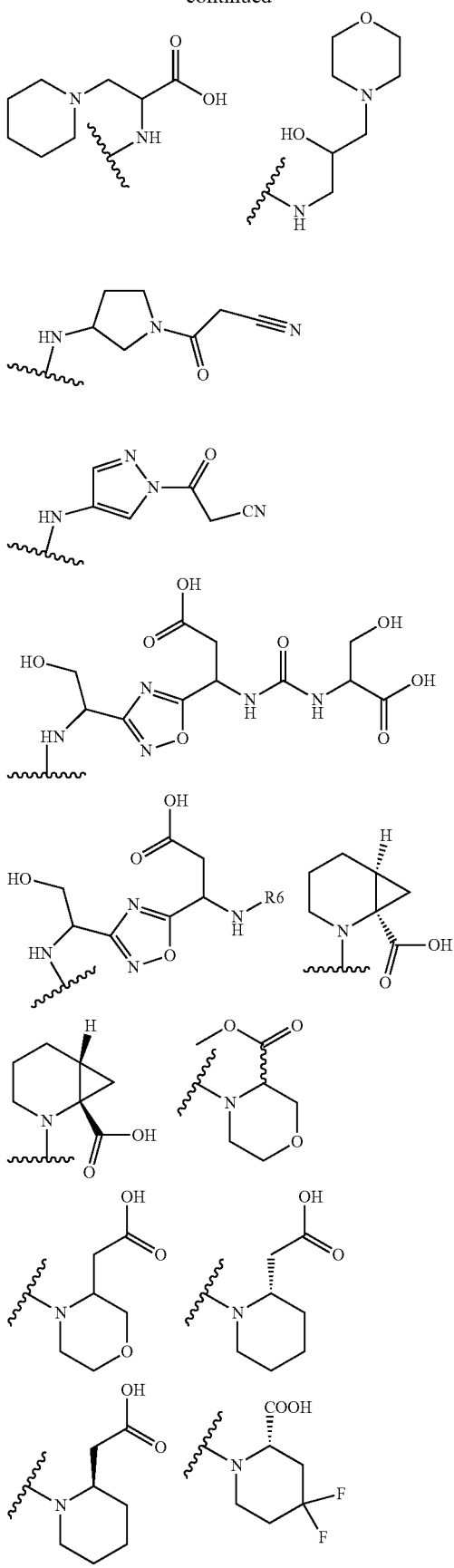

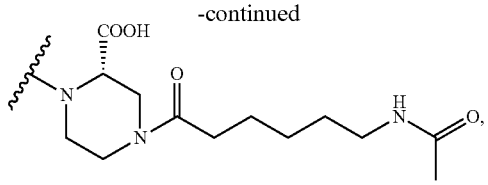

wherein R$_6$ is selected from the group consisting of hydrogen, C$_{1-6}$ alkyl, C(O)C$_{1-6}$ alkyl, and combinations thereof, wherein C$_{1-6}$ alkyl, and C(O)C$_{1-6}$ alkyl are optionally substituted with substituents selected from the group consisting of hydroxyl, COOH, NHR$_6$, NHC(O)NHR$_6$, and combinations thereof.

In an embodiment of the present disclosure, there is provided a compound of Formula I as described herein, wherein R$_1$ is selected from hydrogen, C$_{1-4}$ alkyl, C$_{3-6}$ cycloalkyl, C$_{5-6}$ aryl, and 5-9 membered monocyclic or bicyclic heteroaryl with 1-5 heteroatoms selected from N, S or O, wherein C$_{1-4}$ alkyl, C$_{5-6}$ aryl, and 5-9 membered monocyclic or bicyclic heteroaryl, are optionally substituted with one or more groups selected from hydrogen, halogen, hydroxyl, cyano, C$_{1-4}$ alkyl, C$_{1-4}$ alkoxy, C$_{1-4}$ haloalkyl, C$_{1-4}$ haloalkoxy, or C$_{1-6}$ heterocyclyl; R$_2$ is selected from hydrogen, C$_{5-6}$ aryl, and 5-10 membered monocyclic or bicyclic heteroaryl with 1-5 heteroatoms selected from N, S or O, wherein C$_{5-6}$ aryl, and 5-10 membered monocyclic or bicyclic heteroaryl, are optionally substituted with one or more of the groups selected from the group consisting of hydrogen, fluoro, chloro, bromo, iodo, hydroxyl, cyano, C$_{1-4}$ alkyl, C$_{1-4}$ alkoxy, C$_{1-4}$ haloalkyl, C$_{1-4}$ haloalkoxy, C$_{3-6}$ cycloalkyl, C$_{1-4}$ alkylamino, amino C$_{1-6}$ alkyl, C$_{1-4}$ alkoxyamino, C$_{1-4}$ acylamino, C$_{1-6}$ heterocyclyl, COOR$_a$, wherein C$_{1-4}$ alkyl, C$_{1-4}$ alkoxy, C$_{1-6}$ heterocyclyl are optionally substituted with one or more of the groups selected from C$_{1-4}$ alkyl, C$_{3-6}$ cycloalkyl, C$_{1-6}$ heterocyclyl, and C$_{1-4}$ alkoxy wherein C$_{1-6}$ heterocyclyl is optionally substituted with one or more groups selected from hydroxy, halogen, or cyano; R$_3$ and R$_4$ are independently selected from hydrogen, cyano, C$_{1-4}$ alkyl, C$_{1-4}$ alkoxy, C$_{1-4}$ haloalkyl, C$_{1-4}$ haloalkoxy, C$_{3-6}$ cycloalkyl, C$_{1-4}$ alkylamino, C$_{1-4}$ alkoxyamino, or C$_{1-4}$ acylamino; and R$_5$ is selected from

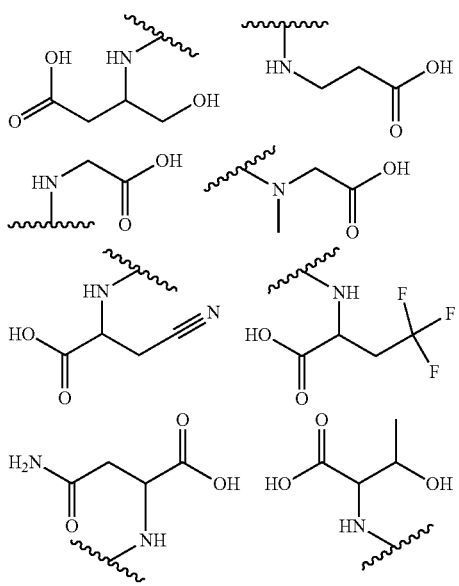

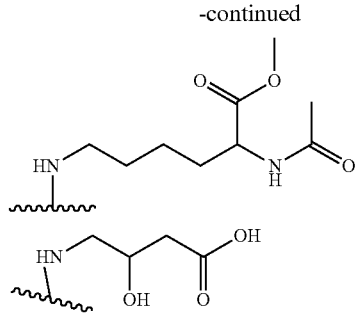

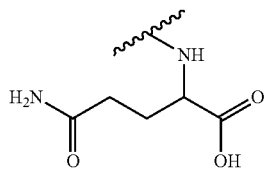

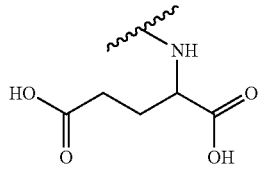

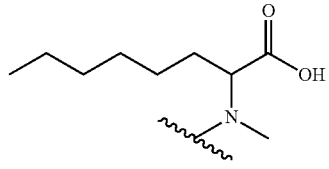

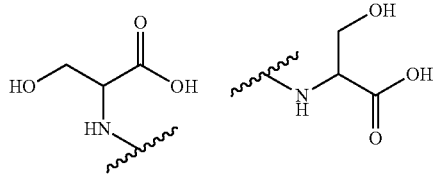

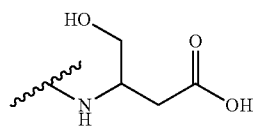

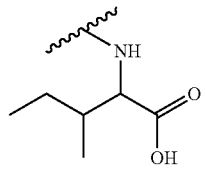

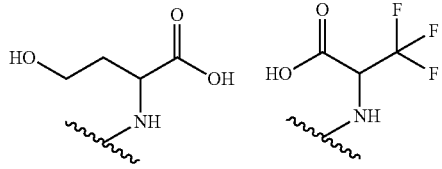

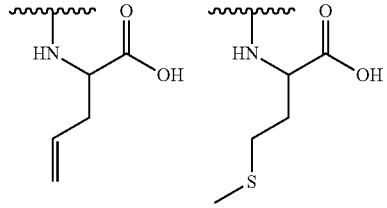

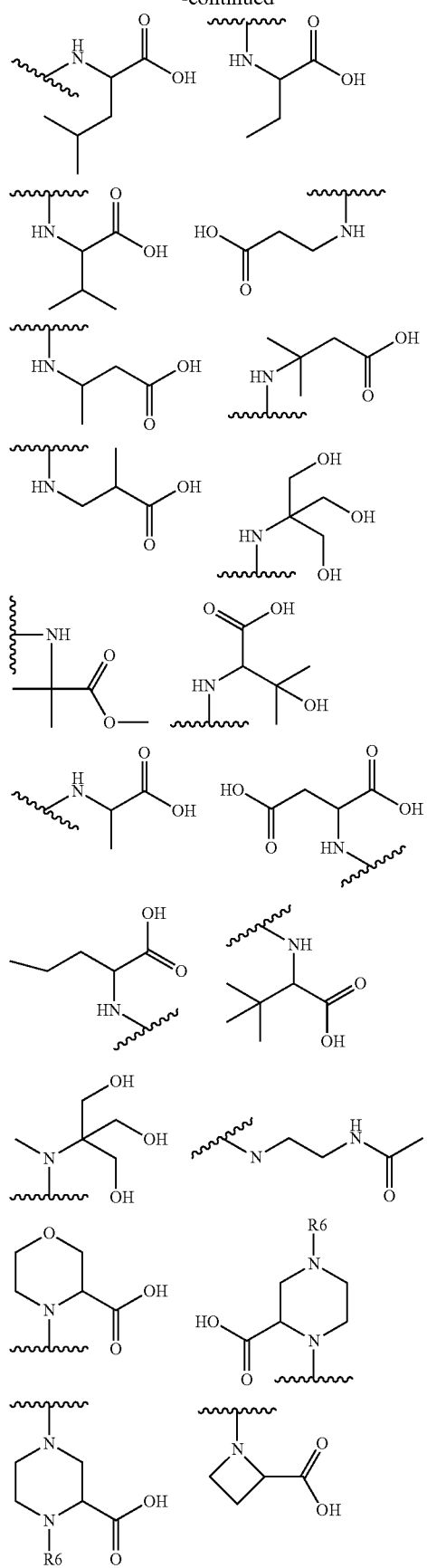
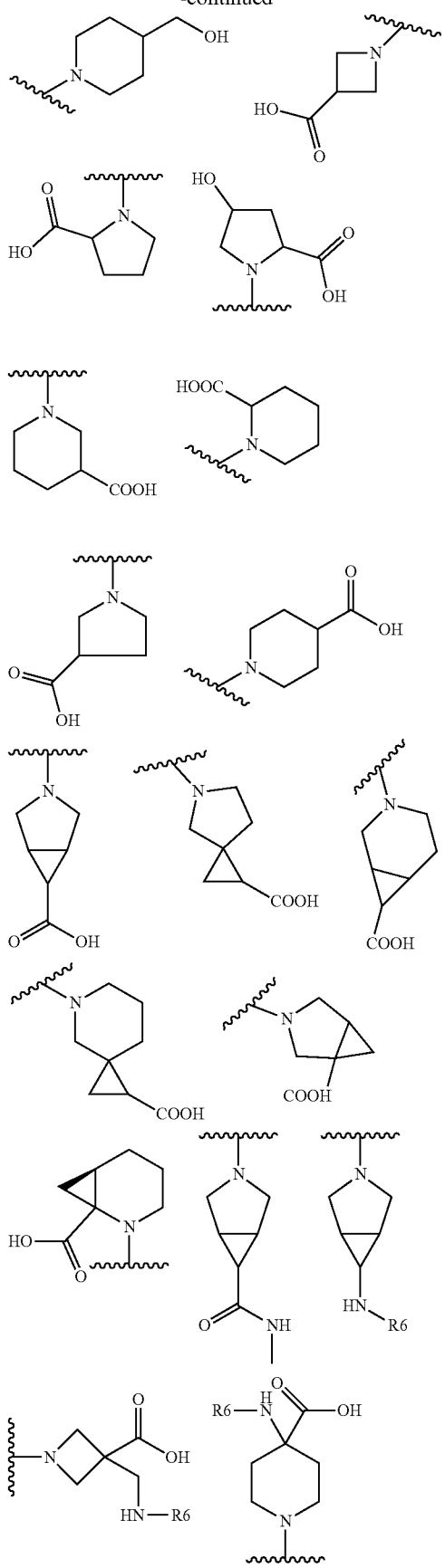

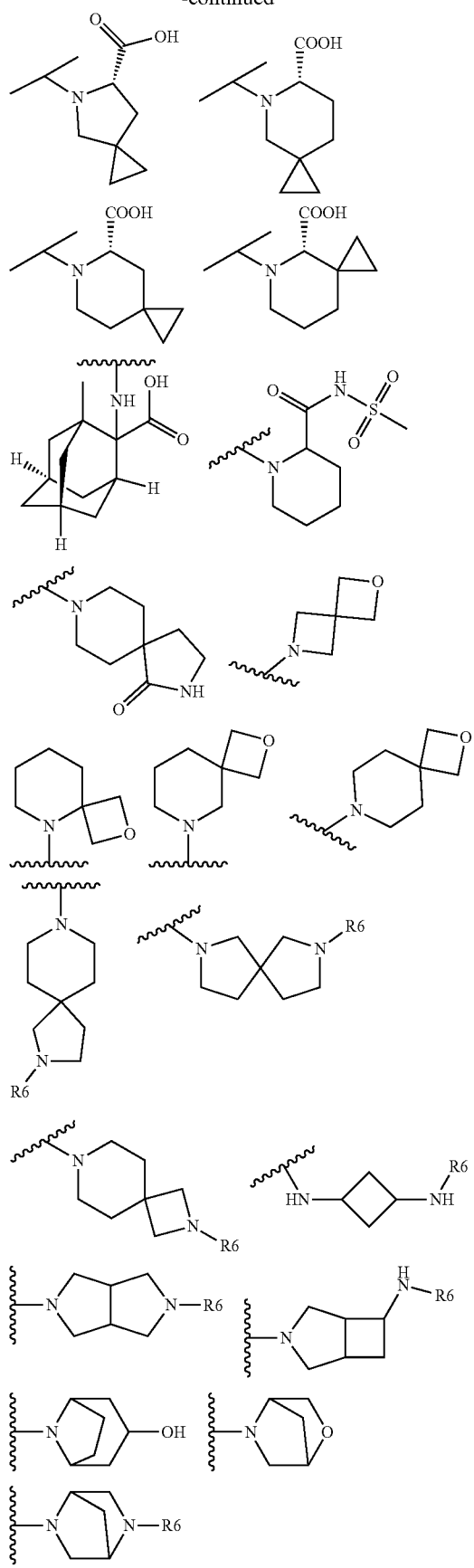
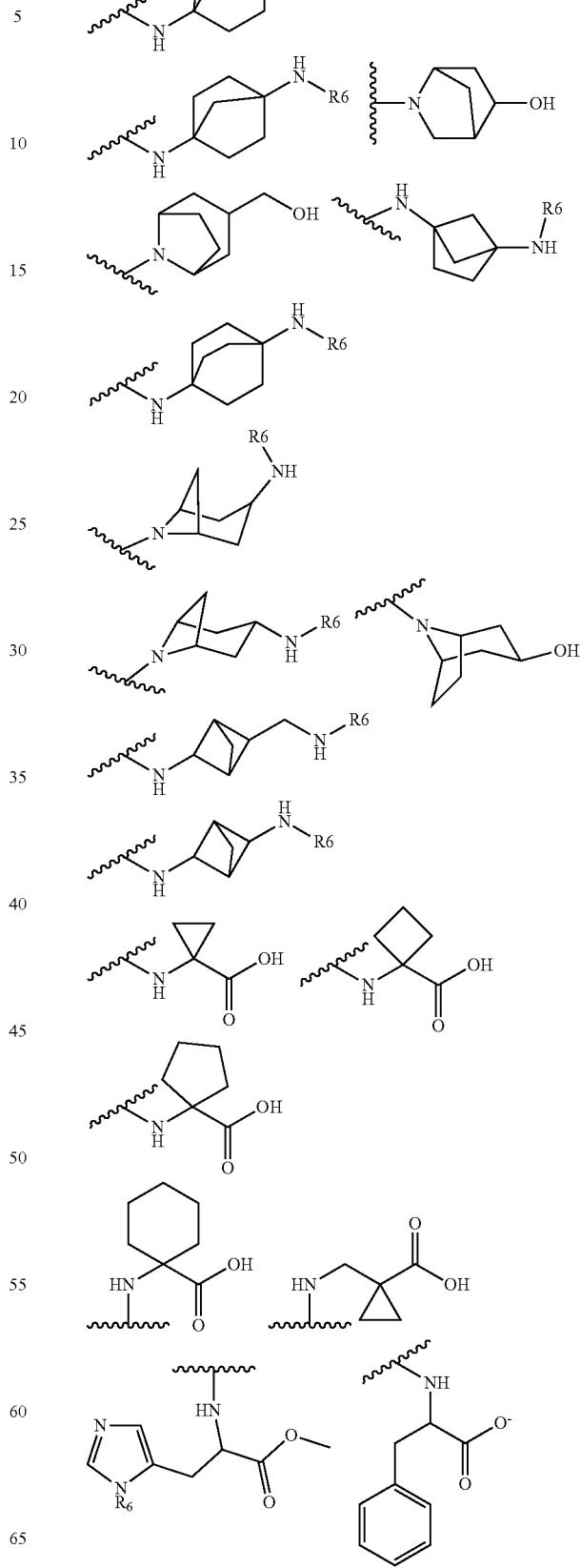

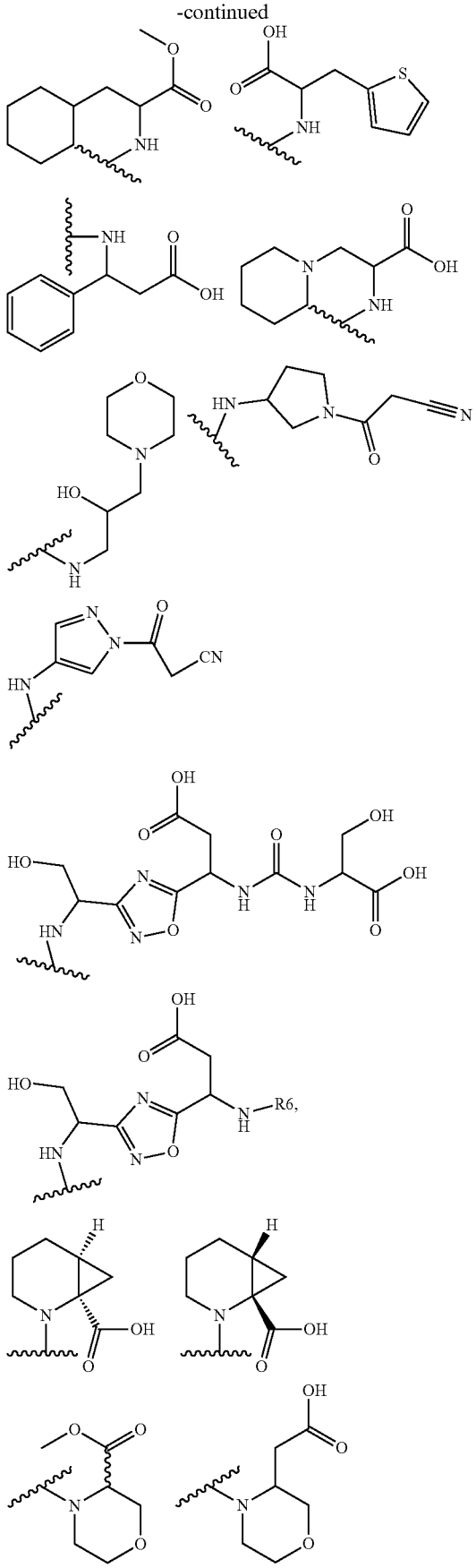

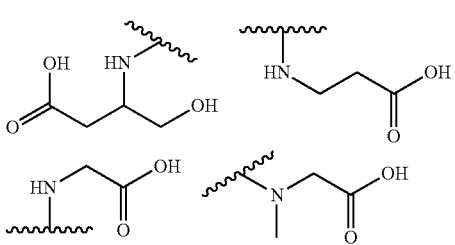

wherein $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided a compound of Formula I as described herein, wherein $R_1$ is selected from hydrogen, $C_{1-6}$ alkyl, $C_{3-6}$ cycloalkyl, $C_{5-6}$ aryl, and 5-9 membered monocyclic or bicyclic heteroaryl with 1-5 heteroatoms selected from N, S or O, wherein $C_{1-6}$ alkyl, $C_{5-6}$ aryl, and 5-9 membered monocyclic or bicyclic heteroaryl, are optionally substituted with one or more of the groups selected from hydrogen, halogen, hydroxyl, cyano, $C_{1-4}$ alkyl, $C_{1-4}$ alkoxy, $C_{1-4}$ haloalkyl, $C_{1-4}$ haloalkoxy, $C_{1-8}$ heterocyclyl, or $COOR_a$, wherein $C_{1-4}$ alkyl, $C_{1-4}$ alkoxy, $C_{1-8}$ heterocyclyl are optionally substituted with one or more of the groups selected from $C_{1-4}$ alkyl, $C_{3-6}$ cycloalkyl, $C_{1-6}$ heterocyclyl, $C_{1-4}$ alkoxy, and $COOR_a$, wherein Ra is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_2$ is selected from $C_{5-6}$ aryl, wherein $C_{5-6}$ aryl is optionally substituted with one or more of the groups selected from hydrogen, fluoro, chloro, bromo, iodo, hydroxyl, and cyano; $R_3$ and $R_4$ are independently selected from the group consisting of hydrogen, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, $C_{1-4}$ acylamino, and combinations thereof; and $R_5$ is selected from

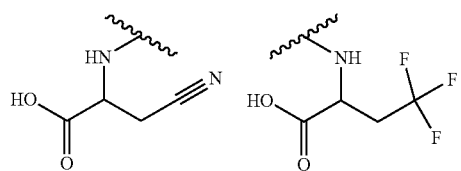
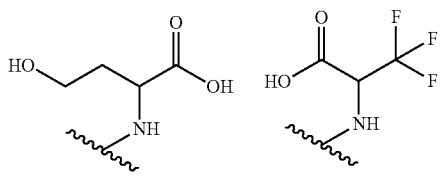
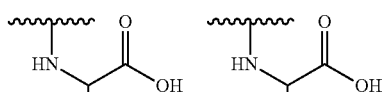
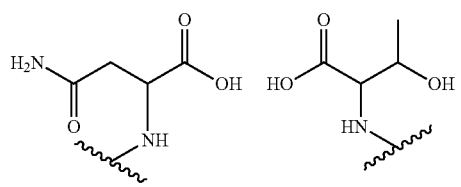
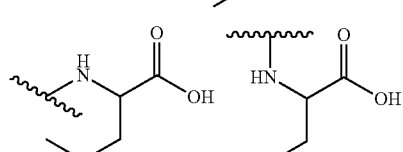
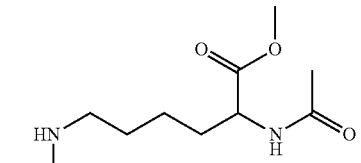
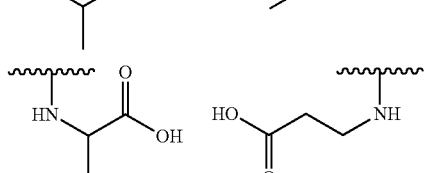
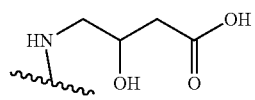
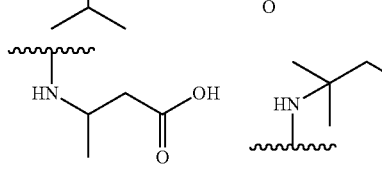
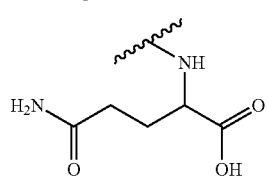
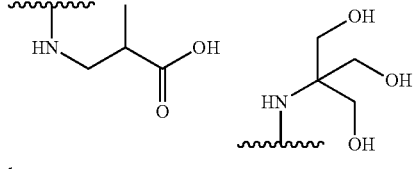
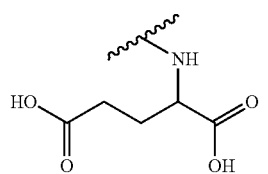
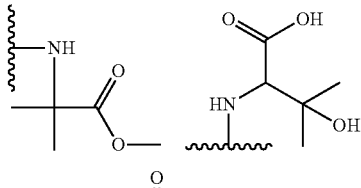
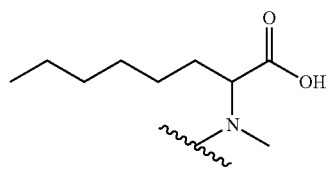
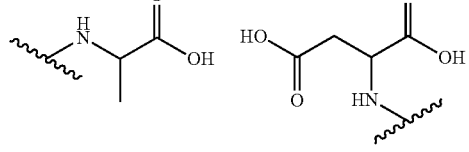
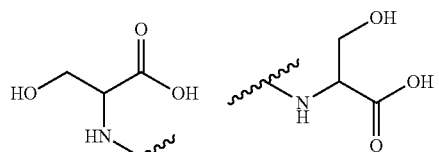
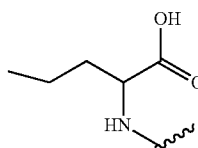
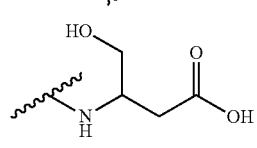
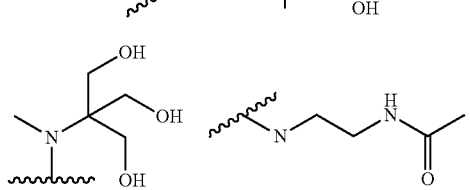
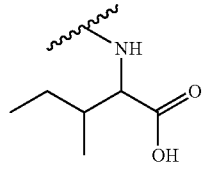

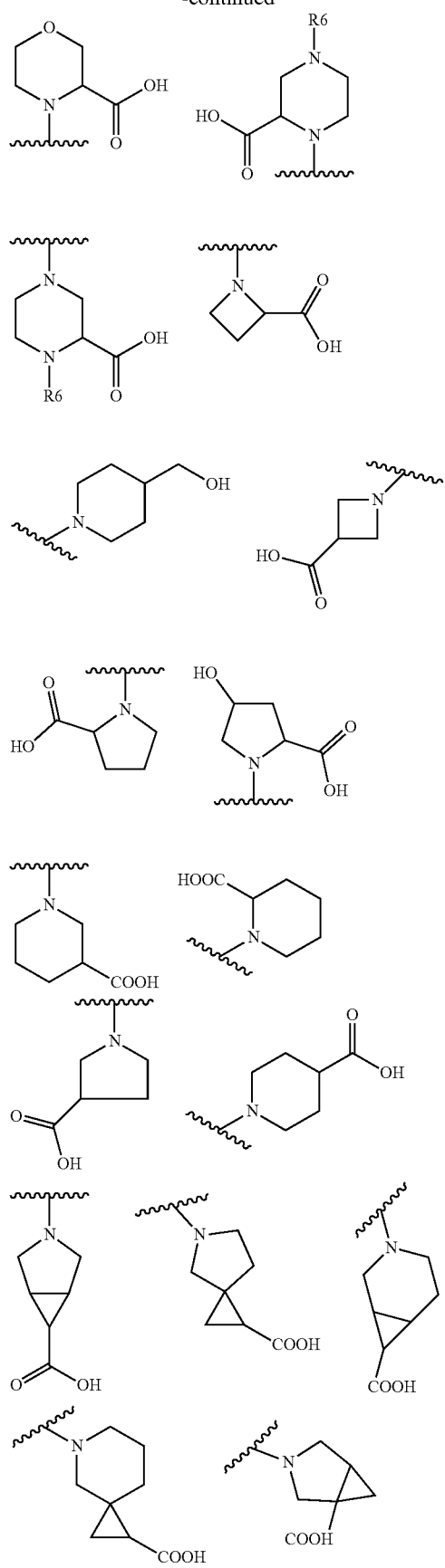
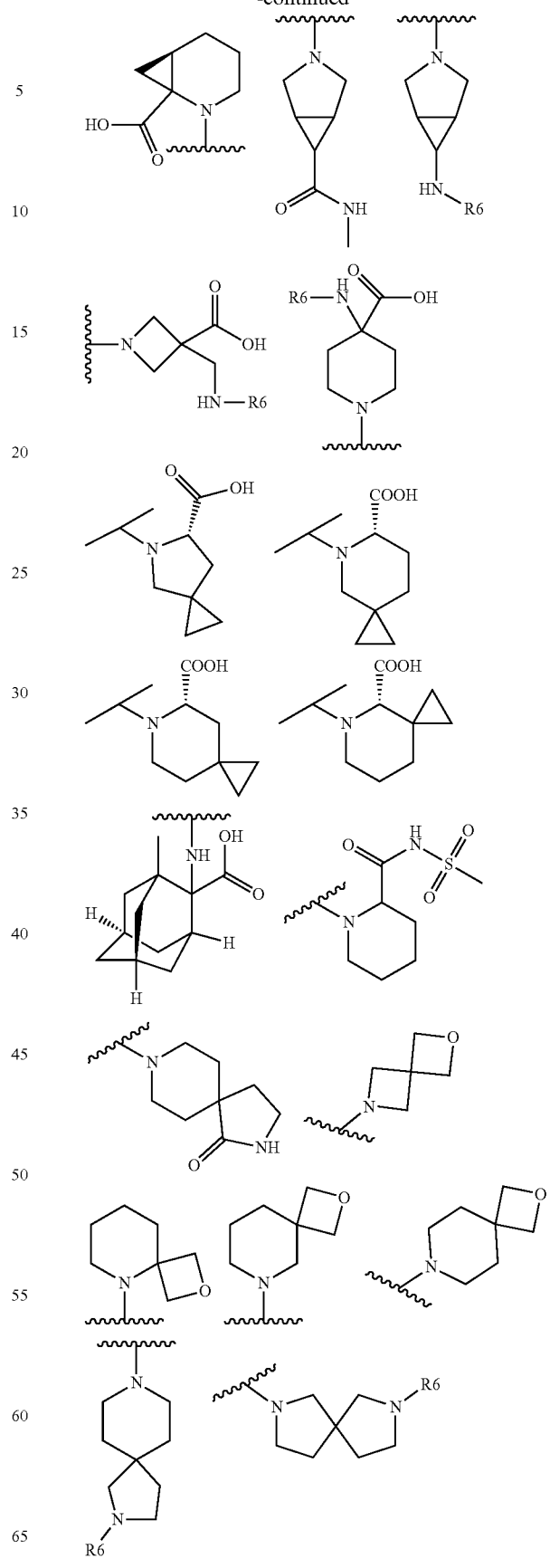

-continued
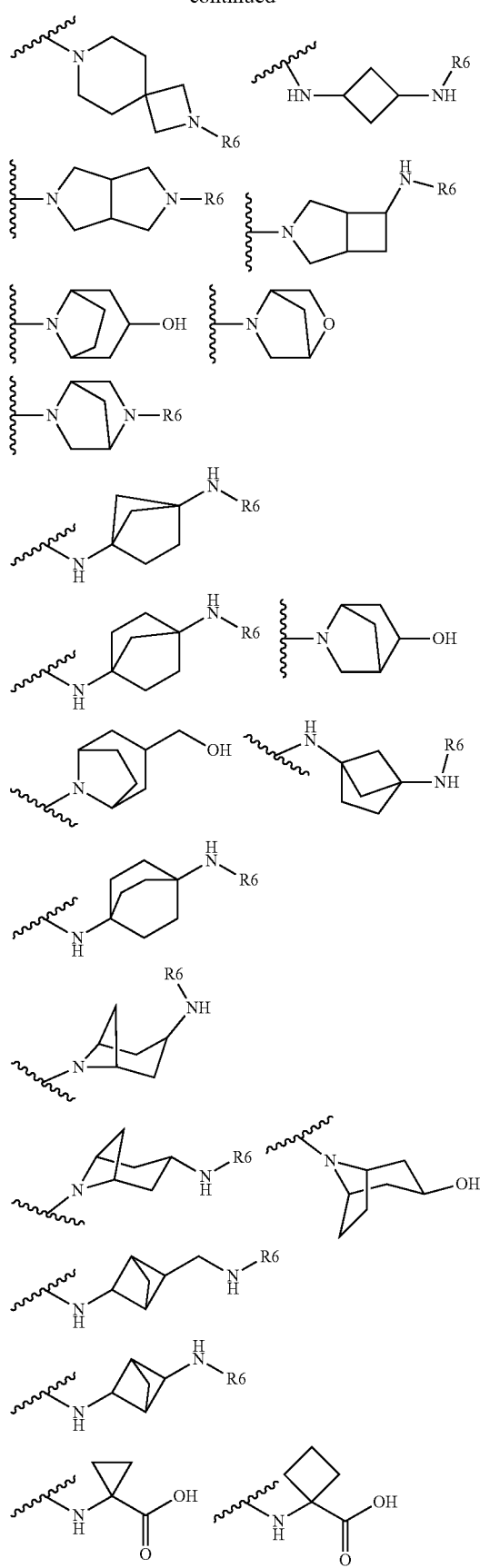
-continued
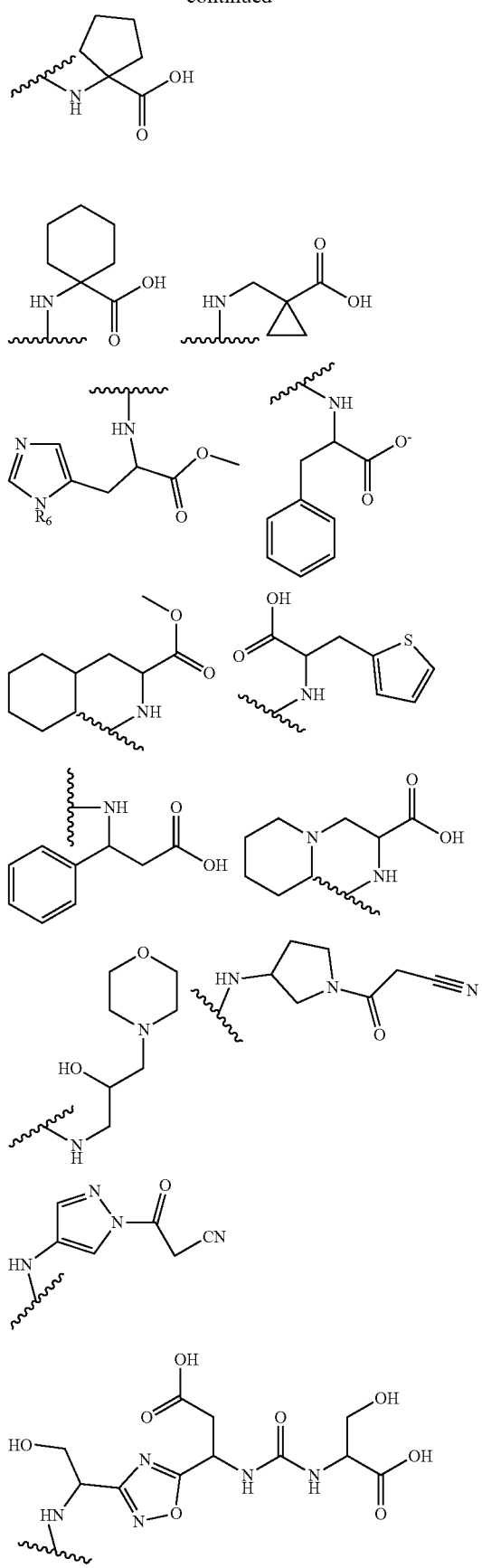

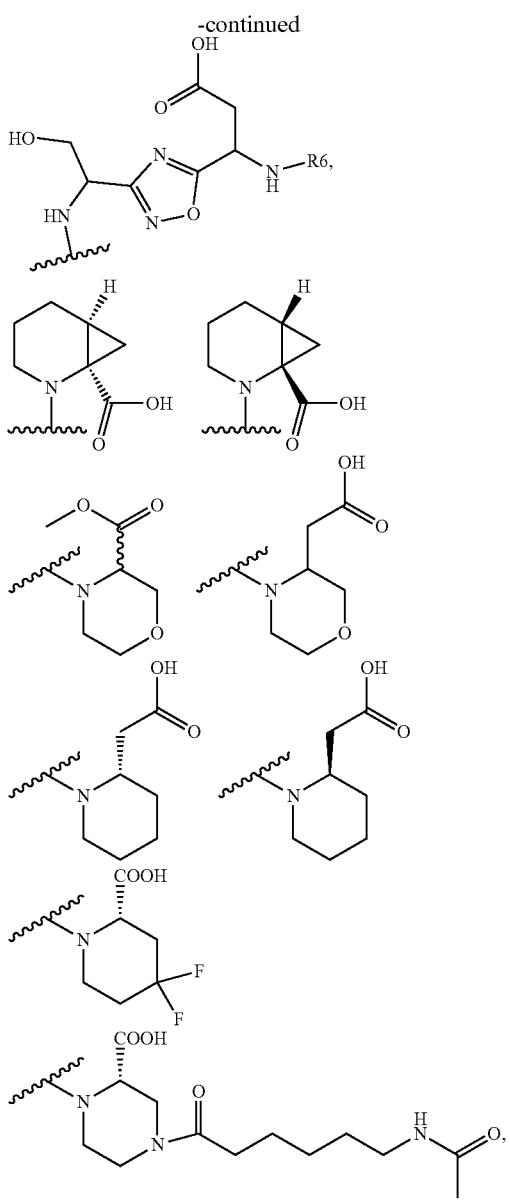

wherein R₆ is selected from the group consisting of hydrogen, $C_{1-6}$ alkyl, $C(O)C_{1-6}$ alkyl, and combinations thereof, wherein $C_{1-6}$alkyl, and $C(O)C_{1-6}$ alkyl are optionally substituted with substituents selected from the group consisting of hydroxyl, COOH, NHR₆, NHC(O)NHR₆, and combinations thereof.

In an embodiment of the present disclosure, there is provided a compound of Formula I as described herein, wherein R₁ is selected from hydrogen, $C_{1-4}$ alkyl, $C_{3-6}$ cycloalkyl, $C_{5-6}$ aryl, and 5-9 membered monocyclic or bicyclic heteroaryl with 1-5 heteroatoms selected from N, S or O, wherein $C_{5-6}$ aryl, and 5-9 membered monocyclic or bicyclic heteroaryl, is optionally substituted with one or more of the groups selected from the group consisting of hydrogen, halogen, hydroxyl, cyano, $C_{1-4}$ alkyl, $C_{1-4}$ alkoxy, $C_{1-4}$ haloalkyl, $C_{1-4}$ haloalkoxy, $C_{1-6}$ heterocyclyl, $COOR_a$, and combinations thereof; wherein $C_{1-4}$ alkyl, $C_{1-4}$ alkoxy, $C_{1-6}$ heterocyclyl is optionally substituted with one or more of the groups selected from $C_{1-4}$ alkyl, $C_{3-6}$ cycloalkyl, $C_{1-6}$ heterocyclyl, $C_{1-4}$ alkoxy, and $COOR_a$; wherein $R_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; R₂ is selected from hydrogen, $C_{5-6}$ aryl, and 5-9 membered monocyclic or bicyclic heteroaryl with 1-5 heteroatoms selected from N, S or O, wherein $C_{5-6}$ aryl, and 5-9 membered monocyclic or bicyclic heteroaryl, is optionally substituted with one or more of the groups selected from the group consisting of hydrogen, fluoro, chloro, bromo, iodo, hydroxyl, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, amino $C_{1-6}$ alkyl, $C_{1-4}$ alkoxyamino, $C_{1-4}$ acylamino, $C_{1-6}$ heterocyclyl, $COOR_a$, and combinations thereof, wherein $C_{1-4}$ alkyl, $C_{1-4}$ alkoxy, $C_{1-6}$ heterocyclyl is optionally substituted with one or more of the groups selected from $C_{1-4}$ alkyl, $C_{3-6}$ cycloalkyl, $C_{1-6}$ heterocyclyl, $C_{1-4}$ alkoxy, and $COOR_a$; wherein $R_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; R₃ is selected from hydrogen, cyano, $C_{1-4}$ alkyl, and $C_{1-4}$ haloalkyl; R₄ is selected from the group consisting of hydrogen, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, $C_{1-4}$ acylamino, and combinations thereof, and R₅ is selected from

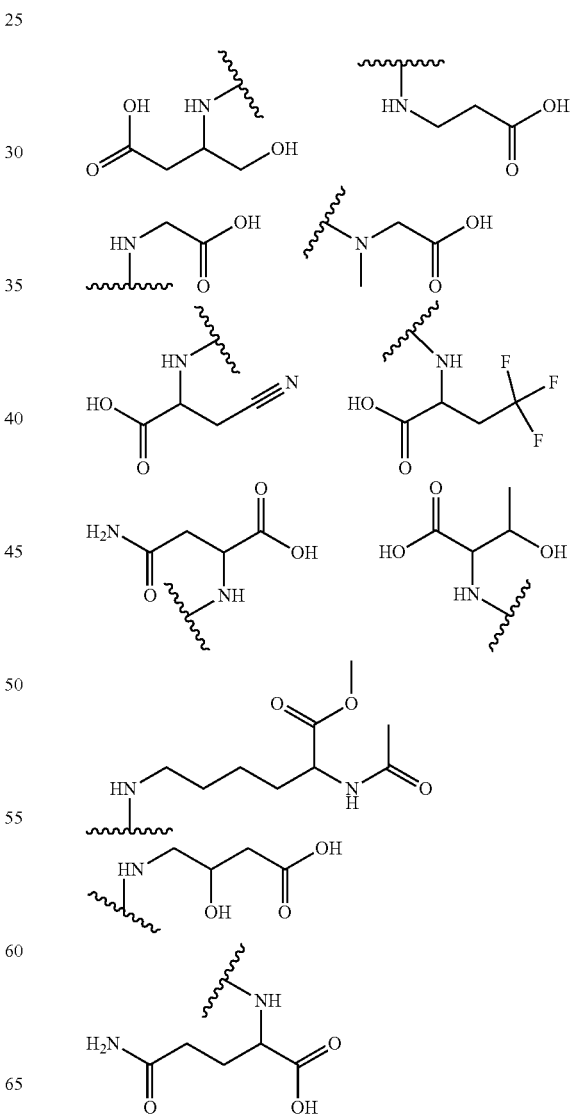

-continued
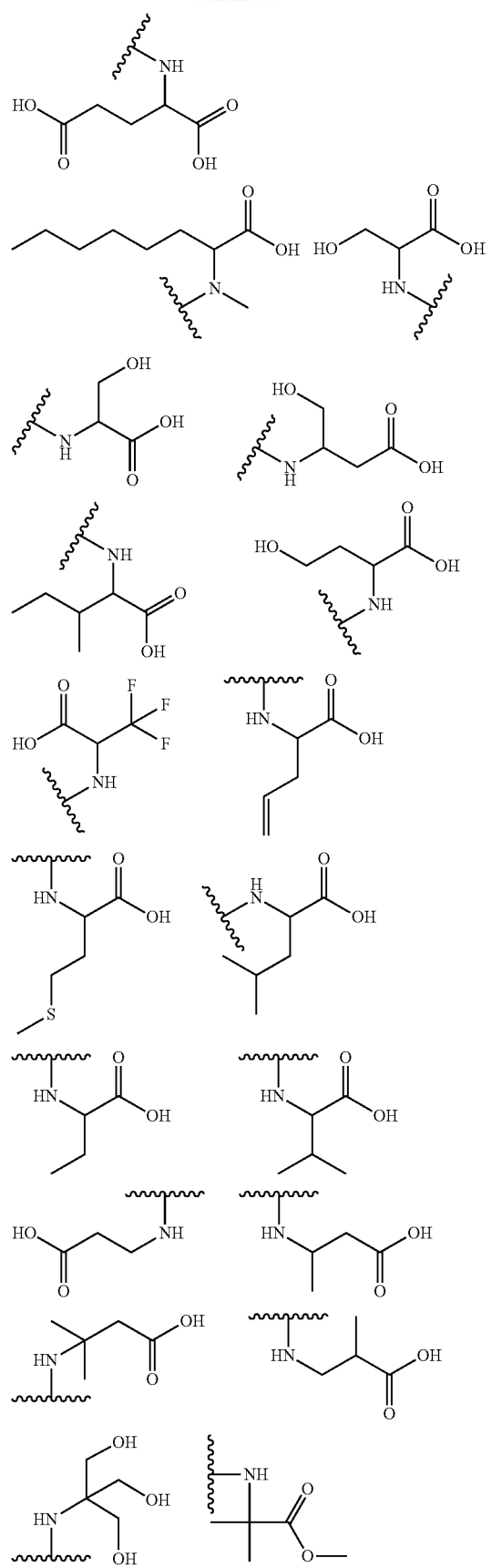
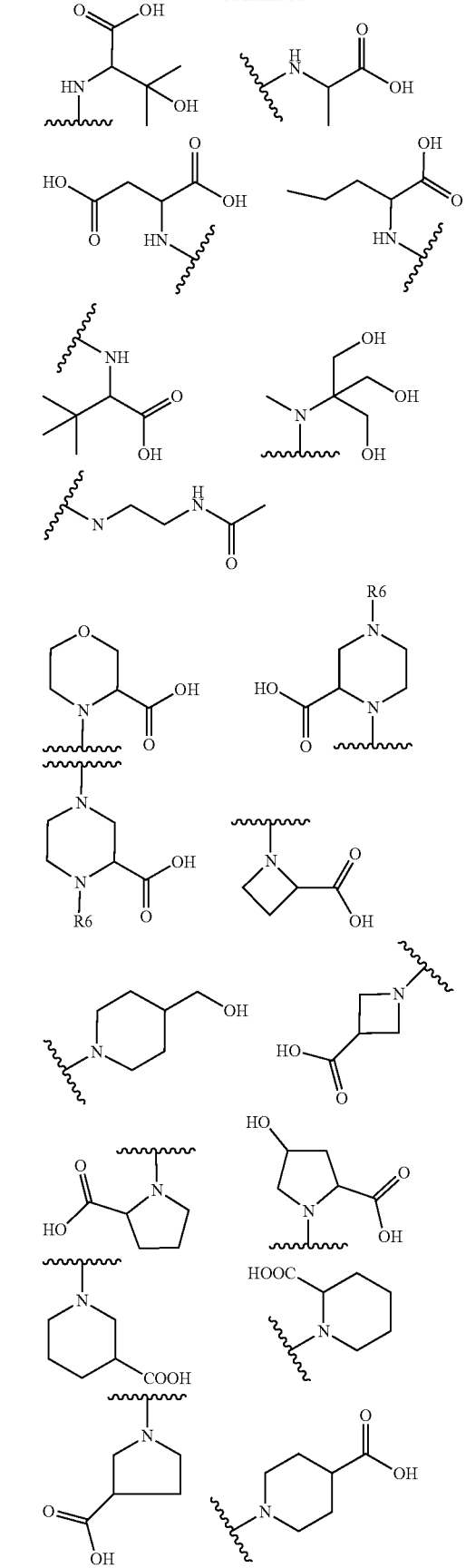

95
-continued
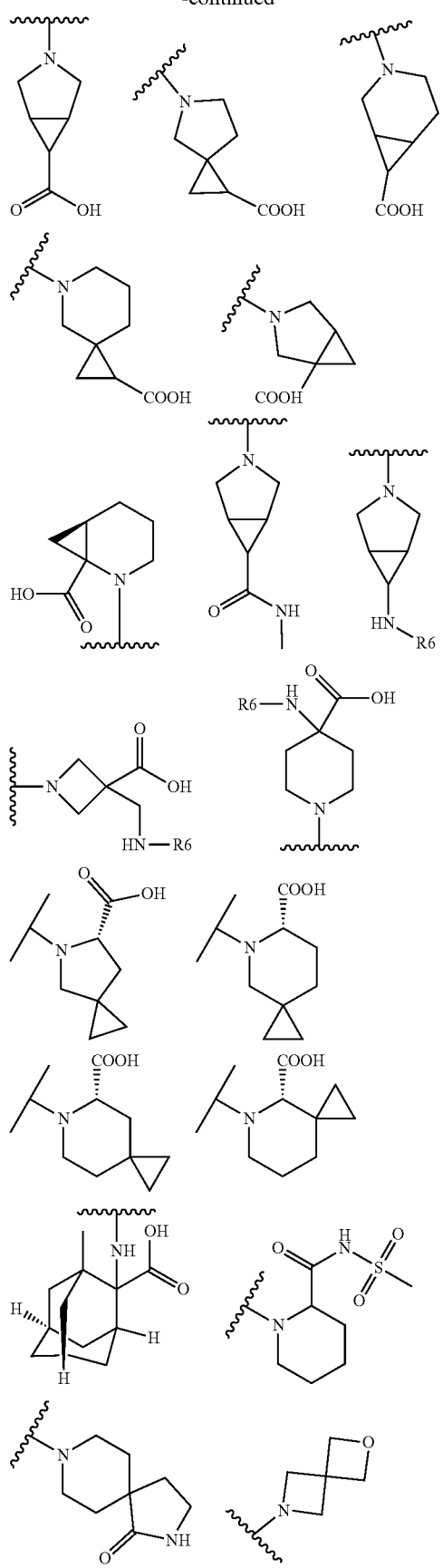
96
-continued
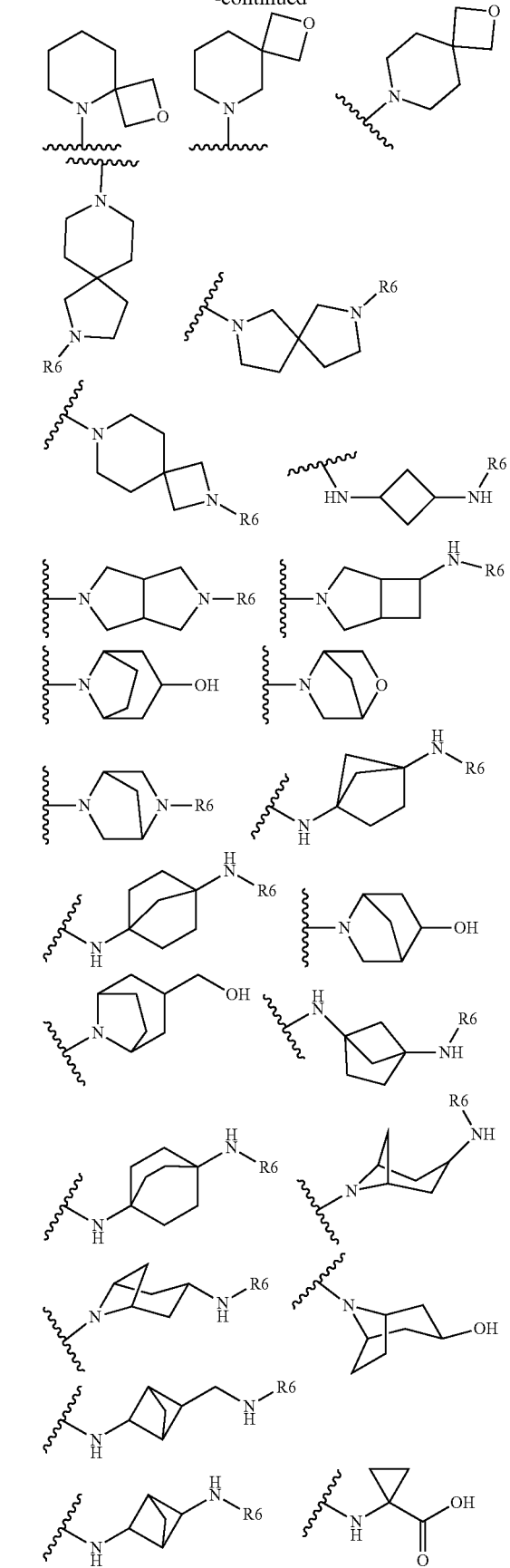

-continued

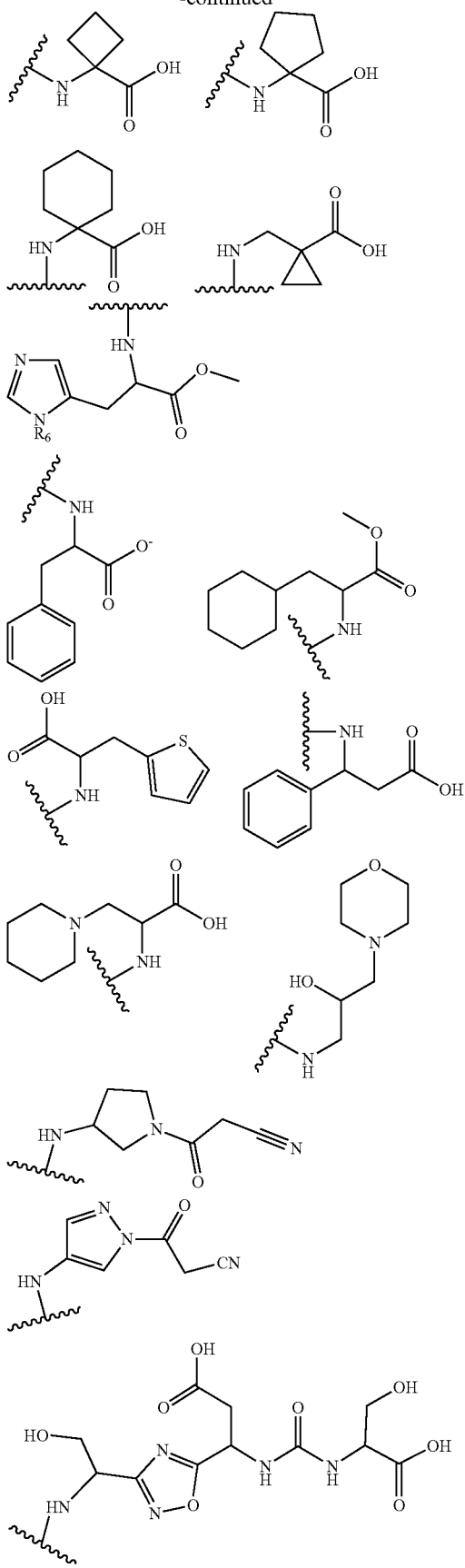
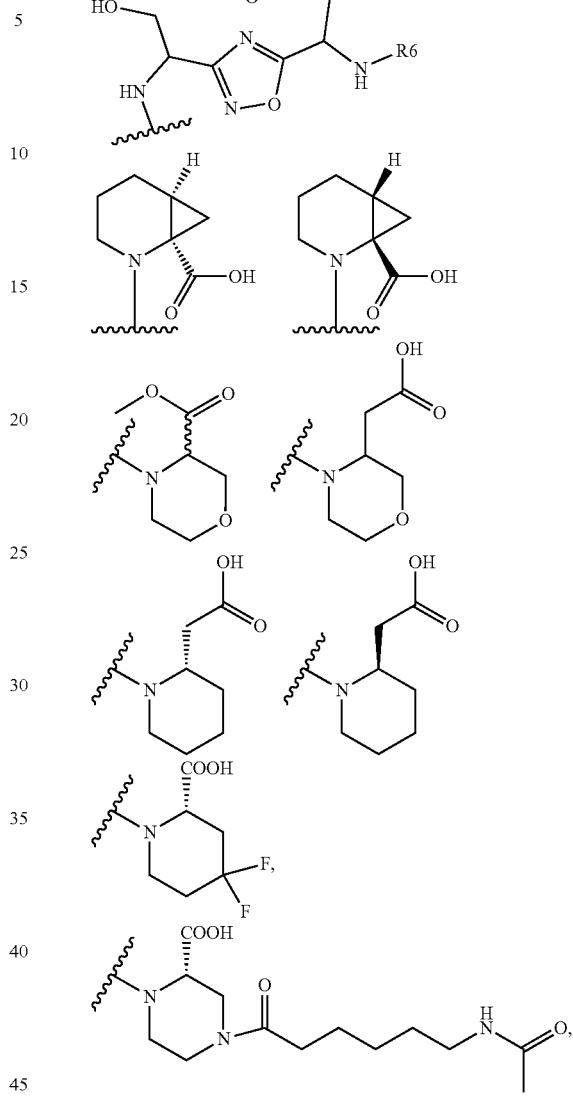

wherein R₆ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, NHR₆, NHC(O)NHR₆, and combinations thereof.

In an embodiment of the present disclosure, there is provided a compound of Formula I as described herein, wherein $R_1$ is selected from hydrogen, $C_{1-4}$ alkyl, $C_{3-6}$ cycloalkyl, $C_{5-6}$ aryl, and 5-9 membered monocyclic or bicyclic heteroaryl with 1-5 heteroatoms selected from N, S or O, wherein $C_{5-6}$ aryl, and 5-9 membered monocyclic or bicyclic heteroaryl, is optionally substituted with one or more of the groups selected from the group consisting of hydrogen, halogen, hydroxyl, cyano, $C_{1-4}$ alkyl, $C_{1-4}$ alkoxy, $C_{1-4}$ haloalkyl, $C_{1-4}$ haloalkoxy, $C_{1-6}$ heterocyclyl, $COOR_a$, and combinations thereof; wherein $C_{1-4}$ alkyl, $C_{1-4}$ alkoxy, $C_{1-6}$ heterocyclyl is optionally substituted with one or more of the groups selected from $C_{1-4}$ alkyl, $C_{3-6}$ cycloalkyl, $C_{1-6}$ heterocyclyl, $C_{1-4}$ alkoxy, and $COOR_a$; wherein $R_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_2$ is selected from hydrogen, $C_{5-6}$ aryl, and 5-9 membered monocyclic or bicyclic heteroaryl with 1-5 heteroatoms selected from N, S or O, wherein $C_{5-6}$ aryl, and 5-9 membered monocyclic or bicyclic heteroaryl, is optionally substituted with one or more of the groups selected from the group consisting of hydrogen, fluoro, chloro, bromo, iodo, hydroxyl, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, amino $C_{1-6}$ alkyl, $C_{1-4}$ alkoxyamino, $C_{1-4}$ acylamino, $C_{1-6}$ heterocyclyl, $COOR_a$, and combinations thereof, wherein $C_{1-4}$ alkoxy, $C_{1-6}$ heterocyclyl is optionally substituted with one or more of the groups selected from $C_{1-4}$ alkyl, $C_{3-6}$ cycloalkyl, $C_{1-6}$ heterocyclyl, $C_{1-4}$ alkoxy, and $COOR_a$; wherein $R_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; $R_3$ is selected from the group consisting of hydrogen, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, $C_{1-4}$ acylamino, and combinations thereof, $R_4$ is selected from hydrogen, $C_{1-4}$ alkyl, $C_{1-4}$ alkoxy, and $C_{1-4}$ alkylamino; and $R_5$ is selected from

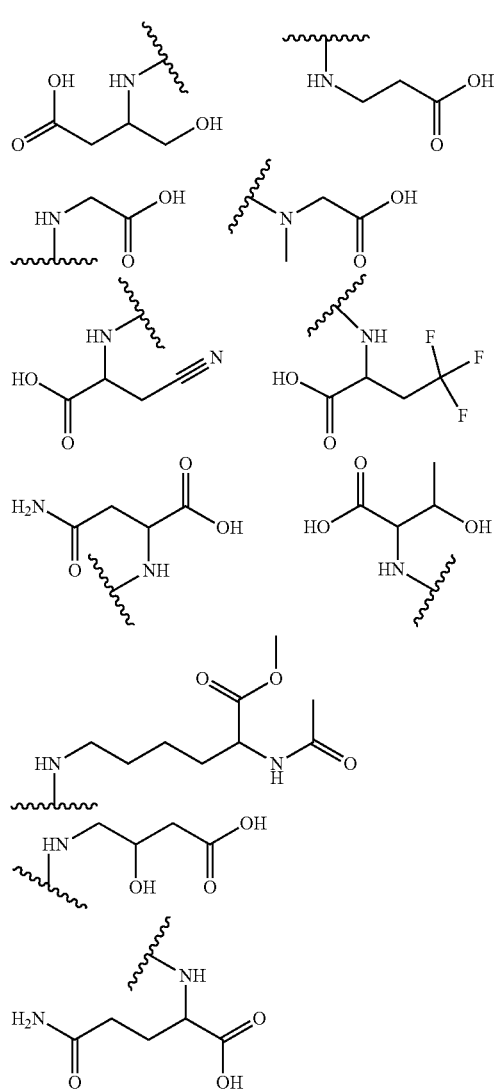
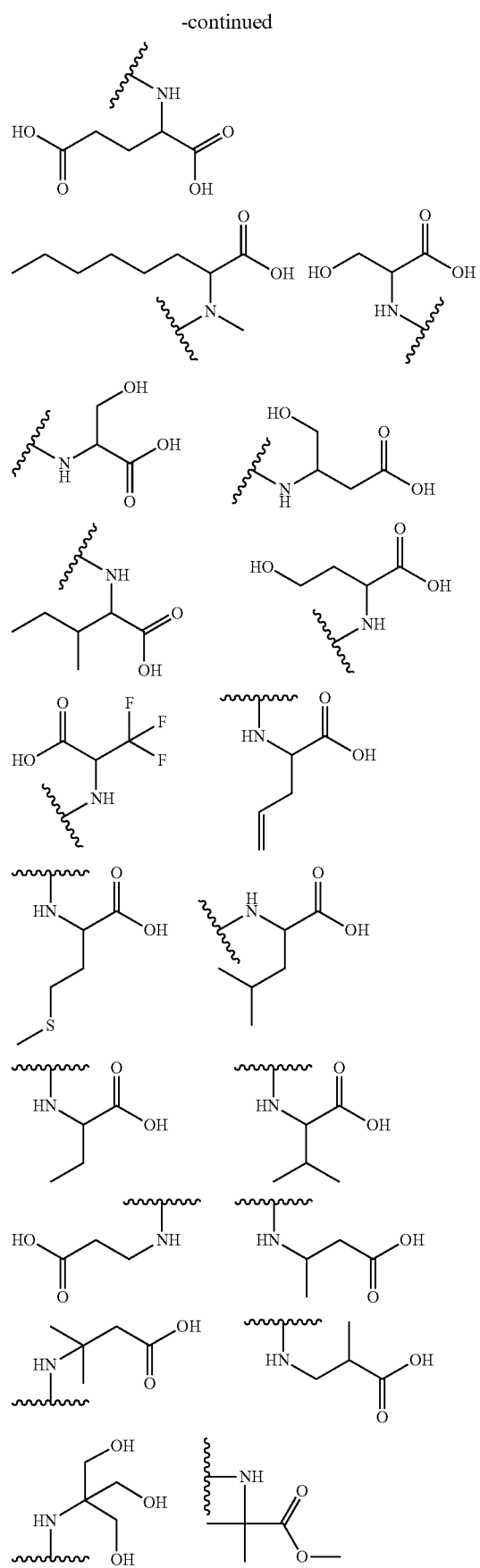

101
-continued
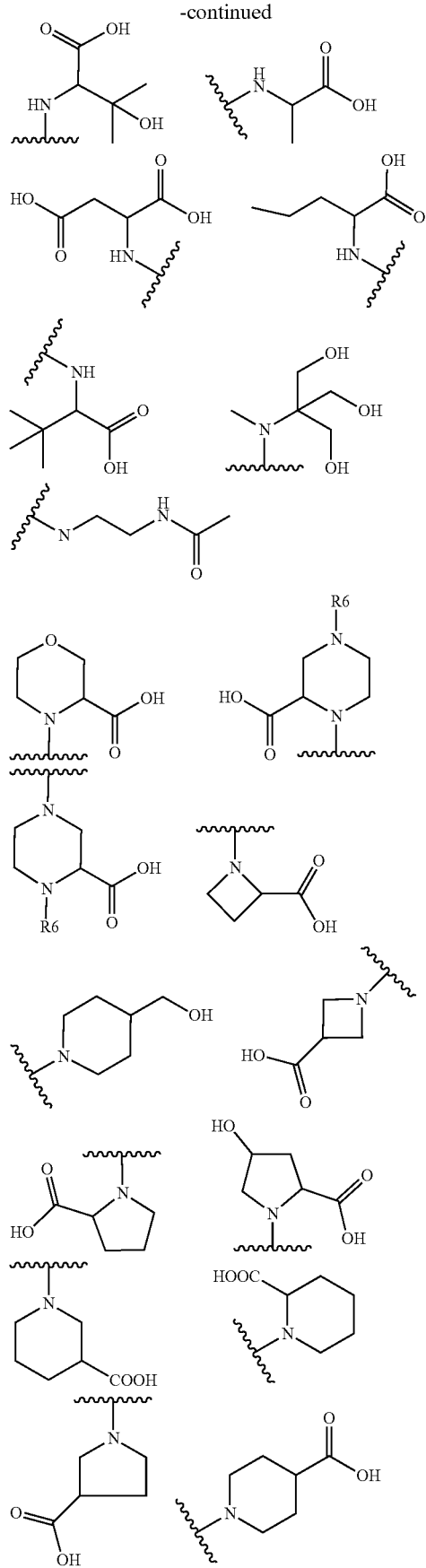
102
-continued
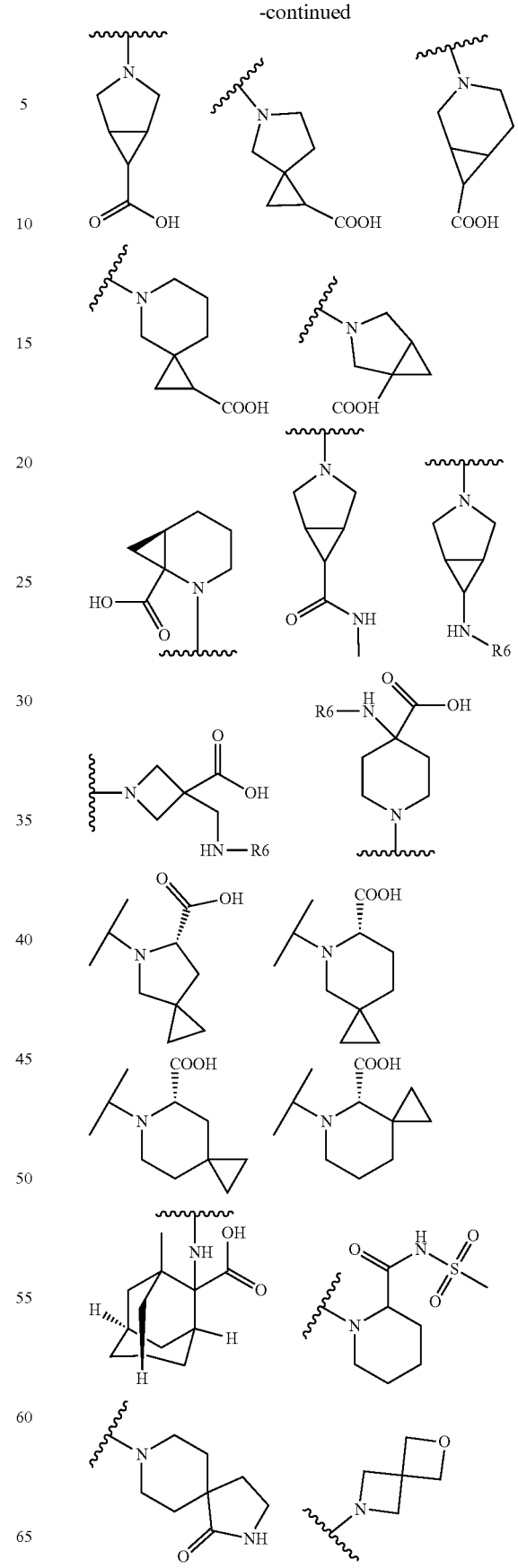

-continued
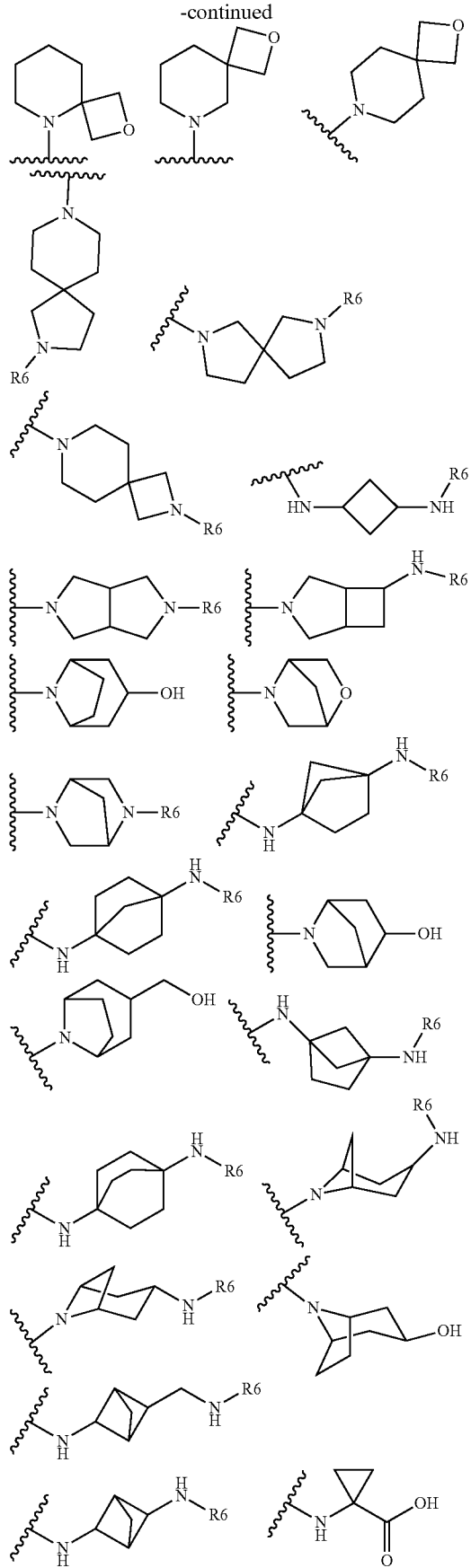
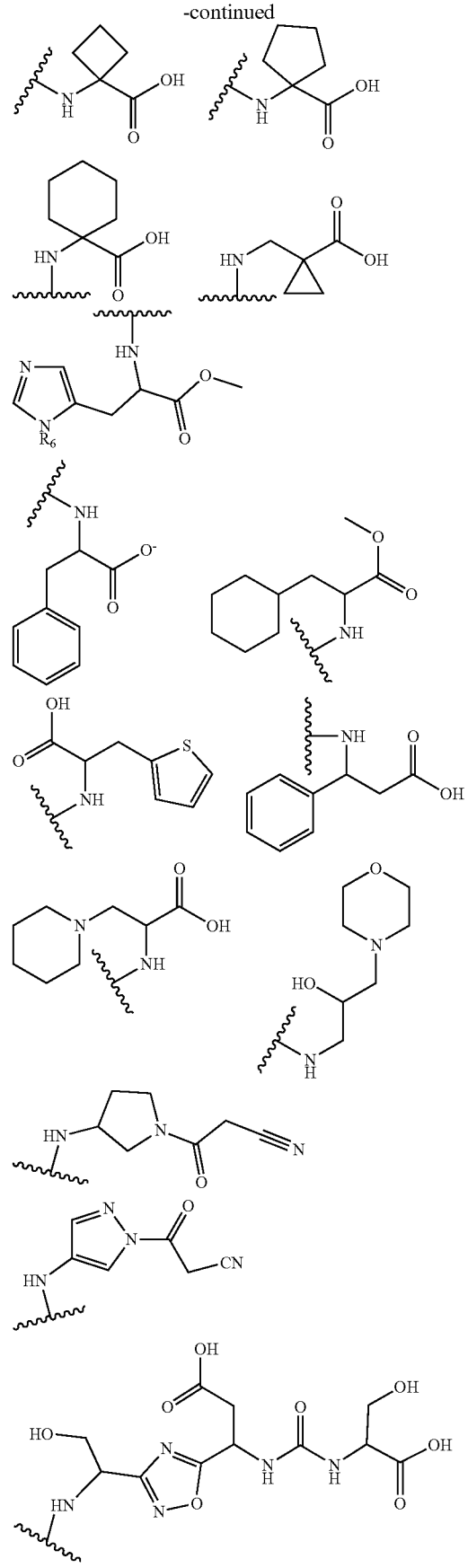

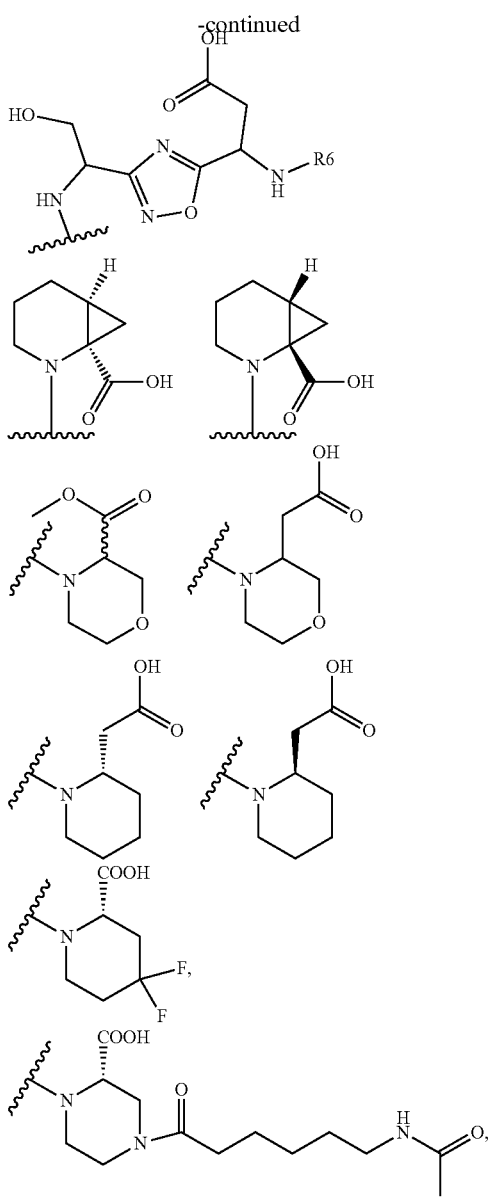

wherein R₆ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, NHR₆, NHC(O)NHR₆, and combinations thereof.

In an embodiment of the present disclosure, there is provided a compound of Formula I as described herein, wherein R₁ is selected from hydrogen, $C_{1-4}$ alkyl, $C_{3-6}$ cycloalkyl, $C_{5-6}$ aryl, and 5-9 membered monocyclic or bicyclic heteroaryl with 1-5 heteroatoms selected from N, S or O, wherein $C_{5-6}$ aryl, and 5-9 membered monocyclic or bicyclic heteroaryl, is optionally substituted with one or more of the groups selected from the group consisting of hydrogen, halogen, hydroxyl, cyano, $C_{1-4}$ alkyl, $C_{1-4}$ alkoxy, $C_{1-4}$ haloalkyl, $C_{1-4}$ haloalkoxy, $C_{1-6}$ heterocyclyl, COOR$_a$, and combinations thereof; wherein $C_{1-4}$ alkyl, $C_{1-4}$ alkoxy, $C_{1-6}$ heterocyclyl is optionally substituted with one or more of the groups selected from $C_{1-4}$ alkyl, $C_{3-6}$ cycloalkyl, $C_{1-6}$ heterocyclyl, $C_{1-4}$ alkoxy, and COOR$_a$; wherein R$_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; R₂ is selected from hydrogen, $C_{5-6}$ aryl, and 5-9 membered monocyclic or bicyclic heteroaryl with 1-5 heteroatoms selected from N, S or O, wherein $C_{5-6}$ aryl, and 5-9 membered monocyclic or bicyclic heteroaryl, is optionally substituted with one or more of the groups selected from the group consisting of hydrogen, fluoro, chloro, bromo, iodo, hydroxyl, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, amino $C_{1-6}$ alkyl, $C_{1-4}$ alkoxyamino, $C_{1-4}$ acylamino, $C_{1-6}$ heterocyclyl, COOR$_a$, and combinations thereof; wherein $C_{1-4}$ alkyl, C14 alkoxy, $C_{1-6}$ heterocyclyl is optionally substituted with one or more of the groups selected from $C_{1-4}$ alkyl, $C_{3-6}$ cycloalkyl, $C_{1-6}$ heterocyclyl, $C_{1-4}$ alkoxy, and COOR$_a$; wherein R$_a$ is independently selected from hydrogen, $C_{1-4}$ alkyl, $C_{3-6}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl; R₃ is selected from the group consisting of hydrogen, cyano, $C_{1-4}$ alkyl, $C_{1-4}$ alkoxy, $C_{1-4}$ haloalkyl, $C_{1-4}$ haloalkoxy, $C_{3-6}$ cycloalkyl, $C_{1-4}$ alkylamino, $C_{1-4}$ alkoxyamino, $C_{1-4}$ acylamino, and combinations thereof; R₄ is selected from hydrogen, $C_{1-4}$ alkyl, $C_{1-4}$ alkoxy, and $C_{1-4}$ alkylamino; and R₅ is selected from

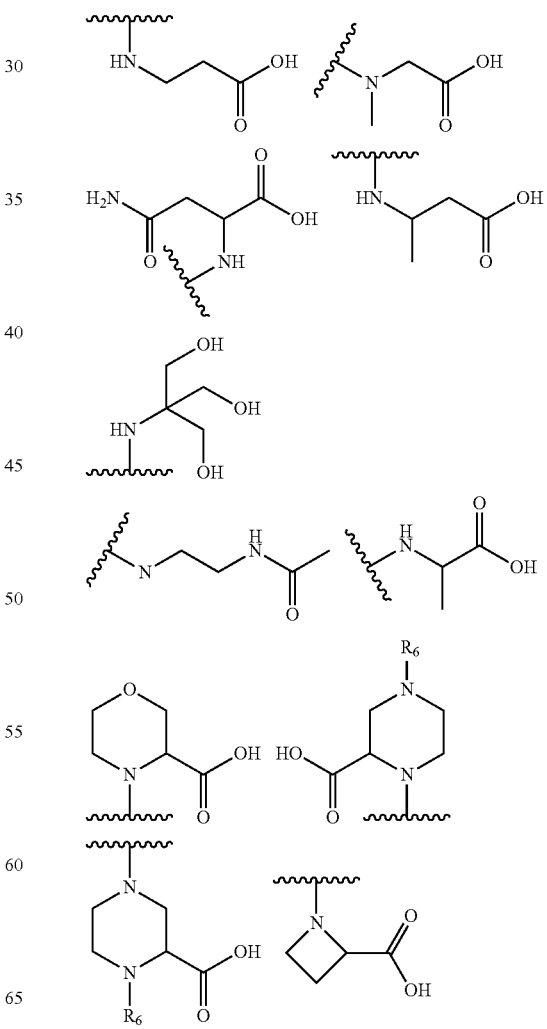

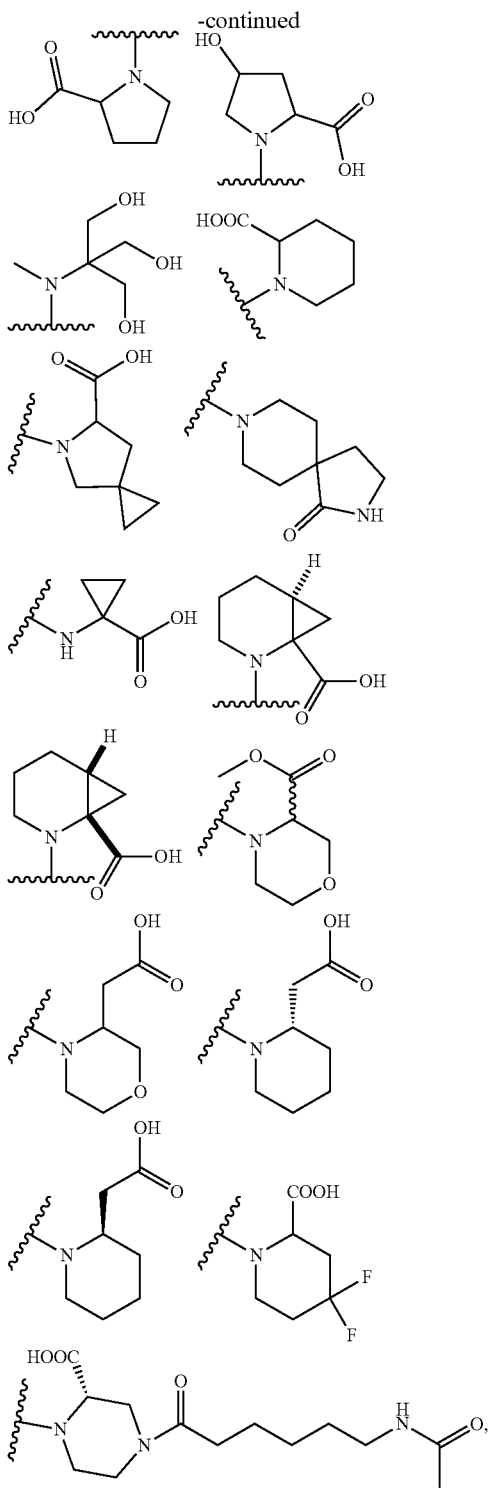

wherein $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment, the present disclosure relates to a compound of Formula I or their polymorphs, stereoisomers, tautomers, prodrugs, solvates, and pharmaceutically acceptable salts thereof, which is selected from a group consisting of:

N-(2-(((2-((4'-fluoro-2-methyl-[1,1'-biphenyl]-3-yl) methoxy)-4-methoxypyrimidin-5-yl)methyl)amino)ethyl) acetamide (Compound-1), N-((4-ethoxy-2-((2-methyl-[1,1'-biphenyl]-3-yl)methoxy) pyrimidin-5-yl)methyl)-N-methyl glycine (Compound-2), N-((4-ethoxy-2-((2-methyl-[1,1'-biphenyl]-3-yl)methoxy) pyrimidin-5-yl)methyl)-N-methyl glycine (Compound-3), (1R,6R)-2-((4,6-dimethoxy-2-((2-methyl-[1,1'-biphenyl]-3-yl)methoxy)pyrimidin-5-yl)methyl)-2-azabicyclo[4.1.0] heptane-1-carboxylic acid (Compound-4), (1S,6R)-2-((4,6-dimethoxy-2-((2-methyl-[1,1'-biphenyl]-3-yl)methoxy)pyrimidin-5-yl)methyl)-2-azabicyclo[4.1.0] heptane-1-carboxylic acid (Compound-5), N-(2-(((4,6-diethoxy-2-((2-methyl-[1,1'-biphenyl]-3-yl) methoxy)pyrimidin-5-yl)methyl)amino)ethyl)acetamide (compound-6), (S)-1-((4-methoxy-2-((2-methyl-[1,1'-biphenyl]-3-yl) methoxy)pyrimidin-5-yl)methyl)piperidine-2-carboxylic acid (Compound-7), (S)-1-((4-((3-cyano-4-fluorobenzyl)oxy)-2-((2-methyl-[1,1'-biphenyl]-3-yl)methoxy)pyrimidin-5-yl)methyl)piperidine-2-carboxylic acid (compound-8), (S)-1-((2-((2-methyl-[1,1'-biphenyl]-3-yl)methoxy)-4-(2,2,2-trifluoroethoxy)pyrimidin-5-yl)methyl)piperidine-2-carboxylic acid (compound-9), (S)-1-((4-(4-hydroxybutoxy)-2-((2-methyl-[1,1'-biphenyl]-3-yl)methoxy)pyrimidin-5-yl)methyl)piperidine-2-carboxylic acid (compound-10), (2S,4R)-1-((2-((3-(2,3-dihydrobenzo[b][1,4]dioxin-6-yl)-2-methylbenzyl)oxy)-4,6-dimethoxypyrimidin-5-yl) methyl)-4-hydroxypyrrolidine-2-carboxylic acid (compound-11), (S)-1-((4-((5-cyanopyridin-3-yl)methoxy)-2-((2-methyl-[1,1'-biphenyl]-3-yl)methoxy)pyrimidin-5-yl)methyl)piperidine-2-carboxylic acid (compound-12), (S)-1-((2-((3'-(3,3-difluoropyrrolidin-1-yl)propoxy)-2,2'-dimethyl-[1,1'-biphenyl]-3-yl)methoxy)-4-methoxypyrimidin-5-yl)methyl)piperidine-2-carboxylic acid (compound-13), N-(2-(((4-methoxy-2-((2-methyl-[1,1'-biphenyl]-3-yl) methoxy)pyrimidin-5-yl)methyl)amino)ethyl)acetamide (Compound-14), (R)-1-((4-methoxy-2-((2-methyl-[1,1'-biphenyl]-3-yl) methoxy)pyrimidin-5-yl)methyl)piperidine-2-carboxylic acid (Compound 15), (S)-1-((2-((4'-fluoro-2-methyl-[1,1'-biphenyl]-3-yl) methoxy)-4-methoxypyrimidin-5-yl)methyl)piperidine-2-carboxylic acid (Compound-16), (S)-1-((2-((3'-fluoro-2-methyl-[1,1'-biphenyl]-3-yl) methoxy)-4-methoxypyrimidin-5-yl)methyl)piperidine-2-carboxylic acid (Compound 17), N-(2-(((2-((3'-fluoro-2-methyl-[1,1'-biphenyl]-3-yl) methoxy)-4-methoxypyrimidin-5-yl)methyl)amino)ethyl) acetamide (Compound-18), (S)-1-((2-((2'-fluoro-2-methyl-[1,1'-biphenyl]-3-yl) methoxy)-4-methoxypyrimidin-5-yl)methyl)piperidine-2-carboxylic acid (Compound 19), N-(2-(((2-((2'-fluoro-2-methyl-[1,1'-biphenyl]-3-yl) methoxy)-4-methoxypyrimidin-5-yl)methyl)amino)ethyl) acetamide (Compound 20), N-(2-(((4-ethoxy-2-((2-methyl-[1,1'-biphenyl]-3-yl) methoxy)pyrimidin-5-yl)methyl)amino)ethyl)acetamide (Compound 21), (S)-1-((4-ethoxy-2-((2-methyl-[1,1'-biphenyl]-3-yl)methoxy)pyrimidin-5-yl)methyl)piperidine-2-carboxylic acid (Compound 22), 1-(((4-ethoxy-2-((2-methyl-[1,1'-biphenyl]-3-yl)methoxy)pyrimidin-5-yl)methyl)amino)cyclopropane-1-carboxylic acid (Compound 23), (3-(((4-ethoxy-2-((2-methyl-[1,1'-biphenyl]-3-yl)methoxy)pyrimidin-5-yl)methyl)amino)propanoic acid (Compound 24), 2-(((4-ethoxy-2-((2-methyl-[1,1'-biphenyl]-3-yl)methoxy)pyrimidin-5-yl)methyl)amino)-2-(hydroxymethyl)propane-1,3-diol (Compound 25), (2-(((4-ethoxy-2-((2-methyl-[1,1'-biphenyl]-3-yl)methoxy)pyrimidin-5-yl)methyl)(methyl)amino)-2-(hydroxymethyl)propane-1,3-diol (Compound 26), (S)-3-(((4-ethoxy-2-((2-methyl-[1,1'-biphenyl]-3-yl)methoxy)pyrimidin-5-yl)methyl)amino)butanoic acid (Compound 27), ((4-ethoxy-2-((2-methyl-[1,1'-biphenyl]-3-yl)methoxy)pyrimidin-5-yl)methyl)-D-alanine (Compound 28), ((4-ethoxy-2-((2-methyl-[1,1'-biphenyl]-3-yl)methoxy)pyrimidin-5-yl)methyl)asparagine (Compound 29), (2R,4R)-1-((4-ethoxy-2-((2-methyl-[1,1'-biphenyl]-3-yl)methoxy)pyrimidin-5-yl)methyl)-4-hydroxypyrrolidine-2-carboxylic acid (Compound 30), 1-((4-ethoxy-2-((2-methyl-[1,1'-biphenyl]-3-yl)methoxy)pyrimidin-5-yl)methyl)azetidine-2-carboxylic acid (Compound 31), N-(2-(((4-(benzyloxy)-2-((2-methyl-[1,1'-biphenyl]-3-yl)methoxy)pyrimidin-5-yl)methyl)amino)ethyl)acetamide (Compound 32), 1-((4-(benzyloxy)-2-((2-methyl-[1,1'-biphenyl]-3-yl)methoxy)pyrimidin-5-yl)methyl)piperidine-2-carboxylic acid (Compound 33), (2S,4R)-1-((4,6-dimethoxy-2-((2-methyl-[1,1'-biphenyl]-3-yl)methoxy)pyrimidin-5-yl)methyl)-4-hydroxypyrrolidine-2-carboxylic acid (Compound 34), 2-(((4,6-dimethoxy-2-((2-methyl-[1,1'-biphenyl]-3-yl)methoxy)pyrimidin-5-yl)methyl)amino)-2-(hydroxymethyl)propane-1,3-diol (Compound 35), ((4,6-dimethoxy-2-((2-methyl-[1,1'-biphenyl]-3-yl)methoxy)pyrimidin-5-yl)methyl)-L-proline (Compound 36), Methyl 4-((4,6-dimethoxy-2-((2-methyl-[1,1'-biphenyl]-3-yl)methoxy)pyrimidin-5-yl)methyl)morpholine-3-carboxylate (Compound 37), 4-((4,6-dimethoxy-2-((2-methyl-[1,1'-biphenyl]-3-yl)methoxy)pyrimidin-5-yl)methyl)morpholine-3-carboxylic acid (Compound 38), (2S,4R)-1-((4,6-diethoxy-2-((2-methyl-[1,1'-biphenyl]-3-yl)methoxy)pyrimidin-5-yl)methyl)-4-hydroxypyrrolidine-2-carboxylic acid (Compound 39), ((S)-1-((4,6-diethoxy-2-((2-methyl-[1,1'-biphenyl]-3-yl)methoxy)pyrimidin-5-yl)methyl)piperidine-2-carboxylic acid (Compound 40), 2-(((4,6-diethoxy-2-((2-methyl-[1,1'-biphenyl]-3-yl)methoxy)pyrimidin-5-yl)methyl)amino)-2-(hydroxymethyl)propane-1,3-diol (Compound 41), 2-(((4,6-dimethoxy-2-((2-methyl-[1,1'-biphenyl]-3-yl)methoxy)pyrimidin-5-yl)methyl)amino)-2-(hydroxymethyl)propane-1,3-diol (Compound 42), (S)-4-((4,6-dimethoxy-2-((2-methyl-[1,1'-biphenyl]-3-yl)methoxy)pyrimidin-5-yl)methyl)morpholine-3-carboxylic acid (Compound 43), 2-(4-((4,6-dimethoxy-2-((2-methyl-[1,1'-biphenyl]-3-yl)methoxy)pyrimidin-5-yl)methyl)morpholin-3-yl)acetic acid (Compound 44), (S)-1-((4,6-dimethoxy-2-((2-methyl-[1,1'-biphenyl]-3-yl)methoxy)pyrimidin-5-yl)methyl)piperidine-2-carboxylic acid (Compound 45), (S)-5-((4,6-dimethoxy-2-((2-methyl-[1,1'-biphenyl]-3-yl)methoxy)pyrimidin-5-yl)methyl)-5-azaspiro[2.4]heptane-6-carboxylic acid (Compound 46), 7-((4,6-dimethoxy-2-((2-methyl-[1,1'-biphenyl]-3-yl)methoxy)pyrimidin-5-yl)methyl)-2,7-diazaspiro[4.5]decan-1-one (Compound 47), rac-(1R,6S)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid (Compound 48), (S)-4-acetyl-1-((4-methoxy-2-((2-methyl-[1,1'-biphenyl]-3-yl)methoxy)pyrimidin-5-yl)methyl)piperazine-2-carboxylic acid (Compound 49), (S)-1-((4-methoxy-2-((2-methyl-[1,1'-biphenyl]-3-yl)methoxy)pyrimidin-5-yl)methyl)piperazine-2-carboxylic acid (Compound 50), (S)-5-((4-methoxy-2-((2-methyl-[1,1'-biphenyl]-3-yl)methoxy)pyrimidin-5-yl)methyl)-5-azaspiro[2.4]heptane-6-carboxylic acid (Compound 51), 7-((4-methoxy-2-((2-methyl-[1,1'-biphenyl]-3-yl)methoxy)pyrimidin-5-yl)methyl)-2,7-diazaspiro[4.5]decan-1-one (Compound 52), N-(2-(((4-((3-cyano-4-fluorobenzyl)oxy)-2-((2-methyl-[1,1'-biphenyl]-3-yl)methoxy)pyrimidin-5-yl)methyl)amino)ethyl)acetamide (Compound 53), (2S,4R)-1-((4-((3-cyano-4-fluorobenzyl)oxy)-2-((2-methyl-[1,1'-biphenyl]-3-yl)methoxy)pyrimidin-5-yl)methyl)-4-hydroxypyrrolidine-2-carboxylicacid (Compound 54), (S)-1-((2-((3-(2,3-dihydrobenzo[b][1,4]dioxin-6-yl)-2-methylbenzyl)oxy)-4,6-dimethoxypyrimidin-5-yl)methyl)piperidine-2-carboxylic acid (Compound 55), N-(2-(((2-((3-(2,3-dihydrobenzo[b][1,4]dioxin-6-yl)-2-methylbenzyl)oxy)-4,6-dimethoxypyrimidin-5-yl)methyl)amino)ethyl)acetamide (Compound 56), N-(2-(((2-(((3',4'-dimethoxy-2-methyl-[1,1'-biphenyl]-3-yl)methoxy)-4,6-dimethoxypyrimidin-5-yl)methyl)amino)ethyl)acetamide (Compound 57), ((2S,4R)-1-((2-((3',4'-dimethoxy-2-methyl-[1,1'-biphenyl]-3-yl)methoxy)-4,6-dimethoxypyrimidin-5-yl)methyl)-4-hydroxypyrrolidine-2-carboxylic acid (Compound 58), (2S,4R)-1-((4-((5-cyanopyridin-3-yl)methoxy)-2-((2-methyl-[1,1'-biphenyl]-3-yl)methoxy)pyrimidin-5-yl)methyl)-4-hydroxypyrrolidine-2-carboxylic acid (Compound 59), (S)-2-(1-((4-methoxy-2-((2-methyl-[1,1'-biphenyl]-3-yl)methoxy)pyrimidin-5-yl)methyl)piperidin-2-yl) acetic acid (Compound 60), (R)-2-(1-((4-methoxy-2-((2-methyl-[1,1'-biphenyl]-3-yl)methoxy)pyrimidin-5-yl)methyl)piperidin-2-yl) acetic acid (Compound 61), (S)-4-(6-acetamidohexanoyl)-1-((4-methoxy-2-((2-methyl-[1,1'-biphenyl]-3-yl)methoxy)pyrimidin-5-yl)methyl)piperazine-2-carboxylic acid (Compound 62), (S)-4,4-difluoro-1-((4-methoxy-2-((2-methyl-[1,1'-biphenyl]-3-yl)methoxy)pyrimidin-5-yl)methyl)piperidine-2-carboxylic acid (Compound 63), (S)-1-((4-methyl-2-((2-methyl-[1,1'-biphenyl]-3-yl)methoxy)pyrimidin-5-yl)methyl)piperidine-2-carboxylic acid (Compound 64), and N-(2-(((4-methyl-2-((2-methyl-[1,1'-biphenyl]-3-yl)methoxy)pyrimidin-5-yl)methyl)amino)ethyl)acetamide (Compound 65).

In an embodiment, the present disclosure relates to a process of preparation of compounds of Formula Ib, Formula Ia, and Formula I as described herein, or its polymorphs, stereoisomers, tautomers, prodrugs, solvates, and pharmaceutically acceptable salts thereof.

In an embodiment of the present disclosure, there is provided a a process of preparation of compounds of Formula Ib, Formula Ia, and Formula I as described herein, wherein said process comprising steps of (a) reacting compounds of Formula IV and Formula B3 in presence of a base, a solvent, and optionally a coupling reagent to obtain compounds of Formula V or Formula XIII; (b) processing the compounds of Formula V and Formula XIII to obtain compounds of Formula VII; and (c) reacting compounds of Formula VII with substituted amines in presence of a reducing agent and a third solvent to obtain compounds of Formula I or Ia or Ib alkyl, $C_{1-10}$ alkoxy, $C_{5-10}$ aryl, and 5-10 membered monocyclic or bicyclic heteroaryl, are optionally substituted with one or more of the groups selected from hydrogen, halogen, hydroxyl, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{1-6}$ alkylamino, $C_{1-6}$ alkoxyamino, $C_{1-6}$ acylamino, $C_{1-10}$ heterocyclyl, or —COOR$_a$, wherein $C_{1-6}$ alkyl, $C_{1-6}$ alkoxy, and $C_{1-10}$ heterocyclyl are optionally substituted with one or more of the groups selected from hydroxy, cyano, $C_{1-6}$ alkyl, $C_{3-6}$ cycloalkyl, $C_{1-6}$ heterocyclyl, $C_{1-6}$ alkoxy, or COOR$_a$, wherein $C_{1-6}$ heterocyclyl is optionally substituted with one or more groups selected from hydroxy, halogen, or cyano; and R$_a$ is selected from hydrogen, halogen, cyano, $C_{1-6}$ alkyl, $C_{3-8}$ cycloalkyl, $C_{5-6}$ aryl, $C_{5-6}$ arylalkyl, $C_{2-6}$ hetero-

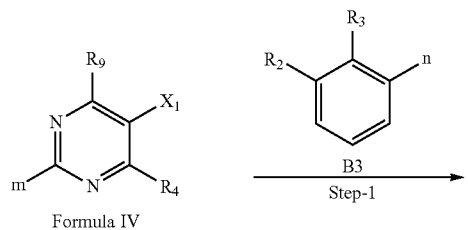

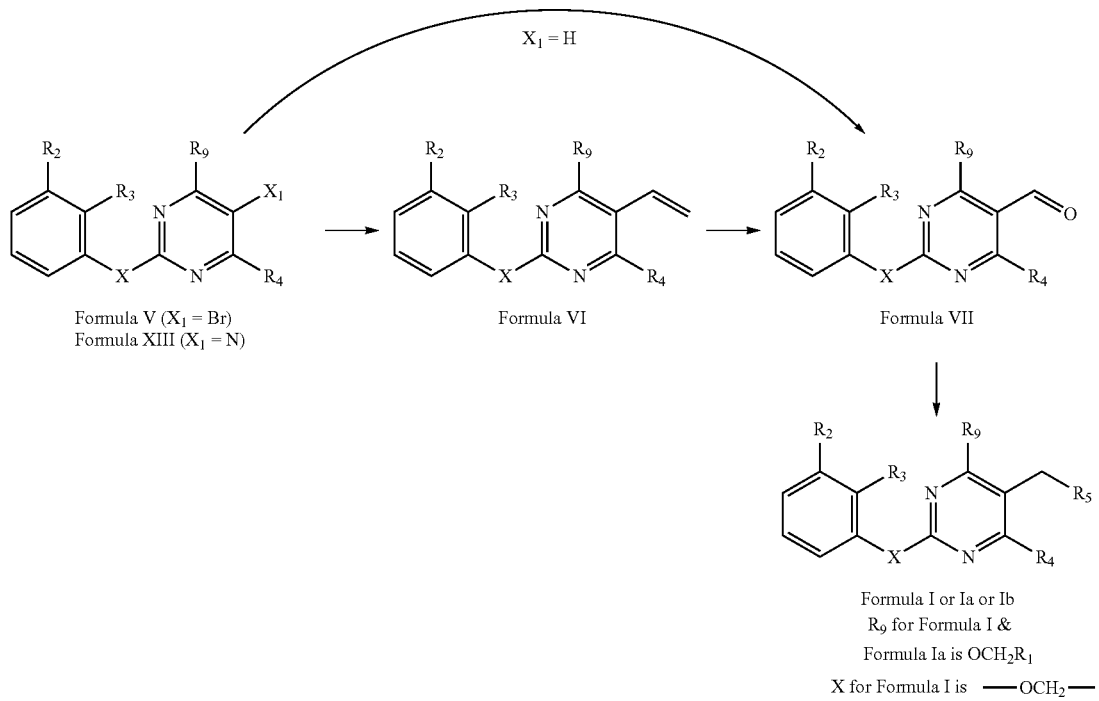

wherein X of Formula V, Formula VI, Formula VII, Formula Ia, and Formula Ib is selected from —CH$_2$O—, —OCH$_2$—, —C(O)NH— or —NHC(O)—; R$_9$, R$_2$, R$_3$, and R$_4$ of Formula Ib, Formula IV, Formula V, Formula VI, Formula VII, and Formula XIII are independently selected from hydrogen, cyano, $C_{1-10}$ alkyl, $C_{1-10}$ alkoxy, $C_{1-6}$ haloalkyl, $C_{1-6}$ haloalkoxy, $C_{3-6}$ cycloalkyl, $C_{1-6}$ alkylamino, amino$C_{1-6}$ alkyl, $C_{1-6}$ alkoxyamino, $C_{1-6}$ acylamino, $C_{5-10}$ aryl, and 5-10 membered monocyclic or bicyclic heteroaryl with 1-5 heteroatoms selected from N, S or O, wherein $C_{1-10}$ cyclyl, $C_{1-6}$ heteroaryl, or $C_{1-6}$ heteroarylalkyl; X of Formula Ib, Formula Ia, Formula V, Formula VI, Formula VII, and Formula XIII is selected from —CH$_2$O—, —OCH$_2$—, —C(O)NH— or —NHC(O)—; R$_5$ of Formula Ib is —NR$_7$R$_8$, wherein R$_7$ and R$_8$ are independently selected from the group consisting of hydrogen, $C_{3-10}$ cycloalkyl, $C_{1-6}$ alkyl, $C_{2-6}$ alkenyl, 5-10 membered monocyclic or bicyclic, saturated or unsaturated heterocyclic ring with 1-3 heteroatoms selected from N, S or O, and combinations thereof, wherein $C_{3-10}$ cycloalkyl, $C_{1-6}$ alkyl, $C_{2-6}$ alkenyl, and the 5-10 membered monocyclic or bicyclic, saturated or unsaturated heterocyclic ring are optionally substituted with one or more substituents selected from oxo, cyano, halogen, hydroxyl, morpholino, $C(O)NH_2$, $C(O)CH_2CN$, $NHR_6$, COOH, $COOR_6$, $NHC(O)R_6$, $C_{1-6}$ alkyl, $C_{1-6}$ haloalkyl, $C_{3-10}$ cycloalkyl, $C_{5-6}$ aryl, $SR_6$, or 5-10 membered monocyclic or bicyclic, saturated or unsaturated heterocyclic ring with 1-3 heteroatoms selected from N, S or O, wherein $C_{1-6}$ alkyl, and the 5-10 membered monocyclic or bicyclic, saturated or unsaturated heterocyclic ring are independently substituted with one or more substituents selected from hydroxyl, and $R_6$; or $R_7$ and $R_8$ can be taken together to form a 4-10 membered monocyclic or bicyclic, saturated or unsaturated heterocyclic ring with 1-3 heteroatoms selected from N, S or O, wherein the 4-10 membered monocyclic or bicyclic, saturated or unsaturated heterocyclic ring is optionally substituted with one or more substituents selected from the group consisting of hydroxyl, halogen, $C_{1-6}$ alkyl, COOH, $R_6$, $NHR_6$, $C(O)NHR_6$, $C(O)NHSO_2R_6$, $C(O)(CH_2)_nNHC(O)CH_3$, and combinations thereof, wherein $C_{1-6}$ alkyl is further substituted with groups selected from hydroxyl. COOH, or $NHR_6$; n is 1-6; and $R_6$ is selected from the group consisting of hydrogen, $C_{1-6}$ alkyl, $C(O)C_{1-6}$ alkyl, and combinations thereof, wherein $C_{1-6}$ alkyl, and $C(O)C_{1-6}$ alkyl are optionally substituted with substituents selected from the group consisting of hydroxyl, COOH, $NHR_6$, $NHC(O)NHR_6$, and combinations thereof.

In an embodiment of the present disclosure, there is provided a process of preparation of compounds of Formula Ib, Formula Ia, and Formula I as described herein, wherein processing the compounds of Formula V to obtain compounds of Formula VII comprises: (a) alkenylation of compounds of Formula V in presence of a second base and a second solvent to obtain compounds of Formula VI; and (b) oxidation of compounds of Formula VI to obtain compounds of Formula VII.

In an embodiment of the present disclosure, there is provided a process of preparation of compounds of Formula Ib, Formula Ia, and Formula I as described herein, wherein processing the compounds of Formula XIII to obtain compounds of Formula VII comprises formylation of compounds of Formula XIII to obtain compounds of Formula VII.

In an embodiment of the present disclosure, there is provided a a process of preparation of compounds of Formula Ib, Formula Ia, and Formula I as described herein, wherein said process comprising steps of (a) reacting compounds of Formula IV and Formula B3 in presence of a base, a solvent, and optionally a coupling reagent to obtain compounds of Formula V or Formula XIII; (b) alkenylation of compounds of Formula V in presence of a second base and a second solvent to obtain compounds of Formula VI; (c) oxidation of compounds of Formula VI to obtain compounds of Formula VII; and (d) reacting compounds of Formula VII with substituted amines in presence of a reducing agent and a third solvent to obtain compounds of Formula I or Ia or Ib.

In an embodiment of the present disclosure, there is provided a a process of preparation of compounds of Formula Ib, Formula Ia, and Formula I as described herein, wherein said process comprising steps of (a) reacting compounds of Formula IV and Formula B3 in presence of a base, a solvent, and optionally a coupling reagent to obtain compounds of Formula V or Formula XIII; (b) formylation of compounds of Formula XIII to obtain compounds of Formula VII; and (c) reacting compounds of Formula VII with substituted amines in presence of a reducing agent and a third solvent to obtain compounds of Formula I or Ia or Ib.

In an embodiment of the present disclosure, there is provided a process of preparation of compounds of Formula Ib, Formula Ia, and Formula I as described herein, wherein the coupling reagent is selected from 1-[Bis(dimethylamino) methylene]-1H-1,2,3-triazolo[4,5-b]pyridinium 3-oxid hexafluorophosphate (HATU), N,N'-Dicyclohexylcarbodiimide (DCC), or Propylphosphonic anhydride; the solvent is selected from the group consisting of methanol, ethanol, isopropyl alcohol, t-butyl alcohol, dichloromethane, ethyl acetate, dioxane, ether, N,N-dimethylformamide, dimethyl sulfoxide, and combinations thereof; the base is selected from the group consisting of sodium hydride, butyllithium, lithium diisopropylamide, potassium carbonate, cesium carbonate, triethylamine, diisopropylethylamine, 4-dimethylaminopyridine, pyridine, and combinations thereof, the second base is selected from the group consisting of butyl lithium, sodium hydride, lithium diisopropylamide, potassium carbonate, cesium carbonate, triethylamine, diisopropylethylamine, 4-dimethylaminopyridine, pyridine, and combinations thereof; the second solvent is selected from the group consisting of N,N-dimethylformamide, dichloromethane, ethyl acetate, dioxane, isopropyl alcohol, ether, t-butyl alcohol, N,N-dimethylformamide, dimethyl sulfoxide, and combinations thereof, the third solvent is selected from the group consisting of acetic acid, methanol, N,N-dimethylformamide, and combinations thereof, and the reducing agent is selected from the group consisting of sodium cyanoborohydride, sodium borohydride, lithiumaluminium hydride, diisobutylaluminium hydride, and combinations thereof.

In an embodiment, the present disclosure relates to pharmaceutical composition comprising a compound of Formula Ib, Formula Ia, and Formula I as described herein, or a pharmaceutically acceptable salt thereof together with a pharmaceutically acceptable carrier, optionally in combination with one or more other pharmaceutical compositions.

In another embodiment, the present disclosure relates to the pharmaceutical composition as described herein, wherein the composition is in the form selected from the group consisting of a tablet, capsule, powder, syrup, solution, aerosol and suspension.

In an embodiment of the present disclosure, there is provided compounds of Formula Ib, Formula Ia, Formula I or a pharmaceutically acceptable salt thereof as described herein, wherein the pharmaceutically acceptable salt selected derived from inorganic bases such as like Li, Na, K, Ca, Mg, Fe, Cu, Zn and Mn; salts of organic bases such as N,N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine, ammonium, substituted ammonium salts, aluminum salts and the like. Salts also include amino acid salts such as glycine, alanine, cystine, cysteine, lysine, arginine, phenylalanine, and guanidine. Salts may include acid addition salts where appropriate which are sulfates, nitrates, phosphates, perchlorates, borates, hydrohalides, acetates, tartrates, maleates, citrates, succinates, palmoates, methanesulfonates, tosylates, benzoates, salicylates, hydroxynaphthoates, benzenesulfonates, ascorbates, glycerophosphates, ketoglutarates.

In an embodiment of the present disclosure, there is provided a method for the treatment and/or prevention of various diseases, including cancer and infectious diseases, the method comprising: administering to a subject suffering from the proliferative disorder or cancer a therapeutically effective amount of the compound of Formula Ib, Formula Ia, and Formula I or the pharmaceutical composition as described herein, with other clinically relevant cytotoxic agents or non-cytotoxic agents to a subject in need thereof.

In an embodiment, the present disclosure relates to a method for the treatment and/or prevention of a proliferative disorder or cancer or HIV or Hepatitis B or Hepatitis C or Hepatitis D or infections both bacterial or viral comprising administering to a subject suffering from the proliferative disorder or cancer a therapeutically effective amount of the compounds of Formula Ib, Formula Ia, Formula I or a pharmaceutically acceptable salt thereof together with a pharmaceutically acceptable carrier, with other clinically relevant cytotoxic agents or non-cytotoxic agents to a subject in need thereof.

The present disclosure provides a method of treatment of a disorder caused by, associated with or accompanied by disruptions of cell proliferation and/or angiogenesis and the subsequent metastasis including administration of a therapeutically effective amount of a compound of Formula I.

The present disclosure provides a method of treatment of cancer in patient including administration of effective amount of compounds of Formula Ib, Formula Ia, and Formula I. The cancer can be either a hematologic malignancy or solid tumor. Hematological malignancy is selected from the group consisting of B-cell lymphoma, T-cell lymphoma and leukemia. In the case of solid tumors, the tumors are selected from the group consisting of breast cancer, lung cancer, ovarian cancer, prostate cancer, head cancer, neck cancer, renal cancer, gastric cancer, colon cancer, pancreatic cancer, and brain cancer.

Compounds of the present disclosure are able to slow tumor growth, stop tumor growth or bring about the regression of tumors and to prevent the formation of tumor metastates (including micrometastates) and the growth of metastates (including micrometastates). In addition they can be used in epidermal hyperproliferation.

The compounds of the Formula I of the present disclosure can be used as a prophylactic or therapeutic agent for cancer. Examples of the cancer include but are not restricted to, breast cancer, prostate cancer, pancreatic cancer, gastric cancer, lung cancer, colon cancer, rectal cancer, esophagus cancer, duodenal cancer, tongue cancer, pharyngeal cancer, brain tumor, neurinoma, non-small cell lung cancer, small cell lung cancer, liver cancer, kidney cancer, bile duct cancer, uterine body cancer, cervical cancer, ovarian cancer, urinary bladder, skin cancer, hemangioma, malignant lymphoma, malignant melanoma, thyroid cancer, bone tumor, vascular fibroma, retinoblastoma, penile cancer, pediatric solid cancer, lymphoma, myeloma and leukemia (including, for example acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL) or hairy cell leukemia).

"Combination therapy" includes the administration of the subject compounds in further combination with other biologically active ingredients (such as, but are not limited to, different antineoplastic agent) and non-drug therapies (such as, but are not limited to, surgery or radiation treatment). The compounds described herein can be used in combination with other pharmaceutically active compounds, preferably, which will enhance the effect of the compounds of the disclosure. The compounds can be administered simultaneously or sequentially to the other drug therapy.

In an embodiment, the present disclosure relates to the use of compounds of Formula Ib, Formula Ia, Formula I or pharmaceutically acceptable salts thereof together with a pharmaceutically acceptable carrier, for the treatment and/or prevention of various diseases including proliferative disorder or cancer; or treatment of cancer together with other clinically relevant cytotoxic agents or non-cytotoxic agents.

In an embodiment, the present disclosure relates to the use of compounds of Formula Ib, Formula Ia, Formula I or pharmaceutically acceptable salts thereof together with a pharmaceutically acceptable carrier, for the treatment and/or prevention of various diseases including proliferative disorder or cancer; or treatment of cancer together with other clinically relevant cytotoxic agents or non-cytotoxic agents, wherein the other clinically relevant cytotoxic agents or non-cytotoxic agents are selected from the group consisting of carboplatin, bortezomib, carfilzomib, lenalidomide, pomalidomide, doxorubicin, daunorubicin, decitabine, denileukin, denileukin diftitox, dexrazoxane, docetaxel, doxorubicin, dromostanolone propionate cyclophosphamide, 5-fluroruracil, imatinib, methotrexate, irinotecan, toptecan, vinblastine, etoposide, vincristine, carmustine, paclitaxel, vorinostat, belinostat, panbinostat, romidepsin, chiadamide, entinostat, mocetinostat, afatinib, bosutinib, cetuximab, enterctinib, lapatinib, nilotinib, pazopanib, ruxlotinib, sorafeenib, sunitinib, vermurafenib, axitinib, gefitinib, cobimetinib, carbozantinib, temozolomide, idarubicin, abarelix, aldesleukin, alemtuzumab, allopurinol, altretamine, anastrozole, asparaginase, bexarotene, baricitinib, bleomycin, busulfan, capecitabine, cladribine, clofarabine, cytarabine, dacarbazine, dactinomycin, sodium, dasatinib, letrozole, tamoxifen, oxaliplatin, procarbazine, zoleronate, and combinations thereof.

In an embodiment, the present disclosure relates to a method for the treatment of cancer as described herein, wherein said method comprising administering a combination of the compounds of Formula Ib, Formula Ia, Formula I or pharmaceutically acceptable salts thereof together with a pharmaceutically acceptable carrier, with other clinically relevant cytotoxic agents or non-cytotoxic agents to a subject in need thereof.

In an embodiment, the present disclosure relates to a method of treatment and/or prevention of various diseases, including cancer and infectious diseases, comprising administering to a subject suffering from the viral infectious diseases such as HIV, Influenza, herpes virus, Hepatitis A, Hepatitis B, Hepatitis C, and Hepatitis D, a therapeutically effective amount of the compound of Formula Ib, Formula Ia, and Formula I or the pharmaceutical composition as described herein, with other clinically relevant anti-viral drugs to a subject in need thereof.

In an embodiment, the present disclosure relates to a method of treatment of cancer as described herein, wherein said method comprising administering a combination of the compounds of Formula Ib, Formula Ia, Formula I or the pharmaceutical composition with other clinically relevant immune checkpoint inhibitors. In another embodiment of the present disclosure, the immune checkpoint inhibitors are selected from the group consisting of CD27, CD28, CD40, CD122, CD96, CD73, CD47, OX40, GITR, CSF1R, JAK, PI3K delta, PI3K gamma, TAM, aiginase, CD137 (4-1BB), ICOS, A2AR, B7-H3, B7-H4, BTLA, CTLA-4, LAG3, TIM3, VISTA, PD-1, PD-L1, PD-L2, and combinations thereof.

In an embodiment, the present disclosure relates to a method of treatment of cancer as described herein, wherein said method comprising administering a combination of the compounds of Formula Ib, Formula Ia, Formula I or the pharmaceutical composition with other clinically relevant immune checkpoint inhibitors such as nivolumab, pembrolizumab, pidilimumab, bms-986016, epacadostat, tremelimumab, CD73 inhibitors and arginase inhibitors to a subject in need of thereof.

In another embodiment, the compounds of the present disclosure may be combined with the antineoplastic agents (e.g. small molecules, cytotoxic reagents, non-cytotoxic reagents, monoclonal antibodies, antisense RNA and fusion proteins) that inhibit one or more biological targets. Such combination may enhance therapeutic efficacy over the efficacy achieved by any of the agents alone and may prevent or delay the appearance of resistant variants.

In another embodiment, the compounds of the present disclosure may be combined with immunoncology drugs not restricting to PD-1, IDO, TDO, Arginase, CD73, TIM3, CTLA4 or any other drugs which is involved in the immune modulation.

In another embodiment, the subject compounds may be combined with CART-T-cell therapy which will enhance the effect of the CART T-cell therapy

EXAMPLES

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Abbreviations:
Ac Acetyl;
$Ac_2O$ Acetic anhydride;
ACN Acetonitrile;
AIBN Azobis(isobutyronitrile);
BINAP 2,2'-Bis(diphenylphosphino)-1,1'-binaphthyl;
BMS Borane-dimethyl sulfide complex;
Bn Benzyl;
Boc Tert-Butoxycarbonyl;
$Boc_2O$ Di-tert-butyl dicarbonate;
BuLi Butyllithium;
CSF Cesium fluoride;
DCE 1,2-Dichloroethane;
DCM Dichloromethane;
DDQ 2,3-Dichloro-5,6-dicyano-1,4-benzoquinone;
DMS Dimethyl sulfide;
ATP Adenosine triphosphate;
Bis-pinacolatodiboron 4,4,4',4',5,5,5',5-Octamethyl-2,2'-bi-1,3,2-dioxaborolane;
BSA Bovine serum albumin;
C18 Refers to 18-carbon alkyl groups on silicon in HPLC stationary phase;
$CH_3CN$ Acetonitrile;
Cy Cyclohexyl;
DCC N,N'-Dicyclohexylcarbodiimide;
DIPEA Hünig's base, N-ethyl-N-(1-methylethyl)-2-propanamine;
Dioxane 1,4-Dioxane;
DMAP 4-dimethylaminopyridine;
DME 1,2-Dimethoxyethane;
DMF N,N-Dimethylformamide;
DMSO Dimethylsulfoxide;
DPPA Diphenyl phosphoryl azide;
EtOAc Ethyl acetate;
EtOH Ethanol;
$Et_2O$ Diethyl ether;
HATU 1-[bis(dimethylamino)methylene]-1H-1,2,3-triazolo[4,5-b]pyridinium 3-oxid hexafluorophosphate;
HOAc Acetic acid;
HPLC High pressure liquid chromatography;
HMDS Hexamethyldisilazide;
IPA Isopropyl alcohol;
LAH Lithium aluminum hydride;
LDA Lithium diisopropylamide;
LHMDS Lithium hexamethyldisilazide;
MeOH Methanol;
MPLC Medium pressure liquid chromatography;
MTBE Methyl tert-butyl ether;
mCPBA m-Chloroperbezoic acid;
NaHMDS Sodium hexamethyldisilazide;
NBS N-bromosuccinimide;
NMR Nuclear magnetic resonance;
$Pd_2(dba)_3$ Tris(dibenzylideneacetone)dipalladium(0);
$Pd(dppf)Cl_2$.DCMComplex [1,1'-Bis(diphenylphosphino)ferrocene]dichloropalladium(II), dichloromethane complex;
RPHPLC Reverse phase high pressure liquid chromatography;
RT Room temperature;
Sat. Saturated;
SGC Silica gel chromatography;
SM Starting material;
T3P propylphosphonic anhydride;
TCL Thin layer chromatography;
TEA Triethylamine;
TFA Trifluoroacetic acid; and
THF Tetrahydrofuran.

The following examples provide the details about the synthesis, activities, and applications of the compounds of the present disclosure. It should be understood the following is representative only, and that the invention is not limited by the details set forth in these examples.

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention.

There is also provided a process as shown in the following Scheme-1, and Scheme-1a for the preparation of compounds of the Formula I, wherein all the groups are as defined earlier.

General Procedure for Synthesis of Compounds of Formula I
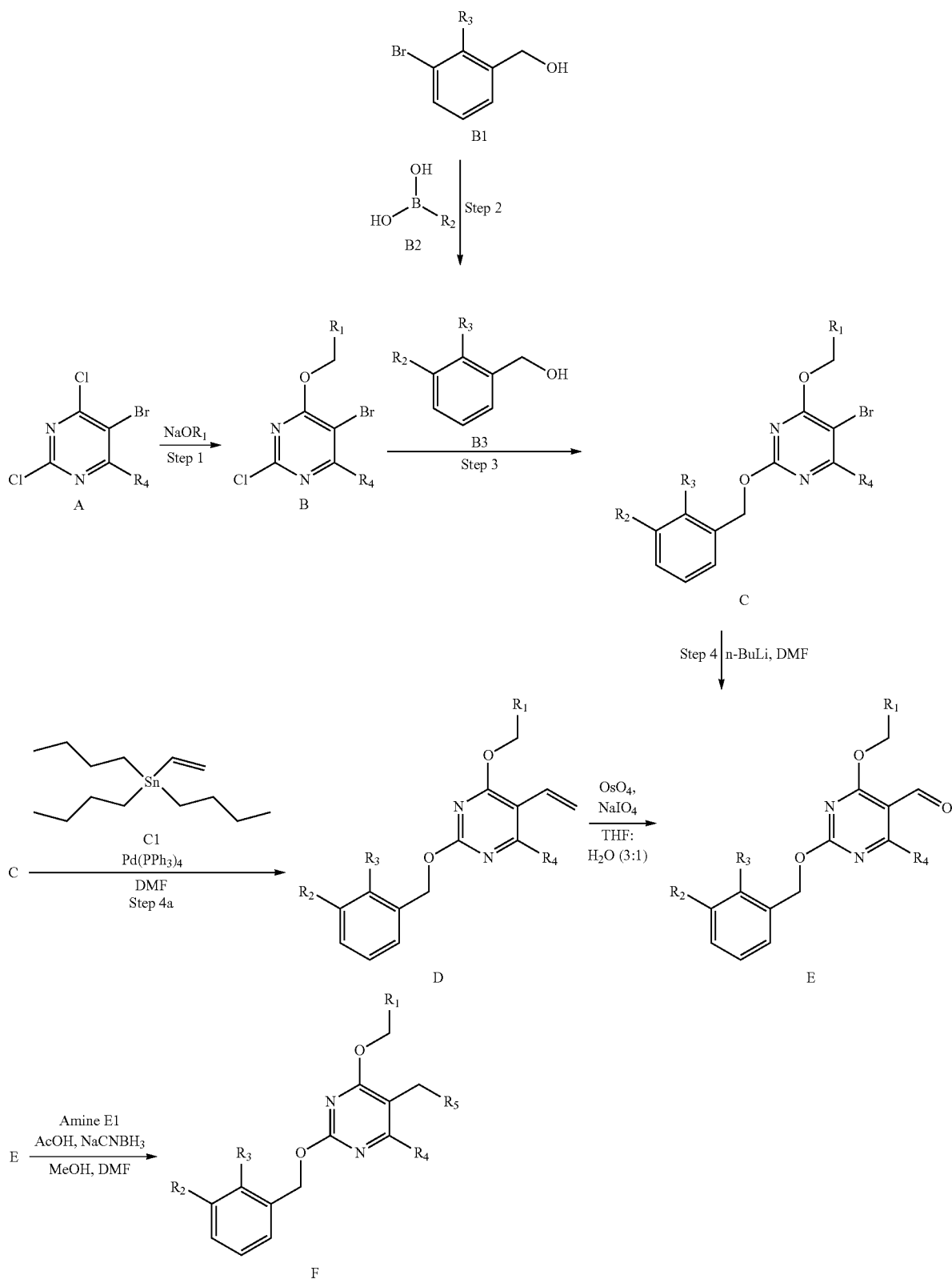

The said process for the preparation of the compounds of Formula I comprises of the following steps:

Step 1: Compound A (5-bromo-2,4-dichloropyrimidine) was reacted with sodium or potassium salt of an alkoxide in a suitable solvent to obtain the corresponding 5-bromo-2-chloro-4-alkoxy pyrimidine (compound B)

Step 2: Compound B3 (2,3 substituted benzyl alcohol) was synthesized by palladium catalyzed Suzuki coupling of substituted bromobenzene B1 with corresponding boronic acids B2 to give B3.

Step 3: Intermediate B3 was further reacted with compound B in presence of base such as sodium hydride to obtain 2-benzyloxy-4-alkoxy-5-bromo pyrimidine (compound C).

Step 4a: The intermediate C was reacted with tributyl (vinyl)stannane (compound C1) to give corresponding vinyl derivative D.

Step 4b: Compound D upon oxidation with sodium metaperiodate and osmium tetroxide gave the corresponding aldehyde E.

Step 4: The aldehyde E can alternatively be synthesised by lithiation of compound C with n-BuLi and quenching with N,N-dimethyl formamide.

Step 5: Reductive amination of intermediate E with various substituted aliphatic, aromatic, heterocyclic and cyclic amines (E1) resulted with compounds (compound F) described in the present invention.

General Procedure for Synthesis of Compounds of Formula I

Scheme 1a

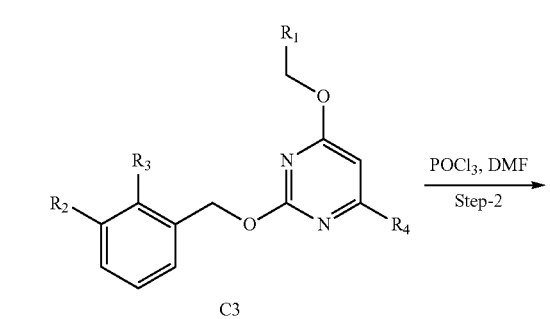

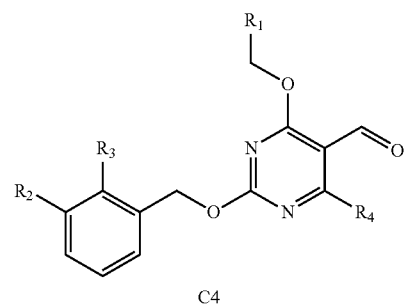

C4

AcOH, NaCNBH3, MeO, DMF | Amine E1 Step-3

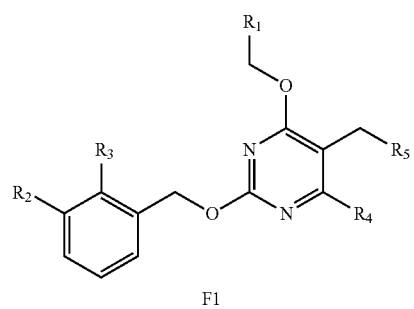

F1

Step 1: Intermediate C2 was reacted with compound B3 in presence of base such as sodium hydride to obtain 2-benzyloxy-4-alkoxy-5-bromo pyrimidine (compound C3).

Step 2: Formylation of on intermediate C3 was performed using POC3 and DMF to obtain intermediate C4.

Step 3: Reductive amination of intermediate C4 with various substituted aliphatic, aromatic, heterocyclic and cyclic amines (E1) resulted with compounds (compound F) described in the present invention.

General Procedure for Synthesis of Compounds of Formula Ib

Using following scheme compounds of the general formula Ib wherein R9 is alkyl or aryl can be prepared Scheme 1b

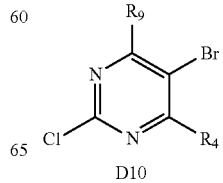

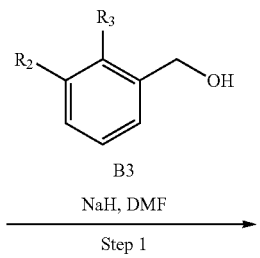

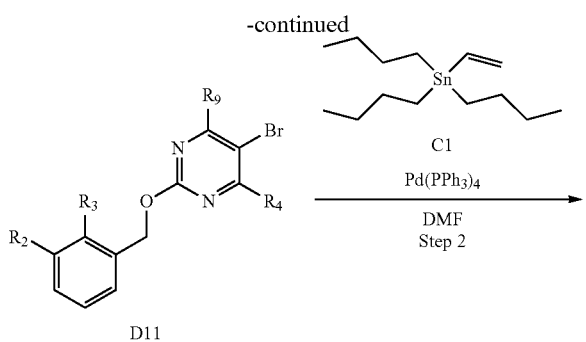

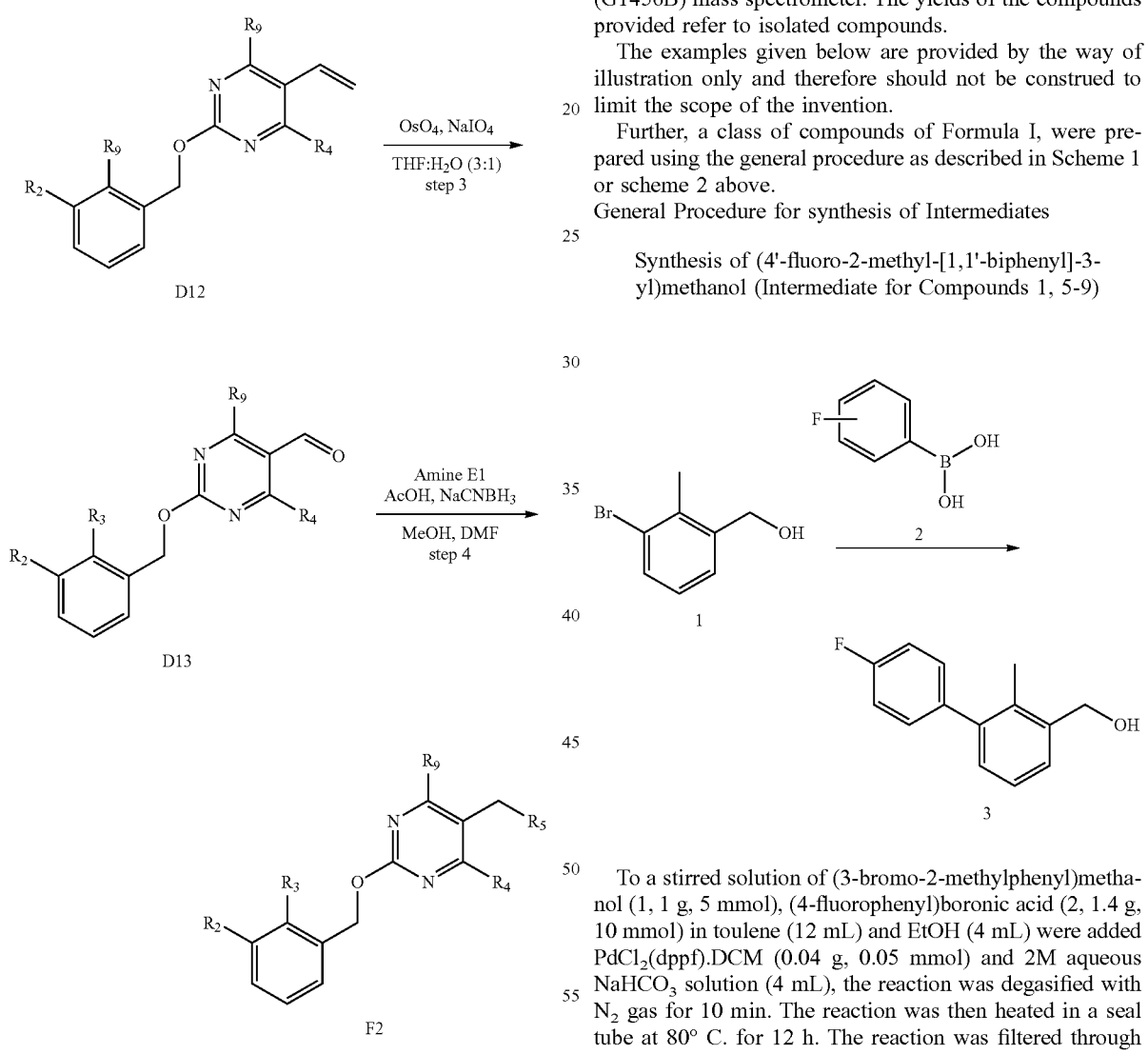

Step 1: B3 was reacted with compound D10 in presence of base such as sodium hydride to obtain pyrimidine derivative compound D11.

Step 2: The intermediate D11 was reacted with tributyl (vinyl)stannane (compound C1) to give corresponding vinyl derivative D12.

Step 3: Compound D12 upon oxidation with sodium metaperiodate and osmium tetroxide gave the corresponding aldehyde D13.

Step 4: Reductive amination of intermediate D13 with various substituted aliphatic, aromatic, heterocyclic and cyclic amines (E1) resulted with compounds (compound F2) described in the present invention.

General Considerations and Analytical Methods:

The compounds used in the reaction processes, if not mentioned otherwise, were commercially available. NMR data were obtained on Varian 400 MHz spectrometer. All compounds were characterized by $^1$H NMR, HPLC and mass spectrometry (LCMS (ES), Liquid chromatography-Mass spectrometry). All $^1$H chemical shifts were reported in parts per million (ppm) and were measured relative to TMS or residual deuterated DMSO as solvent. LCMS (ES) measurements were performed on Agilent-LCMS D-SL (G1456B) mass spectrometer. The yields of the compounds provided refer to isolated compounds.

The examples given below are provided by the way of illustration only and therefore should not be construed to limit the scope of the invention.

Further, a class of compounds of Formula I, were prepared using the general procedure as described in Scheme 1 or scheme 2 above.

General Procedure for synthesis of Intermediates

Synthesis of (4'-fluoro-2-methyl-[1,1'-biphenyl]-3-yl)methanol (Intermediate for Compounds 1, 5-9)

To a stirred solution of (3-bromo-2-methylphenyl)methanol (1, 1 g, 5 mmol), (4-fluorophenyl)boronic acid (2, 1.4 g, 10 mmol) in toulene (12 mL) and EtOH (4 mL) were added PdCl$_2$(dppf).DCM (0.04 g, 0.05 mmol) and 2M aqueous NaHCO$_3$ solution (4 mL), the reaction was degasified with N$_2$ gas for 10 min. The reaction was then heated in a seal tube at 80° C. for 12 h. The reaction was filtered through celite; the filtrate was diluted with water and extracted with ethyl acetate (2×100 mL). The organic layer was then dried over sodium sulfate, evaporated and the crude was purified on combiflash MPLC using 20% ethyl acetate in hexanes as eluent to afford (4'-fluoro-2-methyl-[1,1'-biphenyl]-3-yl) methanol as off-white solid (3, Yield: 0.81 g, 73%). LCMS (ES) m/z=199.1 [M+H—OH]$^+$; $^1$H NMR (400 MHz, DMSO-d$_6$) δ ppm: 2.08 (s, 3H), 4.52 (d, J=5.6 Hz, 2H), 5.09 (t, J=5.2 Hz, 1H), 7.05 (d, J=7.6 Hz, 1H), 7.18-7.25 (m, 3H), 7.27-7.31 (m, 2H), 7.38 (d, J=7.6 Hz, 1H).

Synthesis of (2-methyl-[1,1'-biphenyl]-3-yl)methanol (Intermediate for Compounds 2-4, 10-15)

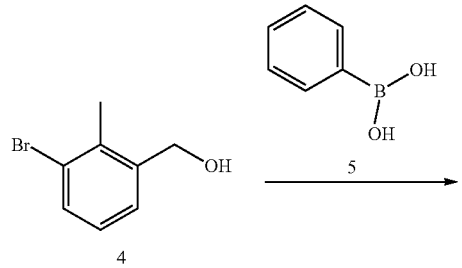

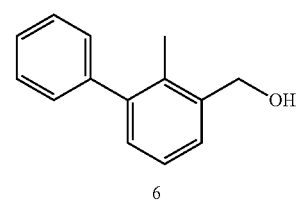

To a stirred solution of (3-bromo-2-methylphenyl)methanol (4, 1 g, 5 mmol), phenyl boronic acid (5, 1.4 g, 10 mmol) in toulene (12 mL) and EtOH (4 mL) were added PdCl$_2$(dppf).DCM (0.04 g, 0.05 mmol) and 2M aqueous NaHCO$_3$ solution (4 mL), the reaction mixture was degasified with nitrogen gas for 10 min. The reaction mixture was then heated in a seal tube at 80° C. for 12 h. The reaction mixture was filtered through celite; the filtrate was diluted with water and extracted with ethyl acetate (2×100 mL). The organic layer was then dried over sodium sulfate, evaporated and the crude was purified on combiflash MPLC using 20% ethyl acetate in hexanes as eluent to afford (2-methyl-[1,1'-biphenyl]-3-yl)methanol as off-white solid (6, Yield: 0.81 g, 73%). LCMS (ES) m/z=199.1 [M+H]+;

Synthesis of N-(2-(((2-((4'-fluoro-2-methyl-[1,1'-biphenyl]-3-yl)methoxy)-4-methoxypyrimidin-5-yl)methyl)amino)ethyl)acetamide (Compound-1)

Scheme 2

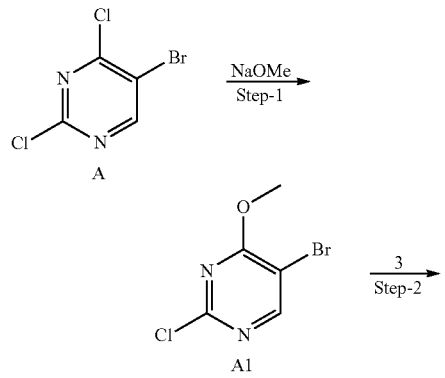

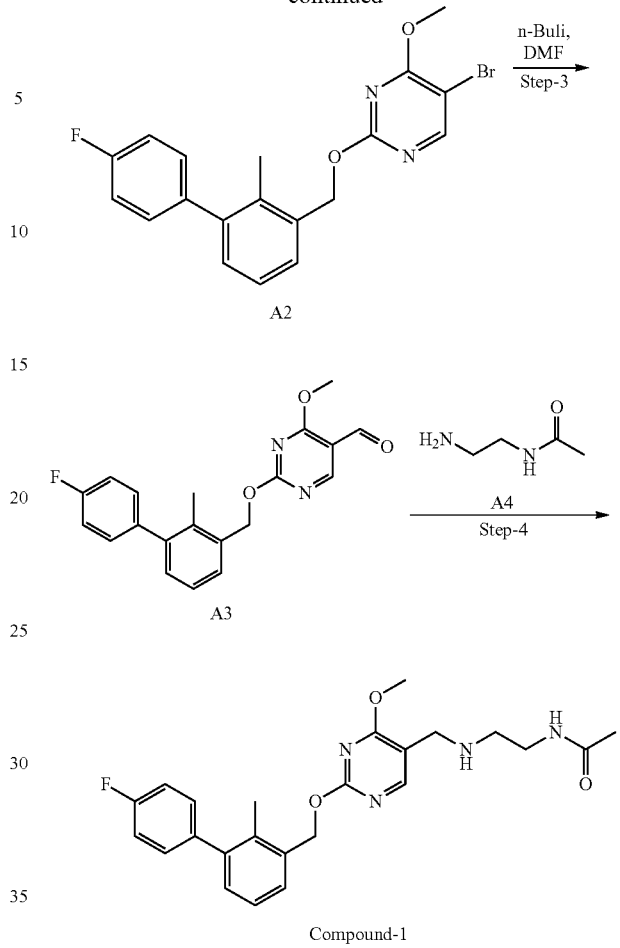

Step 1: Preparation of 5-bromo-2-chloro-4-methoxypyrimidine (A1)

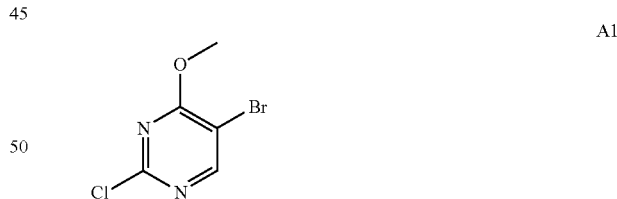

To a stirred solution of 5-bromo-2,4-dichloropyrimidine (A, 5 g, 22.2 mmol) in MeOH (100 mL) was added NaOMe (1.6 g, 28.88 mmol) at 0° C. and the reaction was stirred at r.t for 6 h. The reaction mixture was evaporated; the crude was taken in water and extracted with ethyl acetate (2×150 mL). The combined organic layer was washed with brine solution, dried over sodium sulfate and evaporated. The crude was purified on combiflash MPLC using 2% ethyl acetate in hexanes as eluent to afford 5-bromo-2-chloro-4-methoxypyrimidine as white crystalline solid (A1, yield: 4 g, 82%). LCMS (ES) m/z=222.9, 224.9 [M]$^+$, [M+2H]$^+$; $^1$H NMR (400 MHz, DMSO-d$_6$) δ ppm: 4.01 (s, 3H), 8.69 (s, 1H).

Step 2: Preparation of 5-bromo-2-((4'-fluoro-2-methyl-[1,1'-biphenyl]-3-yl)methoxy)-4-methoxypyrimidine (A2)

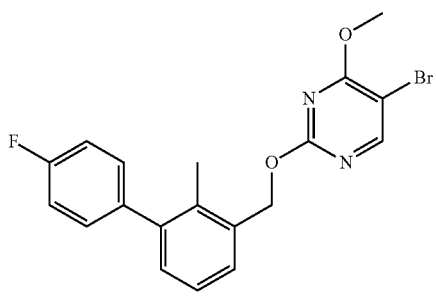

A2

To a stirred solution of (4'-fluoro-2-methyl-[1,1'-biphenyl]-3-yl)methanol (Intermediate 3, 0.5 g, 2.31 mmol) in THF (15 mL) was added 60% NaH in mineral oil (0.184 g, 4.61 mmol) at 0° C. and the reaction was stirred at that temperature for 0.5 h. To the reaction was then added 5-bromo-2-chloro-4-methoxypyrimidine (A1, 0.51 g, 2.31 mmol) in THF (3 mL) at 0° C. and the reaction was stirred at r.t for 4 h. The reaction was quenched with ice, extracted in to ethyl acetate. The organic layer was washed with ice cold water, brine solution and dried over sodium sulfate. The organic layer was then evaporated, the crude was purified on combiflash MPLC using 2.5% ethyl acetate in hexanes as eluent to afford 5-bromo-2-((4'-fluoro-2-methyl-[1,1'-biphenyl]-3-yl)methoxy)-4-methoxypyrimidine as white solid (A2, Yield; 0.8 g, 86%). $^1$H NMR (400 MHz, CDCl$_3$) δ ppm: 2.17 (s, 3H), 3.97 (s, 3H), 5.45 (s, 2H), 7.18 (d, J=7.2 Hz, 1H), 7.22-7.27 (m, 3H), 7.31-7.35 (m, 2H), 7.42 (d, J=7.6 Hz, 1H), 8.51 (s, 1H).

Step 3: Preparation of 2-((4'-fluoro-2-methyl-[1,1'-biphenyl]-3-yl)methoxy)-4-methoxypyrimidine-5-carbaldehyde (A3)

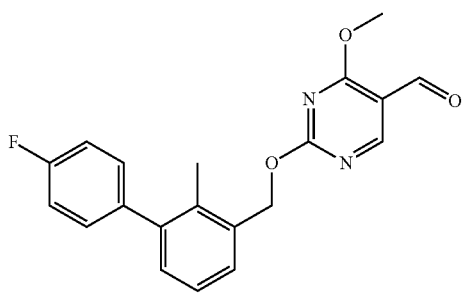

A3

To a stirred solution of 5-bromo-2-((4'-fluoro-2-methyl-[1,1'-biphenyl]-3-yl)methoxy)-4-methoxypyrimidine (A2, 0.3 g, 0.74 mmol) in THF (5 mL) at −78° C. was added n-BuLi (1.2 M solution in hexane, 0.61 mL, 0.74 mmol) and stirred at −78° C. for 10 mins. The reaction turned in to dark brown and the anion generated was quenched with DMF (0.15 mL, 1.48 mmol). The reaction was allowed to come to 0° C., quenched with saturated NH$_4$Cl solution (3 mL). The reaction was diluted with ethyl acetate (20 mL) and the organic layer was separated. The organic layer was dried over sodium sulfate, concentrated to get the crude residue which was purified on combiflash MPLC using 10% ethyl acetate in hexanes as eluent to afford 2-((4'-fluoro-2-methyl-[1,1'-biphenyl]-3-yl)methoxy)-4-methoxypyrimidine-5-carbaldehyde as colorless viscous liquid (A3, yield: 0.12 g, 46%). LCMS (ES) m/z=353.1 [M+H]+; $^1$H NMR (400 MHz, DMSO-d$_6$) δ ppm: 2.19 (s, 3H), 4.04 (s, 3H), 5.56 (s, 2H), 7.20 (d, J=7.6 Hz, 1H), 7.23-7.29 (m, 3H), 7.32-7.35 (m, 2H), 7.45 (d, J=7.6 Hz, 1H), 8.78 (s, 1H), 10.03 (s, 1H).

Step 4: Preparation of N-(2-(((2-((4'-fluoro-2-methyl-[1,1'-biphenyl]-3-yl)methoxy)-4-methoxypyrimidin-5-yl)methyl)amino)ethyl)acetamide (Compound-1)

Compound-1

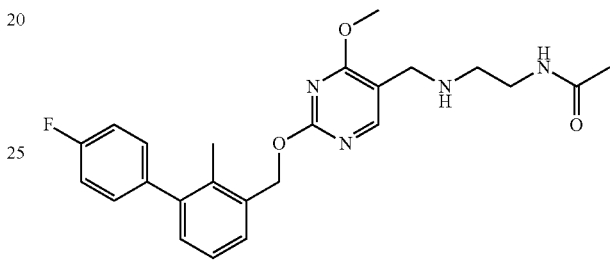

To a solution of 2-((4'-fluoro-2-methyl-[1,1'-biphenyl]-3-yl)methoxy)-4-methoxypyrimidine-5-carbaldehyde (A3, 0.12 g, 0.34 mmol) in MeOH (2 mL) and DMF (2 mL) at 0° C. were added N-(2-aminoethyl)acetamide (A4, 0.2 g, 2.04 mmol) and acetic acid (0.05 mL) simultaneously and the reaction was stirred at r.t for 1 h. The reaction mixture was cooled to 0° C., NaCNBH$_3$ (0.065 g, 1.02 mmol) was added and the reaction was stirred at r.t for 16 h. the reaction mixture was evaporated, the crude was taken in DCM (15 mL) and washed with water and brine solution. The organic layer was dried over sodium sulfate, concentrated to get the crude residue which was purified on combiflash MPLC using 7% methanol in dichloromethane as eluent to afford N-(2-(((2-((4'-fluoro-2-methyl-[1,1'-biphenyl]-3-yl)methoxy)-4-methoxypyrimidin-5-yl)methyl)amino)ethyl)acetamide (Compound-1) as viscous solid (Yield: 0.06 g, 41%). LCMS (ES) m/z=439.2 [M+H]$^+$; $^1$H NMR (400 MHz, DMSO-d$_6$) δ ppm: 1.78 (s, 3H), 2.18 (s, 3H), 2.61-2.69 (m, 1H), 3.16 (d, J=5.6 Hz, 2H), 3.70 (bs, 2H), 3.92 (s, 3H), 5.43 (s, 2H), 7.17 (d, J=6.8 Hz, 1H), 7.23-7.27 (m, 3H), 7.31-7.35 (m, 2H), 7.43 (d, J=7.2 Hz, 1H), 7.82 (bs, 1H), 8.27 (s, 1H); HPLC @ 280 nm, 98.33%.

Synthesis of N-((4-ethoxy-2-((2-methyl-[1,1'-biphenyl]-3-yl)methoxy)pyrimidin-5-yl)methyl)-N-methyl glycine (Compound-2)

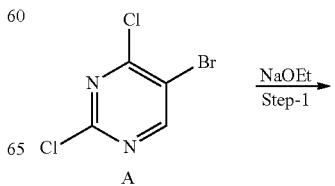

A

-continued

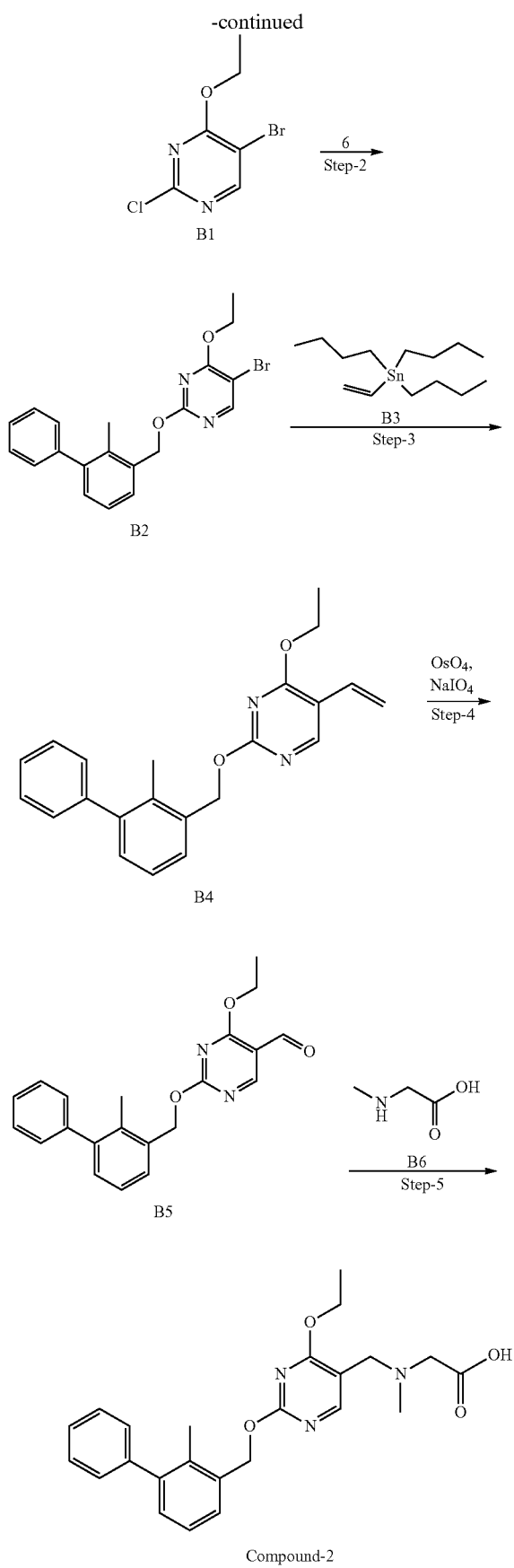

Step 1: Preparation of 5-bromo-2-chloro-4-ethoxypyrimidine (B1)

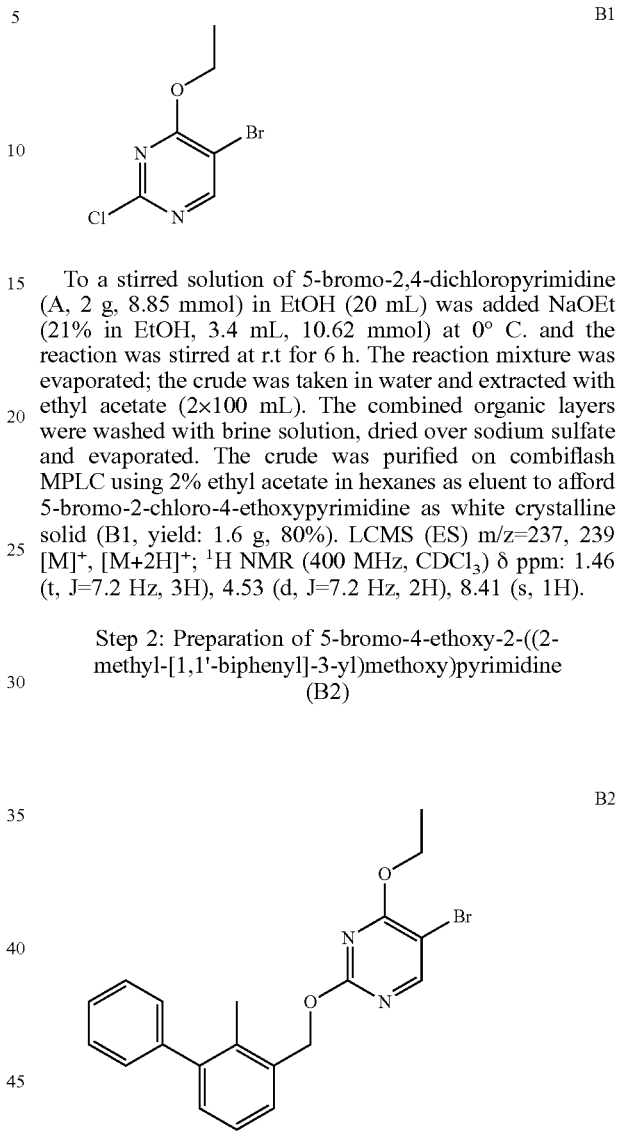

To a stirred solution of 5-bromo-2,4-dichloropyrimidine (A, 2 g, 8.85 mmol) in EtOH (20 mL) was added NaOEt (21% in EtOH, 3.4 mL, 10.62 mmol) at 0° C. and the reaction was stirred at r.t for 6 h. The reaction mixture was evaporated; the crude was taken in water and extracted with ethyl acetate (2×100 mL). The combined organic layers were washed with brine solution, dried over sodium sulfate and evaporated. The crude was purified on combiflash MPLC using 2% ethyl acetate in hexanes as eluent to afford 5-bromo-2-chloro-4-ethoxypyrimidine as white crystalline solid (B1, yield: 1.6 g, 80%). LCMS (ES) m/z=237, 239 [M]$^+$, [M+2H]$^+$; $^1$H NMR (400 MHz, CDCl$_3$) δ ppm: 1.46 (t, J=7.2 Hz, 3H), 4.53 (d, J=7.2 Hz, 2H), 8.41 (s, 1H).

Step 2: Preparation of 5-bromo-4-ethoxy-2-((2-methyl-[1,1'-biphenyl]-3-yl)methoxy)pyrimidine (B2)

To a stirred solution of (2-methyl-[1,1'-biphenyl]-3-yl) methanol (6, 0.83 g, 4.21 mmol) in THF (20 mL) was added 60% NaH in mineral oil (0.36 g, 8.42 mmol) at 0° C. and the reaction mixture was stirred at that temperature for 0.5 h. To the reaction mixture was then added 5-bromo-2-chloro-4-ethoxypyrimidine (B1, 1.0 g, 4.21 mmol) in THF (5 mL) at 0° C. and the reaction mixture was stirred at r.t for 4 h. The reaction mixture was quenched with ice, extracted in to ethyl acetate. The organic layers were washed with ice cold water, brine solution and dried over sodium sulfate. The organic layer was then evaporated, the crude was purified on combiflash MPLC using 2% ethyl acetate in hexanes as eluent to afford 5-bromo-4-ethoxy-2-((2-methyl-[1,1'-biphenyl]-3-yl) methoxy)pyrimidine as white solid (B2, Yield: 0.6 g, 32%). LCMS (ES) m/z=399, 401 [M+2H]$^+$; $^1$H NMR (400 MHz, CDCl$_3$) δ ppm: 1.44 (t, J=7.6 Hz, 3H), 2.27 (s, 3H), 4.50 (q, J=7.2 Hz, 2H), 5.44 (s, 2H), 7.21-7.23 (m, 2H), 7.29 (d, J=7.2 Hz, 2H), 7.32-7.35 (m, 1H), 7.39-7.44 (m, 3H), 8.32 (s, 1H).

Step 3: Preparation of 4-ethoxy-2-((2-methyl-[1,1'-biphenyl]-3-yl)methoxy)-5-vinylpyrimidine (B4)

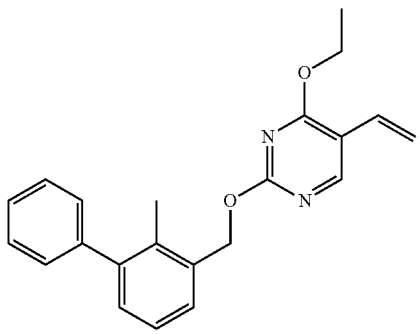

B4

To a stirred solution of 5-bromo-4-ethoxy-2-((2-methyl-[1,1'-biphenyl]-3-yl)methoxy)pyrimidine (B2, 4.4 g, 11.03 mmol) in DMF (60 mL) was added tributyl vinyl tin (B3, 5 mL 16.48 mmol), the reaction mixture was degasified with nitrogen gas for 10 min. Then Pd(PPh$_3$)$_4$ (1.3 g 1.13 mmol) was added and the reaction was heated at 100° C. for 16 h. The reaction was filtered through celite; the filtrate was diluted with water and extracted with ethyl acetate (2×100 mL). The organic layer was then dried over sodium sulfate, evaporated and the crude was purified on combiflash MPLC using 10% ethyl acetate in hexanes as eluent to afford 4-ethoxy-2-((2-methyl-[1,1'-biphenyl]-3-yl)methoxy)-5-vinylpyrimidine as yellow oily liquid (B4, Yield: 1.7 g, 32%). LCMS (ES) m/z=347.1 [M+H]$^+$; $^1$H NMR (400 MHz, DMSO-d$_6$) δ ppm: 1.34 (t, J=7.2 Hz, 3H), 2.18 (s, 3H), 4.39-4.45 (m, 2H), 5.27-5.30 (m, 1H), 5.44 (s, 2H), 5.85-5.90 (m, 1H), 6.57-6.65 (m, 1H), 7.16-7.30 (m, 4H), 7.34-7.46 (m, 4H), 8.46 (s, 1H).

Step 4: Preparation of 4-ethoxy-2-((2-methyl-[1,1'-biphenyl]-3-yl)methoxy)pyrimidine-5-carbaldehyde (B5)

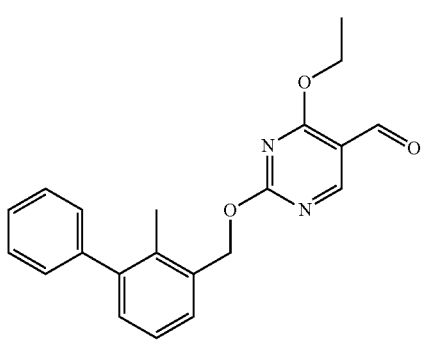

B5

To a stirred solution of 4-ethoxy-2-((2-methyl-[1,1'-biphenyl]-3-yl)methoxy)-5-vinylpyrimidine (B4, 2.2 g, 6.36 mmol) in THF (40 mL) and water (20 mL), was added OsO$_4$ (4 mL, 0.63 mmol) and stirred for 15 min, followed by the addition of NaIO$_4$ (2.8 g, 13.14 mmol) at 0° C. The reaction was allowed to stir at room temperature for 16 h. The reaction mixture was diluted with water and extracted with ethyl acetate (2×100 mL). The organic layer was then dried over sodium sulfate, evaporated and the crude was purified on combiflash MPLC using 13% ethyl acetate in hexanes as eluent to afford 4-ethoxy-2-((2-methyl-[1,1'-biphenyl]-3-yl)methoxy)pyrimidine-5-carbaldehyde as off-white solid (B5, Yield: 1.1 g, 50%). LCMS (ES) m/z=349.3 [M+H]$^+$; $^1$H NMR (400 MHz, DMSO-d$_6$) δ ppm: 1.36 (t, J=7.2 Hz, 3H), 2.20 (s, 3H), 4.50-4.55 (m, 2H), 5.55 (s, 2H), 7.19-7.30 (m, 4H), 7.35-7.45 (m, 4H), 8.77 (s, 1H), 10.03 (s, 1H).

Step 5: Preparation of N-((4-ethoxy-2-((2-methyl-[1,1'-biphenyl]-3-yl)methoxy)pyrimidin-5-yl)methyl)-N-methylglycine (Compound-2)

To a solution of 4-ethoxy-2-((2-methyl-[1,1'-biphenyl]-3-yl)methoxy)pyrimidine-5-carbaldehyde (B5, 0.15 g, 0.43 mmol) in MeOH (2 mL) and DMF (2 mL) at 0° C. was added methylglycine (B6, 0.12 g, 1.35 mmol) and acetic acid (0.1 mL) simultaneously and the reaction was stirred at r.t for 1 h. The reaction mixture was cooled to 0° C., NaCNBH$_3$ (0.08 g, 1.29 mmol) was added and the reaction mixture was stirred at r.t for 16 h. The reaction mixture was evaporated; the crude was taken in DCM (15 mL) and washed with water and brine solution. The organic layer was dried over sodium sulfate, concentrated to get the crude residue which was purified on combiflash MPLC using 10% methanol in dichloromethane as eluent to afford N-((4-ethoxy-2-((2-methyl-[1,1'-biphenyl]-3-yl)methoxy)pyrimidin-5-yl)methyl)-N-methylglycine (Compound-2) as viscous solid (Yield: 0.035 g, 19%). LCMS (ES) m/z=422.2 [M+H]$^+$; $^1$H NMR (400 MHz, DMSO-d$_6$) δ ppm: 1.22-1.31 (m, 3H), 2.18 (s, 3H), 2.28 (s, 3H), 3.15 (s, 2H), 3.59 (s, 3H), 4.34-4.39 (m, 2H), 5.41 (s, 2H), 7.16-7.18 (m, 1H), 7.23-7.30 (m, 3H) 7.36-7.48 (m, 4H), 8.23 (s, 1H): HPLC @ 254 nm, 99.38%.

Synthesis of N-((4-ethoxy-2-((2-methyl-[1,1'-biphenyl]-3-yl)methoxy)pyrimidin-5-yl)methyl)-N-methyl glycine (Compound-3)

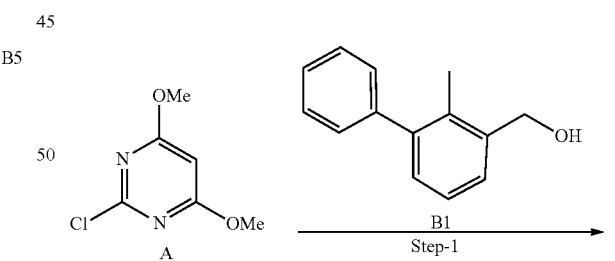

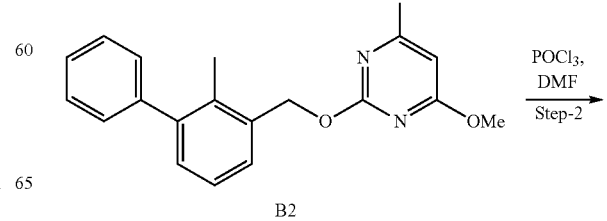

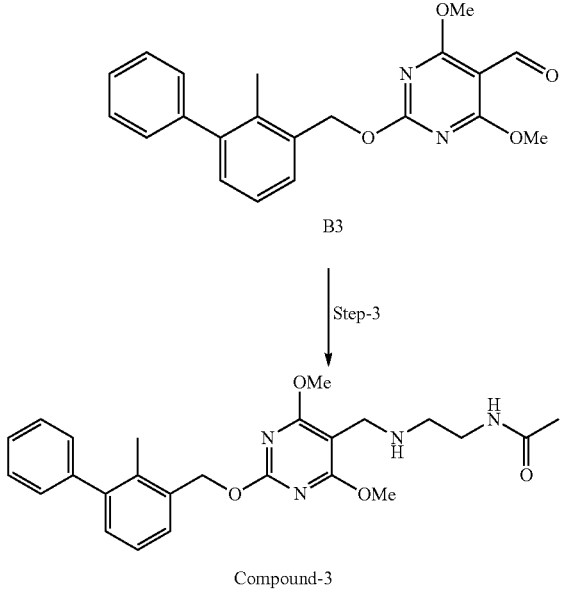

Compound-3

Step 1: Preparation of 4,6-dimethoxy-2-((2-methyl-[1,1'-biphenyl]-3-yl)methoxy)pyrimidine To a stirred solution of (2-methyl-[1,1'-biphenyl]-3-yl)methanol (1 g, 5.05 mmol) in DMF (15 mL) was added NaH (0.24 g, 6.06 mmol) at 0° C. and the reaction was stirred for 30 min at room temperature. To the reaction was then added 2-chloro-4,6-dimethoxypyrimidine (0.97 g, 5.55 mmol) in DMF (5 mL) at 0° C. and the reaction mixture was stirred at room temperature for 2 h. The reaction mixture was quenched with ice, extracted with ethyl acetate. The organic layer was washed with ice cold water, brine solution and dried over sodium sulphate. The organic layer was then evaporated, the crude was purified on combiflash MPLC using 3% ethyl acetate in hexane as eluent to afford 4,6-dimethoxy-2-((2-methyl-[1,1'-biphenyl]-3-yl)methoxy)pyrimidine as colorless viscous oil (1.4 g, 83%). LCMS (ES) m/z=337 [M+H]$^+$; $^1$H NMR (400 MHz, DMSO-d$_6$) δ ppm 2.16 (s, 3H), 3.86 (s, 6H), 5.42 (s, 2H), 5.87 (s, 1H), 7.18 (d, J=7.2 Hz, 1H), 7.24-7.30 (m, 3H), 7.36-7.37 (m, 1H), 7.39-7.43 (m, 3H).

Step 2: Preparation of 4,6-dimethoxy-2-((2-methyl-[1,1'-biphenyl]-3-yl)methoxy)pyrimidine-5-carbaldehyde To a stirred solution of 4,6-dimethoxy-2-((2-methyl-[1,1'-biphenyl]-3-yl)methoxy)pyrimidine (0.8 g, 2.38 mmol) in DMF (6 mL) was added POCl$_3$ (5 mL 16.48 mmol) the reaction was degasified with N$_2$ gas for 10 min, Pd(Pph$_3$)$_4$ (0.7 mL, 7.82 mmol) was added and the reaction mixture was stirred at room temperature for 16 h. The reaction mixture was poured onto ice, basified with saturated NaHCO$_3$ solution and solid precipitated was filtered and dried under vacuum to afford the crude product. The crude was purified on combiflash MPLC using 20% ethyl acetate in hexanes as eluent to give 4,6-dimethoxy-2-((2-methyl-[1,1'-biphenyl]-3-yl)methoxy)pyrimidine-5-carbaldehyde as white solid (0.38 g, 44%). LCMS (ES) m/z=365.1 [M+H]$^+$; $^1$H NMR (400 MHz, DMSO-d$_6$) δ ppm 2.21 (s, 3H), 3.99 (s, 6H), 5.55 (s, 2H), 7.20 (d, J=7.2 Hz, 1H), 7.26-7.30 (m, 3H), 7.34-7.38 (m, 1H), 7.42-7.47 (m, 3H), 10.05 (s, 1H).

Step 3: Preparation of N-(2-(((4,6-dimethoxy-2-((2-methyl-[1,1'-biphenyl]-3-yl)methoxy)pyrimidin-5-yl)methyl)amino)ethyl)acetamide To a solution of 4,6-dimethoxy-2-((2-methyl-[1,1'-biphenyl]-3-yl)methoxy)pyrimidine-5-carbaldehyde (0.19 g, 0.52 mmol) in MeOH (3 mL) and DMF 3 mL) at 0° C. were added N-(2-aminoethyl)acetamide (0.203 g, 1.56 mmol) and acetic acid (0.1 mL) simultaneously and the reaction mixture was stirred at room temperature for 1 h. The reaction mixture was cooled to 0° C., NaCNBH$_3$ (0.09 g, 1.56 mmol) was added and the reaction mixture was stirred at room temperature for 16 h. The reaction mixture was evaporated, the crude was taken in DCM (15 mL) and washed with water and brine solution. The organic layer was dried over sodium sulphate, concentrated to give the crude residue which was purified on combiflash MPLC using 10% methanol in dichloromethane as eluent to afford N-(2-(((4,6-dimethoxy-2-((2-methyl-[1,1'-biphenyl]-3-yl)methoxy)pyrimidin-5-yl)methyl)amino)ethyl) acetamide as off-white solid (0.05 g, 23%). LCMS (ES) m/z=451.2 [M+H]$^+$; $^1$H NMR (400 MHz, DMSO-d$_6$) δ ppm 1.76 (s, 3H), 2.20 (s, 3H), 3.14 (s, 1H), 2.52-2.54 (m, 2H), 3.10 (q, J=6 Hz, 2H), 3.58 (s, 2H), 3.89 (s, 6H), 5.44 (s, 2H), 7.17 (d, J=7.2 Hz, 1H), 7.23-7.29 (m, 3H), 7.33-7.37 (m, 1H), 7.43 (t, J=7.6 Hz, 3H), 7.76 (bs, 1H): HPLC @ 254 nm, 98.47%.

Synthesis of (1R,6R)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid (Compound-4) and (1S,6R)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid (Compound-5)

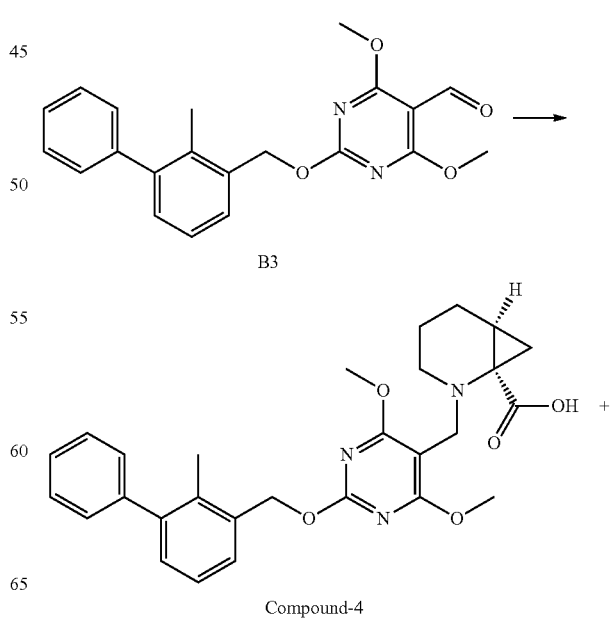

Compound-4

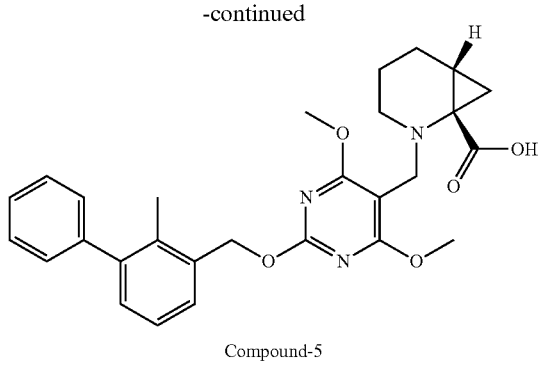

Compound-5

To a solution of 4,6-dimethoxy-2-((2-methyl-[1,1'-biphenyl]-3-yl)methoxy)pyrimidine-5-carbaldehyde (0.2 g, 0.54 mmol) in MeOH (4 mL) and DMF (4 mL), rac-(1R,6S)-2-azabicyclo[4.1.0]heptane-1-carboxylic acid hydrochloride (97 mg, 0.54 mmol), triethylamine (81 mg, 0.81 mmol) were added and stirred for 5 minutes. To this mixture, acetic acid (0.1 mL) was added and the reaction was stirred at room temperature for 2 h. To this reaction mixture, NaCNBH$_3$ (101 mg, 1.6 mmol) was added and continued stirring at r.t for 16 h. The reaction mixture was diluted with water (100 mL) and extracted with 10% MeOH in DCM (2×150 mL). The combined organic layer was washed with water (40 mL) and brine solution (40 mL), dried over sodium sulphate and concentrated to get the crude residue which was purified on combiflash chromatography using 8% methanol in dichloromethane as eluent to afford rac-(1R,6S)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid as light white solid (yield: 165 mg, 62%). The racemic mixture was purified by Supercritical Fluid Chromatography (Waters SFC 200q, column: CHIRALCEL OJ-H (250*21 mm), 5 μm) using CO$_2$ and 0.2% TEA in MeOH as mobile phase (method: 60 gm (CO$_2$)_15% (Co-Solvent)_100bar (ABPR)) with a loading of 5.0 mg/injection in a 5 minutes stagged cycle time. Two peaks were collected at 6.8 minutes (Peak-1, isomer-1) and 8.3 minutes (Peak-2, isomer-2) and concentrated to give compound-4 (73 mg) and compound-5 (82 mg).

Peak-1: (1R,6R)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid (Compound-4)

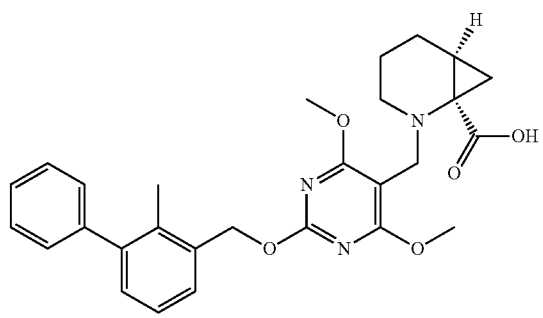 [SMILES: COc1nc(OCc2cccc(-c3ccccc3)c2C)nc(OC)c1CN1CCC[C@H]2C[C@]21C(=O)O]

LCMS (ES) m/z=490.39 [M+H]$^+$; $^1$H NMR (400 MHz, DMSO-d$_6$): δ 1.09-1.18 (m, 1H), 1.26-1.22 (m, 2H), 1.35-1.36 (m, 1H), 1.51-1.59 (m, 1H), 1.77-1.83 (m, 2H), 2.22 (s, 3H), 2.49 (m, 2H), 3.36 (m, 1H), 3.65 (m, 1H), 3.92 (s, 6H), 5.46 (s, 2H), 7.19-7.21 (m, 1H), 7.26-7.32 (m, 3H), 7.35-7.39 (m, 1H), 7.44-7.48 (m, 3H), 11.82 (bs, 1H). HPLC @214 nm, 98.96%.

Peak-2: (1S,6R)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid (Compound-5)

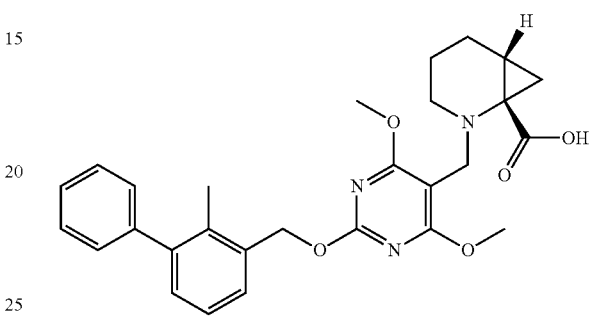

LCMS (ES) m/z=490.39 [M+H]$^+$; $^1$H NMR (400 MHz, DMSO-d$_6$): δ 1.15-1.26 (m, 3H), 1.35-1.36 (m, 1H), 1.51-1.59 (m, 1H), 1.77-1.83 (m, 2H), 2.22 (s, 3H), 2.49 (m, 2H), 3.36 (m, 1H), 3.65 (m, 1H), 3.92 (s, 6H), 5.46 (s, 2H), 7.19-7.21 (m, 1H), 7.26-7.32 (m, 3H), 7.35-7.39 (m, 1H), 7.44-7.48 (m, 3H), 11.82 (bs, 1H). HPLC (214 nm, 99.23%.

Synthesis of N-(2-(((4,6-diethoxy-2-((2-methyl-[1,1'-biphenyl]-3-yl)methoxy)pyrimidin-5-yl)methyl)amino)ethyl) acetamide (Compound-6)

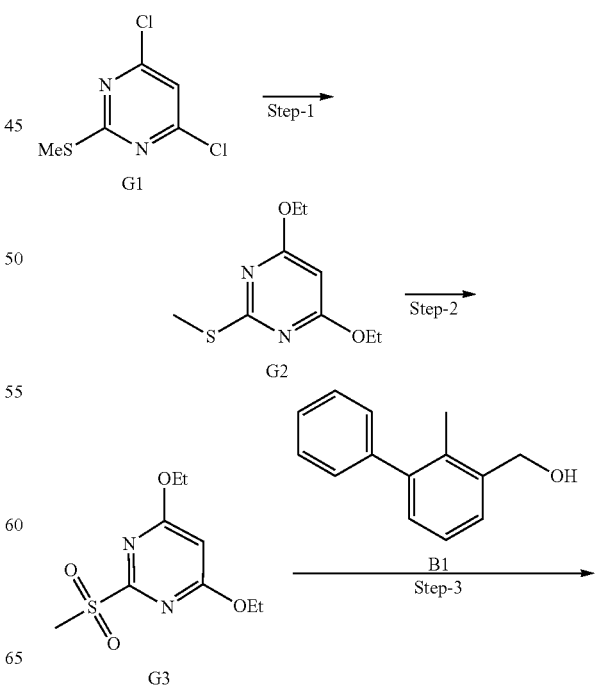

-continued

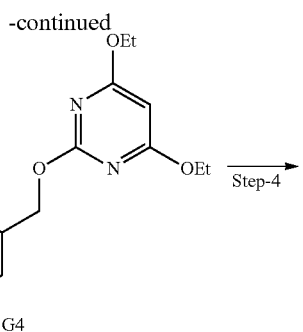

G4

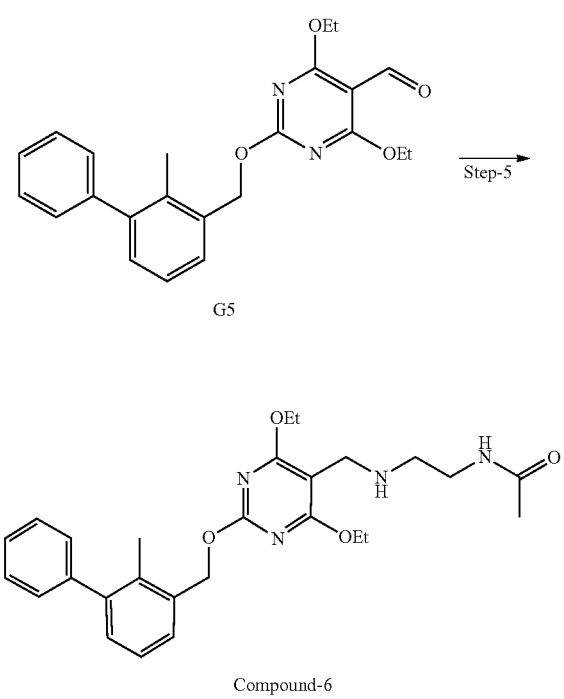

G5

Compound-6

Step 1: Preparation of
4,6-diethoxy-2-(methylthio)pyrimidine

To a stirred solution of 4,6-dichloro-2-(methylthio)pyrimidine (5 g, 25 mmol) in EtOH (30 mL) at 0° C., NaOEt (21% in EtOH, 20 mL, 56 mmol) was added and the reaction was stirred at room temperature for 6 h. The reaction mixture was evaporated and the crude was taken in water (100 mL) and extracted with ethyl acetate (2×300 mL). The combined organic layers were washed with brine solution, dried over sodium sulfate and evaporated to afford 4,6-diethoxy-2-(methylthio)pyrimidine as white solid (yield: 4.7 g, 85.5%). $^1$H NMR (400 MHz, CDCl$_3$): δ 1.37 (d, J=7.04 Hz, 6H), 2.51 (s, 3H), 4.32-4.37 (t, J=7.04 Hz, 4H), 5.67 (s, 1H).

Step 2: Preparation of
4,6-diethoxy-2-(methylsulfonyl)pyrimidine

To a stirred solution of 4,6-diethoxy-2-(methylthio)pyrimidine (51 g, 4 mmol) in DCM (30 mL) at 0° C., mCPBA (4.31 g, 24 mmol) was added and the reaction mixture was stirred at room temperature for 20 h. The reaction mixture was quenched with ice cold water (30 mL) and extracted with DCM (3×100 mL). The organic layer was washed with saturated sodium bicarbonate solution, and brine solution, dried over sodium sulphate and concentrated under vacuum. The crude product was purified by flash chromatography using 8% ethyl acetate in hexane as eluent to afford 4,6-diethoxy-2-(methylsulfonyl)pyrimidine as white solid (yield: 1 g, 81%). $^1$H NMR (400 MHz, CDCl$_3$): δ 1.41 (d, J=7.08 Hz, 6H), 3.30 (s, 3H), 4.32-4.48 (t, J=7.12 Hz, 4H), 6.12 (s, 1H).

Step 3: Preparation of 4,6-diethoxy-2-((2-methyl-[1,1'-biphenyl]-3-yl) methoxy)pyrimidine To a stirred solution of 4,6-diethoxy-2-(methylsulfonyl) pyrimidine (4.5 g, 18.2 mmol) in DMF (40 mL), (2-methyl-[1,1'-biphenyl]-3-yl)methanol (3.62 g, 18.2 mmol) and potassium carbonate (2.53 g, 18.2 mmol) were added and the reaction mixture was heated at 80° C. for 8 h. The reaction mixture was diluted with water (50 mL) and extracted with ethyl acetate (2×100 mL). The organic layer was then dried over sodium sulfate, evaporated to give crude product. The crude product was purified by flash chromatography using 10% ethyl acetate in hexane as eluent to afford 4,6-diethoxy-2-((2-methyl-[1,1'-biphenyl]-3-yl)methoxy)pyrimidine as white solid (yield: 3.5 g, 52%). LCMS (ES) m/z=365.21 [M+H]$^+$, purity @ 214 nm, 89.77%. $^1$H NMR (400 MHz, DMSO-d$_6$) δ ppm: 1.30 (m, 6H), 2.20 (s, 3H), 4.29-4.33 (m, 4H), 5.40 (s, 2H), 7.20 (m, 1H), 7.25-7.30 (m, 3H), 7.39 (m, 1H), 7.44-7.48 (m, 4H).

Step 4: Preparation of 4,6-diethoxy-2-((2-methyl-[1,1'-biphenyl]-3-yl) methoxy)pyrimidine-5-carbaldehyde A solution of phosphoryl chloride (5 ml) in DMF (10 mL) at 0° C. under nitrogen atmosphere was stirred for 1 h. A solution of 4,6-diethoxy-2-((2-methyl-[1,1'-biphenyl]-3-yl) methoxy)pyrimidine (3.5 g, 9.6 mmol) in DCE (30 mL) was added drop wise. Then the reaction mixture was stirred at room temperature for 30 min after that it was heated at 80° C. for 3 h. After completion of reaction, the reaction mixture was concentrated in vacuo and diluted with DCM (50 mL). The organic layer was washed with water (25 mL), brine solution, dried over sodium sulphate, filtered and concentrated in vacuo to give crude product which was purified by silica gel chromatography (10% EtOAc in Hexane) to afford 4,6-diethoxy-2-((2-methyl-[1,1'-biphenyl]-3-yl)methoxy) pyrimidine-5-carbaldehyde as white solid (yield: 1.5 g, 39%). $^1$H NMR (400 MHz, DMSO-d$_6$): δ 1.34 (t, J=7.08 Hz, 6H), 2.22 (s, 3H), 4.46-4.51 (m, 4H), 5.52 (s, 2H), 7.21 (m, 1H), 7.26-7.30 (m, 3H), 7.40 (m, 1H), 7.44-7.48 (m, 3H), 10.07 (s, 1H).

Step 5: Preparation of N-(2-(((4,6-diethoxy-2-((2-methyl-[1,1'-biphenyl]-3-yl)methoxy)pyrimidin-5-yl)methyl)amino)ethyl)acetamide To a solution of 4,6-diethoxy-2-((2-methyl-[1,1'-biphenyl]-3-yl)methoxy)pyrimidine-5-carbaldehyde (0.15 g, 0.38 mmol) in MeOH (3 mL) and DMF (3 mL) at room temperature, N-(2-aminoethyl)acetamide (60 mg, 0.57 mmol) and acetic acid (0.1 mL) were added simultaneously and the reaction mixture was stirred at room temperature for 2 h. To this reaction mixture, NaCNBH$_3$ (0.08 g, 1.29 mmol) was added and stirred at room temperature for 16 h. The reaction mixture was diluted with water (10 mL) and extracted in DCM:MeOH (9:1) (3×25 mL). The organic layer was washed with water, brine solution, dried over sodium sulphate and concentrated to give the crude residue which was purified on flash chromatography using 8% methanol in dichloromethane as eluent to afford N-(2-(((4,6-diethoxy-2-((2-methyl-[1,1'-biphenyl]-3-yl)methoxy)pyrimidin-5-yl)methyl)amino)ethyl)acetamide as white solid (Yield: 0.091 g, 49%). LCMS (ES) m/z=479.24 [M+H]⁺; ¹H NMR (400 MHz, DMSO-d₆): δ 1.19-1.30 (t, 6H), 1.82 (s, 3H), 2.19 (s, 3H), 2.93 (m, 2H), 3.30 (m, 2H), 3.89 (s, 2H), 4.35-4.40 (q, 4H), 5.43 (s, 2H), 7.21 (m, 1H), 7.26-7.30 (m, 3H), 7.40 (m, 1H), 7.44-7.48 (m, 3H), 8.03 (s, 1H), 8.23 (bs, 1H). HPLC @ 214 nm, 98.19%.

Synthesis of (S)-1-((4-methoxy-2-((2-methyl-[1,1'-biphenyl]-3-yl) methoxy)pyrimidin-5-yl)methyl) piperidine-2-carboxylic acid (Compound-7)

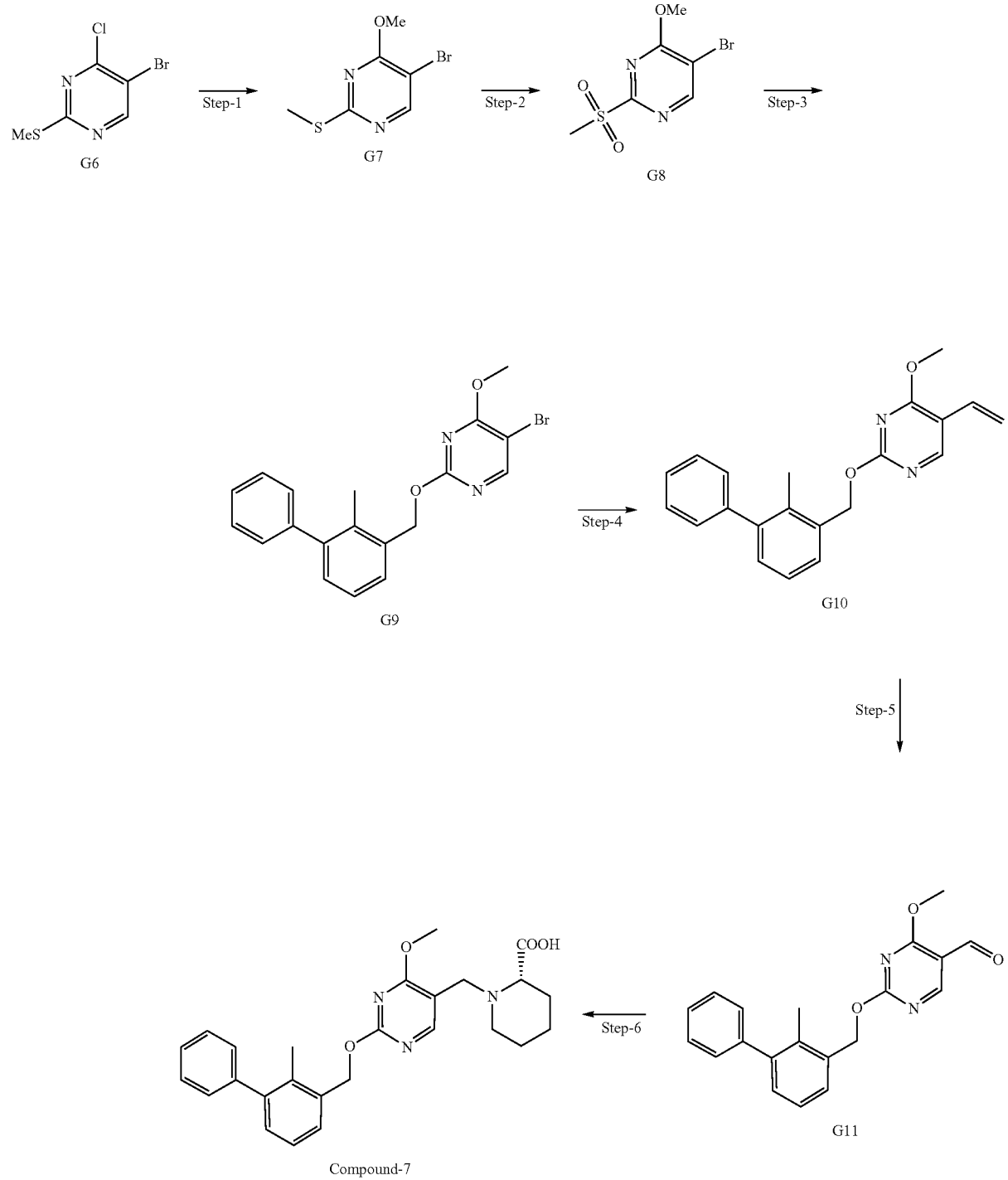

Compound-7

Step 1: Synthesis of 5-bromo-4-methoxy-2-(methylthio)pyrimidine

To a stirred solution of 5-bromo-4-chloro-2-(methylthio)pyrimidine (25 g, 105 mmol) in methanol (200 mL) at 0° C., NaOMe (21% in MeOH, 30 mL, 136 mmol) was added and the reaction mixture was stirred at room temperature for 8 h. After completion of the reaction, the reaction mixture was concentrated under vacuum. The crude product was diluted with water (500 mL) and extracted with ethyl acetate (2×900 mL). The combined organic layer was washed with brine solution (100 mL), dried over sodium sulfate and evaporated to afford 5-bromo-4-methoxy-2-(methylthio)pyrimidine as white solid (Yield: 22 g, 89%). LCMS (ES) m/z=235.19 $[M+H]^+$ $^1$H NMR (400 MHz, CDCl$_3$): δ 2.54 (s, 3H), 4.05 (s, 3H), 8.34 (s, 1H).

Step 2: Synthesis of 5-bromo-4-methoxy-2-(methylthio)pyrimidine

To a stirred solution of 5-bromo-4-methoxy-2-(methylthio)pyrimidine (140 g, 595 mmol) in DCM (2 L) at 0° C., meta-chloroperbenzoic acid (308 g, 1780 mmol) was added and the reaction mixture was stirred at room temperature for 20 h. The reaction mixture was quenched with ice cold water (1 L) and extracted with DCM (3×2 L). The combined organic layer was washed with saturated sodium bicarbonate solution (1 L), brine solution (500 mL) and dried over sodium sulfate. The organic layer was then evaporated and the crude product was purified on combiflash chromatography using 8% ethyl acetate in hexane as eluent to afford 5-bromo-4-methoxy-2-(methylsulfonyl)pyrimidine as white solid (yield: 72 g, 45.38%). LCMS (ES) m/z=267.25 $[M+H]^+$ $^1$H NMR (400 MHz, DMSO-d$_6$): δ 3.40 (s, 3H), 4.11 (s, 3H), 9.02 (s, 1H).

Step 3: Synthesis of 5-bromo-4-methoxy-2-((2-methyl-[1,1'-biphenyl]-3-yl)methoxy)pyrimidine To a stirred solution of 5-bromo-4-methoxy-2-(methylsulfonyl)pyrimidine (80 g, 299 mmol) in DMF (400 mL), (2-methyl-[1,1'-biphenyl]-3-yl)methanol (59.49 g, 300 m mol) and potassium carbonate (123 g, 900 mmol) were added and the reaction mixture was heated at 80° C. for 12 h. After completion of the reaction, the reaction mixture was diluted with water (1 L) and extracted with ethyl acetate (2×2 L). The combined organic layer was then dried over sodium sulfate, filtered and evaporated to give crude product. The crude product was purified on combiflash chromatography using 10% ethyl acetate in hexane as eluent to afford 5-bromo-4-methoxy-2-((2-methyl-[1,1'-biphenyl]-3-yl)methoxy)pyrimidine as white solid (yield: 47 g, 40.8%). LCMS (ES) m/z=385.37 $[M+H]^+$ $^1$H NMR (400 MHz, CDCl$_3$): δ 2.28 (s, 3H), 4.05 (s, 3H), 5.46 (s, 2H), 7.21-7.25 (m, 2H), 7.31-7.34 (m, 2H), 7.36-7.39 (m, 1H), 7.41-7.46 (m, 3H), 8.33 (s, 1H).

Step 4: Synthesis of 4-methoxy-2-((2-methyl-[1,1'-biphenyl]-3-yl)methoxy)-5-vinylpyrimidine To a stirred solution of 5-bromo-4-methoxy-2-((2-methyl-[1,1'-biphenyl]-3-yl) methoxy)pyrimidine (48 g, 124 mmol) in DMF (150 mL), tributyl vinyl tin (71.1 g, 220 mmol) was added and the reaction mixture was degassed with nitrogen gas for 10 min. To this mixture, Pd(PPh$_3$)$_4$ (7.1 g 6.2 mmol) was added and the reaction mixture was heated at 100° C. for 16 h. After completion of the reaction, the reaction mixture was filtered through celite and the filtrate was diluted with water (500 mL) and extracted with ethyl acetate (2×1 L). The combined organic layer was dried over sodium sulfate, evaporated and the crude product was purified on combiflash chromatography using 3% ethyl acetate in hexane as eluent to afford 4-methoxy-2-((2-methyl-[1,1'-biphenyl]-3-yl)methoxy)-5-vinylpyrimidine as yellow oily liquid (yield: 30 g, 72.8%). LCMS (ES) m/z=333.47 $[M+H]^+$ $^1$H NMR (400 MHz, DMSO-d$_6$): δ 2.21 (s, 3H), 3.92 (s, 3H), 5.31 (d, J=11.6 Hz, 1H), 5.55 (s, 2H), 5.89 (d, J=16.6 Hz, 1H), 6.62-6.69 (m, 1H), 7.21-7.31 (m, 4H), 7.37-7.46 (m, 4H), 8.51 (s, 1H).

Step 5: Synthesis of 4-methoxy-2-((2-methyl-[1,1'-biphenyl]-3-yl) methoxy)pyrimidine-5-carbaldehyde To a stirred solution of 4-methoxy-2-((2-methyl-[1,1'-biphenyl]-3-yl)methoxy)-5-vinylpyrimidine (24 g, 72 mmol) in THF (80 mL) and water (80 mL) at 0° C., OsO$_4$ (73 mL, 2.5 wt % solution in tert-butanol, 7.2 mmol) was added and stirred for 15 min. To this mixture, NaIO$_4$ (23 g, 108 mmol) was added and the reaction mixture was allowed to stir at room temperature for 16 h. After completion of the reaction, the reaction mixture was diluted with water (300 mL) and extracted with ethyl acetate (2×800 mL). The organic layer was dried over sodium sulfate, filtered and evaporated to give crude product. The crude product was purified on combiflash chromatography using 12% ethyl acetate in hexane as eluent to afford 4-methoxy-2-((2-methyl-[1,1'-biphenyl]-3-yl) methoxy)pyrimidine-5-carbaldehyde as off-white solid (yield: 18 g, 60%). LCMS (ES) m/z=335.38 $[M+H]^+$ $^1$H NMR (400 MHz, CDCl$_3$): δ 2.29 (s, 3H), 4.13 (s, 3H), 5.58 (s, 2H), 7.24-7.31 (m, 3H), 7.35-7.45 (m, 5H), 8.81 (s, 1H), 10.18 (s, 1H).

Step 6: Synthesis of (S)-1-((4-methoxy-2-((2-methyl-[1,1'-biphenyl]-3-yl)methoxy)pyrimidin-5-yl)methyl)piperidine-2-carboxylic acid To a solution of 4-methoxy-2-((2-methyl-[1,1'-biphenyl]-3-yl) methoxy)pyrimidine-5-carbaldehyde (30 g, 89 mmol) in EtOH (45 mL) and DMF (45 mL), (S)-piperidine-2-carboxylic acid (11.58 g, 89 mmol) and acetic acid (0.3 mL) were added simultaneously and the reaction was stirred at room temperature for 2 h. To this reaction mixture, NaCNBH$_3$ (16.91 g, 269 mmol) was added and continued stirring at room temperature for 16 h. The reaction mixture was diluted with water (100 mL) and extracted in 10% MeOH in DCM (2×150 mL). The combined organic layer was washed with water (40 mL) and brine solution (40 mL), dried over sodium sulphate and concentrated to give crude product (16 g) which was purified on combiflash chromatography using 8% methanol in dichloromethane as eluent to afford (S)-1-((4-methoxy-2-((2-methyl-[1,1'-biphenyl]-3-yl) methoxy)pyrimidin-5-yl)methyl)piperidine-2-carboxylic acid as light yellow solid (yield: 10.5 g, 26.1%). LCMS (ES) m/z=448.24 $[M+H]^+$ and purity @ 214 nm, 99.36%. $^1$H NMR (400 MHz, DMSO-d$_6$): δ 1.35 (m, 1H), 1.46 (m, 3H), 1.70 (m, 2H), 2.20 (m, 4H), 2.89 (m, 1H), 3.07 (br, 1H), 3.55 (d, 1H), 3.66 (d, 1H), 3.90 (s, 3H), 5.43 (s, 2H), 7.21 (m, 1H), 7.26-7.30 (m, 3H), 7.37 (m, 1H), 7.44-7.48 (m, 3H), 8.25 (s, 1H).

Synthesis of (S)-1-((4-((3-cyano-4-fluorobenzyl)oxy)-2-((2-methyl-[1,1'-biphenyl]-3-yl)methoxy)pyrimidin-5-yl)methyl)piperidine-2-carboxylic acid (Compound-8)

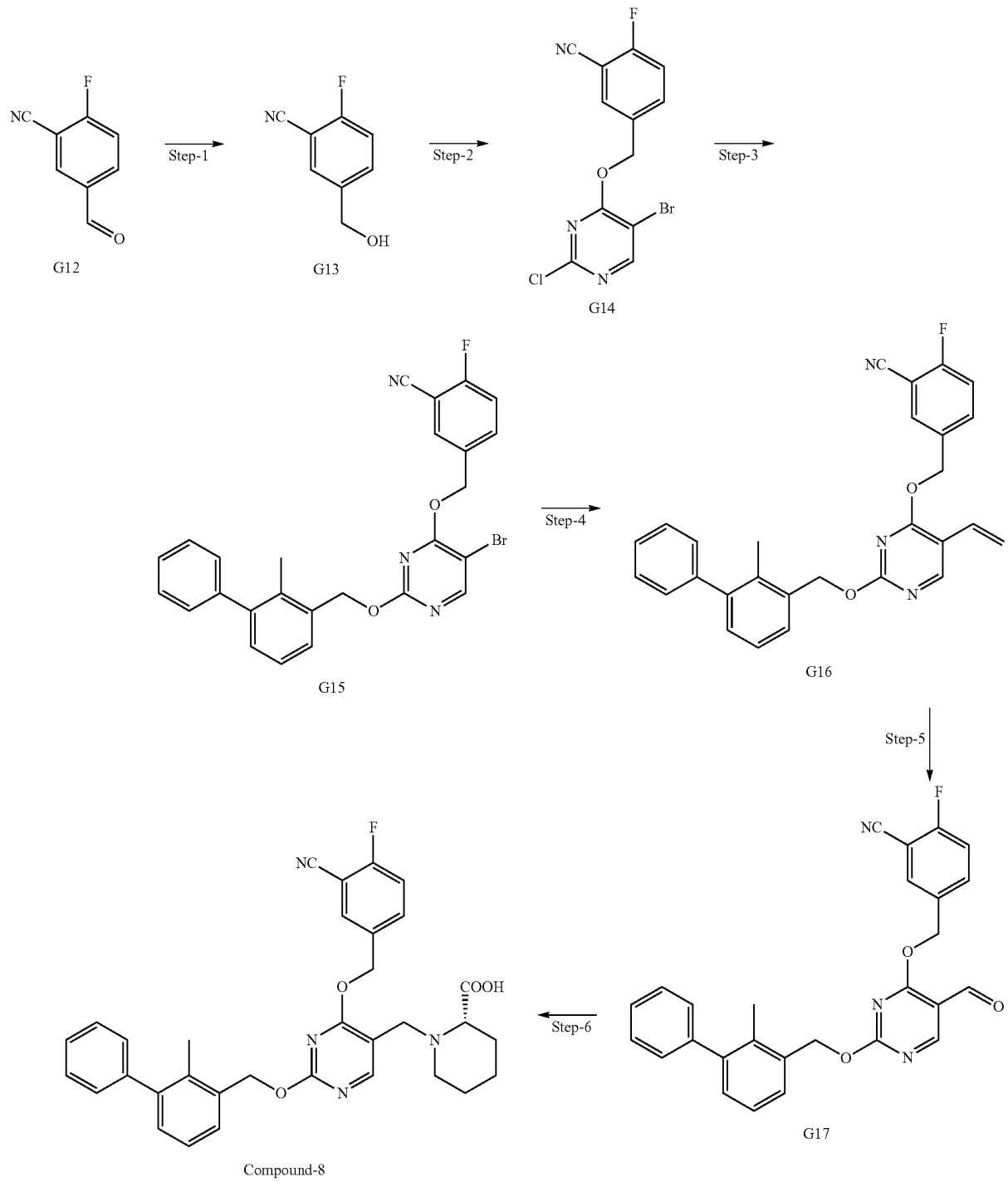

Step 1: Synthesis of 2-fluoro-5-(hydroxymethyl)benzonitrile (2)

To a stirred solution of 2-fluoro-5-formylbenzonitrile (10 g g, 67 mmol) in ethanol (100 mL) at 0° C., sodium borohydride (3.0 g, 80 mmol) was added and continued stirring at 0° C. for 2 h. After TLC showed completion, the reaction mixture was quenched with ice cold water (50 mL) and extracted with DCM (2×50 mL). The organic layer was dried over sodium sulfate and concentrated to obtain 2-fluoro-5-(hydroxymethyl)benzonitrile as white solid (yield: 10 g, 100%). $^1$H NMR (400 MHz, CDCl$_3$): δ 2.33 (s, 1H), 4.69 (s, 2H), 7.21 (s, 1H), 7.57-7.63 (m, 2H).

Step 2: Synthesis of 5-(((5-bromo-2-chloropyrimidin-4-yl)oxy)methyl)-2-fluorobenzonitrile To a stirred solution of 2-fluoro-5-(hydroxymethyl)benzonitrile (5.0 g, 34 mmol) in THF (200 mL) at 0° C., sodium hydride (1.36 g, 60% in mineral oil, 34 mmol) was added and stirred at 0° C. for 1 h. To this mixture, 5-bromo-2,4-dichloropyrimidine (7.5 g, 34 mmol) was added and the reaction mixture was stirred at room temperature for 5 h. After completion, the reaction mixture was quenched with ice cold water (100 mL) and extracted with 10% IPA in chloroform (4×100 mL). The combined organic layer was dried over sodium sulphate and concentrated. The crude was purified by column chromatography (silicagel, 100-200#) using 20% EtOAc in hexane to obtain 5-(((5-bromo-2-chloropyrimidin-4-yl)oxy)methyl)-2-fluorobenzonitrile as white solid (Yield: 4.9 g, 65%). LCMS (ES) m/z=342.19 [M+H]$^+$; $^1$H NMR (400 MHz, DMSO-d$_6$): δ 5.51 (s, 2H), 7.59 (m, 1H), 7.91 (m, 1H), 8.06 (m, 1H), 8.78 (bs, 1H).

Step 3: Synthesis of 5-(((5-bromo-2-((2-methyl-[1,1'-biphenyl]-3-yl)methoxy)pyrimidin-4-yl)oxy)methyl)-2-fluorobenzonitrile To a stirred solution of (2-methyl-[1,1'-biphenyl]-3-yl)methanol (2.7 g, 14 mmol) in DMF (100 mL) at 0° C., sodium hydride (0.67 g, 60% in mineral oil, 17 mmol) was added and stirred at room temperature for 30 min. To this mixture, 5-(((5-bromo-2-chloropyrimidin-4-yl)oxy)methyl)-2-fluorobenzonitrile (5.5 g, 16 mmol) was added and allowed to stir at room temperature for 16 h. After completion of the reaction, the reaction mixture was diluted with water (100 mL) and extracted with ethyl acetate (2×200 mL). The combined organic layer was then dried over sodium sulfate, filtered and evaporated to give crude product. The crude product was purified on column chromatography (silicagel, 100-200 mesh) using 15% ethyl acetate in hexane as eluent to afford 5-(((5-bromo-2-((2-methyl-[1,1'-biphenyl]-3-yl)methoxy)pyrimidin-4-yl)oxy)methyl)-2-fluorobenzonitrile as white solid (yield: 2.8 g, 41%). LCMS (ES) m/z=504.32 [M+H]$^+$; $^1$H NMR (400 MHz, DMSO-d$_6$): δ 2.21 (s, 3H), 5.38 (s, 2H), 5.53 (s, 2H), 7.21-7.23 (m, 1H), 7.31-7.34 (m, 3H), 7.36-7.39 (m, 1H), 7.41-7.45 (m, 3H), 7.56 (m, 1H), 7.89 (m, 1H), 8.05 (m, 1H), 8.58 (s, 1H). HPLC purity a 214 nm, 88.94%.

Step 4: Synthesis of 2-fluoro-5-(((2-((2-methyl-[1,1'-biphenyl]-3-yl)methoxy)-5-vinylpyrimidin-4-yl)oxy)methyl)benzonitrile To a stirred solution of 5-(((5-bromo-2-((2-methyl-[1,1'-biphenyl]-3-yl)methoxy)pyrimidin-4-yl)oxy)methyl)-2-fluorobenzonitrile (2.8 g, 5.5 mmol) in DMF (30 mL), tributyl vinyl tin (4.4 g, 13 mmol) was added and the reaction mixture was degassed with nitrogen gas for 10 min. To this mixture, Pd(PPh$_3$)$_4$ (0.6 g 0.5 mmol) was added and the reaction mixture was heated at 100° C. for 3 h. After completion of the reaction, the reaction mixture was filtered through celite and the filtrate was diluted with water (50 mL) and extracted with ethyl acetate (2×100 mL). The combined organic layer was dried over sodium sulfate, evaporated and the crude product was purified on combiflash chromatography using 25% ethyl acetate in hexane as eluent to afford 2-fluoro-5-(((2-((2-methyl-[1,1'-biphenyl]-3-yl)methoxy)-5-vinylpyrimidin-4-yl)oxy)methyl)benzonitrile as off-white solid (yield: 1.6 g, 66.6%). LCMS (ES) m/z=452.42 [M+H]$^+$; $^1$H NMR (400 MHz, CDCl$_3$): δ 2.26 (s, 3H), 5.30 (d, J=11.6 Hz, 1H), 5.42 (s, 2H), 5.52 (s, 2H), 5.80 (d, J=16.8 Hz, 1H), 6.68 (m, 1H), 7.21-7.23 (m, 1H), 7.31-7.34 (m, 3H), 7.36-7.39 (m, 1H), 7.41-7.45 (m, 4H), 7.72 (m, 1H), 7.78 (m, 1H), 8.32 (s, 1H). HPLC purity @ 214 nm, 94.70%.

Step 5: Synthesis of 2-fluoro-5-(((5-formyl-2-((2-methyl-[1,1'-biphenyl]-3-yl)methoxy)pyrimidin-4-yl)oxy)methyl)benzonitrile To a stirred solution of 2-fluoro-5-(((2-((2-methyl-[1,1'-biphenyl]-3-yl)methoxy)-5-vinylpyrimidin-4-yl)oxy)methyl)benzonitrile (1.6 g, 3 mmol) in acetone (80 mL) and water (16 mL) at 0° C., OsO$_4$ (3 mL, 2.5 wt % solution in tert-Butanol, 0.3 mmol) and N-Methylmorpholine N-oxide (1.0 g, 8.7 mmol) were added and stirred for 15 min. To this mixture, NaIO$_4$ (2.1 g, 10 mmol) was added and the reaction mixture was allowed to stir at room temperature for 16 h. After completion of the reaction, the reaction mixture was diluted with water (100 mL) and extracted with DCM (2×100 mL). The organic layer was dried over sodium sulfate, filtered and evaporated to give crude product. The crude product was purified on combiflash chromatography using 30% ethyl acetate in hexane as eluent to afford 2-fluoro-5-(((5-formyl-2-((2-methyl-[1,1'-biphenyl]-3-yl)methoxy)pyrimidin-4-yl)oxy)methyl)benzonitrile as dark solid (yield: 0.2 g, 15.3%). LCMS (ES) m/z=454.37 [M+H]$^+$; $^1$H NMR (400 MHz, DMSO-d$_6$): δ 2.23 (s, 3H), 5.55 (s, 2H), 5.62 (s, 2H), 7.22-7.32 (m, 4H), 7.38 (m, 1H), 7.46 (m, 2H), 7.52 (m, 1H), 7.59 (m, 1H), 7.93 (m, 1H), 8.08 (m, 1H), 8.85 (s, 1H), 10.07 (s, 1H).

Step 6: Synthesis of (S)-1-((4-((3-cyano-4-fluorobenzyl)oxy)-2-((2-methyl-[1,1'-biphenyl]-3-yl)methoxy)pyrimidin-5-yl)methyl)piperidine-2-carboxylic acid To a solution of 2-fluoro-5-(((5-formyl-2-((2-methyl-[1,1'-biphenyl]-3-yl)methoxy)pyrimidin-4-yl)oxy)methyl)benzonitrile (1 g, 0.22 mmol) in MeOH (2 mL) and DMF (2 mL), (S)-piperidine-2-carboxylic acid (20 mg, 0.19 mmol) and acetic acid (1 drop) were added simultaneously and the reaction was stirred at room temperature for 2 h. To this reaction mixture, NaCNBH$_3$ (30 mg, 0.6 mmol) was added and continued stirring at room temperature for 16 h. The reaction mixture was diluted with water (10 mL) and extracted in 10% MeOH in DCM (2×10 mL). The combined organic layer was washed with water (3 mL) and brine solution (3 mL), dried over sodium sulphate and concentrated to give crude product which was purified on prep-TLC using 10% methanol in dichloromethane as eluent to afford (S)-1-((4-((3-cyano-4-fluorobenzyl)oxy)-2-((2-methyl-[1,1'-biphenyl]-3-yl)methoxy)pyrimidin-5-yl)methyl)piperidine-2-carboxylic acid as white solid (yield: 20 mg, 16.1%). LCMS (ES) m/z=567.29 [M+H]$^+$; $^1$H NMR (400 MHz, DMSO-d$_6$): δ 1.33 (m, 1H), 1.39 (m, 3H), 1.72 (m, 2H), 2.19 (s, 3H), 2.30 (m, 1H), 2.87 (m, 1H), 3.20 (m, 1H), 3.55 (d, J=14.4 Hz, 1H), 3.66 (d, J=14.4 Hz, 1H), 5.40 (s, 2H), 5.48 (s, 2H), 7.21 (m, 1H), 7.26-7.30 (m, 3H), 7.37 (m, 1H), 7.43-7.47 (m, 3H), 7.55 (t, J=9.2 Hz, 1H), 7.89 (m, 1H), 8.04 (m, 1H), 8.26 (s, 1H). HPLC purity @ 214 nm, 91.83%.

Synthesis of (S)-1-((2-((2-methyl-[1,1'-biphenyl]-3-yl)methoxy)-4-(2,2,2-trifluoroethoxy)pyrimidin-5-yl)methyl)piperidine-2-carboxylic acid (compound-9)

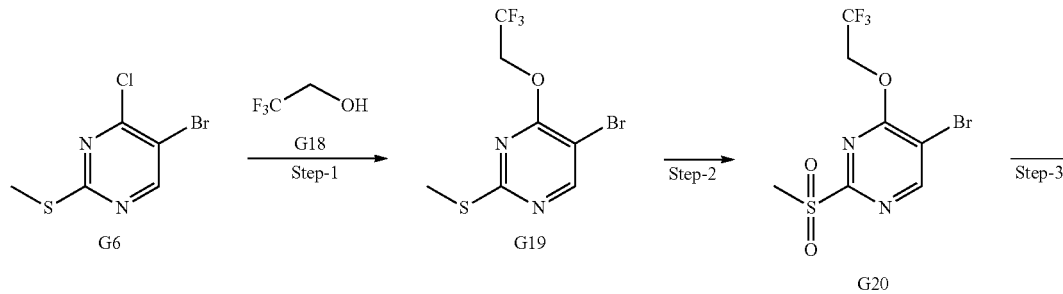

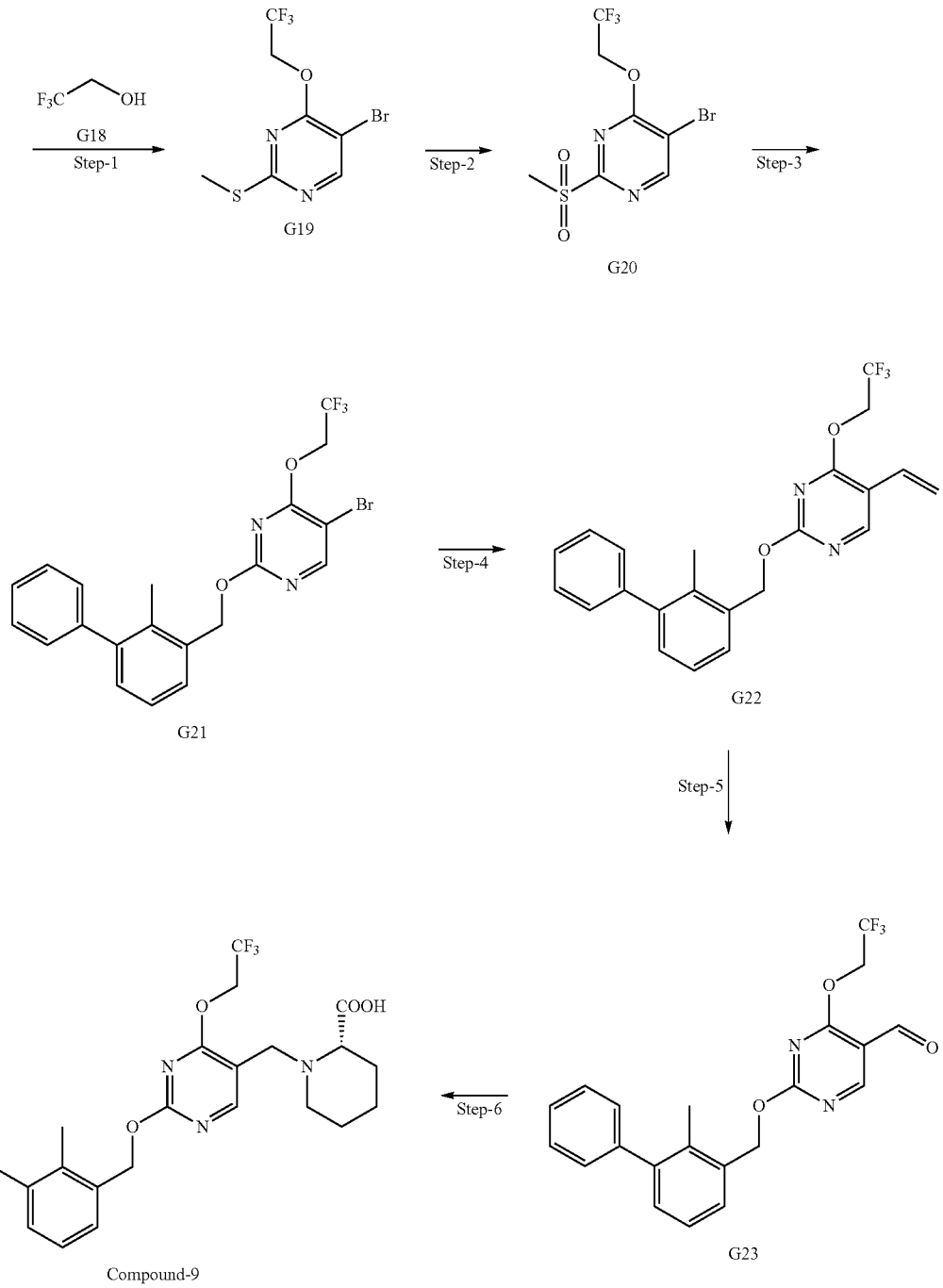

Step 1: Synthesis of 5-bromo-2-(methylsulfonyl)-4-(2,2,2-trifluoroethoxy)pyrimidine To a stirred solution of 5-bromo-4-chloro-2-(methylthio)pyrimidine (6 g, 25 mmol) in THF (200 mL) at 0° C., NaH (1.48 g, 60% in mineral oil, 37 mmol) was added and the reaction was stirred at 0° C. for 1 h. To this mixture, a solution of 2,2,2-trifluoroethan-1-ol (5.7 g, 25 mmol) in THF (20 mL) was added and the reaction was stirred at room temperature for 2 h. After completion of the reaction, the reaction mixture was quenched with ice cold water (250 mL) and extracted with ethyl acetate (2×500 mL). The combined organic layer was washed with brine solution (200 mL), dried over sodium sulfate and evaporated to afford 5-bromo- 2-(methylsulfonyl)-4-(2,2,2-trifluoroethoxy)pyrimidine as white solid (yield: 8 g, Crude). LCMS (ES) m/z=303.26; $^1$H NMR (400 MHz, DMSO-d$_6$): δ 2.50 (s, 3H), 5.12-5.19 (m, 2H), 8.69 (s, 1H).

Step 2: Synthesis of 5-bromo-2-(methylsulfonyl)-4-(2,2,2-trifluoroethoxy)pyrimidine To a stirred solution of 5-bromo-2-(methylthio)-4-(2,2,2-trifluoroethoxy)pyrimidine (8 g, 26.4 mmol) in DCM (150 mL) at 0° C., meta-chloroperbenzoic acid (11.4 g, 66 mmol) was added and the reaction was stirred at room temperature for 20 h. The reaction mixture was quenched with ice cold water (100 mL) and extracted with DCM (3×200 mL). The combined organic layer was washed with saturated sodium bicarbonate solution (300 mL), brine solution (100 mL) and dried over sodium sulfate. The organic layer was evaporated and the crude was purified on combiflash chromatography using 8% ethyl acetate in hexane as eluent to afford 5-bromo-2-(methylsulfonyl)-4-(2,2,2-trifluoroethoxy)pyrimidine as white solid (Yield: 8.4 g, 95%). LCMS (ES) m/z=335.23 [M+H]$^+$ $^1$H NMR (400 MHz, DMSO-d$_6$): δ 3.34 (s, 3H), 5.23-5.29 (m, 2H), 9.16 (s, 1H).

Step 3: Synthesis of 5-bromo-2-((2-methyl-[1,1'-biphenyl]-3-yl)methoxy)-4-(2,2,2-trifluoroethoxy)pyrimidine To a stirred solution of 5-bromo-2-(methylsulfonyl)-4-(2,2,2-trifluoroethoxy)pyrimidine (5 g, 25 mmol) in DMF (70 mL), (2-methyl-[1,1'-biphenyl]-3-yl)methanol (8.4 g, 25 mmol) and potassium carbonate (5.1 g, 37.5 mol) were added and the reaction mixture was heated at 80° C. for 12 h. After completion of the reaction, the reaction mixture was diluted with water (150 mL) and extracted with ethyl acetate (2×250 mL). The combined organic layer was washed with ice cold water (250 mL), brine solution (250 mL) and dried over sodium sulfate. Organic layer was evaporated and the crude was purified on combiflash chromatography using 10% ethyl acetate in hexane as eluent to afford 5-bromo-2-((2-methyl-[1,1'-biphenyl]-3-yl)methoxy)-4-(2,2,2-trifluoroethoxy)pyrimidine as colourless viscous liquid (yield: 5.6 g, 53%). LCMS (ES) m/z=453.29 [M+H]$^+$, $^1$H NMR (400 MHz, DMSO-d$_6$): δ 2.20 (s, 3H), 5.10-5.22 (m, 2H), 5.58 (s, 2H), 7.19-7.21 (m, 1H), 7.24-7.27 (m, 3H), 7.31-7.37 (m, 1H), 7.39-7.47 (m, 3H), 8.67 (s, 1H).

Step 4: Synthesis of 2-((2-methyl-[1,1'-biphenyl]-3-yl)methoxy)-4-(2,2,2-trifluoroethoxy)-5-vinylpyrimidine To a stirred solution of 5-bromo-2-((2-methyl-[1,1'-biphenyl]-3-yl)methoxy)-4-(2,2,2-trifluoroethoxy)pyrimidine (5.5 g, 12 mmol) in DMF (50 mL), tributyl vinyl tin (9.6 g, 30 mmol) was added and the reaction mixture was degassed with nitrogen gas for 10 min. To this mixture, Pd(PPh$_3$)$_4$ (1.3 g 1.2 mmol) was added and the reaction was heated at 100° C. for 8 h. After completion of the reaction, the reaction mixture was filtered through celite and the filtrate was diluted with water (200 mL) and extracted with ethyl acetate (2×500 mL). The combined organic layer was dried over sodium sulfate, evaporated and the crude was purified on combiflash chromatography using 3% ethyl acetate in hexane as eluent to afford 2-((2-methyl-[1,1'-biphenyl]-3-yl)methoxy)-4-(2,2,2-trifluoroethoxy)-5-vinylpyrimidine as yellow oily liquid (yield: 3.1 g, 64.5%). LCMS (ES) m/z=401.13 [M+H]$^+$, 1H NMR (400 MHz, DMSO-d$_6$): δ 2.20 (s, 3H), 5.10-5.18 (m, 2H), 5.42 (d, J=12 Hz, 1H), 5.49 (s, 2H), 5.99 (d, J=16.6 Hz, 1H), 6.60-6.71 (m, 1H), 7.21-7.19 (m, 1H), 7.26-7.31 (m, 3H), 7.36-7.39 (m, 1H), 7.43-7.47 (m, 3H), 8.51 (s, 1H).

Step 5: synthesis of 2-((2-methyl-[1,1'-biphenyl]-3-yl)methoxy)-4-(2,2,2-trifluoroethoxy)pyrimidine-5-carbaldehyde To a stirred solution of 2-((2-methyl-[1,1'-biphenyl]-3-yl)methoxy)-4-(2,2,2-trifluoroethoxy)-5-vinylpyrimidine (7, 0.5 g, 1.2 mmol) in THF (20 mL) and water (6 mL) at 0° C., OsO$_4$ (1 mL, 2.5 wt % solution in tert-butanol, 0.12 mmol) was added and stirred for 15 min. To this mixture, NaIO$_4$ (0.21 g, 1.87 mmol) was added and the reaction was allowed to stir at room temperature for 16 h. After completion, the reaction mixture was diluted with water (100 mL) and extracted with ethyl acetate (2×200 mL). The organic layer was then dried over sodium sulfate, evaporated and the crude was purified on combiflash chromatography using 12% ethyl acetate in hexanes as eluent to afford 2-((2-methyl-[1,1'-biphenyl]-3-yl)methoxy)-4-(2,2,2-trifluoroethoxy)pyrimidine-5-carbaldehyde as gray solid (Yield: 0.45 g, 95%). LCMS (ES) m/z=403.57 [M+H]$^+$ $^1$H NMR (400 MHz, DMSO-d$_6$): δ 2.21 (s, 3H), 5.19-5.26 (m, 2H), 5.61 (s, 2H), 7.22-7.7.23 (m, 1H), 7.27-7.32 (m, 3H), 7.38-7.40 (m, 1H), 7.44-7.47 (m, 3H), 8.92 (s, 1H), 10.05 (s, 1H).

Step 6: (S)-1-((2-((2-methyl-[1,1'-biphenyl]-3-yl)methoxy)-4-(2,2,2-trifluoroethoxy)pyrimidin-5-yl)methyl)piperidine-2-carboxylic acid To a solution of 2-((2-methyl-[1,1'-biphenyl]-3-yl)methoxy)-4-(2,2,2-trifluoroethoxy)pyrimidine-5-carbaldehyde (0.2 g, 0.51 mmol) in MeOH (3 mL) and DMF (3 mL), (S)-piperidine-2-carboxylic acid (0.1 g, 0.77 mmol) and acetic acid (0.1 mL) were added simultaneously and the reaction was stirred at room temperature for 2 h. To this reaction mixture, NaCNBH$_3$ (97 mg, 15 mmol) was added and continued stirring at room temperature for 16 h. The reaction mixture was diluted with water (10 mL) and extracted in 10% MeOH in DCM (2×20 mL). The combined organic layer was washed with water (5 mL) and brine solution (5 mL), dried over sodium sulphate and concentrated to get the crude residue which was purified on combiflash chromatography using 8% methanol in dichloromethane as eluent to afford (S)-1-((2-((2-methyl-[1,1'-biphenyl]-3-yl)methoxy)-4-(2,2,2-trifluoroethoxy)pyrimidin-5-yl)methyl)piperidine-2-carboxylic acid as white solid (Yield: 50 mg, 18.7%). LCMS (ES) m/z=516.35 [M+H]$^+$ and purity @ 214 nm, 99.86%; $^1$H NMR (400 MHz, DMSO-d$_6$): δ 1.40-1.44 (m, 4H), 1.74 (m, 2H), 2.20 (s, 3H), 2.32 (m, 1H), 2.88 (m, 1H), 3.21 (m, 1H), 3.55 (d, J=14.4 Hz, 1H), 3.68 (d, J=14.4 Hz, 1H), 5.01-5.10 (m, 2H), 5.46 (s, 2H), 7.19-7.21 (m, 1H), 7.26-7.30 (m, 3H), 7.37 (m, 1H), 7.44-7.48 (m, 3H), 8.37 (s, 1H).

Synthesis of (S)-1-((4-(4-hydroxybutoxy)-2-((2-methyl-[1,1'-biphenyl]-3-yl)methoxy)pyrimidin-5-yl)methyl)piperidine-2-carboxylic acid (Compound-10)
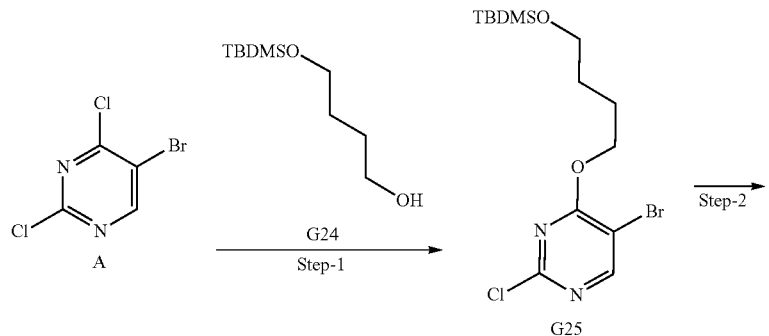
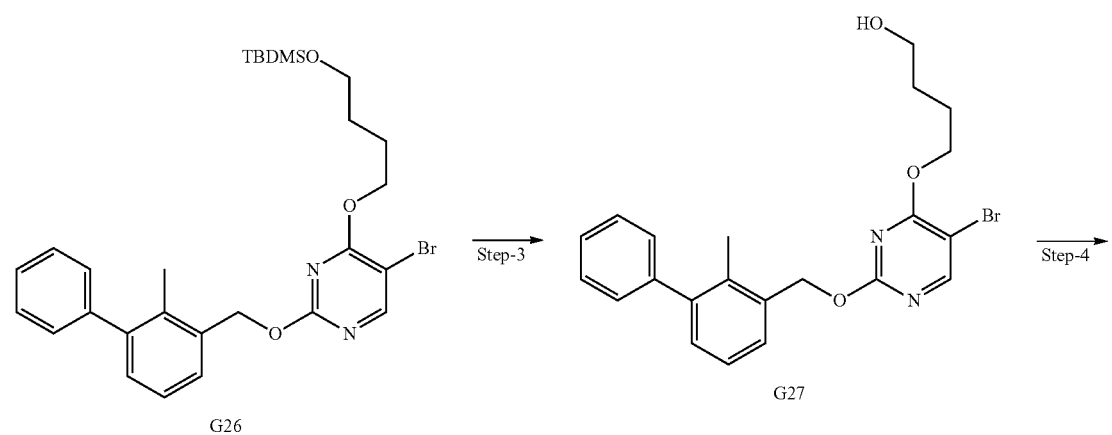
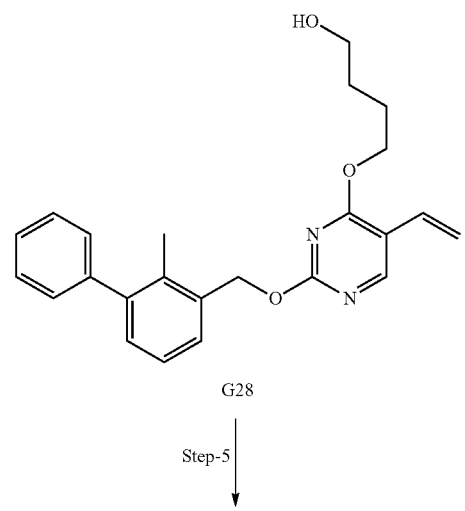

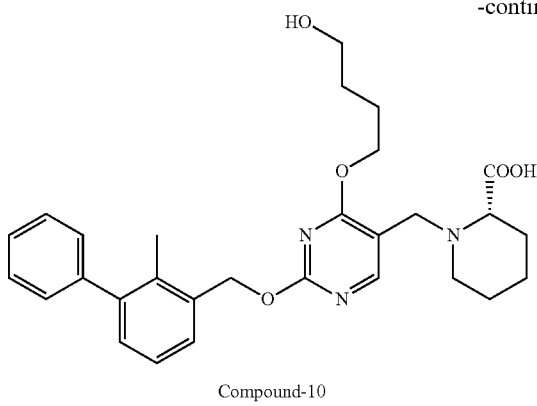

Compound-10

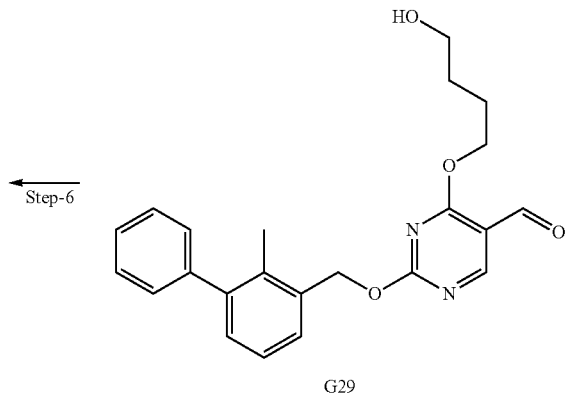

G29

Step-6 (arrow from G29 to Compound-10)

Step-1: Synthesis of 5-bromo-4-(4-((tert-butyldimethylsilyl)oxy)butoxy)-2-chloropyrimidine To a solution of 4-((tert-butyldimethylsilyl)oxy)butan-1-ol (8.52 g, 41.73 mmol) in THF (100 mL) at 0° C., sodium hydride (2.5 g, 60% in mineral oil, 62.7 mmol) was added and stirred the reaction mixture for 10 minutes. To this mixture, 5-bromo-2,4-dichloropyrimidine (9.5 g, 41.73 mmol) was added and stirred the mixture at room temperature for 3 h. After completion of reaction, the reaction mixture was quenched with ice cold water (100 mL) and extracted the mixture with EtOAc (3×100 mL). The combined organic layer was dried over sodium sulfate, filtered and concentrated. The crude product was purified by flash chromatography using 20% EtOAc in hexane as eluent to obtain 5-bromo-4-(4-((tert-butyldimethylsilyl)oxy)butoxy)-2-chloropyrimidine as sticky solid (Yield: 16 g, 97%).

Step 2: Synthesis of 5-bromo-4-(4-((tert-butyldimethylsilyl)oxy)butoxy)-2-((2-methyl-[1,1'-biphenyl]-3-yl)methoxy)pyrimidine To a stirred solution of (2-methyl-[1,1'-biphenyl]-3-yl)methanol (8.01 g, 40.4 mmol) in THF (100 mL) at 0° C., sodium hydride (2.42 g, 60% in mineral oil, 60.6 mmol) was added and stirred at room temperature for 30 min. To this mixture, 5-bromo-4-(4-((tert-butyldimethylsilyl)oxy)butoxy)-2-chloropyrimidine (16 g, 40.4 mmol) was added and allowed to stir at room temperature for 3 h. After completion of the reaction, the reaction mixture was diluted with water (100 mL) and extracted with ethyl acetate (2×200 mL). The combined organic layer was then dried over sodium sulfate, filtered and evaporated to give crude product. The crude product was purified on column chromatography (silicagel, 100-200#) using 20% ethyl acetate in hexane as eluent to afford 5-bromo-4-(4-((tert-butyldimethylsilyl)oxy)butoxy)-2-((2-methyl-[1,1'-biphenyl]-3-yl)methoxy)pyrimidine as yellow viscous liquid (Yield: 11.04 g, 49%). LCMS (ES) m/z=557.40 [M+H]$^+$; $^1$H NMR (400 MHz, DMSO-d$_6$): δ 0.016 (s, 6H), 0.83 (s, 9H), 1.60 (m, 2H), 1.72 (m, 2H), 2.20 (s, 3H), 3.62 (m, 2H), 4.44 (m, 2H), 5.47 (s, 2H), 7.21-7.23 (m, 1H), 7.25-7.31 (m, 3H), 7.37-7.49 (m, 4H), 8.47 (s, 1H).

Step 3: Synthesis of 4-((5-bromo-2-((2-methyl-[1,1'-biphenyl]-3-yl)methoxy)pyrimidin-4-yl)oxy)butan-1-ol To a solution of 5-bromo-4-(4-((tert-butyldimethylsilyl)oxy)butoxy)-2-((2-methyl-[1,1'-biphenyl]-3-yl)methoxy) pyrimidine (5.5 g, 9.86 mmol) in THF (50 mL) at 0° C., TBAF (1M solution in THF, 1 eq) was added and stirred the mixture at room temperature for 3 h. After completion of the reaction, the reaction mixture was diluted with water (50 mL) and extracted with EtOAc (3×100 mL). The combined organic layer was then dried over sodium sulfate, filtered and evaporated to give crude product. The crude product was purified on column chromatography (silicagel, 100-200#) using 20% ethyl acetate in hexane as eluent to afford 4-((5-bromo-2-((2-methyl-[1,1'-biphenyl]-3-yl)methoxy) pyrimidin-4-yl)oxy)butan-1-ol as yellow viscous liquid (Yield: 2.03 g, 46%). LCMS (ES) m/z=443.37 [M+H]$^+$; $^1$H NMR (400 MHz, DMSO-d$_6$): δ 1.65 (m, 2H), 1.76 (m, 2H), 2.19 (s, 3H), 3.44 (m, 2H), 4.42 (m, 2H), 4.46 (m, 1H), 5.43 (s, 2H), 7.21-7.23 (m, 1H), 7.25-7.31 (m, 3H), 7.39-7.52 (m, 4H), 8.53 (s, 1H). HPLC purity @214 nm: 98.91%.

Step 4: Synthesis of 4-((2-((2-methyl-[1,1'-biphenyl]-3-yl)methoxy)-5-vinylpyrimidin-4-yl)oxy)butan-1-ol To a stirred solution of 4-((5-bromo-2-((2-methyl-[1,1'-biphenyl]-3-yl)methoxy)pyrimidin-4-yl)oxy)butan-1-ol (1.0 g, 2.26 mmol) in DMF (15 mL), tributyl vinyl tin (1.79 g, 5.64 mmol) was added and the reaction mixture was degassed with nitrogen gas for 10 min. To this mixture, Pd(PPh$_3$)$_4$ (0.3 g 0.23 mmol) was added and the reaction mixture was heated at 100° C. for 3 h. After completion of the reaction, the reaction mixture was filtered through celite and the filtrate was diluted with water (50 mL) and extracted with ethyl acetate (2×100 mL). The combined organic layer was dried over sodium sulfate, evaporated and the crude product was purified on combiflash chromatography using 25% ethyl acetate in hexane as eluent to afford 4-((2-((2-methyl-[1,1'-biphenyl]-3-yl)methoxy)-5-vinylpyrimidin-4-yl)oxy)butan-1-ol as yellow solid (Yield: 0.7 g, 79%). LCMS (ES) m/z=391.47 [M+H]$^+$; $^1$H NMR (400 MHz, DMSO-d$_6$): δ 1.56 (m, 2H), 1.77 (m, 2H), 2.20 (s, 3H), 3.43 (m, 2H), 4.40 (m, 2H), 4.45 (m, 1H), 5.30 (d, J=12 Hz, 1H), 5.45 (s, 2H), 5.90 (d, J=17.6 Hz, 1H), 6.62 (m, 1H), 7.19 (m, 1H), 7.25-7.32 (m, 3H), 7.36-7.39 (m, 1H), 7.43-7.47 (m, 3H), 8.48 (s, 1H).

Step 5: Synthesis of 4-(4-hydroxybutoxy)-2-((2-methyl-[1,1'-biphenyl]-3-yl)methoxy)pyrimidine-5-carbaldehyde To a stirred solution 4-((2-((2-methyl-[1,1'-biphenyl]-3-yl)methoxy)-5-vinylpyrimidin-4-yl)oxy)butan-1-ol (0.7 g, 1.79 mmol) in THF (10 mL) and water (10 mL) at 0° C., OsO₄ (1.8 mL, 2.5 wt % solution in tert-butanol, 0.18 mmol) was added and stirred for 15 min. To this mixture, NaIO₄ (0.57 g, 2.7 mmol) was added and the reaction mixture was allowed to stir at room temperature for 5 h. After completion of the reaction, the reaction mixture was diluted with water (30 mL) and extracted with DCM (2×50 mL). The organic layer was dried over sodium sulfate, filtered and evaporated to give crude product. The crude product was purified on column chromatography (silicagel, 100-200#) using 40% ethyl acetate in hexane as eluent to afford 4-(4-hydroxybutoxy)-2-((2-methyl-[1,1'-biphenyl]-3-yl)methoxy)pyrimidine-5-carbaldehyde as sticky oily compound (Yield: 0.5 g, 62%). LCMS (ES) m/z=393.38 [M+H]⁺; ¹H NMR (400 MHz, DMSO-d₆): δ 1.56 (m, 2H), 1.77 (m, 2H), 2.22 (s, 3H), 3.44 (m, 2H), 4.42 (m, 1H), 4.51 (m, 2H), 5.56 (s, 2H), 7.21 (m, 1H), 7.27-7.33 (m, 3H), 7.36 (m, 1H), 7.39-7.46 (m, 3H), 8.79 (s, 1H), 10.06 (s, 1H). HPLC purity @ 214 nm, 99.52%.

Step 6: Synthesis of (S)-1-((4-(4-hydroxybutoxy)-2-((2-methyl-[1,1'-biphenyl]-3-yl)methoxy)pyrimidin-5-yl)methyl)piperidine-2-carboxylic acid To a solution of 4-(4-hydroxybutoxy)-2-((2-methyl-[1,1'-biphenyl]-3-yl)methoxy)pyrimidine-5-carbaldehyde (0.24 g, 0.61 mmol) in MeOH (2 mL) and DMF (2 mL), (S)-piperidine-2-carboxylic acid (79 mg, 0.61 mmol) and acetic acid (1 drop) were added simultaneously and the reaction mixture was stirred at room temperature for 2 h. To this reaction mixture, NaCNBH₃ (115 mg, 1.83 mmol) was added and continued stirring at room temperature for 16 h. The reaction mixture was diluted with saturated sodium bicarbonate solution (10 mL) and extracted with DCM (2×25 mL). The combined organic layer was washed with water (5 mL) and brine solution (5 mL), dried over sodium sulphate and concentrated to give crude product which was purified flash chromatography using 10% methanol in dichloromethane as eluent to afford (S)-1-((4-(4-hydroxybutoxy)-2-((2-methyl-[1,1'-biphenyl]-3-yl)methoxy)pyrimidin-5-yl)methyl)piperidine-2-carboxylic acid as white solid (Yield: 250 mg, 80.8%). LCMS (ES) m/z=506.43 [M+H]⁺; ¹H NMR (400 MHz, DMSO-d₆): δ 1.33-1.54 (m, 7H), 1.74 (m, 4H), 2.20 (s, 3H), 2.30 (m, 1H), 2.91 (m, 1H), 3.17 (m, 1H), 3.43 (m, 2H), 3.55 (d, J=14 Hz, 1H), 3.66 (d, J=14 Hz, 1H), 4.33 (m, 2H), 5.42 (s, 2H), 7.18 (m, 1H), 7.25-7.32 (m, 3H), 7.37 (m, 1H), 7.43-7.47 (m, 3H), 8.23 (s, 1H). HPLC purity @ 214 nm, 97.43%.

Synthesis of (2S,4R)-1-((2-((3-(2,3-dihydrobenzo[b][1,4]dioxin-6-yl)-2-methylbenzyl)oxy)-4,6-dimethoxypyrimidin-5-yl)methyl)-4-hydroxypyrrolidine-2-carboxylic acid (Compound-11)

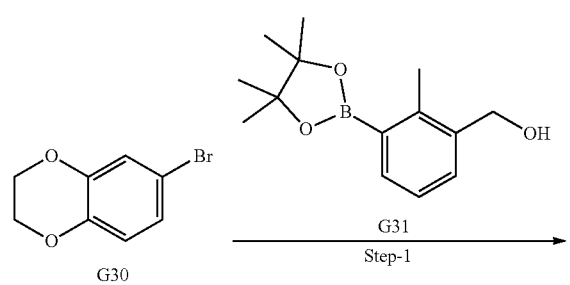

Step-1: Synthesis of (3-(2,3-dihydrobenzo[b][1,4]dioxin-6-yl)-2-methylphenyl)methanol To a solution of 6-bromo-2,3-dihydrobenzo[b][1,4]dioxine (6 g, 0.027 mol) and (2-methyl-3-(4,4,5,5-tetramethyl-1,3,2-dioxaborolan-2-yl)phenyl)methanol (8.3 g, 33 mmol) in Toluene:Ethanol:water (1:1:1) (120 mL) at room temperature, potassium carbonate (11.5 g, 83 mmol) was added and degassed the mixture at room temperature for 15 min using nitrogen. To this mixture, Pd(dppf)Cl₂-DCM complex (1.4 g, 1.3 mmol) was added and the reaction mixture was degassed again for 10 min using nitrogen. After stirring the reaction mixture at 95° C. for 12 h, the mixture was cooled to room temperature and filtered through celite pad. The filtrate was diluted with water (100 mL) and the aqueous mixture was extracted with EtOAc (2×500 mL). The organic layer was washed with brine (500 mL), dried over sodium sulfate and concentrated to get crude compound. The resulting crude was purified by column chromatography (silica gel, 100-200 mesh) using hexanes as eluent to afford (3-(2, 3-dihydrobenzo[b][1,4]dioxin-6-yl)-2-methylphenyl)
methanol (Yield: 7 g, 97.9%) as light red liquid. $^1$H NMR
(400 MHz, DMSO-d$_6$): δ 2.12 (s, 3H), 4.27 (m, 4H), 4.52
(m, 2H), 5.75 (s, 1H), 6.90 (m, 2H), 7.05 (m, 1H), 7.16 (m,
1H), 7.20 (m, 1H), 7.36 (m, 1H).

Step-2: Synthesis of 2-((3-(2,3-dihydrobenzo[b][1,
4]dioxin-6-yl)-2-methylbenzyl)oxy)-4,6-dimethoxy-
pyrimidine To a stirred solution of (3-(2,3-dihydrobenzo[b][1,4]di-
oxin-6-yl)-2-methylphenyl)methanol (8.2 g, 32 mmol) in
DMF (40 mL), 4,6-dimethoxy-2-(methylsulfonyl)pyrimi-
dine (7 g, 32 mmol) and potassium carbonate (13.2 g, 96
mmol) were added and the reaction mixture was heated at
80° C. for 12 h. After completion of reaction, the reaction
mixture was diluted with water (150 mL) and extracted with
ethyl acetate (2×250 mL). The combined organic layer was
washed with ice cold water (250 mL), brine solution (250
mL) and dried over sodium sulfate, evaporated and the crude
was purified on combiflash chromatography using 10%
ethyl acetate in hexane as eluent to afford 2-((3-(2,3-dihy-
drobenzo[b][1,4]dioxin-6-yl)-2-methylbenzyl)oxy)-4,6-di-
methoxy pyrimidine as colourless viscous liquid (Yield: 9 g,
71.4%).

Step-3: Synthesis of 2-((3-(2,3-dihydrobenzo[b][1,
4]dioxin-6-yl)-2-methylbenzyl)oxy)-4,6-dimethoxy-
pyrimidine-5-carbaldehyde A solution of phosphoryl chloride (8 mL) in DMF (8 mL)
at 0° C. under nitrogen atmosphere was stirred for 1 h, it was
added to a solution of 2-((3-(2,3-dihydrobenzo[b][1,4]di-
oxin-6-yl)-2-methylbenzyl)oxy)-4,6-dimethoxypyrimidine
(3 g, 7.6 mmol) in DCE (30 mL) drop wise. Then reaction
mixture was stirred at room temperature for 30 min and then
heated at 80° C. for 3 h. After completion of reaction, the
reaction mixture was concentrated in vacuo and diluted with
DCM (100 mL). The organic mixture was washed with
water (25 mL), brine solution (25 mL), dried over sodium
sulphate, filtered and concentrated in vacuo to give a crude
product which was purified by silica gel chromatography
(10% EtOAc in Hexanes) to afford 2-((3-(2,3-dihydrobenzo
[b][1,4]dioxin-6-yl)-2-methylbenzyl)oxy)-4,6-dimethoxy-
pyrimidine-5-carbaldehyde as light yellow solid (Yield: 1.5
g, 46.8%). LCMS (ES) m/z=423.36 [M+H]+ and purity @
214 nm, 98.13%. 1H NMR (400 MHz, DMSO-d$_6$): δ 2.24 (s,
3H), 4.00 (s, 6H), 4.28 (s, 4H), 5.54 (s, 2H), 6.73-6.77 (m,
2H), 6.92 (d, J=8.0 Hz, 1H), 7.17-7.19 (m, 1H), 7.22-7.26
(m, 1H), 7.44 (d, J=7.6 Hz, 1H), 10.07 (s, 1H).

Step-4: Preparation of (2S,4R)-1-((2-((3-(2,3-dihyd-
robenzo[b][1,4]dioxin-6-yl)-2-methylbenzyl)oxy)-4,
6-dimethoxypyrimidin-5-yl)methyl)-4-hydroxypyr-
rolidine-2-carboxylic acid To a solution of 2-((3-(2,3-dihydrobenzo[b][1,4]dioxin-
6-yl)-2-methylbenzyl)oxy)-4,6-dimethoxypyrimidine-5-car-
baldehyde (0.5 g, 1.1 mmol) in DMF (8 mL), (2S,4R)-4-
hydroxypyrrolidine-2-carboxylic acid (0.15 g, 1.1 mmol),
NaCNBH$_3$ (0.2 g, 3.3 mmol) and acetic acid (0.1 mL) were
added simultaneously and the reaction was heated at 70° C.
for 4 h. The reaction mixture was diluted with water (100
mL) and extracted in 10% MeOH in DCM (2×150 mL). The
combined organic layer was washed with water (40 mL) and
brine solution (40 mL), dried over sodium sulphate and
concentrated to get the crude residue which was purified on
combiflash chromatography using 8% methanol in dichlo-
romethane as eluent to afford (2S,4R)-1-((2-((3-(2,3-dihyd-
robenzo[b][1,4]dioxin-6-yl)-2-methylbenzyl)oxy)-4,6-di-
methoxypyrimidin-5-yl)methyl)-4-hydroxypyrrolidine-2-
carboxylic acid as white solid (Yield: 0.29 g, 49%). LCMS
(ES) m/z=538.34 [M+H]+ and purity @ 214 nm, 98.13%. $^1$H
NMR (400 MHz, DMSO-d$_6$): δ 1.91 (m, 2H), 2.23 (s, 3H),
3.25-3.41 (m, 3H), 3.78-3.86 (m, 2H), 3.90 (s, 6H), 4.16 (m,
1H), 4.27 (s, 4H), 4.98 (bs, 1H), 5.44 (s, 2H), 6.73-6.77 (m,
2H), 6.92 (d, J=8.12 Hz, 1H), 7.15-7.17 (m, 1H), 7.22-7.26
(m, 1H), 7.44 (d, J=7.16 Hz, 1H).

Synthesis of (S)-1-((4-((5-cyanopyridin-3-yl)
methoxy)-2-((2-methyl-[1,1'-biphenyl]-3-yl)
methoxy)pyrimidin-5-yl)methyl)piperidine-2-car-
boxylic acid (Compound-12)

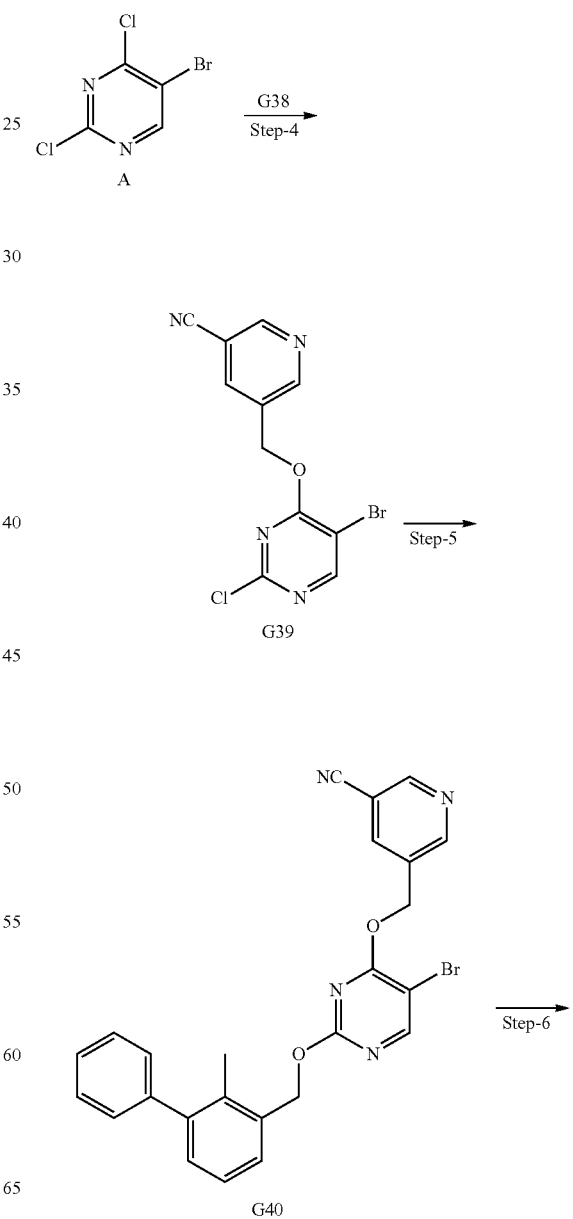

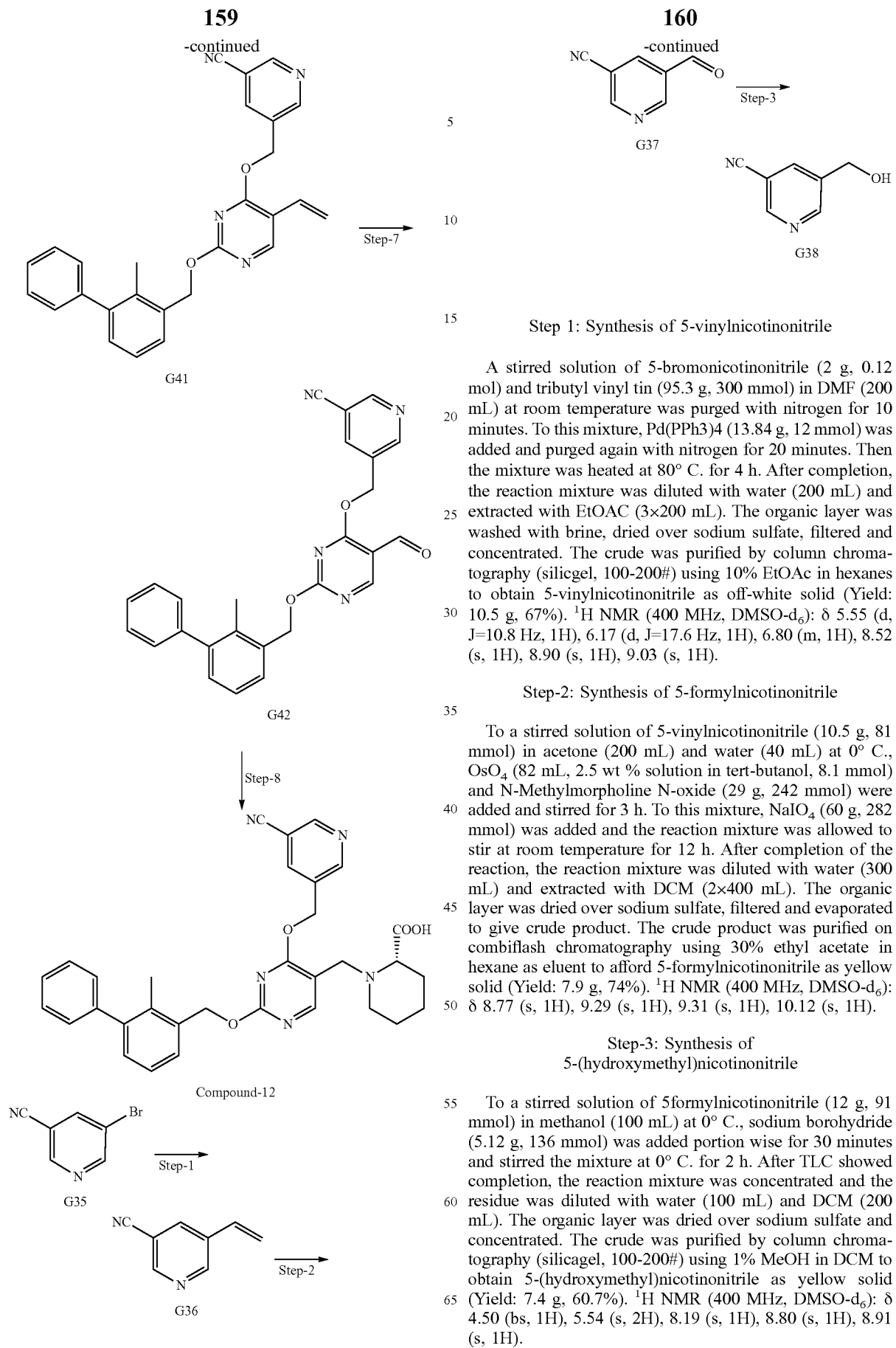

Step 1: Synthesis of 5-vinylnicotinonitrile

A stirred solution of 5-bromonicotinonitrile (2 g, 0.12 mol) and tributyl vinyl tin (95.3 g, 300 mmol) in DMF (200 mL) at room temperature was purged with nitrogen for 10 minutes. To this mixture, Pd(PPh3)4 (13.84 g, 12 mmol) was added and purged again with nitrogen for 20 minutes. Then the mixture was heated at 80° C. for 4 h. After completion, the reaction mixture was diluted with water (200 mL) and extracted with EtOAC (3×200 mL). The organic layer was washed with brine, dried over sodium sulfate, filtered and concentrated. The crude was purified by column chromatography (silicgel, 100-200#) using 10% EtOAc in hexanes to obtain 5-vinylnicotinonitrile as off-white solid (Yield: 10.5 g, 67%). $^1$H NMR (400 MHz, DMSO-$d_6$): δ 5.55 (d, J=10.8 Hz, 1H), 6.17 (d, J=17.6 Hz, 1H), 6.80 (m, 1H), 8.52 (s, 1H), 8.90 (s, 1H), 9.03 (s, 1H).

Step-2: Synthesis of 5-formylnicotinonitrile

To a stirred solution of 5-vinylnicotinonitrile (10.5 g, 81 mmol) in acetone (200 mL) and water (40 mL) at 0° C., OsO$_4$ (82 mL, 2.5 wt % solution in tert-butanol, 8.1 mmol) and N-Methylmorpholine N-oxide (29 g, 242 mmol) were added and stirred for 3 h. To this mixture, NaIO$_4$ (60 g, 282 mmol) was added and the reaction mixture was allowed to stir at room temperature for 12 h. After completion of the reaction, the reaction mixture was diluted with water (300 mL) and extracted with DCM (2×400 mL). The organic layer was dried over sodium sulfate, filtered and evaporated to give crude product. The crude product was purified on combiflash chromatography using 30% ethyl acetate in hexane as eluent to afford 5-formylnicotinonitrile as yellow solid (Yield: 7.9 g, 74%). $^1$H NMR (400 MHz, DMSO-$d_6$): δ 8.77 (s, 1H), 9.29 (s, 1H), 9.31 (s, 1H), 10.12 (s, 1H).

Step-3: Synthesis of 5-(hydroxymethyl)nicotinonitrile

To a stirred solution of 5formylnicotinonitrile (12 g, 91 mmol) in methanol (100 mL) at 0° C., sodium borohydride (5.12 g, 136 mmol) was added portion wise for 30 minutes and stirred the mixture at 0° C. for 2 h. After TLC showed completion, the reaction mixture was concentrated and the residue was diluted with water (100 mL) and DCM (200 mL). The organic layer was dried over sodium sulfate and concentrated. The crude was purified by column chromatography (silicagel, 100-200#) using 1% MeOH in DCM to obtain 5-(hydroxymethyl)nicotinonitrile as yellow solid (Yield: 7.4 g, 60.7%). $^1$H NMR (400 MHz, DMSO-$d_6$): δ 4.50 (bs, 1H), 5.54 (s, 2H), 8.19 (s, 1H), 8.80 (s, 1H), 8.91 (s, 1H).

Step 4: Synthesis of 5-(((5-bromo-2-chloropyrimidin-4-yl)oxy)methyl)nicotinonitrile To a stirred solution of 5-(hydroxymethyl)nicotinonitrile (0.59 g, 4.3 mmol) in THF (20 mL) at 0° C., sodium hydride (0.26 g, 60% in mineral oil, 6.5 mmol) was added and stirred at 0° C. for 30 minutes. To this mixture, a solution of 5-bromo-2,4-dichloropyrimidine (1.0 g, 4.3 mmol) in THF (5 mL) was added and the reaction mixture was stirred at room temperature for 5 h. After completion, the reaction was quenched with ice cold water (100 mL) and extracted with 10% IPA in chloroform (4×100 mL). The combined organic layer was dried over sodium sulphate and concentrated. The crude was purified by column chromatography (silicagel, 100-200#) using 5% MeOH in DCM to obtain 5-(((5-bromo-2-chloropyrimidin-4-yl)oxy)methyl)nicotinonitrile as yellow solid (Yield: 1.0 g, 70%). $^1$H NMR (400 MHz, DMSO-$d_6$): δ 5.59 (s, 2H), 8.43 (s, 1H), 8.80 (s, 1H), 9.00 (s, 1H), 9.05 (s, 1H). HPLC purity @214 nm: 97.07%.

Step 5: Synthesis of 5-(((5-bromo-2-((2-methyl-[1,1'-biphenyl]-3-yl)methoxy)pyrimidin-4-yl)oxy)methyl)nicotinonitrile To a stirred solution of (2-methyl-[1,1'-biphenyl]-3-yl)methanol (0.61 g, 3.1 mmol) in DMF (20 mL) at 0° C., sodium hydride (0.184 g, 60% in mineral oil, 4.6 mmol) was added and stirred at room temperature for 30 min. To this mixture, 5-(((5-bromo-2-chloropyrimidin-4-yl)oxy)methyl)nicotinonitrile (1 g, 3.1 mmol) was added and allowed to stir at room temperature for 3 h. After completion of the reaction, the reaction mixture was diluted with saturated solution of ammonium chloride (20 mL) and diluted with water (50 mL). The aqueous mixture was extracted with ethyl acetate (2×100 mL) and the combined organic layer was then dried over sodium sulfate, filtered and evaporated to give crude product. The crude product was purified on flash chromatography (silicagel) using 50% ethyl acetate in hexane as eluent to afford 5-(((5-bromo-2-((2-methyl-[1,1'-biphenyl]-3-yl)methoxy)pyrimidin-4-yl)oxy)methyl)nicotinonitrile as sticky solid (Yield: 0.7 g, 47%). LCMS (ES) m/z=487.21 [M+H]$^+$; $^1$H NMR (400 MHz, DMSO-$d_6$): δ 2.20 (s, 3H), 5.50 (s, 2H), 5.53 (s, 2H), 7.21-7.23 (m, 1H), 7.27-7.31 (m, 3H), 7.36-7.38 (m, 1H), 7.44-7.47 (m, 3H), 8.43 (m, 1H), 8.59 (s, 1H), 8.98 (s, 1H), 9.01 (s, 1H). HPLC purity @ 254 nm, 97.78%.

Step 4: Synthesis of 5-(((2-((2-methyl-[1,1'-biphenyl]-3-yl)methoxy)-5-vinylpyrimidin-4-yl)oxy)methyl)nicotinonitrile To a stirred solution of 5-(((5-bromo-2-((2-methyl-[1,1'-biphenyl]-3-yl)methoxy)pyrimidin-4-yl)oxy)methyl)nicotinonitrile (0.3 g, 0.62 mmol) in DMF (10 mL), tributyl vinyl tin (0.57 g, 1.86 mmol) was added and the reaction mixture was degassed with nitrogen gas for 10 min. To this mixture, Pd(PPh$_3$)$_4$ (72 mg 0.061 mmol) was added and the reaction mixture was heated at 80° C. for 3 h. After completion of the reaction, the reaction mixture was diluted with water (20 mL) and extracted with ethyl acetate (2×50 mL). The combined organic layer was dried over sodium sulfate, evaporated and the crude product was purified on combiflash chromatography using 30% ethyl acetate in hexane as eluent to afford 5-(((2-((2-methyl-[1,1'-biphenyl]-3-yl)methoxy)-5-vinylpyrimidin-4-yl)oxy)methyl)nicotinonitrile as sticky oil (Yield: 0.225 g, 75%). LCMS (ES) m/z=435.44 [M+H]$^+$; $^1$H NMR (400 MHz, DMSO-$d_6$): δ 2.20 (s, 3H), 5.32 (d, J=11.2 Hz, 1H), 5.52 (s, 4H), 5.89 (d, J=17.6 Hz, 1H), 6.67 (m, 1H), 7.21-7.23 (m, 1H), 7.27-7.31 (m, 3H), 7.36-7.38 (m, 1H), 7.42-7.45 (m, 3H), 8.43 (m, 1H), 8.55 (s, 1H), 8.98 (s, 1H), 9.01 (s, 1H). HPLC purity @ 254 nm, 92.44%.

Step 5: Synthesis of 5-(((5-formyl-2-((2-methyl-[1,1'-biphenyl]-3-yl)methoxy)pyrimidin-4-yloxy)methyl)nicotinonitrile To a stirred solution of 5-(((2-((2-methyl-[1,1'-biphenyl]-3-yl)methoxy)-5-vinylpyrimidin-4-yl)oxy)methyl)nicotinonitrile (220 mg, 0.43 mmol) in acetone (8 mL) and water (2 mL) at 0° C., OsO$_4$ (0.44 mL, 2.5 wt % solution in tert-butanol, 0.043 mmol) and N-methylmorpholine N-oxide (152 mg, 1.35 mmol) were added and stirred for 2 h. To this mixture, NaIO$_4$ (324 mg, 1.513 mmol) was added and the reaction mixture was allowed to stir at room temperature for 3 h. After completion of the reaction, the reaction mixture was diluted with water (25 mL) and extracted with DCM (2×25 mL). The organic layer was dried over sodium sulfate, filtered and evaporated to give crude product. The crude product was purified on combiflash chromatography using 30% ethyl acetate in hexane as eluent to afford 5-(((5-formyl-2-((2-methyl-[1,1'-biphenyl]-3-yl)methoxy)pyrimidin-4-yl)oxy)methyl)nicotinonitrile as yellow solid (Yield: 95 mg, 47%). LCMS (ES) m/z=437.37 [M+H]$^+$; $^1$H NMR (400 MHz, DMSO-$d_6$): δ 2.22 (s, 3H), 5.61 (s, 4H), 7.21-7.23 (m, 1H), 7.27-7.31 (m, 3H), 7.36-7.38 (m, 1H), 7.44-7.52 (m, 3H), 8.47 (m, 1H), 8.85 (s, 1H), 9.01 (s, 1H), 9.03 (s, 1H), 10.07 (s, 1H).

Step 6: Synthesis of (S)-1-((4-((5-cyanopyridin-3-yl)methoxy)-2-((2-methyl-[1,1'-biphenyl]-3-yl)methoxy)pyrimidin-5-yl)methyl)piperidine-2-carboxylic acid To a solution of 5-(((5-formyl-2-((2-methyl-[1,1'-biphenyl]-3-yl)methoxy)pyrimidin-4-yl)oxy)methyl)nicotinonitrile (150 mg, 0.34 mmol) in MeOH (2 mL) and DMF (2 mL), (S)-piperidine-2-carboxylic acid (32 mg, 0.515 mmol) and acetic acid (2 drops) were added simultaneously and the reaction was stirred at room temperature for 3 h. To this reaction mixture, NaCNBH$_3$ (35 mg, 1.03 mmol) was added and continued stirring at room temperature for 5 h. The reaction mixture was diluted with water (10 mL) and extracted with DCM (2×25 mL). The combined organic layer was washed with water (5 mL) and brine solution (5 mL), dried over sodium sulphate and concentrated to give crude product which was purified by flash chromatography using 10% methanol in dichloromethane as eluent to afford (S)-1-((4-((5-cyanopyridin-3-yl)methoxy)-2-((2-methyl-[1,1'-biphenyl]-3-yl)methoxy)pyrimidin-5-yl)methyl)piperidine-2-carboxylic acid as white solid (Yield: 33 mg, 18%). LCMS (ES) m/z=550.22 [M+H]$^+$; $^1$H NMR (400 MHz, DMSO-$d_6$): δ 1.33 (m, 1H), 1.39 (m, 3H), 1.72 (m, 2H), 2.19 (s, 3H), 2.32 (m, 1H), 2.89 (m, 1H), 3.23 (m, 1H), 3.54 (d, J=14.0 Hz, 1H), 3.68 (d, J=14.0 Hz, 1H), 5.48 (s, 4H), 7.21-7.22 (m, 1H), 7.24-7.31 (m, 3H), 7.36-7.38 (m, 1H), 7.43-7.48 (m, 3H), 8.28 (s, 1H), 8.43 (s, 1H), 8.98 (s, 1H), 9.00 (s, 1H). HPLC purity @ 214 nm, 99.32%.

Synthesis of (S)-1-((2-((3'-(3-(3,3-difluoropyrrolidin-1-yl)propoxy)-2,2'-dimethyl-[1,1'-biphenyl]-3-yl)methoxy)-4-methoxypyrimidin-5-yl)methyl)piperidine-2-carboxylic acid (Compound-13)

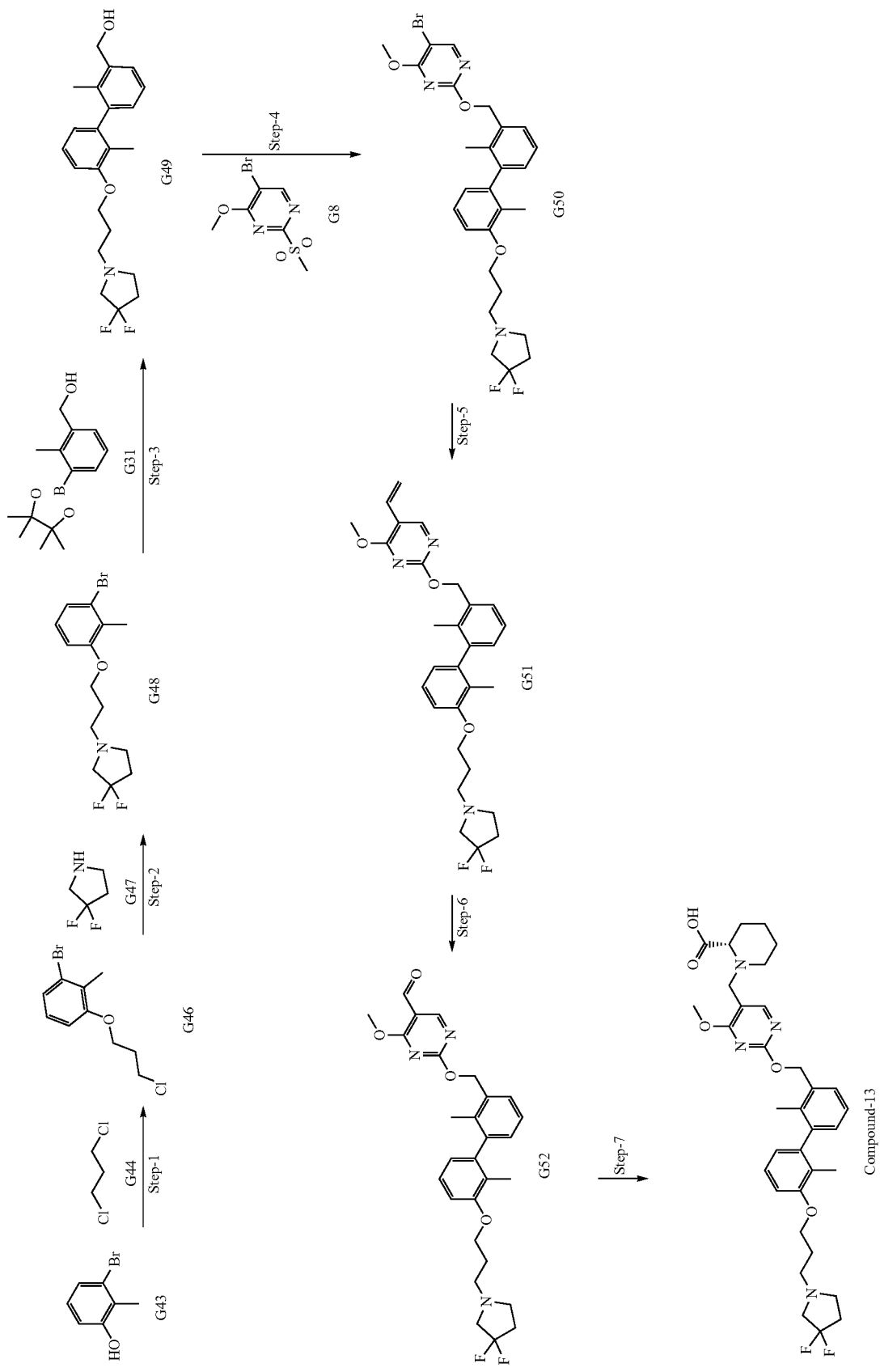

Step-1: Preparation of 1-bromo-3-(3-chloropropoxy)-2-methylbenzene

To a stirred solution of 3-bromo-2-methylphenol (1, 9.8 g, 52 mmol) in DMF (80 mL), 1,3-dichloropropane (73 g, 100 mmol) and potassium carbonate (21.5 g, 156 mmol) were added and stirred the reaction mixture at 80° C. for 12 h under nitrogen atmosphere. After TLC showed completion, the mixture was cooled to room temperature and diluted with EtOAc (100 mL), washed with ice cold water (50 mL) and brine solution (30 mL). The organic phase was dried over sodium sulphate and concentrated in vacuo to give a crude product. The resulting crude was purified by column chromatography (silica gel, 100-200 mesh) using 10% EtOAc in hexanes to afford 1-(3-(3-bromo-2-methylphenoxy) propyl)-3,3-difluoropyrrolidine (Yield: 10.1 g, 73.7%) as yellow liquid. $^1$H NMR (400 MHz, CDCl$_3$): δ 2.25-2.31 (m, 5H), 3.77 (m, 2H), 4.12 (m, 2H), 6.80 (d, J=8.2 Hz, 1H), 6.98-7.02 (m, 1H), 7.17 (d, J=8 Hz, 1H).

Step-2: Preparation of 1-(3-(3-bromo-2-methylphenoxy)propyl)-3,3-difluoropyrrolidine To a stirred solution of 1-bromo-3-(3-chloropropoxy)-2-methylbenzene (10.1 g, 38 mmol) in DMF (60 mL), 3,3-difluoropyrrolidine (11 g, 76 mmol), potassium carbonate (22.5 g, 163 mmol) and sodium iodide (8.5 g, 57 mmol) were added and the reaction mixture was heated at 80° C. for 12 h under nitrogen atmosphere. After TLC showed completion of reaction, the reaction mixture was cooled to room temperature and diluted with EtOAc (100 mL), washed with ice cold water (50 mL), brine solution (50 mL) and the organic phase was dried over sodium sulphate and concentrated in vacuo to give a crude product. The resulting crude was purified by column chromatography (silica gel, 100-200 mesh) using 15% EtOAc in hexanes to afford 1-(3-(3-bromo-2-methylphenoxy) propyl)-3,3-difluoropyrrolidine (7.1 g, 56.3%) as yellow liquid. LCMS (ES) m/z=334.30 [M+H]$^+$ $^1$H NMR (400 MHz, CDCl$_3$): δ 1.96 (m, 2H), 2.22-2.33 (m, 5H), 2.66 (m, 2H), 2.75 (m, 2H), 2.94 (m, 2H), 4.01 (m, 2H), 6.78 (d, J=8.0 Hz, 1H), 6.96-7.00 (m, 1H), 7.15 (d, J=8.0 Hz, 1H).

Step-3: Preparation of (3'-(3-(3,3-difluoropyrrolidin-1-yl)propoxy)-2,2'-dimethyl-[1,1'-biphenyl]-3-yl)methanol To a solution of 1-(3-(3-bromo-2-methylphenoxy)propyl)-3,3-difluoropyrrolidine (2 g, 59 mmol) and (2-methyl-3-(4,4,5,5-tetramethyl-1,3,2-dioxaborolan-2-yl)phenyl) methanol (1.78 g, 71 mmol) in Toluene:Ethanol:water (1:1:1) (30 mL) at room temperature, potassium carbonate (2.47 g, 17 mmol) was added at room temperature and degassed the mixture for 15 min using nitrogen. To this mixture, Pd(dppf)Cl$_2$.DCM (0.24 g, 0.29 mmol) was added and reaction mixture was again degassed for 10 min using nitrogen and heated at 95° C. for 12 h. After completion of the reaction, the reaction mixture was cooled to room temperature and filtered through celite pad. The filtrate was diluted with water (50 mL) and the mixture was extracted with EtOAc (2×100 mL). The organic layer was washed with brine (20 mL), dried over sodium sulfate and concentrated to get crude compound. The resulting crude was purified by column chromatography (silica gel, 100-200 mesh) using 10% EtOAc in hexanes as eluent to afford (3'-(3-(3,3-difluoropyrrolidin-1-yl)propoxy)-2,2'-dimethyl-[1,1'-biphenyl]-3-yl)methanol (Yield: 2 g, 90%) as off white solid. LCMS (ES) m/z=376.18 [M+H]$^+$, $^1$H NMR (400 MHz, DMSO-d$_6$): δ 1.77 (s, 3H), 1.94 (s, 3H), 2.20-2.32 (m, 4H), 2.62-2.68 (m, 4H), 2.92 (m, 2H), 4.06 (m, 2H), 4.54 (m, 2H), 5.09 (m, 1H), 6.64 (d, J=7.44 Hz, 1H), 6.94 (d, J=7.84 Hz, 2H), 7.15-7.22 (m, 2H), 7.39 (d, J=7.44 Hz, 1H).

Step-4: Preparation 5-bromo-2-((3'-(3-(3,3-difluoropyrrolidin-1-yl)propoxy)-2,2'-dimethyl-[1,1'-biphenyl]-3-yl)methoxy)-4-methoxypyrimidine To a stirred solution of (3'-(3-(3,3-difluoropyrrolidin-1-yl)propoxy)-2,2'-dimethyl-[1,1'-biphenyl]-3-yl)methanol (1.41 g, 3.7 mmol) in DMF (30 mL), 5-bromo-4-methoxy-2-(methylsulfonyl)pyrimidine (2 g, 7.49 mmol) and potassium carbonate (3.1 g, 22 mmol) were added and the reaction mixture was heated at 80° C. for 12 h. After completion of reaction, the reaction mixture was diluted with water (60 mL) and extracted with ethyl acetate (2×120 mL). The combined organic layer was washed with ice cold water (50 mL), brine solution (50 mL) and dried over sodium sulfate, evaporated and the crude was purified on combiflash chromatography using 10% ethyl acetate in hexanes as eluent to afford 5-bromo-2-((3'-(3-(3,3-difluoropyrrolidin-1-yl)propoxy)-2,2'-dimethyl-[1,1'-biphenyl]-3-yl)methoxy)-4-methoxypyrimidine as sticky liquid (Yield: 0.7 g, 17%). LCMS (ES) m/z=562.32 [M+H]$^+$ $^1$H NMR (400 MHz, DMSO-d$_6$): δ 1.83 (s, 311), 1.93 (m, 2H), 2.03 (s, 3H), 2.26 (m, 2H), 2.62 (m, 2H), 2.71 (m, 2H), 2.88-2.92 (m, 2H), 3.98 (s, 3H), 4.06 (m, 2H), 5.43 (s, 2H), 6.65 (m, 1H), 6.95 (m, 1H), 7.07 (m, 1H), 7.19-7.39 (m, 2H), 7.43 (m, 1H), 8.53 (s, 1H).

Step-5: Preparation 2-((3'-(3-(3,3-difluoropyrrolidin-1-yl)propoxy)-2,2'-dimethyl-[1,1'-biphenyl]-3-yl)methoxy)-4-methoxy-5-vinylpyrimidine To a stirred solution of 5-bromo-2-((3'-(3-(3,3-difluoropyrrolidin-1-yl)propoxy)-2,2'-dimethyl-[1,1'-biphenyl]-3-yl)methoxy)-4-methoxypyrimidine (0.7 g, 1.24 mmol) in DMF (10 mL), tributyl vinyl tin (1.18 g, 3.7 mmol) was added and the reaction mixture was degassed with nitrogen gas for 10 min. To this mixture, Pd(PPh$_3$)$_4$ (140 mg, 0.12 mmol) was added and the reaction was heated at 100° C. for 8 h. After completion, the reaction mixture was filtered through celite and the filtrate was diluted with water (30 mL) and extracted with ethyl acetate (2×50 mL). The combined organic layer was then dried over sodium sulfate, evaporated and the crude was purified on combiflash chromatography using 3% ethyl acetate in hexanes as eluent to afford 2-((3'-(3-(3,3-difluoropyrrolidin-1-yl)propoxy)-2,2'-dimethyl-[1,1'-biphenyl]-3-yl)methoxy)-4-methoxy-5-vinylpyrimidine as sticky solid (Yield: 0.32 g, 47.5%). LCMS (ES) m/z=510.19 [M+H]$^+$ and purity @ 214 nm, 87.14%.

Step 6: Preparation of 2-((3'-(3-(3,3-difluoropyrrolidin-1-yl)propoxy)-2,2'-dimethyl-[1,1'-biphenyl]-3-yl)methoxy)-4-methoxypyrimidine-5-carbaldehyde To a stirred solution of 2-((3'-(3-(3,3-difluoropyrrolidin-1-yl)propoxy)-2,2'-dimethyl-[1,1'-biphenyl]-3-yl)methoxy)-4-methoxy-5-vinylpyrimidine (0.32 g, 0.62 mmol) in Acetone (10 mL) and water (2 mL) at 0° C., OsO$_4$ (0.6 mL, 2.5 wt % solution in tert-Butanol, 0.062 mmol), N-Methyl-morpholine-N-Oxide (103 mg, 0.87 mmol) was added and stirred for 2 h. To this mixture, NaIO$_4$ (0.22 g, 1 mmol) was added and the reaction was allowed to stir at room temperature for 3 h. After completion of reaction, the reaction mixture was diluted with water (30 mL) and extracted with ethyl acetate (2×100 mL). The organic layer was then dried over sodium sulfate, evaporated and the crude was purified on combiflash chromatography using 12% ethyl acetate in hexanes as eluent to afford 2-((3'-(3-(3,3-difluoropyrrolidin-1-yl)propoxy)-2,2'-dimethyl-[1,1'-biphenyl]-3-yl)methoxy)-4-methoxypyrimidine-5-carbaldehyde as white sticky solid (Yield: 80 mg, 53%). LCMS (ES) m/z=512.45 [M+H]$^+$ and purity @ 214 nm, 95.24%; $^1$H NMR (400 MHz, DMSO-d$_6$) δ ppm: 1.83 (s, 3H), 1.93 (m, 2H), 2.00 (s, 3H), 2.17-2.24 (m, 2H), 2.59 (m, 2H), 2.68-2.70 (m, 2H), 2.89 (m, 2H), 4.04 (m, 2H), 4.06 (s, 3H), 5.57 (s, 2H), 6.66 (d, J=7.6 Hz, 1H), 6.95 (d, J=9.2 Hz, 1H), 7.08 (d, J=7.36 Hz, 1H), 7.17-7.27 (m, 2H), 7.44 (d, J=7.2 Hz, 1H), 8.80 (s, 1H), 10.04 (s, 1H).

Step 7: Preparation of (S)-1-((2-((3'-(3-(3,3-difluoropyrrolidin-1-yl)propoxy)-2,2'-dimethyl-[1,1'-biphenyl]-3-yl)methoxy)-4-methoxypyrimidin-5-yl)methyl)piperidine-2-carboxylic acid To a solution of 2-((3'-(3-(3,3-difluoropyrrolidin-1-yl)propoxy)-2,2'-dimethyl-[1,1'-biphenyl]-3-yl)methoxy)-4-methoxypyrimidine-5-carbaldehyde (70 mg, 0.1368 mmol) in MeOH (3 mL) and DMF (3 mL), (S)-piperidine-2-carboxylic acid (26 mg, 0.2052 mmol) and acetic acid (0.1 mL) were added simultaneously and the reaction was stirred at room temperature for 2 h. To this reaction mixture, NaCNBH$_3$ (25 mg, 0.41 mmol) was added and continued stirring at room temperature for 16 h. The reaction mixture was diluted with water (10 mL) and extracted with 10% MeOH in DCM (2×20 mL). The combined organic layer was washed with water (5 mL) and brine solution (5 mL), dried over sodium sulphate and concentrated to give the crude residue which was purified on combiflash chromatography using 8% methanol in dichloromethane as eluent to afford (S)-1-((2-((3'-(3-(3,3-difluoropyrrolidin-1-yl)propoxy)-2,2'-dimethyl-[1,1'-biphenyl]-3-yl)methoxy)-4-methoxypyrimidin-5-yl)methyl)piperidine-2-carboxylic acid as light white solid (Yield: 33 mg, 39%). LCMS (ES) m/z=625.35 [M+H]$^+$ and purity @ 214 nm, 95.52%; $^1$H NMR (400 MHz, DMSO-d$_6$) δ ppm: 1.35-1.50 (m, 4H), 1.70-1.73 (m, 2H), 1.83 (s, 3H), 1.80-1.93 (m, 2H), 2.00 (s, 3H), 2.17-2.32 (m, 3H), 2.53-2.71 (m, 4H), 2.92 (m, 3H), 3.12 (m, 1H), 3.54-3.66 (m, 2H), 3.89 (s, 3H), 4.06 (m, 2H), 5.43 (s, 2H), 6.67 (d, J=7.48 Hz, 1H), 6.95 (d, J=8.21 Hz, 1H), 7.05 (d, J=7.36 Hz, 1H), 7.17-7.27 (m, 2H), 7.44 (d, J=7.48 Hz, 1H), 8.24 (s, 1H).

Following compounds were synthesized using the similar procedure as exemplified for Compound-1 to Compound-13 above.

N-(2-(((4-methoxy-2-((2-methyl-[1,1'-biphenyl]-3-yl)methoxy)pyrimidin-5-yl)methyl)amino)ethyl)acetamide (Compound-14)

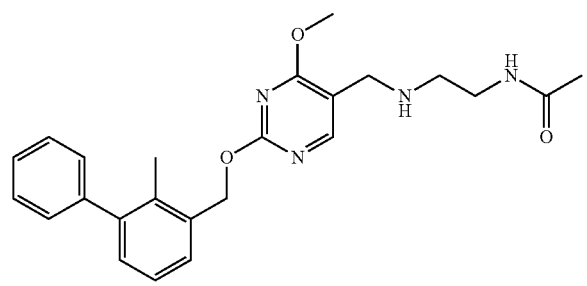 [SMILES: COc1nc(OCc2cccc(-c3ccccc3)c2C)ncc1CNCCNC(C)=O]

LCMS (ES) m/z=421.3 [M+H]$^+$; $^1$HNMR (400 MHz, DMSO-d$_6$): δ 1.73 (s, 3H), 2.19 (s, 3H), 3.08-3.12 (m, 2H), 3.55 (s, 3H), 3.91 (s, 3H), 5.42 (s, 2H), 7.17 (d, J=7.6 Hz, 1H), 7.24 (d, J=7.6 Hz, 1H), 7.29 (d, J=7.2 Hz, 2H), 7.36. (d, J=7.2 Hz, 1H), 7.41-7.45 (m, 3H), 7.73 (bs, 1H), 8.22 (s, 1H).

Compound-15: (R)-1-((4-methoxy-2-((2-methyl-[1,1'-biphenyl]-3-yl)methoxy)pyrimidin-5-yl)methyl)piperidine-2-carboxylic acid

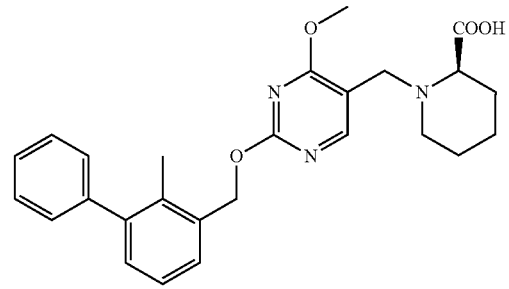 [SMILES: COc1nc(OCc2cccc(-c3ccccc3)c2C)ncc1CN1CCCC[C@@H]1C(=O)O]

LCMS (ES) m/z=448.24 [M+H]$^+$ and purity @ 214 nm, 99.9%; $^1$H NMR (400 MHz, DMSO-d$_6$): δ 1.35 (m, 1H), 1.46 (m, 3H), 1.70 (m, 2H), 2.20 (m, 4H), 2.89 (m, 1H), 3.07 (bs, 1H), 3.55 (d, J=14 Hz, 1H), 3.66 (d, J=14 Hz, 1H), 3.90 (s, 3H), 5.43 (s, 2H), 7.21 (m, 1H). 7.26-7.30 (m, 3H), 7.37 (m, 1H), 7.44-7.48 (m, 3H), 8.25 (s, 1H).

(S)-1-((2-((4'-fluoro-2-methyl-[1,1'-biphenyl]-3-yl)methoxy)-4-methoxypyrimidin-5-yl)methyl)piperidine-2-carboxylic acid (Compound 16)

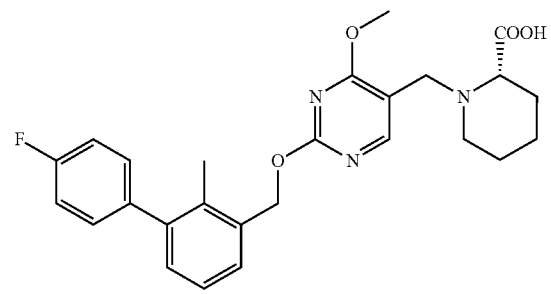 [SMILES: COc1nc(OCc2cccc(-c3ccc(F)cc3)c2C)ncc1CN1CCCC[C@H]1C(=O)O]

LCMS (ES) m/z=466.3 [M+H]$^+$; $^1$HNMR (400 MHz, DMSO-d$_6$): δ 1.33 (bs, 1H), 1.45 (s, 3H), 1.71 (bs, 2H), 2.18 (s, 3H), 2.20-2.25 (m, 1H), 2.86-2.89 (m, 1H), 3.05-3.15 (m, 1H), 3.51-3.64 (m, 2H), 3.88 (s, 3H), 5.41 (s, 2H), 7.17 (d, J=7.6 Hz, 1H), 7.23-7.27 (m, 3H), 7.31-7.35 (m, 2H), 7.43 (d, J=7.2 Hz, 1H), 8.23 (s, 1H).

169

(S)-1-((2-((3'-fluoro-2-methyl-[1,1'-biphenyl]-3-yl)methoxy)-4-methoxypyrimidin-5-yl)methyl)piperidine-2-carboxylic acid (Compound 17)

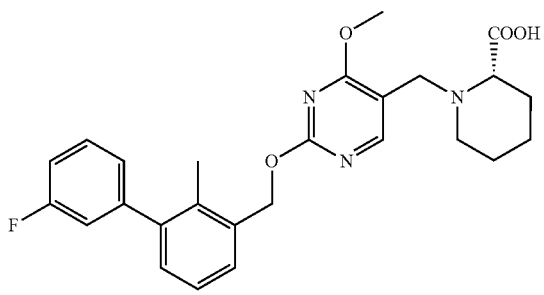 [SMILES: COc1nc(OCc2cccc(-c3cccc(F)c3)c2C)ncc1CN1CCCC[C@H]1C(=O)O]

LCMS (ES) m/z=466.2 [M+H]$^+$; $^1$HNMR (400 MHz, DMSO-d$_6$): δ 1.35 (bs, 1H), 1.40-1.50 (m, 3H), 1.65-1.78 (m, 2H), 2.20 (s, 3H), 2.30-2.47 (m, 1H), 2.86-2.89 (m, 1H), 3.10 (bs, 1H), 3.52-3.55 (m, 1H), 3.61-3.64 (m, 1H), 3.88 (s, 3H), 5.42 (s, 2H), 7.14 (d, J=8 Hz, 2H), 7.19-7.20 (m, 2H), 7.27 (t, J=7.2 Hz, 2H), 7.44-7.50 (m, 2H), 8.23 (s, 1H).

N-(2-(((2-((3'-fluoro-2-methyl-[1,1'-biphenyl]-3-yl)methoxy)-4-methoxypyrimidin-5-yl)methyl)amino)ethyl)acetamide (Compound-18)

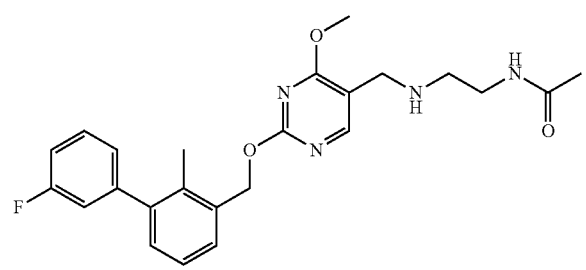 [SMILES: COc1nc(OCc2cccc(-c3cccc(F)c3)c2C)ncc1CNCCNC(C)=O]

LCMS (ES) m z=439.2 [M+H]$^+$: $^1$HNMR (400 MHz, DMSO-d$_6$): δ 1.77 (s, 3H), 2.19 (s, 3H), 2.54 (t, J=6.4 Hz, 2H), 3.12 (q, J=6.0 Hz, 2H), 3.59 (s, 2H), 3.91 (s, 3H), 5.42 (s, 2H), 7.13 (d, J=8.0 Hz, 2H), 7.18-7.20 (m, 2H), 7.26 (t, J=7.6 Hz, 1H), 7.44-7.50 (m, 2H), 7.76 (bs, 1H), 8.24 (s, 1H).

(S)-1-((2-((2'-fluoro-2-methyl-[1,1'-biphenyl]-3-yl)methoxy)-4-methoxypyrimidin-5-yl)methyl)piperidine-2-carboxylic acid (Compound 19)

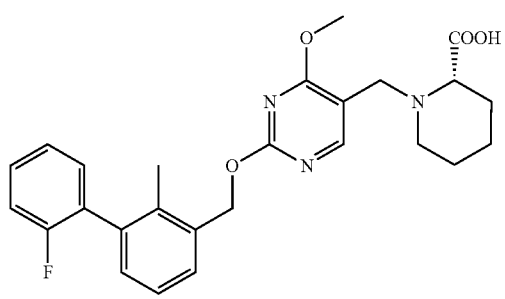 [SMILES: COc1nc(OCc2cccc(-c3ccccc3F)c2C)ncc1CN1CCCC[C@H]1C(=O)O]

170

LCMS (ES) m/z=466.2 [M+H]$^+$; $^1$HNMR (400 MHz, DMSO-d$_6$): δ 1.33 (bs, 1H), 1.40-1.50 (m, 3H), 1.76-1.78 (m, 2H), 2.11 (s, 3H), 2.23-2.30 (m, 1H), 2.86-2.89 (m, 1H), 3.10 (bs, 1H), 3.51-3.54 (m, 1H), 3.61-3.65 (m, 1H), 3.88 (s, 3H), 5.42 (s, 2H), 7.18 (d, J=7.2, 1H), 7.26-7.29 (m, 4H), 7.43-7.48 (m, 2H), 8.25 (s, 1H).

N-(2-(((2-((2'-fluoro-2-methyl-[1,1'-biphenyl]-3-yl)methoxy)-4-methoxypyrimidin-5-yl)methyl)amino)ethyl)acetamide (Compound 20)

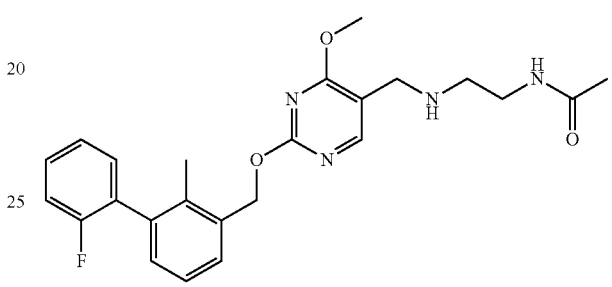

LCMS (ES) m/z=439.2 [M+H]$^+$; $^1$HNMR (400 MHz, DMSO-d$_6$): δ 1.77 (s, 3H), 2.11 (s, 3H), 2.55-2.61 (m, 2H), 3.10-3.15 (m, 2H), 3.32 (s, 1H), 3.62 (s, 2H), 3.91 (s, 3H), 5.43 (s, 2H), 7.18 (d, J=7.2, 1H), 7.26-7.31 (m, 4H), 7.41-7.47 (m, 2H), 7.78 (bs, 1H), 8.25 (s, 1H).

N-(2-(((4-ethoxy-2-((2-methyl-[1,1'-biphenyl]-3-yl)methoxy)pyrimidin-5-yl)methyl)amino)ethyl)acetamide (Compound 21)

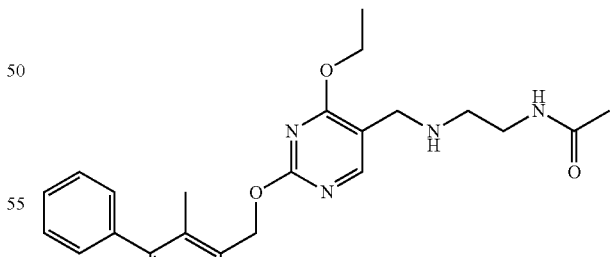

LCMS (ES) m/z=435.3 [M+H]$^+$; $^1$HNMR (400 MHz, DMSO-d$_6$): δ1.30 (t, J=7.2 Hz, 3H), 1.76 (s, 3H), 2.18 (s, 3H), 2.52-2.53 (m, 2H), 3.08-3.13 (m, 2H), 3.56 (s, 2H), 4.37 (q, J=7.2 Hz, 2H), 5.40 (s, 2H), 7.16 (d, J=7.2 Hz, 1H), 7.23-7.29 (m, 3H), 7.35-7.37 (m, 1H), 7.39-7.45 (m, 3H), 7.74 (bs, 1H), 8.22 (s, 1H).

171

(S)-1-(((4-ethoxy-2-((2-methyl-[1,1'-biphenyl]-3-yl)methoxy)pyrimidin-5-yl)methyl)piperidine-2-carboxylic acid (Compound 22)

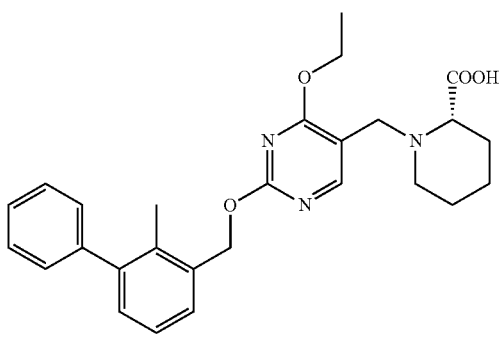 [SMILES: CCOc1nc(OCc2cccc(-c3ccccc3)c2C)ncc1CN1CCCC[C@H]1C(=O)O]

LCMS (ES) m/z=462.2 [M+H]+; 1HNMR (400 MHz, DMSO-d$_6$): δ 1.28 (t, J=7.2 Hz, 3H), 1.35-1.45 (m, 3H), 1.66-1.78 (m, 2H), 2.18 (s, 3H), 2.87-2.90 (m, 2H), 3.09-3.13 (m, 2H), 3.50-3.54 (m, 1H), 3.60-3.63 (m, 1H), 4.35 (q, J=6.8 Hz, 2H), 5.40 (s, 2H), 7.17 (d, J=6.8 Hz, 1H), 7.25-7.30 (m, 3H) 7.34-7.37 (m, 1H), 7.40-7.45 (m, 3H), 8.22 (s, 1H).

1-(((4-ethoxy-2-((2-methyl-[1,1'-biphenyl]-3-yl)methoxy)pyrimidin-5-yl)methyl)amino)cyclopropane-1-carboxylic acid (Compound 23)

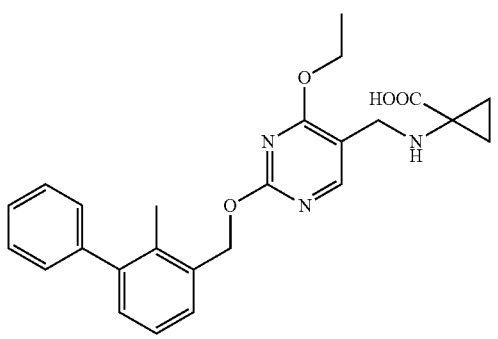 [SMILES: CCOc1nc(OCc2cccc(-c3ccccc3)c2C)ncc1CNC1(C(=O)O)CC1]

LCMS (ES) m/z=434.1 [M+H]+; 1HNMR (400 MHz, DMSO-d$_6$): δ0.88-0.89 (m, 2H), 1.05-1.09 (m, 2H), 1.30 (t, J=6.8 Hz, 3H), 2.17 (s, 3H), 3.67 (s, 3H), 4.35 (q. J=6.8 Hz, 21H), 5.39 (s, 2H) 7.16 (d, J=7.2 Hz, 1H), 7.22-7.29 (m, 3H), 7.34-7.45 (m, 5H), 8.15 (s, 1H).

172

(3-(((4-ethoxy-2-((2-methyl-[1,1'-biphenyl]-3-yl)methoxy)pyrimidin-5-yl)methyl)amino)propanoic acid (Compound 24)

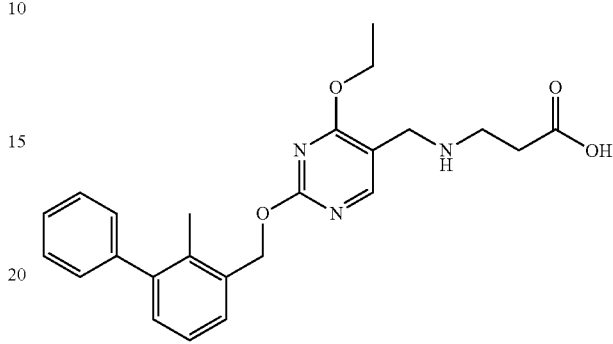

LCMS (ES) m/z=422 [M+H]+; 1HNMR (400 MHz, DMSO-d$_6$): δ1.30 (t, J=6.8 Hz, 3H), 2.18-2.20 (m, 6H), 2.65 (s, 2H), 3.58 (s, 2H), 4.37 (q, J=7.2 Hz, 2H), 5.40 (s, 2H) 7.16 (d, J=7.6 Hz, 1H), 7.23-7.29 (m, 3H) 7.34-7.45 (m, 4H), 8.23 (s, 1H).

2-(((4-ethoxy-2-((2-methyl-[1,1'-biphenyl]-3-yl)methoxy)pyrimidin-5-yl)methyl)amino)-2-(hydroxymethyl)propane-1,3-diol (Compound 25)

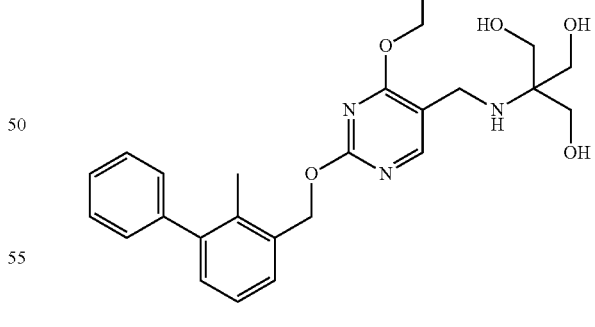

LCMS (ES) m/z=454 [M+H]+; 1HNMR (400 MHz, DMSO-d$_6$): δ1.29 (t, J=6.8 Hz, 3H), 1.77 (bs, 1H), 2.18 (s, 3H), 3.35-3.36 (m, 6H), 3.60 (s, 2H), 4.20 (s, 3H), 4.36 (q, J=7.2 Hz, 2H), 5.40 (s, 2H), 7.16 (d, J=7.6 Hz, 1H), 7.23-7.30 (m, 3H), 7.34-7.45 (m, 4H), 8.25 (s, 1H).

173

(2-(((4-ethoxy-2-((2-methyl-[1,1'-biphenyl]-3-yl)methoxy)pyrimidin-5-yl)methyl)(methyl)amino)-2-(hydroxymethyl)propane-1,3-diol (Compound 26)

174

((4-ethoxy-2-((2-methyl-[1,1'-biphenyl]-3-yl)methoxy)pyrimidin-5-yl)methyl)-D-alanine (Compound 28)

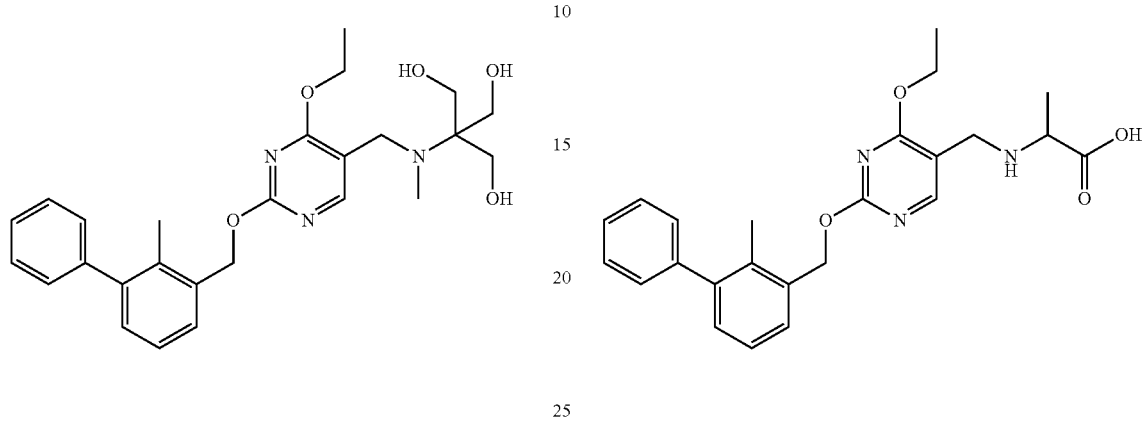

LCMS (ES) m/z=468.2 [M+H]$^+$; $^1$HNMR (400 MHz, DMSO-d$_6$): δ1.30 (t, J=7.2 Hz, 3H), 2.18 (s, 6H), 3.50-3.51 (m, 6H), 3.66 (s, 2H), 4.20 (s, 3H), 4.35 (q, J=6.8 Hz, 2H), 5.40 (s, 2H), 7.17 (d, J=7.8 Hz, 1H), 7.23-7.30 (m, 3H) 7.34-7.45 (m, 4H), 8.25 (s, 1H).

LCMS (ES) m/z=422.1 [M+H]$^+$; $^1$HNMR (400 MHz, DMSO-d$_6$): δ 1.23-1.22 (m, 3H), 1.31 (s, 3H), 2.18 (s, 3H), 3.20-3.17 (m, 3H), 3.75-3.63 (m, 2H), 4.39-4.37 (m, 2H), 5.42 (s, 2H) 7.18-7.16 (m, 1H), 7.30-7.23 (m, 3H) 7.43-7.36 (m, 4H), 8.28 (s, 1H).

(S)-3-(((4-ethoxy-2-((2-methyl-[1,1'-biphenyl]-3-yl)methoxy)pyrimidin-5-yl)methyl)amino)butanoic acid (Compound 27)

((4-ethoxy-2-((2-methyl-[1,1'-biphenyl]-3-yl)methoxy)pyrimidin-5-yl)methyl)asparagine (Compound 29)

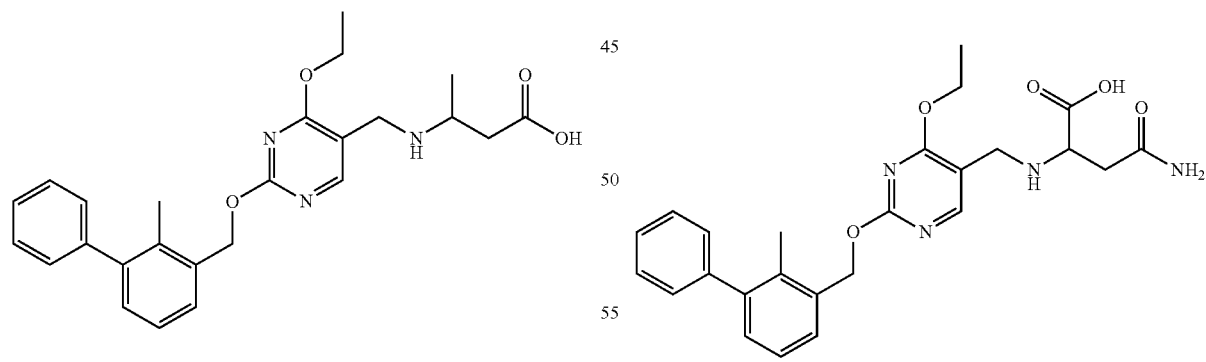

LCMS (ES) m/z=436.52 [M+H]$^+$; $^1$HNMR (400 MHz, DMSO-d$_6$): δ 1.09 (d, J=6.4 Hz, 3H) 1.30-1.26 (m, 2H), 1.33-1.30 (m, 3H), 2.22-2.18 (m, 5H), 2.97-2.94 (m, 1H), 3.74-3.61 (m, 2H), 4.39-4.37 (m, 2H), 5.42 (s, 2H), 7.18-7.16 (m, 1H), 7.30-7.23 (m, 3H) 7.45-7.40 (m, 4H), 8.28 (s, 1H).

LCMS (ES) m/z=464.52 [M+H]$^+$; $^1$HNMR (400 MHz, DMSO-d$_6$): δ 1.31 (t, J=7.2 Hz, 3H), 2.18 (s, 3H), 3.38 (bs, 2H), 3.77-3.68 (m, 2H), 4.40-4.35 (m, 2H), 5.42 (s, 2H), 6.93 (s, 1H), 7.30-7.23 (m, 3H) 7.50-7.34 (m, 4H), 8.28 (s, 1H).

175

(2R,4R)-1-((4-ethoxy-2-((2-methyl-[1,1'-biphenyl]-3-yl)methoxy)pyrimidin-5-yl)methyl)-4-hydroxypyrrolidine-2-carboxylic acid (Compound 30)

176

N-(2-(((4-(benzyloxy)-2-((2-methyl-[1,1'-biphenyl]-3-yl)methoxy)pyrimidin-5-yl)methyl)amino)ethyl)acetamide (Compound 32)

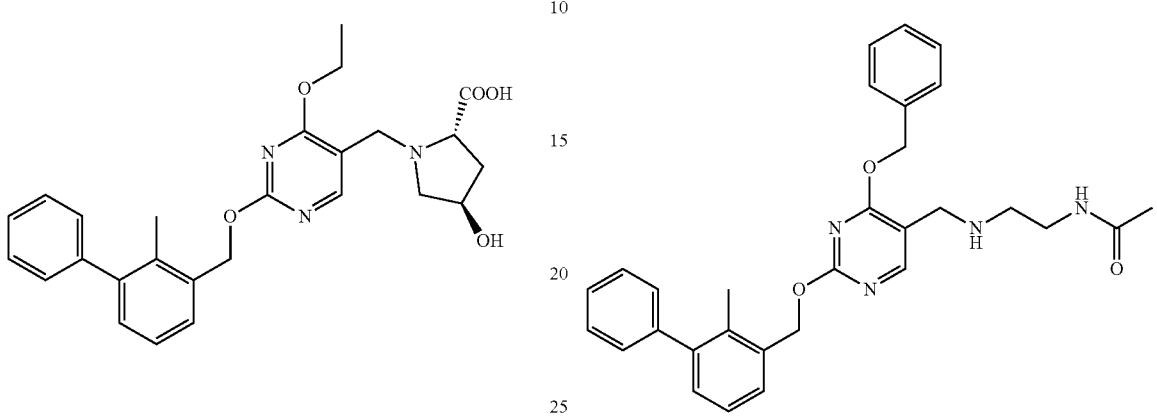

LCMS (ES) m/z=464.2 [M+H]⁺; ¹HNMR (400 MHz, DMSO-d₆): δ 1.33 (t, J=7.2 Hz, 3H), 1.98-1.90 (m, 2H), 2.13 (s, 3H), 2.42-2.39 (m, 1H) 3.21-3.17 (m, 2H), 3.46-3.42 (m, 2H), 3.79-3.73 (m, 2H), 4.17 (s, 1H), 4.38-4.33 (m, 2H), 5.41 (s, 2H), 7.17-7.16 (m, 1H), 7.30-7.23 (m, 3H), 7.37-7.33 (m, 1H), 7.45-7.40 (m, 3H), 8.23 (s, 1H).

LCMS (ES) m/z=496.61 [M+H]⁺; ¹HNMR (400 MHz, DMSO-d₆): δ 1.72 (s, 3H), 2.17 (s, 3H), 2.555-2.53 (m, 3H), 3.14-3.08 (m, 2H), 3.64 (s, 2H), 5.47-5.37 (m, 4H) 7.17-7.16 (m, 2H), 7.34-7.27 (m, 3H) 7.36-7.34 (m, 5H), 7.45-7.37 (m, 4H), 8.26 (s, 1H).

1-((4-ethoxy-2-((2-methyl-[1,1'-biphenyl]-3-yl)methoxy)pyrimidin-5-yl)methyl)azetidine-2-carboxylic acid (Compound 31)

1-((4-(benzyloxy)-2-((2-methyl-[1,1'-biphenyl]-3-yl)methoxy)pyrimidin-5-yl)methyl)piperidine-2-carboxylic acid (Compound 33)

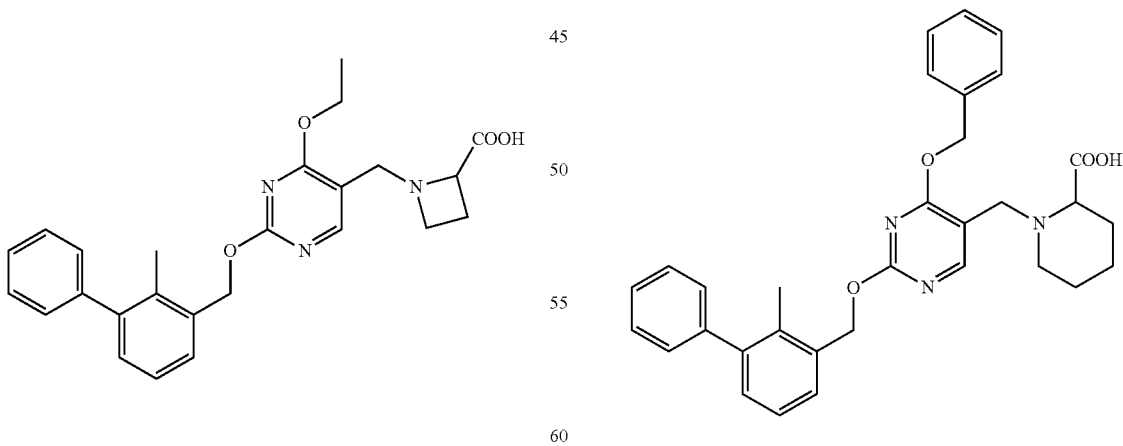

LCMS (ES) m/z=433.51 [M+H]⁺; ¹HNMR (400 MHz, DMSO-d₆): δ 1.29 (q, J=4.2 Hz, 3H), 2.05-1.82 (m, 2H), 2.18 (s, 3H), 3.20-3.11 (m, 4H), 3.74-3.70 (m, 1H), 4.38-4.32 (m, 2H), 5.39 (s, 2H), 7.30-7.15 (m, 5H), 7.45-7.37 (m, 5H), 8.20 (s, 1H).

LCMS (ES) m/z=523.63 [M+H]⁺; ¹HNMR (400 MHz, DMSO-d₆): δ 1.21 (s, 1H), 1.43-1.39 (m, 4H), 1.72-1.70 (m, 2H), 2.17 (s, 3H), 2.30-2.21 (m, 1H), 2.86-2.85 (m, 1H), 3.16-3.15 (m, 2H), 3.67-3.51 (m, 2H), 5.41 (d, J=5.6 Hz, 2H), 7.18-7.16 (m, 2H), 7.34-7.27 (m, 3H), 7.36-7.34 (m, 5H), 7.45-7.37 (m, 4H), 8.25 (s, 1H).

177

(2S,4R)-1-((4,6-dimethoxy-2-((2-methyl-[1,1'-biphenyl]-3-yl)methoxy)pyrimidin-5-yl)methyl)-4-hydroxypyrrolidine-2-carboxylic acid (Compound 34)

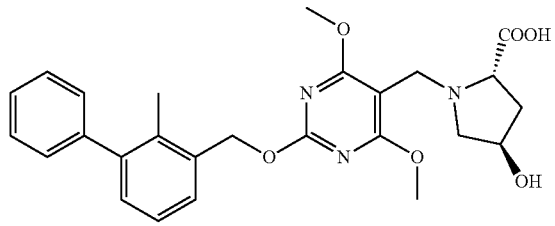 [SMILES: COc1nc(OCc2cccc(-c3ccccc3)c2C)nc(OC)c1CN1C[C@H](O)C[C@H]1C(=O)O]

LCMS (ES) m/z=480.2 [M+H]$^+$; $^1$HNMR (400 MHz, DMSO-d$_6$): δ 1.88-1.90 (m, 2H), 2.21 (s, 3H), 3.14 (s, 1H), 3.35-3.19 (m, 1H), 3.76-3.83 (m, 3H), 3.88 (s, 6H), 4.15 (bs, 1H), 4.94 (bs, 1H), 5.44 (s, 2H), 7.18 (d, J=7.6 Hz, 1H), 7.24-7.30 (m, 3H) 7.33-7.37 (m, 1H), 7.41-7.46 (m, 3H).

2-(((4,6-dimethoxy-2-((2-methyl-[1,1'-biphenyl]-3-yl)methoxy)pyrimidin-5-yl)methyl)amino)-2-(hydroxymethyl)propane-1,3-diol (Compound 35)

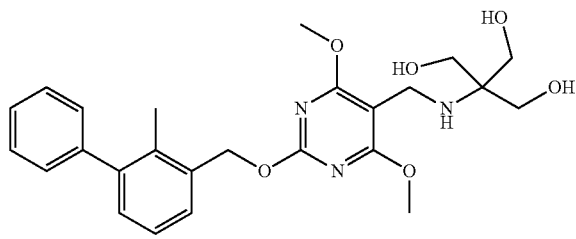 [SMILES: COc1nc(OCc2cccc(-c3ccccc3)c2C)nc(OC)c1CNC(CO)(CO)CO]

LCMS (ES) m/z=470.2 [M+H]$^+$; $^1$HNMR (400 MHz, DMSO-d$_6$): δ 2.20 (s, 3H), 3.34 (d, J=4.8 Hz, 6H), 3.54 (s, 2H), 3.88 (s, 6H), 4.12, bs, 3H), 5.43 (s, 2H), 7.16 (d, J=7.6 Hz, 1H), 7.24-7.30 (m, 3H), 7.34-7.39 (m, 1H), 7.43 (t, J=7.6 Hz, 3H).

((4,6-dimethoxy-2-((2-methyl-[1,1'-biphenyl]-3-yl)methoxy)pyrimidin-5-yl)methyl)-L-proline (Compound 36)

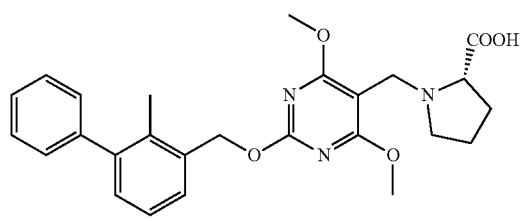 [SMILES: COc1nc(OCc2cccc(-c3ccccc3)c2C)nc(OC)c1CN1CCC[C@H]1C(=O)O]

LCMS (ES) m/z=464.4 [M+H]$^+$; $^1$HNMR (400 MHz, DMSO-d$_6$): δ 1.55-1.89 (m, 3H), 2.01-2.22 (m, 1H), 2.21 (s, 3H), 2.65 (bs, 1H), 3.05-3.09 (m, 1H), 3.18-3.29 (m, 1H), 3.86 (s, 2H), 3.90 (S, 6H), 5.45 (s, 2H), 7.19 (d, J=7.6 Hz, 1H), 7.25-7.30 (m, 3H), 7.34-7.38 (m, 1H), 7.42-7.47 (m, 3H).

178

Methyl 4-((4,6-dimethoxy-2-((2-methyl-[1,1'-biphenyl]-3-yl)methoxy)pyrimidin-5-yl)methyl) morpholine-3-carboxylate (Compound 37)

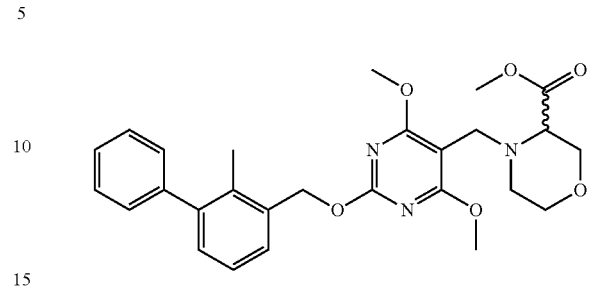

LCMS (ES) m/z=494.4 [M+H]$^+$; $^1$HNMR (400 MHz, DMSO-d$_6$): δ 2.21 (s, 3H), 2.29-2.32 (m, 1H), 3.09 (t, J=8.4 Hz, 1H), 3.16-3.27 (m, 1H), 3.45-3.50 (m, 1H), 3.52-3.69 (m, 7H), 3.85 (s, 6H), 5.44 (s, 2H), 7.18 (d, J=8 Hz, 1H), 7.24-7.38 (m, 3H), 7.34-7.38 (m, 1H), 7.42-7.46 (m, 3H).

4-((4,6-dimethoxy-2-((2-methyl-[1,1'-biphenyl]-3-yl)methoxy)pyrimidin-5-yl)methyl)morpholine-3-carboxylic acid (Compound 38)

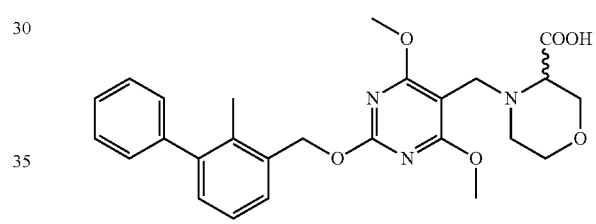

LCMS (ES) m/z=480 [M+H]$^+$; $^1$HNMR (400 MHz, DMSO-d$_6$): δ 2.21 (s, 3H), 2.29-2.32 (m, 1H), 2.99-3.04 (m, 1H), 3.42-3.49 (m, 2H), 3.51-3.64 (m, 3H), 3.66-3.72 (m, 2H), 3.85 (s, 6H), 5.43 (s, 2H), 7.18 (d, J=8 Hz, 1H), 7.24-7.38 (m, 3H), 7.34-7.38 (m, 1H), 7.42-7.46 (m, 3H).

(2S,4R)-1-((4,6-diethoxy-2-((2-methyl-[1,1'-biphenyl]-3-yl)methoxy)pyrimidin-5-yl)methyl)-4-hydroxypyrrolidine-2-carboxylic acid (Compound 39)

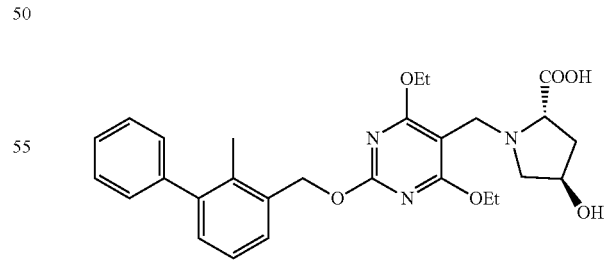

LCMS (ES) m/z=508.19 [M+H]$^+$; $^1$H NMR (400 MHz, DMSO-d$_6$): δ 1.30-1.32 (t, 6H), 1.93 (m, 2H), 2.21 (s, 3H), 2.66 (m, 1H), 3.23-3.27 (bs, 1H), 3.36-3.46 (bs, 1H), 3.82 (d, 1H), 3.92 (d, 1H), 4.17 (s, 1H), 4.35-4.38 (m, 4H), 4.97 (bs, 1H), 5.43 (s, 2H), 7.20 (m, 1H), 7.26-7.30 (m, 3H), 7.40 (m, 1H), 7.44-7.48 (m, 3H). HPLC @ 214 nm, 99.78%.

((S)-1-((4,6-diethoxy-2-((2-methyl-[1,1'-biphenyl]-3-yl)methoxy)pyrimidin-5-yl)methyl)piperidine-2-carboxylic acid (Compound 40)

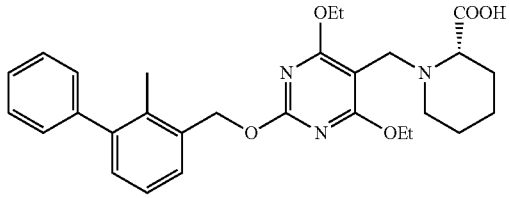 [SMILES: CCOc1nc(OCc2cccc(-c3ccccc3)c2C)nc(OCC)c1CN1CCCC[C@H]1C(=O)O]

LCMS (ES) m/z=506.19 [M+H]$^+$; $^1$H NMR (400 MHz, DMSO-d$_6$): δ 1.26-1.28 (m, 6H), 1.33 (m, 2H), 1.46 (m, 2H), 1.70 (s, 2H), 2.21 (s, 3H), 2.37 (m, 1H), 3.00 (s, 1H), 3.11 (s, 1H), 3.62 (d, J=13.2 Hz, 1H), 3.74 (d, J=13.2 Hz, 1H), 4.33 (m, 4H), 5.41 (s, 2H), 7.20 (m, 1H), 7.26-7.30 (m, 3H), 7.40 (m, 1H), 7.44-7.48 (m, 3H). HPLC @ 214 nm, 99.60%.

2-(((4,6-diethoxy-2-((2-methyl-[1,1'-biphenyl]-3-yl)methoxy)pyrimidin-5-yl)methyl)amino)-2-(hydroxymethyl)propane-1,3-diol (Compound 41)

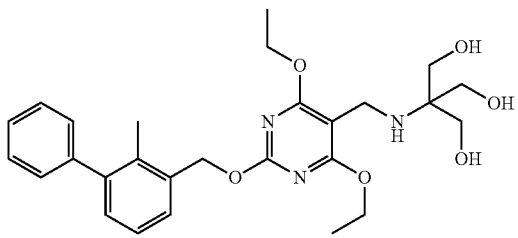 [SMILES: CCOc1nc(OCc2cccc(-c3ccccc3)c2C)nc(OCC)c1CNC(CO)(CO)CO]

LCMS (ES) m/z=498.2 [M+H]J; $^1$H NMR (400 MHz, DMSO-d$_6$): δ 1.28 (m, 6H), 2.21 (s, 3H), 3.40 (m, 4H), 3.56 (bs, 2H), 4.15 (bs, 2H), 4.33-4.38 (m, 4H), 5.42 (m, 2H), 7.20 (m, 1H), 7.26-7.30 (m, 3H), 7.40 (m, 1H), 7.44-7.48 (m, 3H). HPLC @ 214 nm, 99.77%.

2-(((4,6-dimethoxy-2-((2-methyl-[1,1'-biphenyl]-3-yl)methoxy)pyrimidin-5-yl)methyl)amino)-2-(hydroxymethyl)propane-1,3-diol (Compound 42)

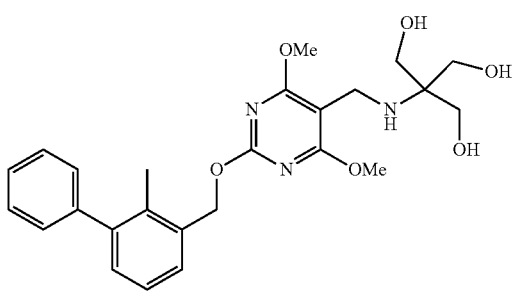 [SMILES: COc1nc(OCc2cccc(-c3ccccc3)c2C)nc(OC)c1CNC(CO)(CO)CO]

LCMS (ES) m/z=470.362 [M+H]$^+$; $^1$H NMR (400 MHz, DMSO-d$_6$): δ 2.22 (s, 3H), 3.38 (m, 3H), 3.57 (m, 2H), 3.90 (s, 6H), 4.71 (bs, 2H), 5.45 (s, 2H), 7.20 (m, 1H), 7.26-7.30 (m, 3H), 7.37 (m, 1H), 7.44-7.48 (m, 3H). HPLC @ 214 nm, 97.42%.

(S)-4-((4,6-dimethoxy-2-((2-methyl-[1,1'-biphenyl]-3-yl)methoxy)pyrimidin-5-yl)methyl)morpholine-3-carboxylic acid (Compound 43)

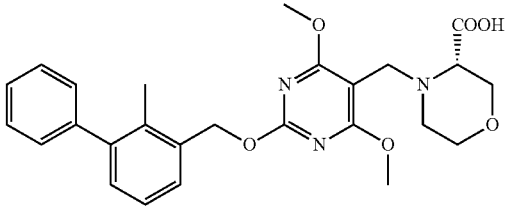 [SMILES: COc1nc(OCc2cccc(-c3ccccc3)c2C)nc(OC)c1CN1CCOC[C@H]1C(=O)O]

LCMS (ES) m/z=480.25 [M+H]$^+$; $^1$H NMR (400 MHz, DMSO-d$_6$): δ 2.22 (s, 3H), 3.03 (m, 2H), 3.32 (m, 1H), 3.50 (m, 1H), 3.59 (m, 3H), 3.67 (m, 2H), 3.87 (s, 6H), 5.45 (s, 2H), 7.20 (m, 1H), 7.26-7.30 (m, 3H), 7.37 (m, 1H), 7.44-7.48 (m, 3H). HPLC @ 214 nm, 98.9%.

2-(4-((4,6-dimethoxy-2-((2-methyl-[1,1'-biphenyl]-3-yl)methoxy)pyrimidin-5-yl)methyl)morpholin-3-yl)acetic acid (Compound 44)

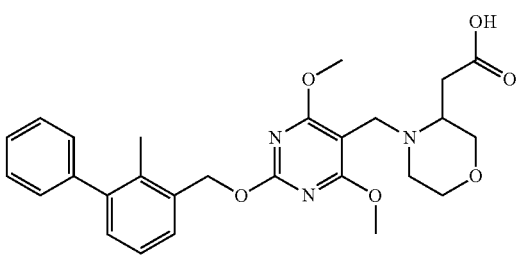 [SMILES: COc1nc(OCc2cccc(-c3ccccc3)c2C)nc(OC)c1CN1CCOCC1CC(=O)O]

LCMS (ES) m/z=494.30 [M+H]$^+$; $^1$H NMR (400 MHz, DMSO-d$_6$) δ ppm: 2.20 (m, 5H), 2.50 (m, 1H), 2.71 (m, 2H), 3.22 (m, 2H), 3.40-3.63 (m, 4H), 3.88 (s, 6H). 5.45 (s, 2H), 7.20 (m, 1H), 7.26-7.30 (m, 3H), 7.39 (m, 1H), 7.44-7.48 (m, 3H). HPLC @ 214 nm, 98.43%.

(S)-1-((4,6-dimethoxy-2-((2-methyl-[1,1'-biphenyl]-3-yl)methoxy)pyrimidin-5-yl)methyl)piperidine-2-carboxylic acid (Compound 45)

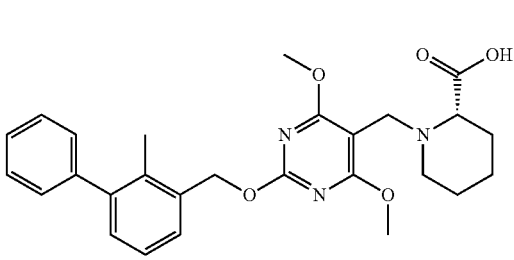 [SMILES: COc1nc(OCc2cccc(-c3ccccc3)c2C)nc(OC)c1CN1CCCC[C@H]1C(=O)O]

LCMS (ES) m/z=478.36 [M+H]$^+$; $^1$H NMR (400 MHz, DMSO-d$_6$): δ 1.23-1.31 (m, 4H), 1.63 (m, 1H), 1.71 (m, 1H), 2.23 (s, 3H), 2.33 (m, 1H), 3.03-2.97 (m, 2H), 3.63 (m, 1H), 3.77 (m, 1H), 3.91 (s, 6H), 5.45 (s, 2H), 7.20 (m, 1H), 7.26-7.32 (m, 3H), 7.37 (m, 1H), 7.44-7.48 (m, 3H). HPLC @ 214 nm, 99.83%.

(S)-5-((4,6-dimethoxy-2-((2-methyl-[1,1'-biphenyl]-3-yl)methoxy)pyrimidin-5-yl)methyl)-5-azaspiro[2.4]heptane-6-carboxylic acid (Compound 46)

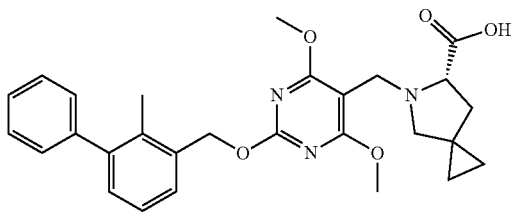 [SMILES: COc1nc(OCc2cccc(-c3ccccc3)c2C)nc(OC)c1CN1CC2(CC2)C[C@H]1C(=O)O]

LCMS (ES) m/z=490.39 [M+H]+; 1H NMR (400 MHz, DMSO-d6): δ 0.42-0.55 (m, 4H), 1.23 (m, 2H), 1.71-1.75 (m, 1H), 2.23 (s, 3H), 2.27 (m, 1H), 2.87 (m, 1H), 2.94 (m, 1H), 3.59 (m, 1H), 3.97 (s, 6H), 5.47 (s, 2H), 7.19-7.21 (m, 1H), 7.26-7.32 (m, 3H), 7.35-7.39 (m, 1H), 7.43-7.47 (m, 3H). HPLC @ 214 nm, 99.30%.

7-((4,6-dimethoxy-2-((2-methyl-[1,1'-biphenyl]-3-yl)methoxy)pyrimidin-5-yl)methyl)-2,7-diazaspiro[4.5]decan-1-one (Compound 47)

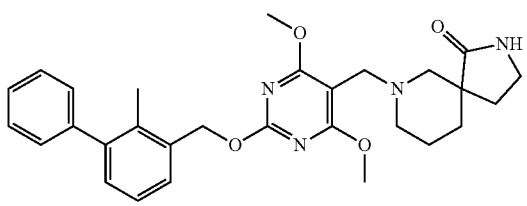 [SMILES: COc1nc(OCc2cccc(-c3ccccc3)c2C)nc(OC)c1CN1CCCC2(CCNC2=O)C1]

LCMS (ES) m/z=503.44 [M+H]+; 1H NMR (400 MHz, DMSO-d6) δ: 1.33-1.47 (m, 4H), 1.78-1.97 (m, 3H), 2.07-2.05 (m, 1H), 2.22 (s, 3H), 2.39 (m, 1H), 2.72 (m, 1H), 3.09 (m, 2H), 3.33 (m, 2H), 3.88 (s, 6H), 5.45 (s, 2H), 7.19-7.21 (m, 1H), 7.26-7.32 (m, 3H), 7.35-7.39 (m, 1H), 7.43-7.47 (m, 4H). HPLC @ 214 nm, 99.84%.

rac-(1R,6S)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid (Compound 48)

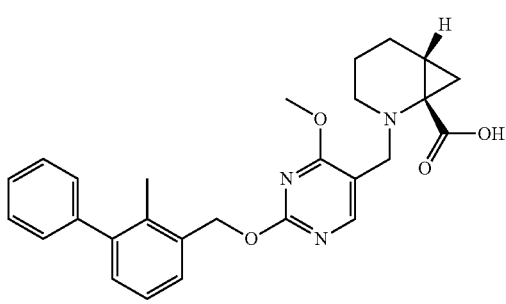 [SMILES: COc1nc(OCc2cccc(-c3ccccc3)c2C)ncc1CN1CCC[C@@H]2C[C@@]21C(=O)O]

LCMS (ES) m/z=460.43 [M+H]+; 1H NMR (400 MHz, DMSO-d6): δ 0.99-1.00 (m, 1H), 1.19-1.22 (m, 2H), 1.56-1.59 (m, 2H), 1.80-1.84 (m, 1H), 2.21 (s, 3H), 2.33-2.36 (m, 1H), 2.53 (m, 2H), 3.67-3.55 (m, 2H), 3.89 (s, 3H), 5.51 (s, 2H), 7.19-7.21 (m, 1H), 7.26-7.32 (m, 3H), 7.35-7.39 (m, 1H), 7.43-7.47 (m, 3H), 8.37 (s, 1H), 11.82 (bs, 1H). HPLC @ 214 nm, 99.23%.

(S)-4-acetyl-1-((4-methoxy-2-((2-methyl-[1,1'-biphenyl]-3-yl)methoxy)pyrimidin-5-yl)methyl)piperazine-2-carboxylic acid (Compound 49)

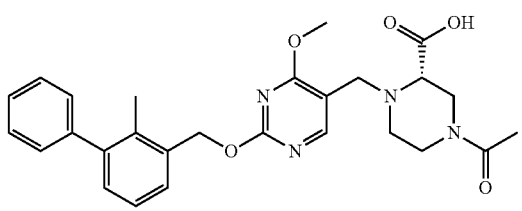 [SMILES: COc1nc(OCc2cccc(-c3ccccc3)c2C)ncc1CN1CCN(C(C)=O)C[C@H]1C(=O)O]

LCMS (ES) n/z=491.46 [M+H]+; 1H NMR (400 MHz, DMSO-d6): δ 1.95 (m, 3H), 2.20 (s, 3H), 2.32 (bs, 1H), 2.84-3.01 (m, 2H), 3.15 (m, 1H), 3.45 (m, 1H), 3.55-3.79 (m, 2H), 3.89 (m, 5H), 5.49 (s, 2H), 7.17-7.19 (m, 1H), 7.26-7.32 (m, 3H), 7.35-7.39 (m, 1H), 7.43-7.47 (m, 3H), 8.26 (bs, 1H). HPLC @ 214 nm, 99.86%.

(S)-1-((4-methoxy-2-((2-methyl-[1,1'-biphenyl]-3-yl)methoxy)pyrimidin-5-yl)methyl)piperazine-2-carboxylic acid (Compound 50)

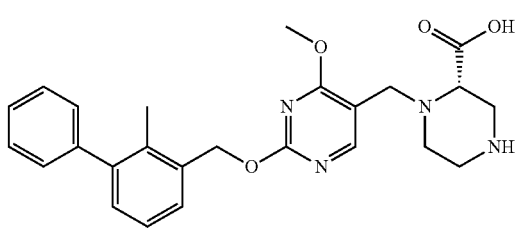 [SMILES: COc1nc(OCc2cccc(-c3ccccc3)c2C)ncc1CN1CCNC[C@H]1C(=O)O]

LCMS (ES) m/z=449.23[M+H]+; 1H NMR (400 MHz, DMSO-d6): δ 2.21 (s, 3H), 2.49 (m, 1H), 2.66-2.88 (m, 3H), 2.98-2.95 (m, 1H), 3.09 (m, 1H), 3.12 (m, 1H), 3.54-3.57 (m, 1H), 3.66-3.69 (m, 1H), 3.89 (s, 3H), 5.49 (s, 2H), 7.17-7.19 (m, 1H), 7.24-7.32 (m, 3H), 7.35-7.39 (m, 1H), 7.43-7.47 (m, 3H), 8.31 (bs, 1H). HPLC @214 nm, 97.83%.

(S)-5-((4-methoxy-2-((2-methyl-[1,1'-biphenyl]-3-yl)methoxy)pyrimidin-5-yl)methyl)-5-azaspiro[2.4]heptane-6-carboxylic acid (Compound 51)

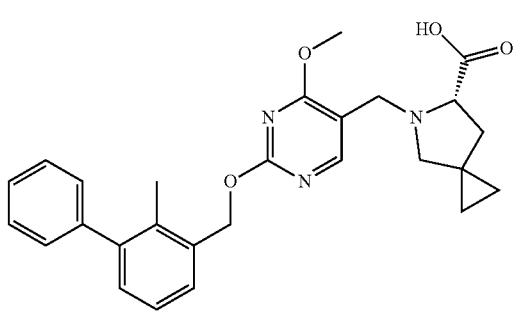 [SMILES: COc1nc(OCc2cccc(-c3ccccc3)c2C)ncc1CN1CC2(CC2)C[C@H]1C(=O)O]

LCMS (ES) m/z=460.36 [M+H]⁺; ¹H NMR (400 MHz, DMSO-d₆): δ 0.42-0.51 (m, 4H), 1.73-1.78 (m, 1H), 2.14 (m, 1H), 2.23 (s, 3H), 2.68 (m, 1H), 2.78 (m, 11H), 3.57 (m, 1H), 3.74 (m, 1H), 3.88 (m, 1H), 3.91 (s, 3H), 5.51 (s, 2H), 7.19-7.21 (m, 1H), 7.24-7.32 (m, 3H), 7.35-7.39 (m, 1H), 7.43-7.49 (m, 3H), 8.30 (s, 1H). HPLC purity @ 214 nm, 99.70%.

7-((4-methoxy-2-((2-methyl-[1,1'-biphenyl]-3-yl)methoxy)pyrimidin-5-yl)methyl)-2,7-diazaspiro[4.5]decan-1-one (Compound 52)

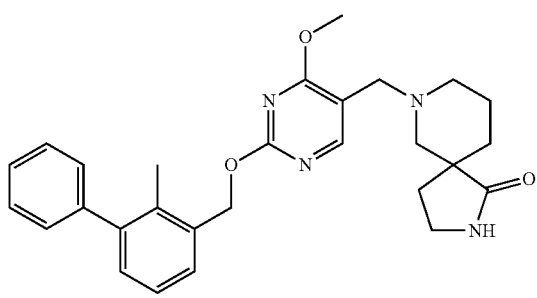 [SMILES: COc1nc(OCc2cccc(-c3ccccc3)c2C)ncc1CN1CCCC2(CCNC2=O)C1]

LCMS (ES) m/z=473.44 [M+H]⁺; ¹H NMR (400 MHz, DMSO-d₆) δ: 1.33-1.51 (m, 4H), 1.76-1.89 (m, 2H), 1.95-2.03 (m, 2H), 2.21 (s, 3H), 2.43 (m, 1H), 2.76 (m, 1H), 2.96-3.06 (m, 2H), 3.36 (m, 2H), 3.89 (s, 3H), 5.44-5.52 (m, 2H), 7.19-7.21 (m, 1H), 7.24-7.32 (m, 3H), 7.35-7.39 (m, 1H), 7.43-7.49 (m, 4H), 8.21 (s, 1H). HPLC purity @ 214 nm, 95.84%.

N-(2-(((4-((3-cyano-4-fluorobenzyl)oxy)-2-((2-methyl-[1,1'-biphenyl]-3-yl)methoxy)pyrimidin-5-yl)methyl)amino)ethyl)acetamide (Compound 53)

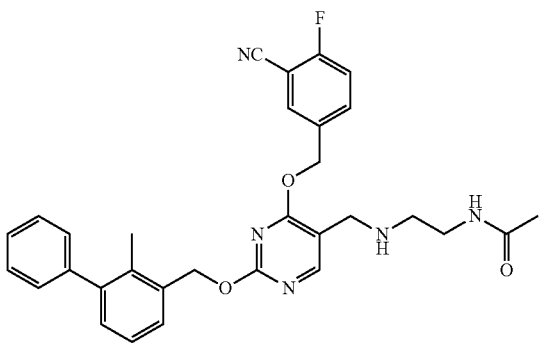 [SMILES: CC(=O)NCCNCc1cnc(OCc2cccc(-c3ccccc3)c2C)nc1OCc1ccc(F)c(C#N)c1]

LCMS (ES) m/z=540.32 [M+H]⁺; ¹H NMR (400 MHz, DMSO-d₆): δ 1.75 (s, 3H), 2.19 (s, 3H), 2.55 (m, 2H), 3.10 (m, 2H), 3.64 (s, 2H), 5.40 (s, 2H), 5.48 (s, 2H), 7.21 (m, 1H), 7.26-7.31 (m, 3H), 7.37 (m, 1H), 7.43-7.47 (m, 3H), 7.55 (t, J=9.2 Hz, 1H), 7.77 (m, 1H), 7.88 (m, 1H), 8.04 (m, 1H), 8.30 (s, 1H). HPLC purity @214 nm, 96.36%.

(2S,4R)-1-((4-((3-cyano-4-fluorobenzyl)oxy)-2-((2-methyl-[1,1'-biphenyl]-3-yl)methoxy)pyrimidin-5-yl)methyl)-4-hydroxypyrrolidine-2-carboxylic acid (Compound 54)

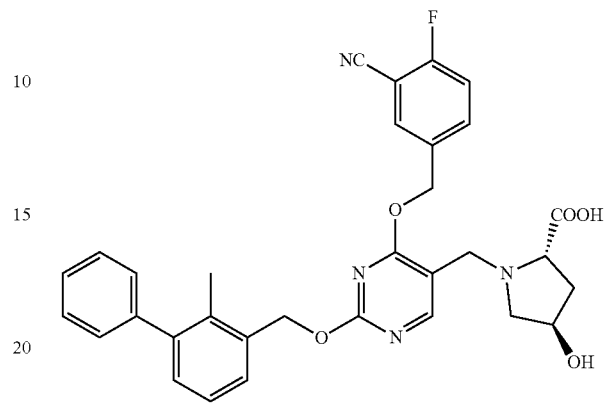

LCMS (ES) m/z=569.28 [M+H]⁺; ¹H NMR (400 MHz, DMSO-d₆): δ 1.87-2.02 (m, 2H), 2.20 (s, 3H), 2.40 (m, 1H), 3.18 (m, 1H), 3.46 (m, 1H), 3.70 (d, J=14 Hz, 1H), 3.82 (d, J=14 Hz, 1H), 4.20 (m, 1H), 4.90 (bs, 1H), 5.40 (s, 2H), 5.48 (s, 2H), 7.21 (m, 1H), 7.26-7.31 (m, 3H), 7.37 (m, 1H), 7.43-7.47 (m, 3H), 7.55 (t, J=9.2 Hz, 1H), 7.88 (m, 1H), 8.04 (m, 1H), 8.32 (s, 1H). HPLC purity d) 214 nm, 98.12%.

(S)-1-((2-((3-(2,3-dihydrobenzo[b][1,4]dioxin-6-yl)-2-methylbenzyl)oxy)-4,6-dimethoxypyrimidin-5-yl)methyl)piperidine-2-carboxylic acid (Compound 55)

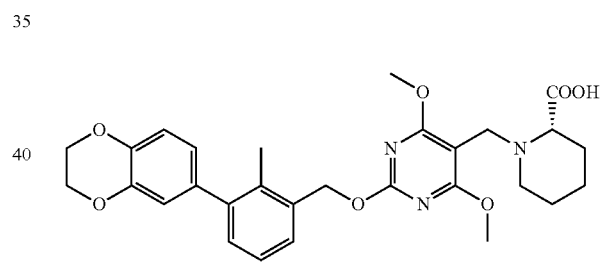

LCMS (ES) m/z=536.26 [M+H]⁺ and purity @ 214 nm, 98.69%. ¹H NMR (400 MHz, DMSO-d₆): δ 1.49-1.44 (m, 2H), 1.63-1.70 (m, 2H), 1.89 (s, 2H), 2.23 (s, 3H), 2.30 (m, 1H), 2.96-3.04 (bs, 2H), 3.63-3.76 (m, 2H), 3.87 (s, 6H), 4.27 (s, 4H), 5.43 (s, 2H), 6.73-6.77 (m, 2H), 6.92 (d, J=8.12 Hz, 1H), 7.15-7.17 (m, 1H), 7.22-7.26 (m, 1H), 7.44 (d, J=7.16 Hz, 1H).

N-(2-(((2-((3-(2,3-dihydrobenzo[b][1,4]dioxin-6-yl)-2-methylbenzyl)oxy)-4,6-dimethoxypyrimidin-5-yl)methyl)amino)ethyl)acetamide (Compound 56)

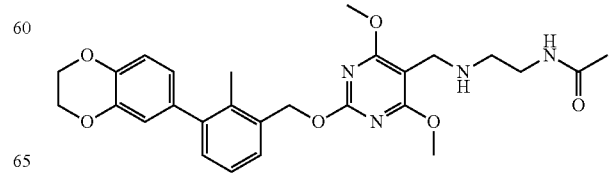

LCMS (ES) m/z=509.23 [M+H]⁺ and purity @ 214 nm, 96.7%. ¹H NMR (400 MHz, DMSO-d₆): δ 1.82 (s, 3H), 2.23 (s, 3H), 2.82 (bs, 2H), 3.24-3.25 (m, 2H), 3.83 (m, 2H), 3.94 (s, 6H), 4.27 (s, 4H), 5.47 (s, 2H), 6.73-6.77 (m, 2H), 6.92 (d, J=8.12 Hz, 1H), 7.15-7.17 (m, 1H), 7.22-7.26 (m, 1H), 7.44 (d, J=7.16 Hz, 1H), 7.95-7.97 (m, 1H).

N-(2-(((2-((3',4'-dimethoxy-2-methyl-[1,1'-biphenyl]-3-yl)methoxy)-4,6-dimethoxypyrimidin-5-yl)methyl)amino)ethyl)acetamide (Compound 57)

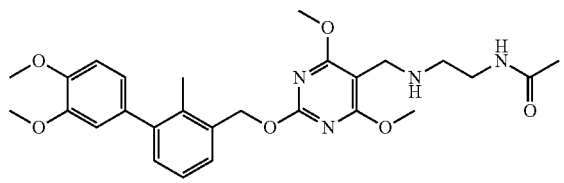 [SMILES: COc1nc(OCc2cccc(-c3ccc4c(c3)OCCO4)c2C)nc(OC)c1CNCCNC(C)=O]

LCMS (ES) m/z=511.33 [M+H]⁺ and purity @ 214 nm, 95.1%. ¹H NMR (400 MHz, DMSO-d₆): δ 1.78 (s, 3H), 2.25 (s, 3H), 2.56 (m, 2H), 3.13 (m, 2H), 3.60 (m, 2H), 3.76 (s, 3H), 3.79 (s, 3H), 3.90 (s, 6H), 5.44 (s, 2H), 6.82 (d, J=8.12 Hz, 1H), 6.86 (s, 1H), 7.02 (d, J=8.2 Hz, 1H), 7.20-7.21 (m, 2H), 7.45 (d, J=7 Hz, 1H), 7.81 (bs, 1H).

((2S,4R)-1-((2-((3',4'-dimethoxy-2-methyl-[1,1'-biphenyl]-3-yl)methoxy)-4,6-dimethoxypyrimidin-5-yl)methyl)-4-hydroxypyrrolidine-2-carboxylic acid (Compound 58)

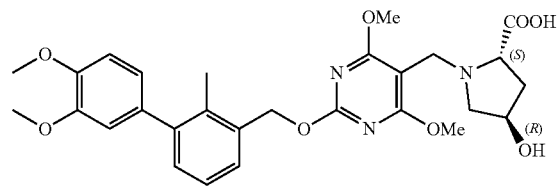

LCMS (ES) m/z=540.33 [M+H]⁺ and purity @ 214 nm, 99.69%. ¹H NMR (400 MHz, DMSO-d₆): δ 1.85-1.91 (m, 2H), 2.25 (s, 3H), 2.50 (s, 2H), 3.35-3.41 (m, 2H), 3.76-3.82 (m, 8H), 3.90 (s, 6H), 4.18 (m, 1H), 4.99 (bs, 1H), 5.45 (s, 2H), 6.82 (d, J=8.12 Hz, 1H), 6.86 (s, 1H), 7.08 (d, J=8.2 Hz, 1H), 7.20-7.21 (m, 2H), 7.45 (d, J=7 Hz, 1H).

(2S,4R)-1-((4-((5-cyanopyridin-3-yl)methoxy)-2-((2-methyl-[1,1'-biphenyl]-3-yl)methoxy)pyrimidin-5-yl)methyl)-4-hydroxypyrrolidine-2-carboxylic acid (Compound 59)

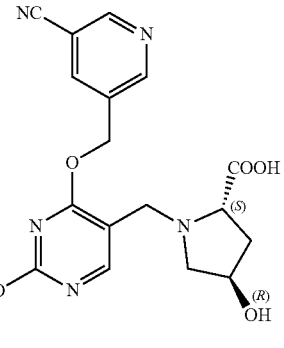

LCMS (ES) m/z=552.0 [M+H]⁺; ¹H NMR (400 MHz, DMSO-d₆): δ 1.93-2.00 (m, 2H), 2.20 (s, 3H), 2.40 (m, 1H), 3.18 (m, 1H), 3.47 (m, 1H), 3.71 (d, J=14 Hz, 1H), 3.82 (d, J=14 Hz, 1H), 4.20 (m, 1H), 4.91 (bs, 1H), 5.48 (s, 4H), 7.18-7.20 (m, 1H), 7.24-7.32 (m, 3H), 7.36-7.38 (m, 1H), 7.43-7.47 (m, 3H), 8.32 (s, 1H), 8.43 (s, 1H), 8.98 (s, 1H), 9.00 (s, 1H). HPLC purity @ 214 nm, 99.59%.

(S)-2-(1-((4-methoxy-2-((2-methyl-[1,1'-biphenyl]-3-yl)methoxy)pyrimidin-5-yl)methyl)piperidin-2-yl)acetic acid (Compound 60)

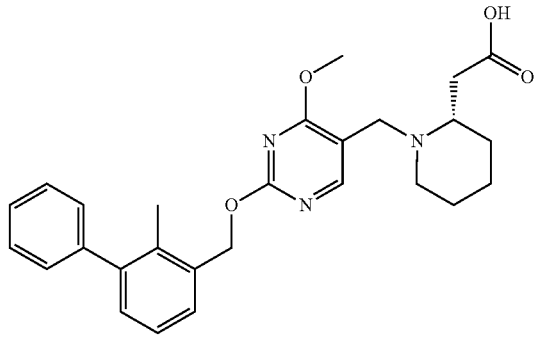 [SMILES: COc1nc(OCc2cccc(-c3ccccc3)c2C)ncc1CN1CCCC[C@H]1CC(=O)O]

LCMS (ES) m/z=462.38 [M+H]; ¹H NMR (400 MHz, DMSO-d₆): δ 1.33-1.36 (m, 2H), 1.46 (m, 3H), 1.70 (m, 1H), 2.20 (s, 3H), 2.23-2.32 (m, 2H), 2.63 (m, 2H), 2.87 (m, 1H), 3.40 (d, J=14 Hz, 1H), 3.68 (d, J=14 Hz, 1H), 3.90 (s, 3H), 5.43 (s, 2H), 7.18 (m, 1H), 7.26-7.32 (m, 3H), 7.37 (m, 1H), 7.44-7.48 (m, 3H), 8.25 (s, 1H). HPLC @ 214 nm, 96%.

The Compounds 61-63 were prepared in a similar manner as Compound 60.

(R)-2-(1-((4-methoxy-2-((2-methyl-[1,1'-biphenyl]-3-yl)methoxy)pyrimidin-5-yl)methyl)piperidin-2-yl)acetic acid (Compound 61)

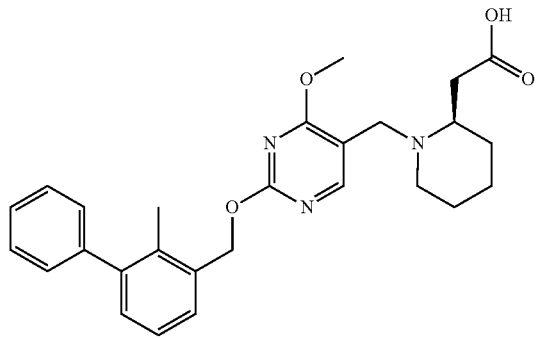 [SMILES: COc1nc(OCc2cccc(-c3ccccc3)c2C)ncc1CN1CCCC[C@@H]1CC(=O)O]

LCMS (ES) m/z=462.23 [M+H]⁺.

(S)-4-(6-acetamidohexanoyl)-1-((4-methoxy-2-((2-methyl-[1,1'-biphenyl]-3-yl)methoxy)pyrimidin-5-yl)methyl)piperazine-2-carboxylic acid (Compound 62)

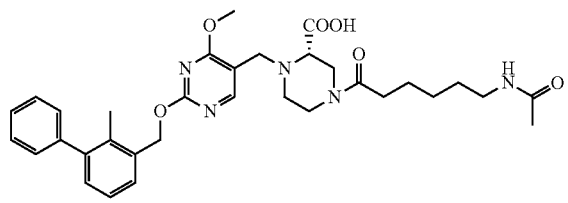 [SMILES: COc1nc(OCc2cccc(-c3ccccc3)c2C)ncc1CN1CCN(C(=O)CCCCCNC(C)=O)C[C@H]1C(=O)O]

LCMS (ES) mz=604.3 [M+H]⁺.

(S)-4,4-difluoro-1-((4-methoxy-2-((2-methyl-[1,1'-biphenyl]-3-yl)methoxy)pyrimidin-5-yl)methyl)piperidine-2-carboxylic acid (Compound 63)

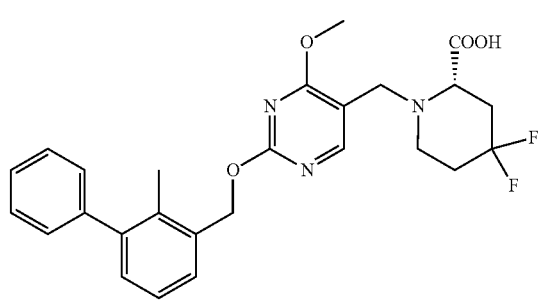 [SMILES: COc1nc(OCc2cccc(-c3ccccc3)c2C)ncc1CN1CCC(F)(F)C[C@H]1C(=O)O]

LCMS (ES) m/z=484.3 [M+H]⁺.

Synthesis of (S)-1-((4-methyl-2-((2-methyl-[1,1'-biphenyl]-3-yl)methoxy)pyrimidin-5-yl)methyl)piperidine-2-carboxylic acid (Compound-64)

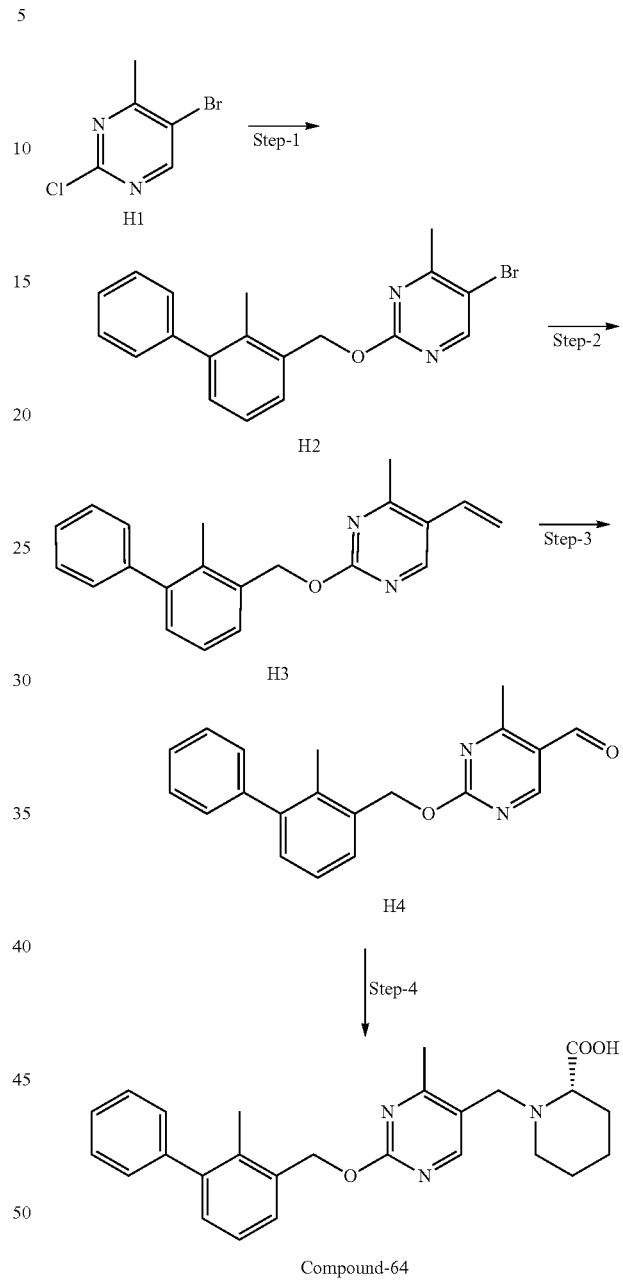

Step 1: Synthesis of 5-bromo-4-methyl-2-((2-methyl-[1,1'-biphenyl]-3-yl)methoxy)pyrimidine To a stirred solution of (2-methyl-[1,1'-biphenyl]-3-yl)methanol (7.1 g, 0.036 mol) in DMF (60 mL) at 0° C., sodium hydride (1.73 g, 60% in mineral oil, 0.043 mol) was added and stirred at room temperature for 30 minutes. To this mixture, 5-bromo-2-chloro-4-methylpyrimidine (5 g, 0.024 mol) was added and allowed to stir at room temperature for 16 h. After completion of the reaction, the reaction mixture was diluted with water (50 mL) and extracted with ethyl acetate (2×100 mL). The combined organic layer was then dried over sodium sulfate, filtered and evaporated to give crude product. The crude product was purified on column chromatography (silicagel, 100-200#) using 10% ethyl acetate in hexane as eluent to afford 5-bromo-4-methyl-2-((2-methyl-[1,1'-biphenyl]-3-yl)methoxy)pyrimidine as off-white solid (Yield: 1.5 g, 17%). LCMS (ES) m/z=369.01 [M+H]$^+$; $^1$H NMR (400 MHz, CDCl3): δ 2.31 (s, 3H), 2.58 (s, 3H), 5.47 (s, 2H), 7.21-7.23 (m, 2H), 7.25-7.30 (m, 2H), 7.35 (m, 1H), 7.39-7.43 (m, 2H), 7.49 (m, 1H), 8.47 (s, 1H). HPLC purity @ 214 nm, 99.78%.

Step 2: Synthesis of 4-methyl-2-((2-methyl-[1,1'-biphenyl]-3-yl)methoxy)-5-vinylpyrimidine To a stirred solution of 5-bromo-4-methyl-2-((2-methyl-[1,1'-biphenyl]-3-yl)methoxy)pyrimidine (1.5 g, 0.0041 mol) in DMF (20 mL), tributyl vinyl tin (3.2 g, 0.011 mol) was added and the reaction mixture was degassed with nitrogen gas for 10 min. To this mixture, Pd(PPh$_3$)$_4$ (0.46 g 0.4 mmol) was added and the reaction mixture was heated at 100° C. for 2 h. After completion of the reaction, the reaction mixture was filtered through celite and the filtrate was diluted with water (50 mL) and extracted with ethyl acetate (2×100 mL). The combined organic layer was dried over sodium sulfate, evaporated and the crude product was purified on combiflash chromatography using 25% ethyl acetate in hexane as eluent to afford 4-methyl-2-((2-methyl-[1,1'-biphenyl]-3-yl)methoxy)-5-vinylpyrimidine as yellowish liquid (Yield: 1.2 g, 92%). LCMS (ES) m/z=317.42 [M+H]; $^1$H NMR (400 MHz, DMSO-d$_6$): δ 2.20 (s, 3H), 2.46 (s, 3H), 5.30 (d, J=11.2 Hz, 1H), 5.45 (s, 2H), 5.78 (d, J=17.6 Hz, 1H), 6.82 (m, 1H), 7.19 (m, 1H), 7.25-7.32 (m, 3H), 7.36-7.39 (m, 1H), 7.43-7.47 (m, 3H), 8.67 (s, 1H). HPLC purity @ 214 nm, 99.04%.

Step 3: Synthesis of 4-methyl-2-((2-methyl-[1,1'-biphenyl]-3-yl)methoxy)pyrimidine-5-carbaldehyde To a stirred solution 4-methyl-2-((2-methyl-[1,1'-biphenyl]-3-yl)methoxy)-5-vinylpyrimidine (0.9 g, 0.003 mol) in THF (25 mL) and water (25 mL) at 0° C., OsO$_4$ (42 mL, 2.5 wt % solution in tert-butanol, 0.0042 mol) was added and stirred for 15 min. To this mixture, NaIO$_4$ (0.89 g, 0.0042 mol) was added and the reaction mixture was allowed to stir at room temperature for 5 h. After completion of the reaction, the reaction mixture was diluted with water (50 mL) and extracted with DCM (2×50 mL). The organic layer was dried over sodium sulfate, filtered and evaporated to give crude product. The crude product was purified on column chromatography (silicagel, 100-200#) using 20% ethyl acetate in hexane as eluent to afford 4-methyl-2-((2-methyl-[1,1'-biphenyl]-3-yl)methoxy)pyrimidine-5-carbaldehyde as off-white solid (Yield: 0.64 g, 73%). LCMS (ES) m/z=319.36 [M+H]$^+$; $^1$H NMR (400 MHz, DMSO-d$_6$): δ 2.22 (s, 3H), 2.73 (s, 3H), 5.57 (s, 2H), 7.21 (m, 1H), 7.27-7.33 (m, 3H), 7.38 (m, 1H), 7.46 (m, 3H), 8.99 (s, 1H), 10.12 (s, 1H). HPLC purity @214 nm, 97.18%.

Step 4: Synthesis of (S)-1-((4-methyl-2-((2-methyl-[1,1'-biphenyl]-3-yl)methoxy)pyrimidin-5-yl) methyl)piperidine-2-carboxylic acid To a solution of 4-methyl-2-((2-methyl-[1,1'-biphenyl]-3-yl)methoxy)pyrimidine-5-carbaldehyde (0.2 g, 0.62 mmol) in MeOH (2 mL) and DMF (2 mL), (S)-piperidine-2-carboxylic acid (73 mg, 0.56 mmol) and acetic acid (1 drop) were added simultaneously and the reaction was stirred at room temperature for 2 h. To this reaction mixture, NaCNBH$_3$ (110 mg, 1.86 mmol) was added and continued stirring at room temperature for 16 h. The reaction mixture was diluted with water (10 mL) and extracted in 10% MeOH in DCM (2×10 mL). The combined organic layer was washed with water (3 mL) and brine solution (3 mL), dried over sodium sulphate and concentrated to give crude product which was purified on prep-TLC using 10% methanol in dichloromethane as eluent to afford (S)-1-((4-methyl-2-((2-methyl-[1,1'-biphenyl]-3-yl)methoxy)pyrimidin-5-yl) methyl)piperidine-2-carboxylic acid as white solid (Yield: 90 mg, 35%). LCMS (ES) m/z=432.25 [M+H]$^+$; $^1$H NMR (400 MHz, DMSO-d$_6$): δ 1.33-1.42 (m, 4H), 1.72 (m, 2H), 2.16 (m, 1H), 2.20 (s, 3H), 2.49 (s, 3H), 2.78 (m, 1H), 3.08 (m, 1H), 3.39 (m, 1H), 3.75 (m, 1H), 5.41 (s, 2H), 7.18 (m, 1H), 7.25-7.32 (m, 3H), 7.37 (m, 1H), 7.43-7.47 (m, 3H), 8.31 (s, 1H). HPLC purity @ 214 nm, 99.20%.

The Compound 65 was also prepared in a similar manner as Compound 64 above.

N-(2-(((4-methyl-2-((2-methyl-[1,1'-biphenyl]-3-yl) methoxy)pyrimidin-5-yl)methyl)amino)ethyl)acetamide (Compound 65)

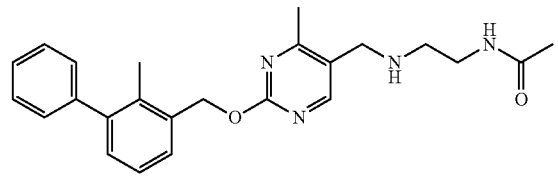 [SMILES: CC(=O)NCCNCc1cnc(OCc2cccc(-c3ccccc3)c2C)nc1C]

LCMS (ES) m/z=405.24 [M+H]$^+$; $^1$H NMR (400 MHz, DMSO-d$_6$): δ 1.78 (s, 3H), 2.20 (s, 3H), 2.45 (s, 3H), 2.55 (m, 2H), 3.13 (m, 2H), 3.64 (s, 2H), 5.42 (s, 2H), 7.18 (m, 1H), 7.25-7.32 (m, 3H), 7.37 (m, 1H), 7.43-7.47 (m, 3H), 7.77 (bs, 1H), 8.37 (s, 1H). HPLC purity @ 214 nm, 98.84%.

Example 5

General Procedure for Biological Evaluation

PD-L1 Enzyme Assay: Homogenous Time-Resolved Fluorescence (HTRF) Binding Assay

All binding studies were performed using PD-1/PD-L1 Binding Assay Kit from CisBio (Catalog #63ADK000CPAPEG), according to the manufacturer's protocol. The interaction between Tag1-PD-1 and Tag2-PD-1 was detected by anti-Tag1-Eu$^{3+}$ (HTRF donor) and anti-Tag2-XL665 (HTRF acceptor). When the donor and acceptor antibodies were brought to close proximity due to PD-1 and PD-L1 binding, excitation of the donor antibody triggered fluorescent resonance energy transfer (FRET) towards the acceptor antibody, which in turn emitted specifically at 665 nm. This specific signal is positively proportional to PD-1/PD-L1 interaction. The compounds blocking PD-1/PD-L1 interaction will cause a reduction in HTRF signal. The necessary reagents were mixed in the following order: 2 μl compounds (or diluents buffer), 4 μl PD-L1 protein, 4 μl PD-1 protein. After an incubation of 15 minutes, 5 μl of anti-Tag1-Eu$^{3+}$ and 5 μl of anti-Tag2-XL665 were added. The plate was sealed and incubated at RT for 1 h. The fluorescence emission was read at two different wavelengths (665 nm and 620 nm) on a BMG PheraStar® multiplate reader. Results were calculated from the 665 nm and 620 nm fluorescence signal and expressed in HTRF ratio=(665 nm/620 nm)×104.

Evaluation of Biological Activity:

Table 1, below, shows the biological activity of compounds of the present disclosure in PD1/PD-L1 inhibition assay. Compounds having $IC_{50}$<100 nM are designated as "A"; 100-500 nM are designated as "B"; and >500 nM are designated as "C" respectively.

TABLE 1

Biochemical PD1/PD-L1 inhibiton data

| Compound | PD1/PD-L1 Activity |
|---|---|
| 1 | C |
| 2 | C |
| 3 | A |
| 4 | A |
| 5 | B |
| 6 | B |
| 7 | A |
| 8 | C |
| 9 | C |
| 10 | B |
| 11 | A |
| 12 | C |
| 13 | B |
| 14 | B |
| 15 | B |
| 16 | C |
| 17 | B |
| 18 | B |
| 19 | B |
| 20 | C |
| 21 | C |
| 22 | B |
| 23 | B |
| 24 | C |
| 25 | A |
| 26 | B |
| 27 | C |
| 28 | B |
| 29 | B |
| 30 | B |
| 31 | B |
| 32 | C |
| 33 | C |
| 34 | A |
| 35 | A |
| 36 | B |
| 37 | C |
| 38 | A |
| 39 | B |
| 40 | B |
| 41 | B |
| 42 | A |
| 43 | A |
| 44 | B |
| 45 | A |
| 46 | A |
| 47 | A |
| 48 | C |
| 49 | C |
| 50 | C |
| 51 | C |
| 52 | C |
| 53 | C |
| 54 | B |
| 55 | A |
| 56 | A |
| 57 | C |
| 58 | C |
| 59 | C |
| 60 | B |
| 64 | A |
| 65 | B |

Table 1 illustrates that most of the tested compounds were found to be effectively blocking the PD1/PD-L1 when evaluated through Homogenous Time-Resolved Fluorescence (HTRF) binding assay. The $IC_{50}$ values display the efficacy of the compounds in inhibiting the PD1/PD-L1 activation. $IC_{50}$ value indicates how much of a particular drug or a compound is needed to inhibit a 50% of the interaction of PD1/PD-L1. A low value of $IC_{50}$ denotes high inhibition efficacy of the test compound (Compounds 1-65 as described hereinabove). However, in the above Table 1, high efficacy is denoted by "A", "B", and "C", wherein "A" having least value of $IC_{50}$ and thus most effective.

The above mentioned compounds have potency to be developed as drugs to alleviate the PD1/PD-L1 activity and thus treating cancer, and other diseases or conditions associated with activation of PD1/PD-L1.

Example 6

Pharmacokinetics Evaluation of Compound-45: Animal Experiments Details

Institutional Animal Ethical Committee (IAEC) of Jubilant Biosys (IAEC/JDC/2018/158) nominated by CPCSEA (Committee for the Purpose of Control and Supervision of Experiments on Animals) approved the mice pharmacokinetic experiments. Male Balb/c mice (~6-8 weeks old with body weight range of 22-25 g) were procured from Vivo Biotech, Hyderabad, India. Animals were quarantined in Jubilant Biosys Animal House for a period of 7 days with a 12:12 h light:dark cycles, and prior study the animals were stratified as per body weight. Animals had free access to feed (Altromin Spezialfutter GmbH & Co. KG., Im Seelenkamp 20, D-32791, Lage, Germany) and water ad-libitum.

Intravenous and oral pharmacokinetics study was done at a dose of 2 and 10 mg/kg and at a dose volume of 10 mL/kg. Serial blood samples (200 μL) were collected from retro-orbital plexus at 0.083 (Only for IV), 0.15, 0.5, 1, 2, 4, 8, 10 (only for PO) and 24 h. Blood samples collected in tubes containing $K_2$.EDTA as anticoagulant and centrifuged for 5 min at 14000 rpm in a refrigerated centrifuge (Biofuge, Heraeus, Germany) maintained at 4° C. for plasma separation.

Group I (PO) (22-25 g) received compound-45 at 10 mg/Kg (suspension formulation prepared using 0.5% methylcellulose and Tween-80; dose volume: 10 mL/Kg), whereas group II received IV (24-25 g) received compound-45 intravenously [5% DMSO, 5% Solutol:absolute alcohol (1:1, v/v) and 90% of normal saline; strength: 0.2 mg/mL; dose volume: 10 mL/Kg] at 2.0 mg/Kg dose. Post-dosing serial blood samples (200 μL), sparse sampling was done and at each time point three mice were used for blood sampling) were collected at regular intervals using heparinized capillaries through retro-orbital plexus into polypropylene tubes containing K2.EDTA solution as an anti-coagulant. Animals were allowed to eat feed 2 h post dose of compound-45. Blood concentration-time data of compound-45 was analyzed by non-compartmental method using Phoenix WinNonlin Version 7.0.

The results are tabulated in Table 2 below.

TABLE 2

Pharmacokinetics evaluation of Compound-45

SAMPLE PROCESSING

| | |
|---|---|
| Plasma volume for analysis | 50 μL |
| Extraction method | Protein precipitation (Acetonitrile, 0.3 mL) |
| Stock solution concentration/Date | 2059 μg/mL |
| Linearity range | 4.32-2882 ng/mL |
| Quality control levels | 13.0, 1297 and 2594 ng/mL |
| Internal standard concentration | 100 ng/mL (Loperamide) |

ANALYTICAL DETAILS

| | |
|---|---|
| Instrument Id | JB/DMPK/0002 (LC-MS/MS) (Model: API 4000 from Sciex ) |
| Quantitation software used | Analyst 1.6.2 |
| MRM transition (analyte) | Q1-m/z 478, Q3-m/z 349 |
| MRM transition (internal standard) | Q1-m/z 477, Q3-m/z 210 |
| Mobile phase | A-acetonitrile; B-0.2% formic acid in water (Gradient) |
| Analytical column | Atlantis dC18 (50 × 4.6 mm, 3 μm) |
| Flow rate | 1.0 mL/min |
| Injection volume | 5 μL |
| Run time | 3.5 min |
| Retention time | Analyte (compound-45-1.94 min IS (Loperamide)-1.79 min |
| Regression value/Weighing factor | 0.9982/1/$x^2$ |
| PK software used | Phoenix WinNonlin 7.0 |

Example 7

ADME and Pharamcokinetics of Compound-45
Metabolic Stability in Liver Microsomes Procedure: Potassium phosphate buffer (66.7 mM, pH 7.4) containing mouse or rat or dog or monkey or human liver microsomes (0.5 mg/mL) was pre-incubated separately with compound (1 μM) and positive control (verapamil, 1 μM) in a 37° C. water bath for 5 min. The reactions were initiated by adding 20 μL of 10 mM NADPH. Reactions without NADPH (0 and 30 min) were also incubated to rule out non-NADPH metabolism or chemical instability in the incubation buffer. All reactions were terminated using 200 μL of ice-cold acetonitrile containing internal standard at 0, 5, 15 and 30 min. The vials were centrifuged at 3000 rpm for 15 min. The reaction mixtures (obtained from the above studies) were extracted, processed and analyzed by LC-MS [Shimadzu SIL LC series (Kyoto, Japan) was coupled to an API-4000 Mass Spectrometer (MDS Sciex, Toronto, Canada)] to monitor the disappearance of compound.

Conclusion: Metabolic stability of compound-45 in different species of liver microsomes compound-45 was found to be highly stable (>80%) in mice, rat, dog and human liver microsomes.

Caco-2 Permeability

Procedure: Caco-2 human intestinal epithelial cells were plated in 24-Transwell® dual chamber plates (Millipore, Billerica, Mass., USA) (cell density of 80,000 cells/cm$^2$ on day-1). The permeability studies were conducted with the monolayers cultured for 21 to 22 days in culture. The integrity of each Caco-2 cell monolayer was certified by trans epithelial electrical resistance (TEER) test (pre-experiment) and by determining the permeability of reference compound i.e., Lucifer yellow. Caco-2 cell monolayers with TEER values greater than 500 Ωcm$^2$ were considered for experimentation. Digoxin (5 μM) was used as a positive control for P-gp substrate. The concentrations of compound used in the assay was 5 μM. HBSS Buffer was used as the medium for the transport assay and the final concentration of DMSO in spiking solution was 0.05%. The bi-directional permeability study was initiated by adding an appropriate volume of HBSS buffer containing compound to respective apical and basolateral chambers (n=3). An aliquot of sample (100 μL) was taken from both chambers at 0 and 60 min of the incubation period and to this equal volume of acetonitrile was added, mixed gently and centrifuged at 4000 rpm for 10 min. An aliquot of 100 μL was subsequently transferred to the auto-sampler and 10 μL was injected for analysis on LC-MS/MS.

Conclusion:

Compound-45 was found to be medium permeable and high efflux in caco-2 assay and may be a substrate of an active efflux transporter.

Plasma Protein Binding

Procedure:

To evaluate the ability of compound to bind the plasma proteins, the most common approach of plasma protein binding using equilibrium dialysis was used. Compound was tested at a final concentration of 3 μM in mouse, rat, human or dog plasma. An aliquot of 150 μL plasma containing compound was added in first half (plasma side) of the well of 96-well micro-equilibrium dialysis device. An aliquot of 150 μL of 100 mM sodium phosphate buffer pH 7.4 was added in the second half (buffer side) of the well of 96-well HT equilibrium dialysis device. The plate containing plasma and buffer was equilibrated at 37±1° C. for 4.5 h, with constant shaking at 120 rpm on an orbital shaker. Samples were collected from respective halves after the completion of incubation time. The proteins were precipitated using organic solvents. The samples were subjected to centrifugation and the supernatants were analyzed analysis on LC-MS/MS.

Conclusion:

Compound-45 had a high binding in mouse plasma with fraction unbound of 0.039. The stability and recovery of compound-45 in plasma was good.

CYP Inhibition

Procedure:

CYP inhibition potential of compound was assessed in human liver microsomes (procured from GIBCO Invitrogen) against CYP3A4, 2D6, 2C9, 2C19 and 1A2 in the following sequential steps. Standard reaction mixture (final volume 300 μL) contained 66.7 M potassium phosphate buffer (pH 7.4), protein (0.1, 0.25, 0.5, 0.5 and 0.5 mg/mL concentration for CYP3A4, 2D6, 2C9 2C19 and 1A2 respectively) and compound (at eight different concentration levels ranging from 0.091 to 20.0 PM, added as 0.9 μL DMSO solution with a final DMSO concentration of 0.1%). The mixtures were pre-incubated at 37±1° C. for 5 min. The reaction (in duplicate) was initiated by addition of 30 μL of NADPH (10 mM). Reaction was terminated at 10 min by adding 300 μL of acetonitrile. The activity of liver microsomes was confirmed with positive controls i.e., monitoring the hydroxylation of midazolam for CYP 3A4, hydroxylation of bufuralol for CYP 2D6, hydroxylation of diclofenac for CYP 2C9, hydroxylation of omeprazole for CYP2C19 and O-Deethylation for CYP 1A2. The reaction mixtures (obtained from the above studies) were extracted, processed and analyzed by LC-MS [Shimadzu SIL LC series (Kyoto, Japan) was coupled to an API-4000 Mass Spectrometer (MDS Sciex, Toronto, Canada)].

Conclusion:

The predicted IC$_{50}$ values of compound-45 were determined for CYP-specific hydroxylation of midazolam, bufuralol, diclofenac and omeprazole for CYP 3A4, 2D6 and 2C9 respectively. compound-45 did not show notable inhibition against these enzymes and the predicted $IC_{50}$ values of compound-45 were found to be >10 uM respectively, indicating it is a weak inhibitor against tested CYPs.

PK profile:

TABLE 3

Pharmacokinetic parameters of Compound 45 in Balb C mice after an oral dose of 10 mg/Kg.

| Parameter | Unit | Value |
|---|---|---|
| $t_{1/2, \beta}$ | (h) | 6.32 |
| $AUC_{0-t}$ | (ng · h/mL) | 20307 |
| $AUC_{0-\infty}$ | (ng · h/mL) | 21117 |
| $C_{max}$ | (ng/mL) | 4841 |
| $t_{max}$ | (h) | 0.50 |
| $T_{last}$ | (h) | 24.0 |
| Oral bioavailability (F %) | | 90.6 |
| Time points considered for $t_{1/2,\beta}$ calculation | | 8-24 h |

TABLE 4

Pharmacokinetic parameters of Compound 45 in Balb C mice after an IV dose of 2 mg/Kg.

| Parameter | Unit | Value |
|---|---|---|
| $t_{1/2, \beta}$ | (h) | 1.27 |
| $C_{max}$ | (ng/mL) | 2108 |
| $C_0$ | (ng/mL) | 2133 |
| $AUC_{0-t}$ | (ng · h/mL) | 4481 |
| $AUC_{0-\infty}$ | (ng · h/mL) | 4922 |
| CL | (mL/min/Kg) | 6.77 |
| $V_d$ | (L/Kg) | 0.74 |
| $V_{dss}$ | (L/Kg) | 1.20 |
| $T_{last}$ | (h) | 8.00 |
| Time points considered for $t_{1/2,\beta}$ calculation | | 1-4 h |
| $C_0$ calculated manually using initial 3 time points. | | |

$t_{1/2,\beta}$: terminal half life;
$AUC_{0-t}$: area under the plasma concentration-time curve from zero to last measurable time point;
$AUC_{0-\infty}$: area under the plasma concentration-time curve from time zero to infinity;
$C_{max}$: maximum observed plasma concentration;
$t_{max}$: time to the maximum observed plasma concentration;
CL: clearance;
$C_0$: extrapolated concentration at zero time point;
$V_d$: volume of distribution;
$V_{dss}$: volume of distribution at steady state;
$T_{last}$: time of the last point with quantifiable concentration;
F: oral bioavailability.

The profiles of plasma concentration for Compound-45 following single oral and intravenous administration to mice. In the mice, plasma concentrations of compound-45 decreased mono-exponentially manner after 1 mg/kg intravenous administration. The clearance was 6.77 ml/min/kg [8% hepatic blood flow (HBF)]. The in vivo clearance was bit over predicted by the in vitro (microsomes) scaled clearance. compound-45 had a high volume of distribution of 0.74 L/kg in mice, which is 40 times higher than that of total body water (TBW). The terminal $t_{1/2}$ was found to be 1.27 h. Post oral administration maximum plasma concentrations ($C_{max}$: 4841 ng/mL) attained at 0.5 h indicating rapid absorption from gastrointestinal tract. The terminal tin (6.32 h) determined after oral administration was longer than that after intravenous administration (1.27 h), which may indicate multiple sites absorption. The $AUC_{0-\infty}$ attained post oral dose was 21117 ng·h/ml. The oral bioavailability in mice at 10 mg/kg was 91%.

Example 8

In Vivo Efficacy of Compound-45 in RENCA Renal Model (FIG. 1):

RENCA renal cancer cell line was procured from ATCC, USA and grown in the recommended media and culture conditions. Cells in the exponential phase were mixed with equal volume of matrigel in a 1:1 ratio, followed by implantation of $1\times10^6$ cells/100 µl subcutaneously on the right flank of immunocompetent Balb/c mice (1 site/mouse). Tumor cells were engrafted at the site of injection within 1-2 weeks of implantation and treatment was initiated by randomizing mice into study groups of N=10, when the average tumor volume reached 100 mm³. Tumor bearing mice were treated with Vehicle (oral), Vehicle (IP), Compound B (orally at 30 mg/kg dose, twice daily) or Anti-PD-L1 mAb (Clone 10F.9G2, BioXcell) intraperitoneally at 0.1 mg/mouse, Q4D. Tumor volume and mouse body weight was measured three times per week during treatment, until the tumor volume reached a maximum of 2000 mm³. Tumor volume (mm³) was calculated using the formula—(tumor length)× (tumor width)²/2. For pharmacokinetic parameters of Compound B, plasma and tumors were isolated at the end of the study and analyzed. Tumor growth inhibition was calculated after normalizing the tumor volume on a given day to that on day 1 based on the formula below:

% $TGI$=[1−(Treatment $TV_{Final}$−Treatment $TV_{initial}$)/ (Vehicle $TV_{Final}$−Vehicle $TV_{initial}$)]*100

As shown in FIG. 1, Compound-45 show better or similar efficacy compared to PD-L1 monoclonal antibody by oral dosing. There was no significant body weight reduction observed during the dosing regimen.

Advantage

These small molecules are reasonably stable across mice, rat and dog liver microsomes and have very good solubility. These compounds show very good exposure by oral route and are efficacious in syngeneic model by oral dosing. Some of the toxicities observed using PD-L1 monoclonal antibody due to low clearance can be overcome by using these small molecules

What is claimed is:
1. A compound of Formula I

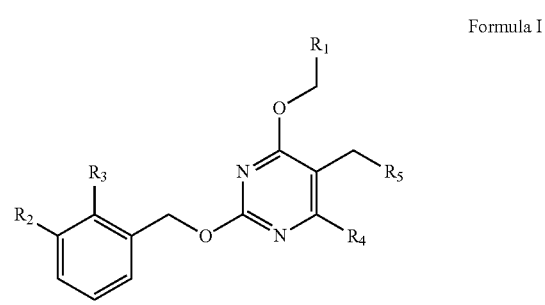

Formula I their stereoisomers and pharmaceutically acceptable salts thereof,
wherein
$R_1$ is selected from hydrogen, $C_{1-10}$ alkyl, $C_{1-6}$ haloalkyl, $C_{5-10}$ aryl and 5-10 membered monocyclic or bicyclic heteroaryl with 1-5 heteroatoms selected from N, S or O,
wherein, $C_{1-10}$ alkyl, $C_{5-10}$ aryl and 5-10 membered monocyclic or bicyclic heteroaryl, are optionally substituted with one or more of the groups selected from hydrogen, halogen, hydroxyl and cyano, $R_2$ is selected from hydrogen, $C_{1-10}$ alkyl, $C_{1-10}$ alkoxy, $C_{5-10}$ aryl and 5-10 membered monocyclic or bicyclic heteroaryl with 1-5 heteroatoms selected from N, S or O, wherein, $C_{1-10}$ alkyl, $C_{5-10}$ aryl and 5-10 membered monocyclic or bicyclic heteroaryl, are optionally substituted with one or more of the groups selected from hydrogen, halogen, $C_{1-6}$ alkyl, $C_{1-6}$ alkoxy and $C_{1-6}$ heterocyclyl, wherein, $C_{1-6}$ alkyl, $C_{1-6}$ alkoxy and $C_{1-6}$ heterocyclyl are optionally substituted with one or more of the groups selected from $C_{1-6}$ alkyl or $C_{1-6}$ heterocyclyl, wherein, $C_{1-6}$ heterocyclyl is optionally substituted with one or more halogen;

$R_3$ and $R_4$ are independently selected from hydrogen, $C_{1-10}$ alkyl and $C_{1-10}$ alkoxy;

O is absent or is oxygen;

$R_5$ is —$NR_7R_8$, wherein, $R_7$ and $R_8$ are selected from the group consisting of hydrogen, $C_{3-10}$ cycloalkyl, $C_{1-6}$ alkyl, 5-10 membered monocyclic or bicyclic, saturated or unsaturated heterocyclic ring with 1-3 heteroatoms selected from N, S or O, and combinations thereof, wherein, $C_{3-10}$ cycloalkyl, $C_{1-6}$ alkyl and the 5-10 membered monocyclic or bicyclic, saturated or unsaturated heterocyclic ring are optionally substituted with one or more substituents selected from oxo, cyano, halogen, hydroxyl, morpholino, $C(O)NH_2$, $C(O)CH_2CN$, $NHR_6$, COOH, $COOR_6$, $NHC(O)R_6$, $C_{1-6}$ alkyl, $C_{1-6}$ haloalkyl, $C_{3-10}$ cycloalkyl, $C_{5-6}$ aryl, $SR_6$ or 5-10 membered monocyclic or bicyclic, saturated or unsaturated heterocyclic ring with 1-3 heteroatoms selected from N, S or O, wherein, $C_{1-6}$ alkyl and the 5-10 membered monocyclic or bicyclic, saturated or unsaturated heterocyclic ring are independently substituted with one or more substituents selected from hydroxyl and $R_6$; or $R_7$ and $R_8$ can be taken together to form a 4-10 membered monocyclic or bicyclic, saturated or unsaturated heterocyclic ring with 1-3 heteroatoms selected from N, S or O, wherein, the 4-10 membered monocyclic or bicyclic, saturated or unsaturated heterocyclic ring is optionally substituted with one or more substituents selected from the group consisting of hydroxyl, halogen, $C_{1-6}$ alkyl, COOH, $R_6$, $NHR_6$, $C(O)NHR_6$, $C(O)NHSO_2R_6$, $C(O)(CH_2)_nNHC(O)CH_3$ and combinations thereof, wherein, $C_{1-6}$ alkyl is further substituted with groups selected from oxo, hydroxyl, COOH, $COOR_6$ or $NHR_6$; n is 1-6; and $R_6$ is selected from the group consisting of hydrogen, $C_{1-6}$ alkyl, $C(O)C_{1-6}$ alkyl and combinations thereof, wherein, $C_{1-6}$ alkyl and $C(O)C_{1-6}$ alkyl are optionally substituted with substituents selected from the group consisting of hydroxyl, COOH, $NHR_6$, $NHC(O)NHR_6$ and combinations thereof.

2. The compound of Formula I as claimed in claim 1, their stereoisomers and pharmaceutically acceptable salts thereof, wherein $R_1$ is selected from hydrogen, $C_{1-6}$ alkyl, $C_{1-4}$ haloalkyl, $C_{5-9}$ aryl and 5-10 membered monocyclic or bicyclic heteroaryl with 1-5 heteroatoms selected from N, S or O, wherein, $C_{1-6}$ alkyl, $C_{5-9}$ aryl and 5-10 membered monocyclic or bicyclic heteroaryl, is optionally substituted with one or more of the groups selected from hydrogen, halogen, hydroxyl and cyano;

$R_2$ is selected from hydrogen, $C_{1-6}$ alkyl, $C_{1-6}$ alkoxy, $C_{5-9}$ aryl and 5-10 membered monocyclic or bicyclic heteroaryl with 1-5 heteroatoms selected from N, S or O, wherein, $C_{1-6}$ alkyl, $C_{5-9}$ aryl, and 5-10 membered monocyclic or bicyclic heteroaryl, is optionally substituted with one or more of the groups selected from hydrogen, halogen, $C_{1-4}$ alkyl, $C_{1-4}$ alkoxy and $C_{1-6}$ heterocyclyl, wherein, $C_{1-4}$ alkyl, $C_{1-4}$ alkoxy and $C_{1-6}$ heterocyclyl are optionally substituted with one or more of the groups selected from $C_{1-4}$ alkyl or $C_{1-6}$ heterocyclyl, wherein, $C_{1-6}$ heterocyclyl is optionally substituted with one or more halogen;

$R_3$ and $R_4$ are independently selected from hydrogen, $C_{1-6}$ alkyl and $C_{1-6}$ alkoxy;

O is absent or is oxygen; and $R_5$ is selected from

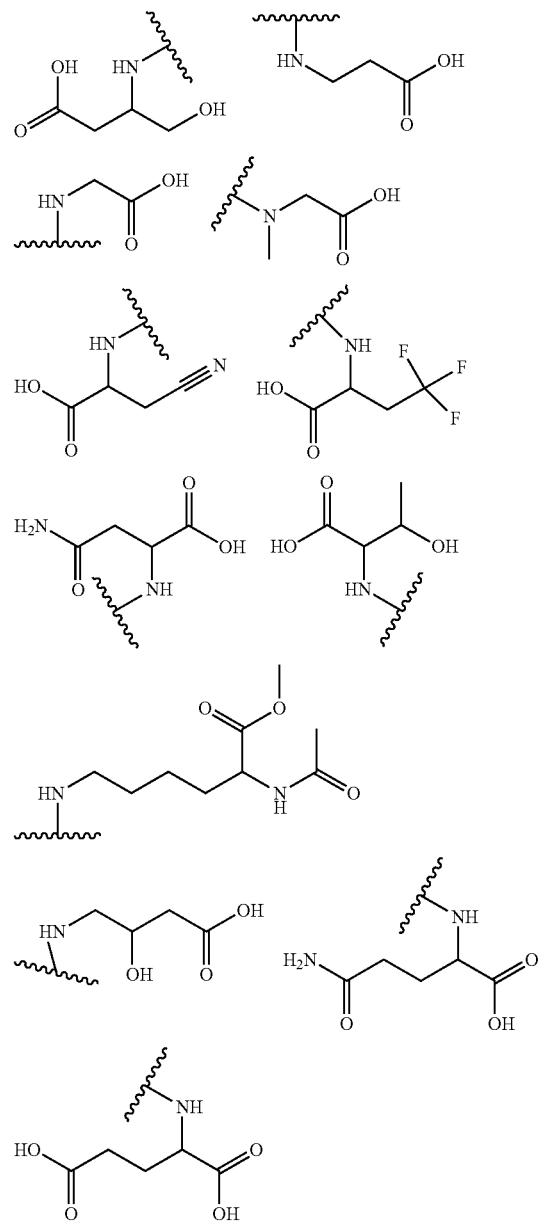

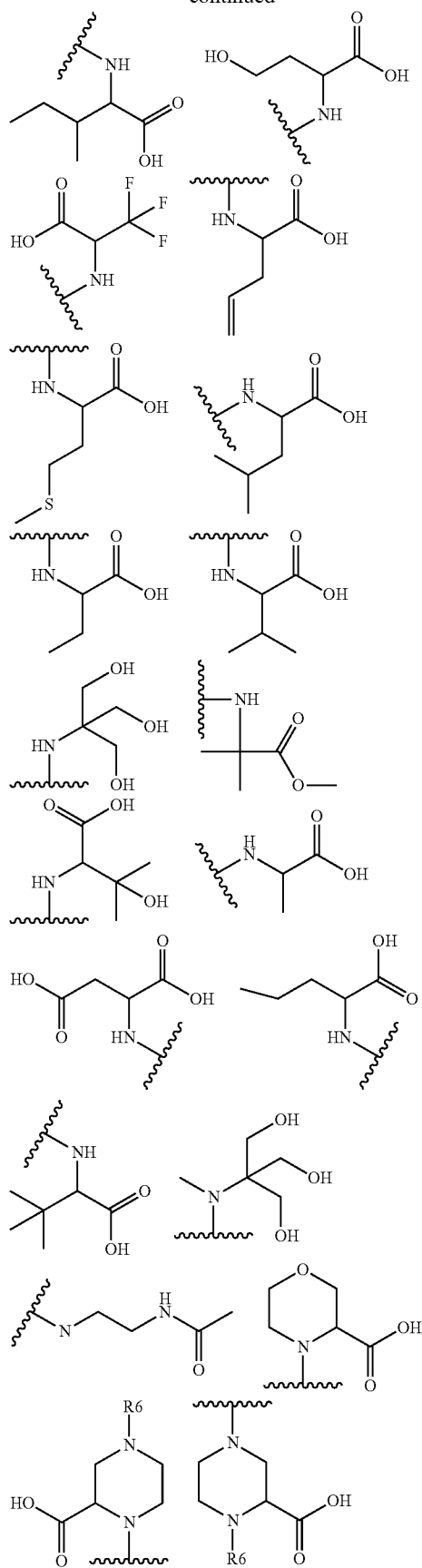
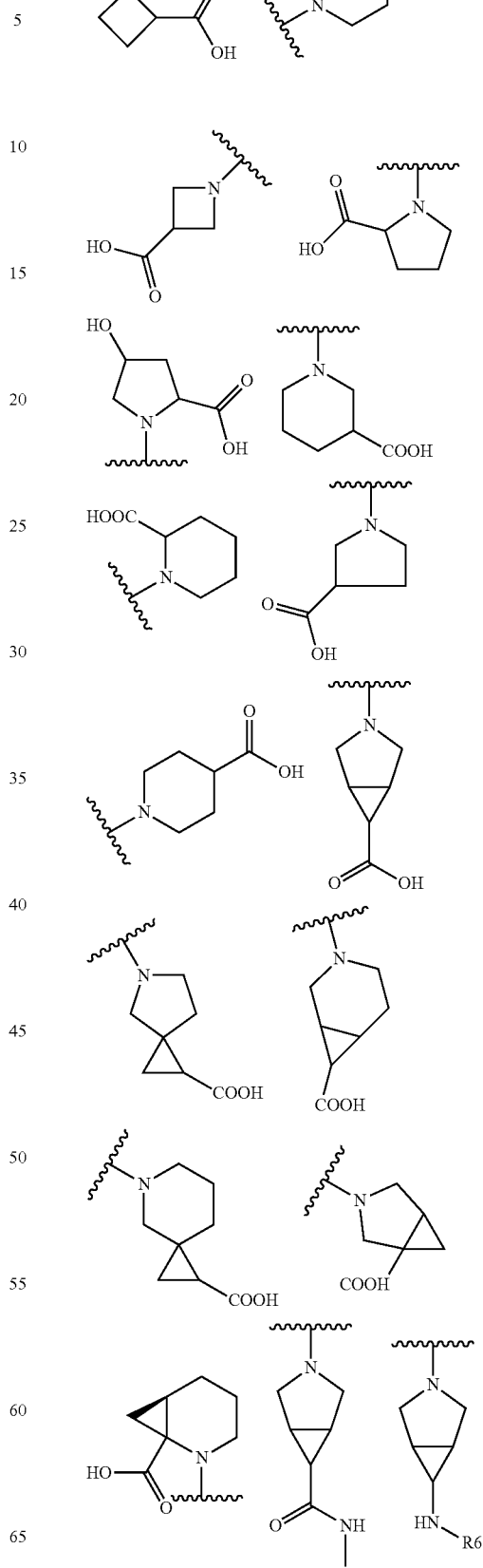

201
-continued
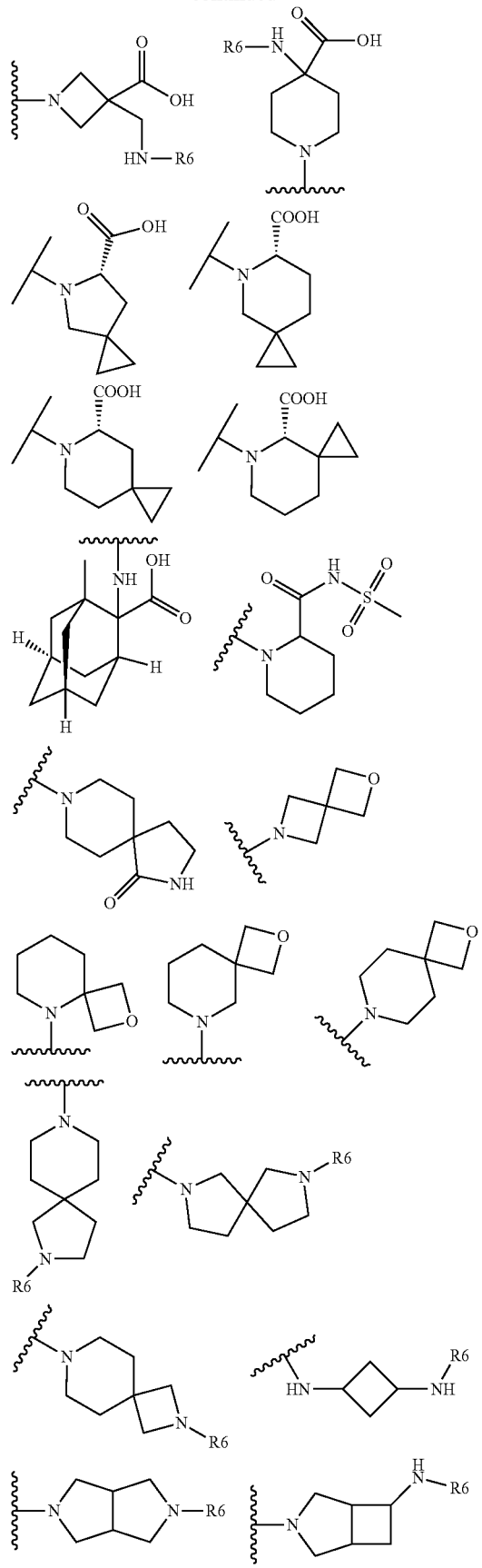
202
-continued
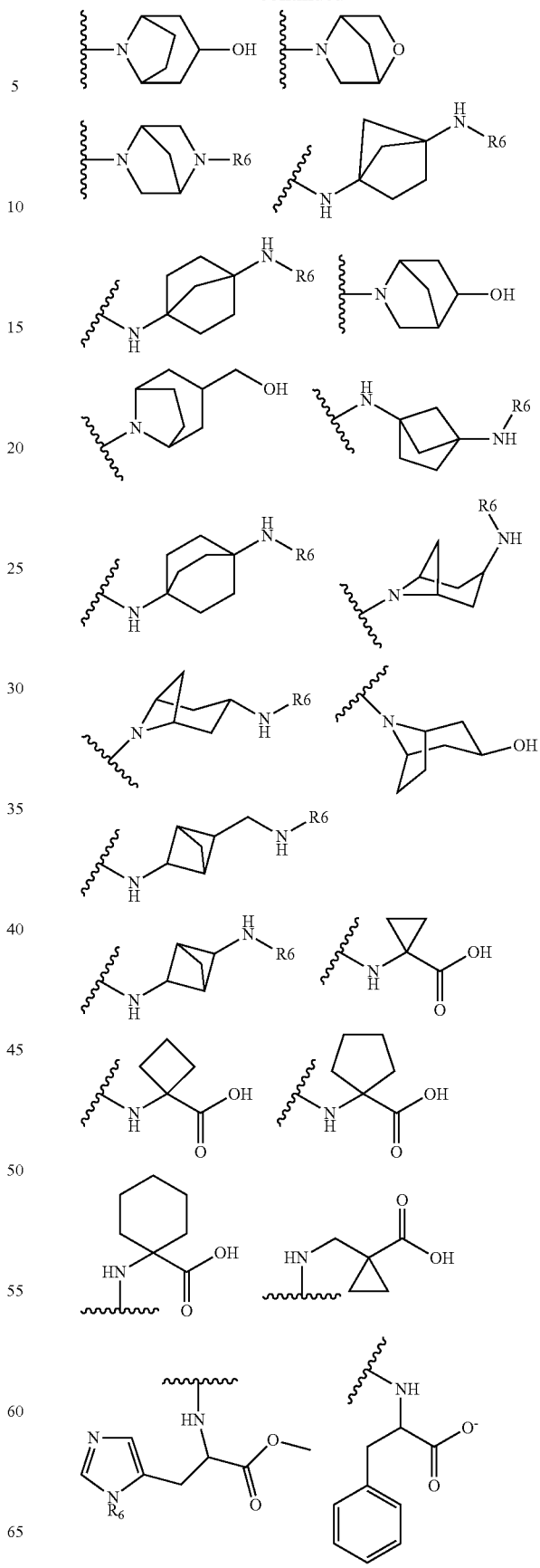

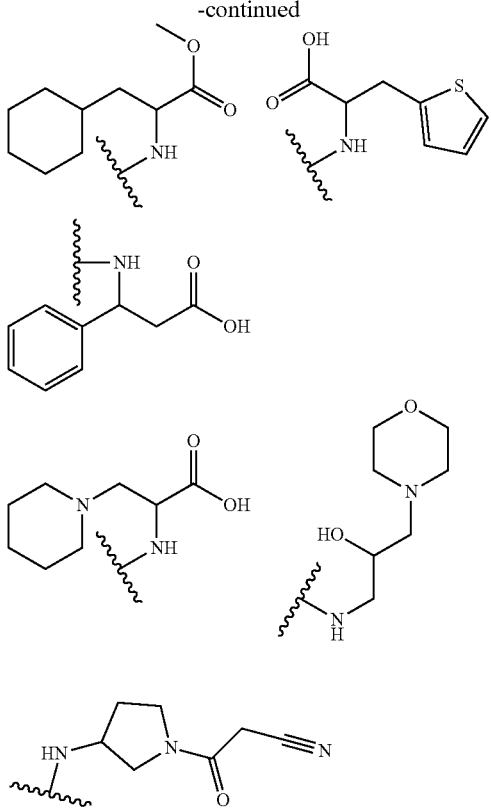
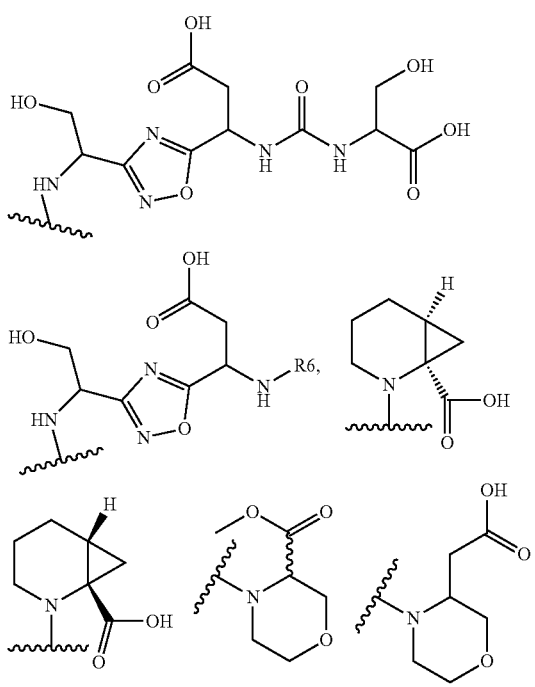

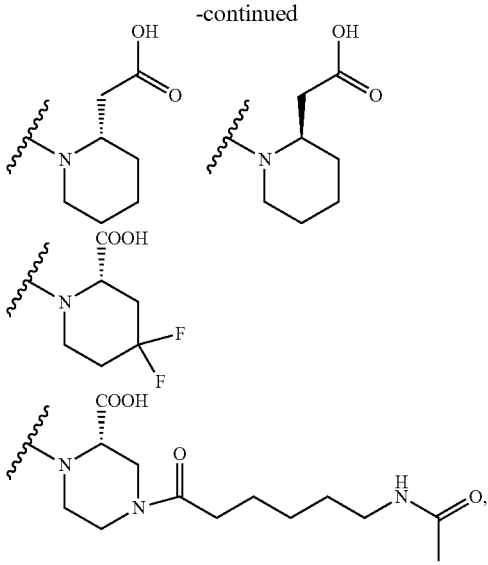
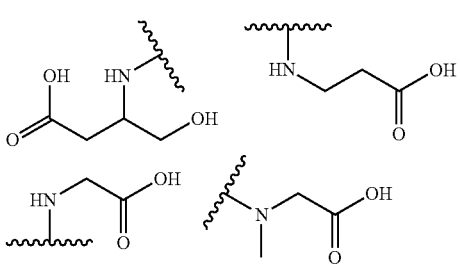

wherein, $R_6$ is selected from the group consisting of hydrogen, $C_{1-6}$ alkyl, $C(O)C_{1-6}$ alkyl and combinations thereof, wherein, $C_{1-6}$ alkyl and $C(O)C_{1-6}$ alkyl are optionally substituted with substituents selected from the group consisting of hydroxyl, COOH, $NHR_6$, $NHC(O)NHR_6$ and combinations thereof.

3. The compound of Formula I as claimed in claim 1, their stereoisomers and pharmaceutically acceptable salts thereof, wherein, $R_1$ is selected from hydrogen, $C_{1-4}$ alkyl, $C_{5-6}$ aryl and 5-9 membered monocyclic or bicyclic heteroaryl with 1-5 heteroatoms selected from N, S or O, wherein, $C_{1-4}$ alkyl, $C_{5-6}$ aryl and 5-9 membered monocyclic or bicyclic heteroaryl, are optionally substituted with one or more groups selected from hydrogen, halogen, hydroxyl and cyano, $R_2$ is selected from hydrogen, $C_{5-6}$ aryl and 5-10 membered monocyclic or bicyclic heteroaryl with 1-5 heteroatoms selected from N, S or O, wherein, $C_{5-6}$ aryl and 5-10 membered monocyclic or bicyclic heteroaryl, is optionally substituted with one or more groups selected from hydrogen, fluoro, chloro, bromo, iodo, $C_{1-4}$ alkyl, $C_{1-4}$ alkoxy and $C_{1-6}$ heterocyclyl, wherein, $C_{1-4}$ alkyl, $C_{1-4}$ alkoxy $C_{1-6}$ heterocyclyl is optionally substituted with one or more of the groups selected from $C_{1-4}$ alkyl and $C_{1-6}$ heterocyclyl, wherein, $C_{1-6}$ heterocyclyl is optionally substituted with one or more halogen;

$R_3$ and $R_4$ are independently selected from hydrogen, $C_{1-4}$ alkyl and $C_{1-4}$ alkoxy;

O is absent or is oxygen;

$R_5$ is selected from

-continued

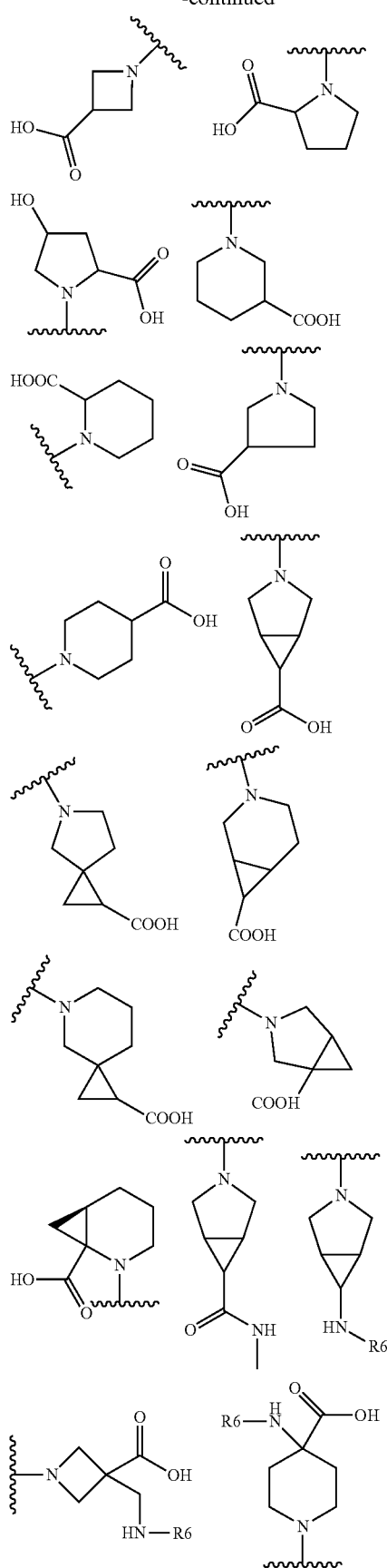
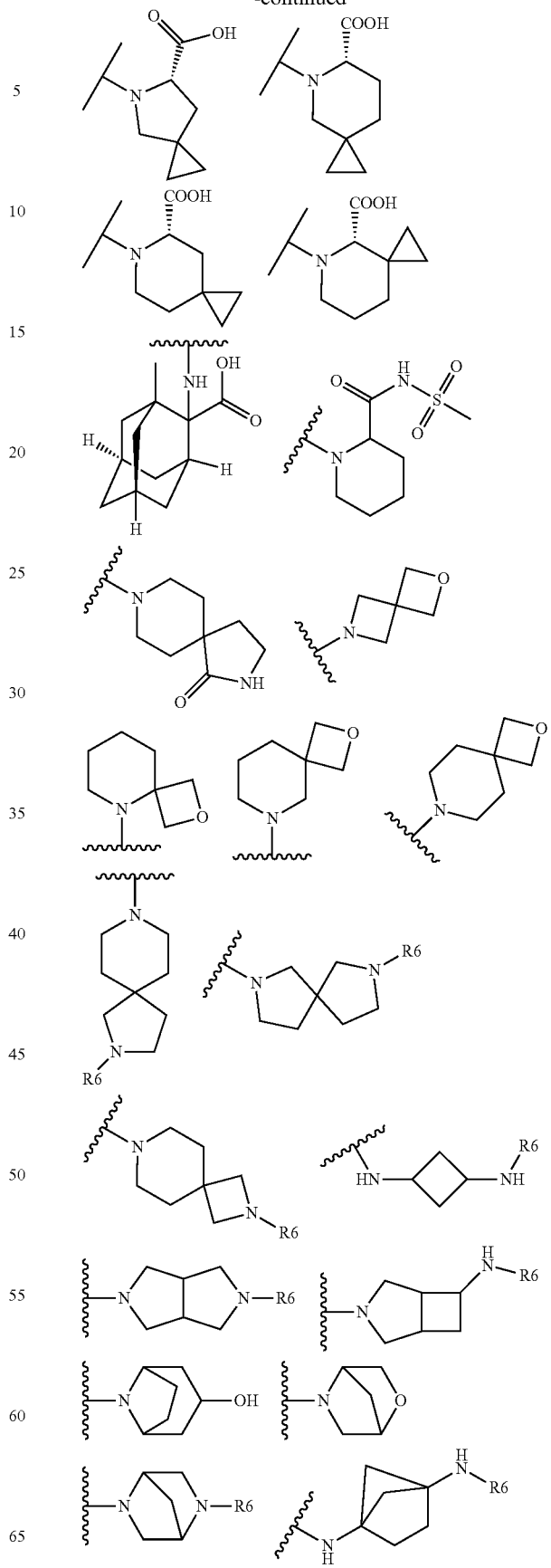

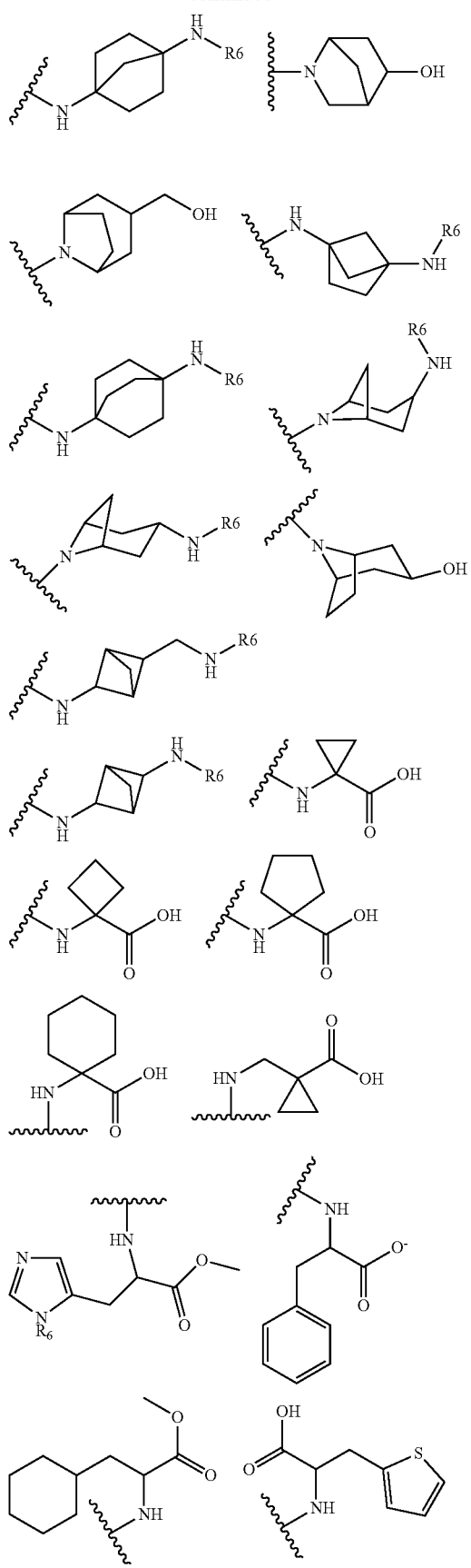
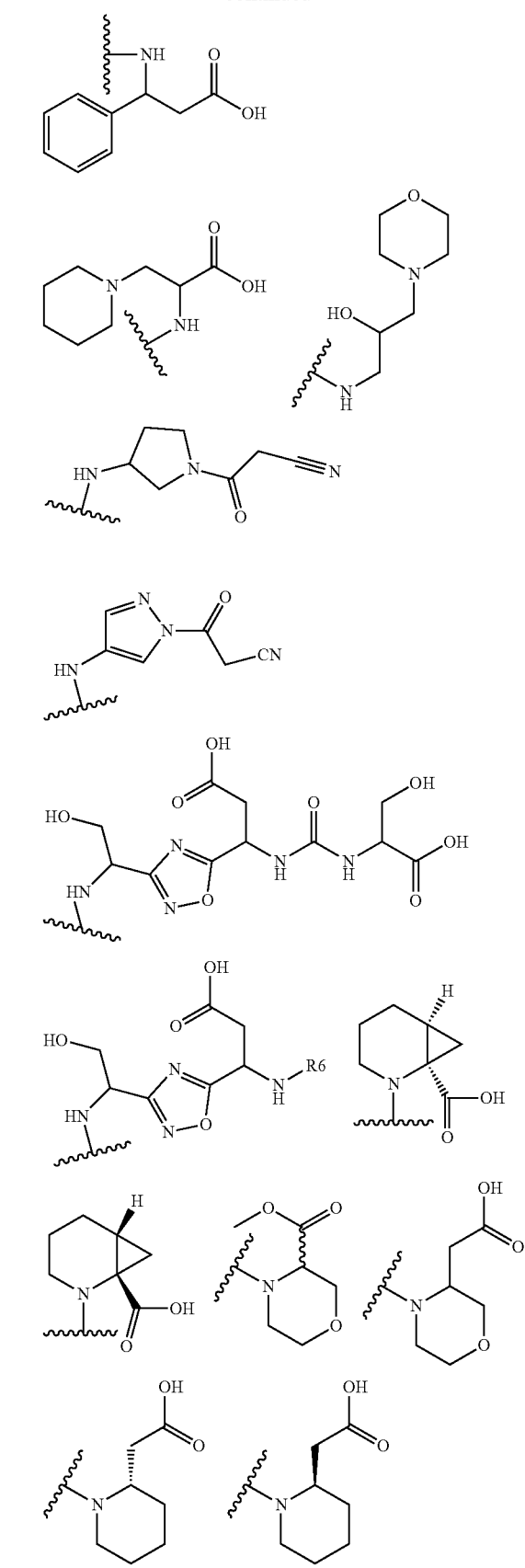

-continued

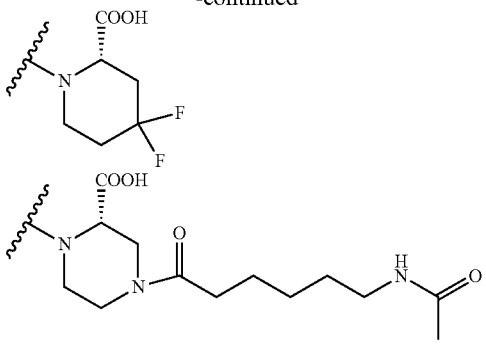

wherein, $R_6$ is selected from the group consisting of hydrogen, $C_{1-6}$ alkyl, $C(O)C_{1-6}$ alkyl and combinations thereof, wherein, $C_{1-6}$ alkyl and $C(O)C_{1-6}$ alkyl are optionally substituted with substituents selected from the group consisting of hydroxyl, COOH, $NHR_6NHC(O)NHR_6$, and combinations thereof.

4. A compound or its stereoisomers and pharmaceutically acceptable salts thereof, which is selected from a group consisting of:

N-(2-(((2-((4'-fluoro-2-methyl-[1,1'-biphenyl]-3-yl)methoxy)-4-methoxypyrimidin-5-yl)methyl)amino)ethyl)acetamide (Compound-1), N-((4-ethoxy-2-((2-methyl-[1,1'-biphenyl]-3-yl)methoxy)pyrimidin-5-yl)methyl)-N-methyl glycine (Compound-2), N-((4-ethoxy-2-((2-methyl-[1,1'-biphenyl]-3-yl)methoxy)pyrimidin-5-yl)methyl)-N-methyl glycine (Compound-3), (1R,6R)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid (Compound-4), (1S,6R)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid (Compound-5), N-(2-(((4,6-diethoxy-2-((2-methyl-[1,1'-biphenyl]-3-yl)methoxy)pyrimidin-5-yl)methyl)amino)ethyl)acetamide (Compound-6), (S)-1-((4-methoxy-2-((2-methyl-[1,1'-biphenyl]-3-yl)methoxy)pyrimidin-5-yl)methyl)piperidine-2-carboxylic acid (Compound-7), (S)-1-((4-((3-cyano-4-fluorobenzyl)oxy)-2-((2-methyl-[1,1'-biphenyl]-3-yl)methoxy)pyrimidin-5-yl)methyl)piperidine-2-carboxylic acid (Compound-8), (S)-1-((2-((2-methyl-[1,1'-biphenyl]-3-yl)methoxy)-4-(2,2,2-trifluoroethoxy)pyrimidin-5-yl)methyl)piperidine-2-carboxylic acid (Compound-9), (S)-1-((4-(4-hydroxybutoxy)-2-((2-methyl-[1,1'-biphenyl]-3-yl)methoxy)pyrimidin-5-yl)methyl)piperidine-2-carboxylic acid (Compound-10), (2S,4R)-1-((2-((3-(2,3-dihydrobenzo[b][1,4]dioxin-6-yl)-2-methylbenzyl)oxy)-4,6-dimethoxypyrimidin-5-yl)methyl)-4-hydroxypyrrolidine-2-carboxylic acid (Compound-11), (S)-1-((4-((5-cyanopyridin-3-yl)methoxy)-2-((2-methyl-[1,1'-biphenyl]-3-yl)methoxy)pyrimidin-5-yl)methyl) piperidine-2-carboxylic acid (Compound-12), (S)-1-((2-((3'-(3-(3,3-difluoropyrrolidin-1-yl)propoxy)-2,2'-dimethyl-[1,1'-biphenyl]-3-yl)methoxy)-4-methoxypyrimidin-5-yl)methyl)piperidine-2-carboxylic acid (Compound-13), N-(2-(((4-methoxy-2-((2-methyl-[1,1'-biphenyl]-3-yl)methoxy)pyrimidin-5-yl)methyl)amino)ethyl)acetamide (Compound-14), (R)-1-((4-methoxy-2-((2-methyl-[1,1'-biphenyl]-3-yl)methoxy)pyrimidin-5-yl)methyl)piperidine-2-carboxylic acid (Compound 15), (S)-1-((2-((4'-fluoro-2-methyl-[1,1'-biphenyl]-3-yl)methoxy)-4-methoxypyrimidin-5-yl)methyl)piperidine-2-carboxylic acid (Compound-16), (S)-1-((2-((3'-fluoro-2-methyl-[1,1'-biphenyl]-3-yl)methoxy)-4-methoxypyrimidin-5-yl)methyl)piperidine-2-carboxylic acid (Compound 17), N-(2-(((2-((3'-fluoro-2-methyl-[1,1'-biphenyl]-3-yl)methoxy)-4-methoxypyrimidin-5-yl)methyl)amino)ethyl)acetamide (Compound-18), (S)-1-((2-((2'-fluoro-2-methyl-[1,1'-biphenyl]-3-yl)methoxy)-4-methoxypyrimidin-5-yl)methyl)piperidine-2-carboxylic acid (Compound 19), N-(2-(((2-((2'-fluoro-2-methyl-[1,1'-biphenyl]-3-yl)methoxy)-4-methoxypyrimidin-5-yl)methyl)amino)ethyl)acetamide (Compound 20), N-(2-(((4-ethoxy-2-((2-methyl-[1,1'-biphenyl]-3-yl)methoxy)pyrimidin-5-yl)methyl)amino)ethyl)acetamide (Compound 21), (S)-1-((4-ethoxy-2-((2-methyl-[1,1'-biphenyl]-3-yl)methoxy)pyrimidin-5-yl)methyl) piperidine-2-carboxylic acid (Compound 22), 1-(((4-ethoxy-2-((2-methyl-[1,1'-biphenyl]-3-yl)methoxy)pyrimidin-5-yl)methyl)amino)cyclopropane-1-carboxylic acid (Compound 23), (3-(((4-ethoxy-2-((2-methyl-[1,1'-biphenyl]-3-yl)methoxy)pyrimidin-5-yl)methyl)amino)propanoic acid (Compound 24), 2-(((4-ethoxy-2-((2-methyl-[1,1'-biphenyl]-3-yl)methoxy)pyrimidin-5-yl)methyl)amino)-2-(hydroxymethyl)propane-1,3-diol (Compound 25), (2-(((4-ethoxy-2-((2-methyl-[1,1'-biphenyl]-3-yl)methoxy)pyrimidin-5-yl)methyl)(methyl)amino)-2-(hydroxymethyl)propane-1,3-diol (Compound 26), (S)-3-(((4-ethoxy-2-((2-methyl-[1,1'-biphenyl]-3-yl)methoxy)pyrimidin-5-yl)methyl)amino)butanoic acid (Compound 27), ((4-ethoxy-2-((2-methyl-[1,1'-biphenyl]-3-yl)methoxy)pyrimidin-5-yl)methyl)-D-alanine (Compound 28), ((4-ethoxy-2-((2-methyl-[1,1'-biphenyl]-3-yl)methoxy)pyrimidin-5-yl)methyl)asparagine (Compound 29), (2R,4R)-1-((4-ethoxy-2-((2-methyl-[1,1'-biphenyl]-3-yl)methoxy)pyrimidin-5-yl)methyl)-4-hydroxypyrrolidine-2-carboxylic acid (Compound 30), 1-((4-ethoxy-2-((2-methyl-[1,1'-biphenyl]-3-yl)methoxy)pyrimidin-5-yl)methyl)azetidine-2-carboxylic acid (Compound 31), N-(2-(((4-(benzyloxy)-2-((2-methyl-[1,1'-biphenyl]-3-yl)methoxy)pyrimidin-5-yl)methyl)amino)ethyl)acetamide (Compound 32), 1-((4-(benzyloxy)-2-((2-methyl-[1,1'-biphenyl]-3-yl)methoxy)pyrimidin-5-yl)methyl)piperidine-2-carboxylic acid (Compound 33), (2S,4R)-1-((4,6-dimethoxy-2-((2-methyl-[1,1'-biphenyl]-3-yl)methoxy)pyrimidin-5-yl)methyl)-4-hydroxypyrrolidine-2-carboxylic acid (Compound 34), 2-(((4,6-dimethoxy-2-((2-methyl-[1,1'-biphenyl]-3-yl)methoxy)pyrimidin-5-yl)methyl)amino)-2-(hydroxymethyl)propane-1,3-diol (Compound 35), ((4,6-dimethoxy-2-((2-methyl-[1,1'-biphenyl]-3-yl)methoxy)pyrimidin-5-yl)methyl)-L-proline (Compound 36), Methyl 4-((4,6-dimethoxy-2-((2-methyl-[1,1'-biphenyl]-3-yl)methoxy)pyrimidin-5-yl)methyl) morpholine-3-carboxylate (Compound 37),
4-((4,6-dimethoxy-2-((2-methyl-[1,1'-biphenyl]-3-yl)methoxy)pyrimidin-5-yl)methyl)morpholine-3-carboxylic acid (Compound 38),
(2S,4R)-1-((4,6-diethoxy-2-((2-methyl-[1,1'-biphenyl]-3-yl)methoxy)pyrimidin-5-yl)methyl)-4-hydroxypyrrolidine-2-carboxylic acid (Compound 39),
((S)-1-((4,6-diethoxy-2-((2-methyl-[1,1'-biphenyl]-3-yl)methoxy)pyrimidin-5-yl)methyl)piperidine-2-carboxylic acid (Compound 40),
2-(((4,6-diethoxy-2-((2-methyl-[1,1'-biphenyl]-3-yl)methoxy)pyrimidin-5-yl)methyl)amino)-2-(hydroxymethyl)propane-1,3-diol (Compound 41),
2-(((4,6-dimethoxy-2-((2-methyl-[1,1'-biphenyl]-3-yl)methoxy)pyrimidin-5-yl)methyl)amino)-2-(hydroxymethyl)propane-1,3-diol (Compound 42),
(S)-4-((4,6-dimethoxy-2-((2-methyl-[1,1'-biphenyl]-3-yl)methoxy)pyrimidin-5-yl)methyl)morpholine-3-carboxylic acid (Compound 43),
2-(4-((4,6-dimethoxy-2-((2-methyl-[1,1'-biphenyl]-3-yl)methoxy)pyrimidin-5-yl)methyl)morpholin-3-yl)acetic acid (Compound 44),
(S)-1-((4,6-dimethoxy-2-((2-methyl-[1,1'-biphenyl]-3-yl)methoxy)pyrimidin-5-yl)methyl)piperidine-2-carboxylic acid (Compound 45),
(S)-5-((4,6-dimethoxy-2-((2-methyl-[1,1'-biphenyl]-3-yl)methoxy)pyrimidin-5-yl)methyl)-5-azaspiro[2.4]heptane-6-carboxylic acid (Compound 46),
7-((4,6-dimethoxy-2-((2-methyl-[1,1'-biphenyl]-3-yl)methoxy)pyrimidin-5-yl)methyl)-2,7-diazaspiro[4.5]decan-1-one (Compound 47),
rac-(1R,6S)-2-((4,6-dimethoxy-2-((2-methyl-[1,1'-biphenyl]-3-yl)methoxy)pyrimidin-5-yl)methyl)-2-azabicyclo[4.1.0]heptane-1-carboxylic acid (Compound 48),
(S)-4-acetyl-1-((4-methoxy-2-((2-methyl-[1,1'-biphenyl]-3-yl)methoxy)pyrimidin-5-yl)methyl)piperazine-2-carboxylic acid (Compound 49),
(S)-1-((4-methoxy-2-((2-methyl-[1,1'-biphenyl]-3-yl)methoxy)pyrimidin-5-yl)methyl)piperazine-2-carboxylic acid (Compound 50),
(S)-5-((4-methoxy-2-((2-methyl-[1,1'-biphenyl]-3-yl)methoxy)pyrimidin-5-yl)methyl)-5-azaspiro[2.4]heptane-6-carboxylic acid (Compound 51),
7-((4-methoxy-2-((2-methyl-[1,1'-biphenyl]-3-yl)methoxy)pyrimidin-5-yl)methyl)-2,7-diazaspiro[4.5]decan-1-one (Compound 52),
N-(2-(((4-((3-cyano-4-fluorobenzyl)oxy)-2-((2-methyl-[1,1'-biphenyl]-3-yl)methoxy)pyrimidin-5-yl)methyl)amino)ethyl)acetamide (Compound 53),
(2S,4R)-1-((4-((3-cyano-4-fluorobenzyl)oxy)-2-((2-methyl-[1,1'-biphenyl]-3-yl)methoxy)pyrimidin-5-yl)methyl)-4-hydroxypyrrolidine-2-carboxylicacid (Compound 54),
(S)-1-((2-((3-(2,3-dihydrobenzo[b][1,4]dioxin-6-yl)-2-methylbenzyl)oxy)-4,6-dimethoxypyrimidin-5-yl)methyl)piperidine-2-carboxylic acid (Compound 55),
N-(2-(((2-((3-(2,3-dihydrobenzo[b][1,4]dioxin-6-yl)-2-methylbenzyl)oxy)-4,6-dimethoxypyrimidin-5-yl)methyl)amino)ethyl)acetamide (Compound 56),
N-(2-(((2-((3',4'-dimethoxy-2-methyl-[1,1'-biphenyl]-3-yl)methoxy)-4,6-dimethoxypyrimidin-5-yl)methyl)amino)ethyl)acetamide (Compound 57),
((2S,4R)-1-((2-((3',4'-dimethoxy-2-methyl-[1,1'-biphenyl]-3-yl)methoxy)-4,6-dimethoxypyrimidin-5-yl)methyl)-4-hydroxypyrrolidine-2-carboxylic acid (Compound 58),
(2S,4R)-1-((4-((5-cyanopyridin-3-yl)methoxy)-2-((2-methyl-[1,1'-biphenyl]-3-yl)methoxy)pyrimidin-5-yl)methyl)-4-hydroxypyrrolidine-2-carboxylic acid (Compound 59),
(S)-2-(1-((4-methoxy-2-((2-methyl-[1,1'-biphenyl]-3-yl)methoxy)pyrimidin-5-yl)methyl)piperidin-2-yl) acetic acid (Compound 60),
(R)-2-(1-((4-methoxy-2-((2-methyl-[1,1'-biphenyl]-3-yl)methoxy)pyrimidin-5-yl)methyl)piperidin-2-yl) acetic acid (Compound 61),
(S)-4-(6-acetamidohexanoyl)-1-((4-methoxy-2-((2-methyl-[1,1'-biphenyl]-3-yl)methoxy)pyrimidin-5-yl)methyl)piperazine-2-carboxylic acid (Compound 62),
(S)-4,4-difluoro-1-((4-methoxy-2-((2-methyl-[1,1'-biphenyl]-3-yl)methoxy)pyrimidin-5-yl)methyl)piperidine-2-carboxylic acid (Compound 63),
(S)-1-((4-methyl-2-((2-methyl-[1,1'-biphenyl]-3-yl)methoxy)pyrimidin-5-yl)methyl)piperidine-2-carboxylic acid (Compound 64), and
N-(2-(((4-methyl-2-((2-methyl-[1,1'-biphenyl]-3-yl)methoxy)pyrimidin-5-yl)methyl)amino)ethyl)acetamide (Compound 65).

5. A process of preparation of compounds of Formula I

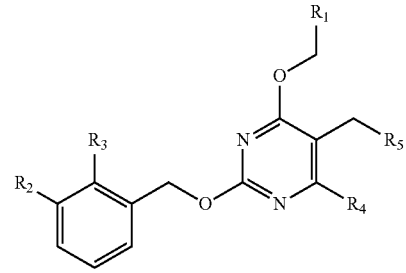

Formula I their stereoisomers and pharmaceutically acceptable salts thereof,
wherein,
$R_1$ is selected from hydrogen, $C_{1-10}$ alkyl, $C_{1-6}$ haloalkyl, $C_{5-10}$ aryl and 5-10 membered monocyclic or bicyclic heteroaryl with 1-5 heteroatoms selected from N, S or O,
wherein, $C_{1-10}$ alkyl, $C_{5-10}$ aryl and 5-10 membered monocyclic or bicyclic heteroaryl, are optionally substituted with one or more of the groups selected from hydrogen, halogen, hydroxyl and cyano,
$R_2$ is selected from hydrogen, $C_{1-10}$ alkyl, $C_{1-10}$ alkoxy, $C_{5-10}$ aryl and 5-10 membered monocyclic or bicyclic heteroaryl with 1-5 heteroatoms selected from N, S or O,
wherein, $C_{1-10}$ alkyl, $C_{5-10}$ aryl and 5-10 membered monocyclic or bicyclic heteroaryl, are optionally substituted with one or more of the groups selected from hydrogen, halogen, $C_{1-6}$ alkyl, $C_{1-6}$ alkoxy and $C_{1-6}$ heterocyclyl,
wherein, $C_{1-6}$ alkyl, $C_{1-6}$ alkoxy and $C_{1-6}$ heterocyclyl are optionally substituted with one or more of the groups selected from $C_{1-6}$ alkyl or $C_{1-6}$ heterocyclyl,
wherein, $C_{1-6}$ heterocyclyl is optionally substituted with one or more halogen;

R$_3$ and R$_4$ are independently selected from hydrogen, C$_{1-10}$ alkyl and C$_{1-10}$ alkoxy;

O is absent or is oxygen;

R$_5$ is —NR$_7$R$_8$, wherein, R$_7$ and R$_8$ are selected from the group consisting of hydrogen, C$_{3-10}$ cycloalkyl, C$_{1-6}$ alkyl, 5-10 membered monocyclic or bicyclic, saturated or unsaturated heterocyclic ring with 1-3 heteroatoms selected from N, S or O, and combinations thereof, wherein, C$_{3-10}$ cycloalkyl, C$_{1-6}$ alkyl and the 5-10 membered monocyclic or bicyclic, saturated or unsaturated heterocyclic ring are optionally substituted with one or more substituents selected from oxo, cyano, halogen, hydroxyl, morpholino, C(O)NH$_2$, C(O)CH$_2$CN, NHR$_6$, COOH, COOR$_6$, NHC(O)R$_6$, C$_{1-6}$ alkyl, C$_{1-6}$ haloalkyl, C$_{3-10}$ cycloalkyl, C$_{5-6}$ aryl, SR$_6$ or 5-10 membered monocyclic or bicyclic, saturated or unsaturated heterocyclic ring with 1-3 heteroatoms selected from N, S or O, wherein, C$_{1-6}$ alkyl and the 5-10 membered monocyclic or bicyclic, saturated or unsaturated heterocyclic ring are independently substituted with one or more substituents selected from hydroxyl and R$_6$; or R$_7$ and R$_8$ can be taken together to form a 4-10 membered monocyclic or bicyclic, saturated or unsaturated heterocyclic ring with 1-3 heteroatoms selected from N, S or O, wherein, the 4-10 membered monocyclic or bicyclic, saturated or unsaturated heterocyclic ring is optionally substituted with one or more substituents selected from the group consisting of hydroxyl, halogen, C$_{1-6}$ alkyl, COOH, R$_6$, NHR$_6$, C(O)NHR$_6$, C(O)NHSO$_2$R$_6$, C(O)(CH$_2$)$_n$NHC(O)CH$_3$ and combinations thereof, wherein, C$_{1-6}$ alkyl is further substituted with groups selected from oxo, hydroxyl, COOH, COOR$_6$ or NHR$_6$; n is 1-6; and R$_6$ is selected from the group consisting of hydrogen, C$_{1-6}$ alkyl, C(O)C$_{1-6}$ alkyl and combinations thereof, wherein, C$_{1-6}$ alkyl and C(O)C$_{1-6}$ alkyl are optionally substituted with substituents selected from the group consisting of hydroxyl, COOH, NHR$_6$, NHC(O)NHR$_6$ and combinations thereof, the process comprising (a) reacting compounds of Formula IV and Formula B$_3$ in presence of a base, a solvent, and optionally a coupling reagent to obtain compounds of Formula V or Formula XIII; (b) processing the compounds of Formula V and Formula XIII to obtain compounds of Formula VI and Formula VII; and (c) reacting compounds of Formula VII with substituted amines in presence of a reducing agent and a third solvent to obtain compounds of Formula I

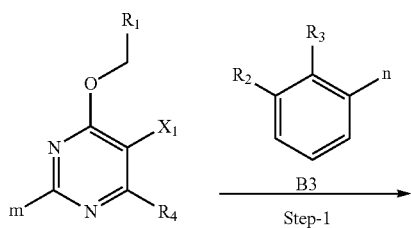

Formula IV

Wherein m is halo, —COOH, —NH$_2$, —O—, —CH$_2$OH and n is halo, —COOH, —NH$_2$, —O—, —CH$_2$OH X$_1$ is H or Br

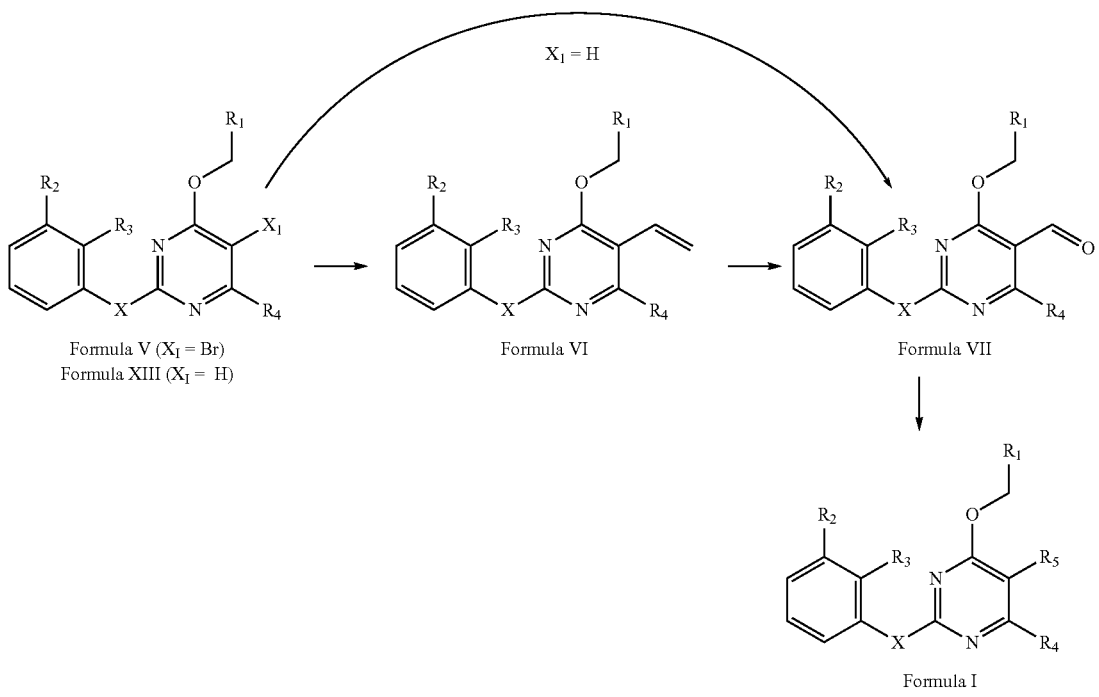

Formula V (X$_1$ = Br)
Formula XIII (X$_1$ = H)

Formula VI

Formula VII

Formula I wherein, $R_1$ of Formula I, Formula IV, Formula V, Formula VI, Formula VII, and Formula XIII are independently selected from hydrogen, $C_{1-10}$ alkyl, $C_{1-6}$ haloalkyl, $C_{5-10}$ aryl and 5-10 membered monocyclic or bicyclic heteroaryl with 1-5 heteroatoms selected from N, S or O, wherein, $C_{1-10}$ alkyl, $C_{5-10}$ aryl and 5-10 membered monocyclic or bicyclic heteroaryl, are optionally substituted with one or more of the groups selected from hydrogen, halogen, hydroxyl and cyano;

$R_2$ of Formula I, Formula V, Formula VI, Formula VII, Formula XIII and Formula $B_3$ are independently selected from hydrogen, $C_{1-10}$ alkyl, $C_{1-10}$ alkoxy, $C_{5-10}$ aryl and 5-10 membered monocyclic or bicyclic heteroaryl with 1-5 heteroatoms selected from N, S or O, wherein, $C_{1-10}$ alkyl, $C_{5-10}$ aryl and 5-10 membered monocyclic or bicyclic heteroaryl, are optionally substituted with one or more of the groups selected from hydrogen, halogen, $C_{1-6}$ alkyl, $C_{1-6}$ alkoxy and $C_{1-6}$ heterocyclyl, wherein, $C_{1-6}$ alkyl, $C_{1-6}$ alkoxy and $C_{1-6}$ heterocyclyl are optionally substituted with one or more of the groups selected from $C_{1-6}$ alkyl or $C_{1-6}$ heterocyclyl, wherein, $C_{1-6}$ heterocyclyl is optionally substituted with one or more halogen;

$R_3$, and $R_4$ of Formula I, Formula IV, Formula V, Formula VI, Formula VII, Formula XIII and Formula $B_3$ independently selected from hydrogen, $C_{1-10}$ alkyl and $C_{1-10}$ alkoxy;

X of Formula I, Formula V, Formula VI, Formula VII, and Formula XIII is —CH$_2$O where O is absent or is oxygen; $R_5$ of Formula I is —NR$_7$R$_8$, wherein, $R_7$ and $R_8$ are independently selected from the group consisting of hydrogen, $C_{3-10}$ cycloalkyl, $C_{1-6}$ alkyl, 5-10 membered monocyclic or bicyclic, saturated or unsaturated heterocyclic ring with 1-3 heteroatoms selected from N, S or O, and combinations thereof, wherein, $C_{3-10}$ cycloalkyl, $C_{1-6}$ alkyl, and the 5-10 membered monocyclic or bicyclic, saturated or unsaturated heterocyclic ring are optionally substituted with one or more substituents selected from oxo, cyano, halogen, hydroxyl, morpholino, C(O)NH$_2$, C(O)CH$_2$CN, NHR$_6$, COOH, COOR$_6$, NHC(O)R$_6$, $C_{1-6}$ alkyl, $C_{1-6}$ haloalkyl, $C_{3-10}$ cycloalkyl, $C_{5-6}$ aryl, SR$_6$ or 5-10 membered monocyclic or bicyclic, saturated or unsaturated heterocyclic ring with 1-3 heteroatoms selected from N, S or O, wherein, $C_{1-6}$ alkyl and the 5-10 membered monocyclic or bicyclic, saturated or unsaturated heterocyclic ring are independently substituted with one or more substituents selected from hydroxyl and R$_6$; or $R_7$ and $R_8$ can be taken together to form a 4-10 membered monocyclic or bicyclic, saturated or unsaturated heterocyclic ring with 1-3 heteroatoms selected from N, S or O, wherein, the 4-10 membered monocyclic or bicyclic, saturated or unsaturated heterocyclic ring is optionally substituted with one or more substituents selected from the group consisting of hydroxyl, halogen, $C_{1-6}$ alkyl, COOH, R$_6$, NHR$_6$, C(O)NHR$_6$, C(O)NHSO$_2$R$_6$, C(O)(CH$_2$)$_n$NHC(O)CH$_3$ and combinations thereof, wherein, $C_{1-6}$ alkyl is further substituted with groups selected from hydroxyl, COOH or NHR$_6$; n is 1-6; and R$_6$ is selected from the group consisting of hydrogen, $C_{1-6}$ alkyl, C(O)$C_{1-6}$ alkyl and combinations thereof, wherein, $C_{1-6}$ alkyl and C(O)$C_{1-6}$ alkyl are optionally substituted with substituents selected from the group consisting of hydroxyl, COOH, NHR$_6$, NHC(O)NHR$_6$ and combinations thereof.

6. The process of claim 5, wherein, processing the compounds of Formula V to obtain compounds of Formula VII comprises: (a) alkenylation of compounds of Formula V in presence of a second base and a second solvent to obtain compounds of Formula VI; and (b) oxidation of compounds of Formula VI to obtain compounds of Formula VII.

7. The process of claim 5, wherein, processing the compounds of Formula XIII to obtain compounds of Formula VII comprises formylation of compounds of Formula XIII to obtain compounds of Formula VII.

8. The process of claim 5, wherein, the coupling reagent is selected from 1-[bis(dimethylamino)methylene]-1H-1,2,3-triazolo[4,5-b]pyridinium 3-oxid hexafluorophosphate (HATU), N,N'-Dicyclohexylcarbodiimide (DCC), or propylphosphonic anhydride; the solvent is selected from the group consisting of methanol, ethanol, isopropyl alcohol, t-butyl alcohol, dichloromethane, ethyl acetate, dioxane, ether, N,N-dimethylformamide, dimethyl sulfoxide, and combinations thereof; the base is selected from the group consisting of sodium hydride, butyllithium, lithium diisopropylamide, potassium carbonate, cesium carbonate, triethylamine, diisopropylethylamine, 4-dimethylaminopyridine, pyridine, and combinations thereof; and the reducing agent is selected from the group consisting of sodium cyanoborohydride, sodium borohydride, lithiumaluminium hydride, diisobutylaluminium hydride, and combinations thereof.

9. A pharmaceutical composition comprising a compound of Formula I or a pharmaceutically acceptable salt thereof of claim 1 and a pharmaceutically acceptable carrier.

10. The pharmaceutical composition of claim 9, wherein, the composition is in a form selected from the group consisting of a tablet, capsule, powder, syrup, solution, aerosol and suspension.

11. A method for the treatment of diseases associated with PD1/PD-L1 activation, comprising administering to a subject suffering from the proliferative disorder or cancer associated with PD1/PD-L1 activation a therapeutically effective amount of the compound of claim 1, to a subject in need thereof.

12. A method for the treatment of cancer, said method comprising administering a compound of Formula I as claimed in claim 1 to a subject in need of said treatment.

13. A method of treatment of cancer of claim 12, wherein, said compound is administered in combination with an immune modulator.

14. A method for the treatment of cancer and an infectious disease, the method comprising administering to a subject suffering from an infectious disease selected from the group consisting of HIV, Influenza, herpes virus, Hepatitis A, Hepatitis B, Hepatitis C, and Hepatitis D, a therapeutically effective amount of the compound of Formula I as claimed in claim 1 to a subject in need thereof.

15. A pharmaceutical composition of claim 9, further comprising one or more other pharmaceutically-active ingredients.

16. The process of claim 6, wherein, the second base is selected from the group consisting of butyl lithium, sodium hydride, lithium diisopropylamide, potassium carbonate, cesium carbonate, triethylamine, diisopropylethylamine, 4-dimethylaminopyridine, pyridine, and combinations thereof, the second solvent is selected from the group consisting of N,N-dimethylformamide, dichloromethane, ethyl acetate, dioxane, isopropyl alcohol, ether, t-butyl alcohol, N,N-dimethylformamide, dimethyl sulfoxide, and combinations thereof, the third solvent is selected from the group consisting of acetic acid, methanol, N,N-dimethylformamide, and combinations thereof.

* * * * *